(12) United States Patent
De Angelis et al.

(10) Patent No.: US 9,040,668 B2
(45) Date of Patent: May 26, 2015

(54) ANTI-SERUM ALBUMIN BINDING VARIANTS

(75) Inventors: Elena De Angelis, Cambridge (GB); Carolyn Enever, Cambridge (GB); Haiqun Liu, Cambridge (GB); Oliver Schon, Cambridge (GB); Malgorzata Pupecka-Swider, Cambridge (GB)

(73) Assignee: Glaxo Group Limited (GB)

( * ) Notice: Subject to any disclaimer, the term of this patent is extended or adjusted under 35 U.S.C. 154(b) by 0 days.

(21) Appl. No.: 13/698,794

(22) PCT Filed: May 20, 2011

(86) PCT No.: PCT/EP2011/058298
§ 371 (c)(1),
(2), (4) Date: Nov. 19, 2012

(87) PCT Pub. No.: WO2011/144751
PCT Pub. Date: Nov. 24, 2011

(65) Prior Publication Data
US 2013/0129746 A1 May 23, 2013

Related U.S. Application Data

(60) Provisional application No. 61/346,519, filed on May 20, 2010.

(51) Int. Cl.
| | | |
|---|---|---|
| *A61K 39/395* | (2006.01) | |
| *A61K 39/00* | (2006.01) | |
| *C12P 21/08* | (2006.01) | |
| *C07K 14/765* | (2006.01) | |
| *C07K 19/00* | (2006.01) | |
| *C07K 16/46* | (2006.01) | |
| *C07K 16/18* | (2006.01) | |
| *A61K 47/48* | (2006.01) | |
| *C07K 16/28* | (2006.01) | |

(52) U.S. Cl.
CPC .............. *C07K 16/18* (2013.01); *C07K 14/765* (2013.01); *A61K 47/48538* (2013.01); *C07K 16/2878* (2013.01); *C07K 2317/21* (2013.01); *C07K 2317/565* (2013.01); *C07K 2317/567* (2013.01); *C07K 2317/569* (2013.01); *C07K 2317/92* (2013.01); *C07K 2317/94* (2013.01); *C07K 2319/00* (2013.01); *C07K 2319/31* (2013.01); *C07K 16/468* (2013.01)

(58) Field of Classification Search
CPC ...... C07K 16/28; C07K 16/48; C07K 16/468; C07K 16/2878; C07K 2317/21; C07K 2317/22; C07K 2317/569; C07K 2317/92; C07K 2319/00; C07K 2319/31; C07K 14/56; A61K 2039/505; A61K 47/48538
See application file for complete search history.

(56) References Cited

U.S. PATENT DOCUMENTS

2011/0301335 A1* 12/2011 Duffield et al. ............ 530/387.3
2011/0305696 A1* 12/2011 De Angelis et al. ........ 424/134.1

FOREIGN PATENT DOCUMENTS

| WO | WO 2008/149147 A2 | 12/2008 |
| WO | WO 2010/094720 A2 | 8/2010 |
| WO | WO 2010/094722 A2 | 8/2010 |
| WO | WO 2010/094723 A2 | 8/2010 |
| WO | WO 2010/108937 A2 | 9/2010 |
| WO | WO 2011/006914 A2 | 1/2011 |
| WO | WO 2011/039096 A1 | 4/2011 |

OTHER PUBLICATIONS

Jespers et al., Nature Biotechnology 22(9): 1161-1165, Sep. 2004.*
Holt, et al., Protein Engineering, Design & Selection, vol. 21, No. 5, 2008, pp. 283-288.

* cited by examiner

*Primary Examiner* — Phuong Huynh
(74) *Attorney, Agent, or Firm* — Jason C. Fedon; William T. Han

(57) ABSTRACT

The invention relates to improved variants of the anti-serum albumin immunoglobulin single variable domain DOM7h-11, as well as ligands and drug conjugates comprising such variants, compositions, nucleic acids, vectors and hosts.

9 Claims, 8 Drawing Sheets

Figure 1A

Block 1 (positions 1–20), Kabat Residue:
D I Q M T Q S P S S L S A S V G D R V T
(positions: 5=T, 10=S, 15=V, 20=T)

Rows DOM7h-11, DOM7h-11-12, DOM7h-11-15, DOM7h-11-18, DOM7h-11-19, DOM7h-11-3: identical to Kabat residue (all dots).

Block 2 (positions 21–40), Kabat Residue:
G I T C R A S Q S I P H I G T M L A W Y
(positions: 25=A, 30=G, 35=W, 40=P; column 40 shows P)
Additional residues shown in row: ... Q Q K P (ending at position 40=P)

DOM7h-11:     R R C A R S I P H T G S L M L A T
DOM7h-11-12:  . . . . . . . . . . . . . . . M .
DOM7h-11-15:  . . . . . . . . . . . . . . . M .
DOM7h-11-18:  . . . . . . . . . . . . . . . M .
DOM7h-11-19:  . . . . . . . . . . . . . . . M .
DOM7h-11-3:   . . . . . . . . . . . . . . . . .

Block 3 (positions 41–60), Kabat Residue:
G K A P L L L I W F G L R S Q S G V P S
(positions: 45=K, 50=F, 55=Q, 60=S)

DOM7h-11:     . . . . . . . . F A W G L R S Q S . . .
DOM7h-11-12:  . . . . . . . . . A . E . . . . . . . .
DOM7h-11-15:  . . . . . . . . . . . . . . . . . . . .
DOM7h-11-18:  . . . . . . . . . . . . . . . . . . . .
DOM7h-11-19:  . . . . . . . . . W N . . . . . . . . .
DOM7h-11-3:   . . . . . . . . . . . . . . . . . . . .

Block 4 (positions 61–80), Kabat Residue:
R F S G S G T D F T L T I S S L Q S L P
(positions: 65=S, 70=D, 75=I, 80=P)

DOM7h-11:     . . . . . . . . . . . . . . . . . . . .
DOM7h-11-12:  . . . . . . . . . . . . . . . . . . . .

Figure 1A

| human | kinetics based on DOM7h-11 lineage (ranges supported by data) | | |
|---|---|---|---|
| | overall range | | |
| | KD: 1 to 10000 | | |
| | Kd:1.5e-4 to 0.1 ; Ka:2e6 to 1e4 | | |
| therapeutic ranges | chronic | intermediate | acute |
| | high affinity | medium affinity | low affinity |
| | KD: 0.1-400 | KD: 400-2000 | KD: 2000-10000 |
| | Kd:1.5e-4 to 8e-3 ; Ka:1e6 to 5e4 | Kd: 8e-3 to 0.08 ; Ka: 2e4 to 5e4 | Kd:0.08 to 0.1 ; Ka: 5e4 to 1e4 |
| optional ranges | KD: 1-200 | KD: 400-1500 | KD: 2000-6000 |
| | Kd:3e-4 to 2e-3; Ka: 1e6 to 5e4 | Kd:8e-3 to 0.08; Ka: 2e4 to 6e4 | Kd:0.08 to 0.1 ; Ka: 5e4 to 2e4 |
| Examples | DOM7h-11-15, DOM7h-14, DOM7h-14-10, DMS7322; DMS7327 | DMS7326; DMS7323 | DOM7h-11 |

Figure 2A

| Cyno | overall range | chronic | | intermediate | | acute | |
|---|---|---|---|---|---|---|---|
| | | high affinity | | medium affinity | | low affinity | |
| therapeutic ranges | KD: 1 to 10000<br>Kd:1.5e-4 to 0.1 ; Ka:2e6 to 1e4 | KD: 0.1-400<br>Kd:1.5e-4 to 8e-3 ; Ka:2e6 to 2e4 | | KD: 400-2000<br>Kd: 8e-3 to 0.08 ; Ka: 2e4 to 5e4 | | KD: 2000-10000<br>Kd:0.08 to 0.1 ; Ka: 5e4 to 1e4 | |
| optional ranges | | KD: 1-200<br>Kd:3e-4 to 2e-3; Ka: 1e6 to 1e4 | | KD: 400-1500<br>Kd:2e-3 to 0.05; Ka: 2e4 to 1e4 | | KD: 2000-6000<br>Kd:0.08 to 0.1 ; Ka: 5e4 to 2e4 | |
| Examples | | DMS7327; DOM7h-11-15; DOM7h-14; DOM7h-14-10; DOM7h-14-18; DMS7321; DMS7322 | | DOM7h-11; DMS7326; DMS7324; | | DMS7325 | |

Figure 2B

| Rat | | | overall range | | |
|---|---|---|---|---|---|
| | | | KD: 1 to 10000 | | |
| | | | Kd: 2e-3 to 0.15 ; Ka: 2e6 to 1e4 | | |
| therapeutic ranges | chronic | | intermediate | | acute |
| | high affinity | | medium affinity | | low affinity |
| | KD: 1-300 | | KD: 300-2000 | | KD: 2000-10000 |
| | Kd:2e-3 to 5e-2 ; Ka:2e6 to 2e5 | | Kd:5e-2 to 0.09 ; Ka:2e5 to 4.5e4 | | Kd:0.09 to 0.15 ; Ka: 4.5e4 to 1.5e4 |
| optional ranges | KD: 20-200 | | KD: 400-1800 | | KD: 2000-6000 |
| | Kd:9e-3 to 2e-2 ; Ka: 1e6 to 1e5 | | Kd: 4e-2 to 0.09; Ka:1e5 to 5e4 | | Kd: 0.1 to 0.14 ; Ka: 5e4 to 3e4 |
| Examples | DOM7h-11-15; DOM7h-11-12; DMS7327; DOM7h-14; DMS7322 | | DMS7326; DOM7h-14-18; DOM7h-14-19; DMS7321; DMS7323 | | DMS7325; DOM7h-11; |

Figure 2C

| Mouse | | | | | |
|---|---|---|---|---|---|
| | | overall range | | | |
| | | KD: 1 to 10000 | | | |
| | | Kd: 2e-3 to 0.15 ; Ka: 2e6 to 1e4 | | | |
| therapeutic ranges | chronic | | intermediate | | acute |
| | high affinity | | medium affinity | | low affinity |
| | KD: 1-100 | | KD: 100-2000 | | KD: 2000-10000 |
| | Kd:2e-3 to 1e-2 ; Ka:2e6 to 1e5 | | Kd:1e-2 to 0.07 ; Ka: 1e5 to 3e4 | | Kd: 0.08 to 0.15; Ka: 4e4 to 1.5e4 |
| optional ranges | KD: 1 to 80 | | KD: 120-2000 | | KD: 4000-10000 |
| | Kd:2e-3 to 1e-2 ; Ka: 2e6 to 1.5e5 | | Kd: 9e-3 to 0.07 ; Ka: 1.3e5 to 3e4 | | Kd:0.1 to 0.15 ; Ka: 2.5e4 to 1.5e4 |
| Examples | DOM7h-11-15; DMS7327; DOM7h-14; DOM7h-14-10; DOM7h-14-18; DOM7h-14-19; DMS7322 | | DMS7321; DMS7323; DMS7324; DOM7h-11-12; DMS7326 | | DMS7325; DOM7h-11 |

ANTI-SERUM ALBUMIN BINDING VARIANTS

This application is a 371 of International Application No. PCT/EP2011/058298, filed 20 May 2011, which claims the benefit of U.S. Provisional Application No. 61/346,519, filed 20 May 2010, both of which are herein incorporated by reference in their entireties.

The invention relates to improved variants of the anti-serum albumin immunoglobulin single variable domain DOM7h-11, as well as ligands and drug conjugates comprising such variants, compositions, nucleic acids, vectors and hosts.

BACKGROUND OF THE INVENTION

WO04003019 and WO2008/096158 disclose anti-serum albumin (SA) binding moieties, such as anti-SA immunoglobulin single variable domains (dAbs), which have therapeutically-useful half-lives. These documents disclose monomer anti-SA dAbs as well as multi-specific ligands comprising such dAbs, e.g., ligands comprising an anti-SA dAb and a dAb that specifically binds a target antigen, such as TNFR1. Binding moieties are disclosed that specifically bind serum albumins from more than one species, e.g. human/mouse cross-reactive anti-SA dAbs.

WO05118642 and WO2006/059106 disclose the concept of conjugating or associating an anti-SA binding moiety, such as an anti-SA immunoglobulin single variable domain, to a drug, in order to increase the half-life of the drug. Protein, peptide and new chemical entity (NCE) drugs are disclosed and exemplified. WO2006/059106 discloses the use of this concept to increase the half-life of insulintropic agents, e.g., incretin hormones such as glucagon-like peptide (GLP)-1. Reference is also made to Holt et al, "Anti-Serum albumin domain antibodies for extending the half-lives of short lived drugs", Protein Engineering, Design & Selection, vol 21, no 5, pp 283-288, 2008. WO2008/096158 discloses DOM7h-11, which is a good anti-SA dAb. It would be desirable to provide improved dAbs that are variants of DOM7h-11 and that specifically bind serum albumin, preferably albumins from human and non-human species, which would provide utility in animal models of disease as well as for human therapy and/or diagnosis. It would also be desirable to provide for the choice between relatively modest- and high-affinity anti-SA binding moieties (dAbs). Such moieties could be linked to drugs, the anti-SA binding moiety being chosen according to the contemplated end-application. This would allow the drug to be better tailored to treating and/or preventing chronic or acute indications, depending upon the choice of anti-SA binding moiety. It would also be desirable to provide anti-SA dAbs, that are monomeric or substantially so in solution. This would especially be advantageous when the anti-SA dAb is linked to a binding moiety, e.g., a dAb, that specifically binds a cell-surface receptor, such as TNFR1, with the aim of antagonizing the receptor. The monomeric state of the anti-SA dAb is useful in reducing the chance of receptor cross-linking, since multimers are less likely to form which could bind and cross-link receptors (e.g., TNFR1) on the cell surface, thus increasing the likelihood of receptor agonism and detrimental receptor signaling.

A number of improved dAbs are disclosed in PCT/EP2010/052008 and PCT/EP2010/052007 the disclosures of which are incorporated by reference.

It would also be desirable to provide improved dAbs that have an improved stability. This would be advantageous in allowing a dAb to have a suitable stability profile or shelf-life. In particular, it would be desirable to provide dAbs having an improved ability to resist unfolding upon exposure to elevated temperatures i.e. improved thermostability. It would also be desirable to provide dAbs that have improved stability when formatted into constructs such as multi-specific ligands or when conjugated to proteins, peptides or NCEs.

SUMMARY OF THE INVENTION

Aspects of the present invention solve these problems.

To this end, the present inventors surprisingly found that mutations can be made to immunoglobulin single variable domain molecules of the DOM7h-11 lineage to give the molecules improved stability as measured by an improved thermostability relative to the parent DOM7h-11 molecules.

In one aspect, there is provided an anti-serum albumin (SA) immunoglobulin single variable domain variant of DOM7h-11 (DOM7h-11 as shown in FIG. 1), said variant having a $T_m$ of at least 54° C. In another aspect, there is provided an anti-serum albumin (SA) immunoglobulin single variable domain variant of DOM7h-11 (DOM7h-11 as shown in FIG. 1), said variant having a $T_m$ of greater than 54° C. The transition midpoint ($T_m$) is the temperature where 50% of the protein is in its native conformation and the other 50% is denatured. Suitably said $T_m$ is measured by Differential Scanning Calorimetry.

In one embodiment, said variant comprises at least one mutation in any of positions 22, 42 or 91 (numbering according to Kabat) compared to DOM7h-11. Suitably, an anti-SA immunoglobulin single variable domain variant is a variant of DOM7h-11-15 (DOM7h-11-15 as shown in FIG. 1 (SEQ ID NO: 7) and comprises at least one mutation in any of positions 22, 42 or 91 (numbering according to Kabat) compared to DOM7h-11-15. In one embodiment, a variant comprises at least one mutation selected from the following:
Position 22=Ser, Phe, Thr, Ala or Cys;
Position 42=Glu or Asp;
Position 91=Thr or Ser;

In other embodiments, there is provided an anti-SA immunoglobulin single variable domain variant wherein position 22 is Ser or Phe; an anti-SA immunoglobulin single variable domain variant wherein position 42 is Glu and position 91 is Thr; an anti-SA immunoglobulin single variable domain variant wherein position 91 is Thr; an anti-SA immunoglobulin single variable domain variant wherein position 22 is Phe. In one embodiment, position 108 is Trp.

Further embodiments provide a variant comprising an amino acid sequence that is identical to the amino acid sequence of a single variable domain selected from DOM7h-11-56 (SEQ ID NO: 412), DOM7h-11-68 (SEQ ID NO: 416), DOM7h-11-79 (SEQ ID NO:418) and DOM7h-11-80 (SEQ ID NO: 419) (or a variant having an amino acid that is at least 95, 96, 97, 98 or 99% identical to the amino acid sequence of the selected amino acid sequence) or has up to 4 changes compared to the selected amino acid sequence.

In particular, it has been found that mutations targeted to the FW3 (positions 57 to 88, numbering according to Kabat) and CDR3 regions (positions 89 to 97, numbering according to Kabat) of DOM7h-11 confer improved stability. Accordingly, in another embodiment, there is provided an anti-SA immunoglobulin single variable domain variant in accordance with an aspect of the invention wherein the variant comprises at least one mutation in the FW3 region (positions 57 to 88, numbering according to Kabat) or in the CDR3 region (positions 89 to 97, numbering according to Kabat) compared to DOM7h-11.

Further embodiments provide an anti-SA immunoglobulin single variable domain variant wherein said variant is a variant of DOM7h-11-15 (DOM7h-11-15 as shown in FIG. 1) and comprises at least one mutation in the FW3 region (positions 57 to 88, numbering according to Kabat) or in the CDR3 region (positions 89 to 97, numbering according to Kabat) compared to DOM7h-11-15. Suitably, said variant comprises at least one mutation at any of positions 77, 83, 93 or 95 (numbering according to Kabat).

In one embodiment, the variant comprises at least one mutation selected from the following:
Position 77=Asn, Gln
Position 83=Val, Ile, Met, Leu, Phe, Ala or Norleucine.
Position 93=Val, Ile, Met, Leu, Phe, Ala or Norleucine.
Position 95=His, Asn, Gln, Lys or Arg.

In another embodiment, an anti-SA immunoglobulin single variable domain in accordance with the invention further comprises a mutation at position 106 or 108 (numbering according to Kabat). Suitably, position 106 is Asn or Gln. Suitably position 108 is Trp, Tyr or Phe.

In further embodiments, there is provided an anti-SA immunoglobulin single variable domain variant wherein position 77 is Asn; an anti-SA single variable domain wherein position 83 is Val; an anti-SA single variable domain wherein position 95 is His; an anti-SA single variable domain wherein position 95 is His; an anti-SA single variable domain wherein position 93 is Val.

In yet further embodiments, there is provided a variant comprising an amino acid sequence that is identical to the amino acid sequence of a single variable domain selected from DOM7h-11-57 (SEQ ID NO: 413), DOM7h-11-65 (SEQ ID NO: 414) or DOM7h-11-67 (SEQ ID NO:415) (or a variant having an amino acid that is at least 95, 96, 97, 98 or 99% identical to the amino acid sequence of the selected amino acid sequence) or has up to 4 changes compared to the selected amino acid sequence, provided that the amino acid sequence of the variant has at least one mutation in the FW3 or CDR3 region.

In further embodiments, there is provided a variant comprising an amino acid sequence that is identical to the amino acid sequence of a single variable domain selected from DOM7h-11-69 (SEQ ID NO: 417), DOM 7h-11-90 (SEQ ID NO: 420), DOM 7h-11-86 (SEQ ID NO: 421), DOM 7h-11-87 (SEQ ID NO: 422), or DOM 7h-11-88 (SEQ ID NO: 423) (or a variant having an amino acid that is at least 95, 96, 97, 98 or 99% identical to the amino acid sequence of the selected amino acid sequence).

Suitably a variant has a $T_m$ of at least 57° C. In another embodiment, a variant has a $T_m$ of greater than 57° C.

In one embodiment, a variant in accordance with any embodiment of the invention has an increased $T_m$ value compared to DOM7h-11. In another embodiment, said variant has an increased $T_m$ value compared to DOM7h-11-15. In another embodiment, there is provided a variant comprising any combination of any of the mutations listed above. Suitably, $T_m$ is measured by DSC in accordance with the methods described herein.

Suitably, a variant in accordance with the invention comprises a binding site that specifically binds human SA with a dissociation constant (KD) of from about 0.1 to about 10000 nM, optionally from about 1 to about 6000 nM, as determined by surface plasmon resonance. The variant of any preceding claim, wherein the variant comprises a binding site that specifically binds human SA with an off-rate constant ($K_d$) of from about $1.5 \times 10^{-4}$ to about 0.1 sec$^{-1}$, optionally from about $3 \times 10^{-4}$ to about 0.1 sec$^{-1}$ as determined by surface plasmon resonance. The variant of any preceding claim, wherein the variant comprises a binding site that specifically binds human SA with an on-rate constant ($K_a$) of from about $2 \times 10^6$ to about $1 \times 10^4 M^{-1}$ sec$^{-1}$, optionally from about $1 \times 10^6$ to about $2 \times 10^4 M^{-1}$ sec$^{-1}$ as determined by surface plasmon resonance.

Advantageously, the variant in accordance with the invention is cross-reactive with serum albumin from a number of different species such as, for example, monkey e.g. Cynomolgus monkey, suncus (shrew), marmoset, ferret, rat, mouse, pig and dog SA.

Accordingly, in one embodiment, the variant in accordance with the invention comprises a binding site that specifically binds Cynomolgus monkey SA with a dissociation constant (KD) of from about 0.1 to about 10000 nM, optionally from about 1 to about 6000 nM, as determined by surface plasmon resonance. The variant of any preceding claim, wherein the variant comprises a binding site that specifically binds Cynomolgus monkey SA with an off-rate constant ($K_d$) of from about $1.5 \times 10^{-4}$ to about 0.1 sec$^{-1}$, optionally from about $3 \times 10^{-4}$ to about 0.1 sec$^{-1}$ as determined by surface plasmon resonance. The variant of any preceding claim, wherein the variant comprises a binding site that specifically binds Cynomolgus monkey SA with an on-rate constant ($K_a$) of from about $2 \times 10^6$ to about $1 \times 10^4 M^{-1}$ sec$^{-1}$, optionally from about $1 \times 10^6$ to about $5 \times 10^3 M^{-1}$ sec$^{-1}$ as determined by surface plasmon resonance. In another aspect, there is provided a multispecific ligand comprising an anti-SA variant in accordance with the invention and a binding moiety that specifically binds a target antigen other than SA. Suitable target antigens are exemplified herein. In one embodiment, the binding moiety that specifically binds a target antigen may be another single domain immunoglobulin molecule. In another embodiment, the binding moiety that specifically binds a target antigen may be a monoclonal antibody. Suitable formats and methods for making dual specific molecules, such as mAbdAb molecules are described, for example in WO2009/068649.

An aspect of the invention provides a fusion product, e.g., a fusion protein or fusion with a peptide or NCE (new chemical entity) drug, comprising a polypeptide, protein, peptide or NCE drug fused or conjugated (for an NCE) to any variant as described above. In another aspect, there is provided a fusion protein, polypeptide fusion or conjugate comprising a polypeptide or peptide drug fused to an anti-serum albumin dAb variant in accordance with the invention, optionally wherein the selected variant is DOM7h-11-56 (SEQ ID NO: 412), DOM7h-11-57 (SEQ ID NO: 413), DOM7h-11-65 (SEQ ID NO: 414), DOM7h-11-67 (SEQ ID NO:415), DOM7h-11-68 (SEQ ID NO:416), DOM7h-11-69 (SEQ ID NO: 417), DOM7h-11-79 (SEQ ID NO:418), DOM7h-11-80 (SEQ ID NO: 419), DOM 7h-11-90 (SEQ ID NO: 420), DOM 7h-11-86 (SEQ ID NO: 421), DOM 7h-11-87 (SEQ ID NO: 422), or DOM 7h-11-88 (SEQ ID NO: 423). Suitably, such a fusion protein comprises a linker (e.g., a linker comprising the amino acid sequence TVA, optionally TVAAPS (SEQ ID NO: 437) between the variant and the drug.

In one embodiment, there is provided a polypeptide fusion or conjugate comprising an anti-serum albumin dAb as disclosed herein and an incretin or insulinotropic agent, e.g., exendin-4, GLP-1(7-37), GLP-1(6-36) or any incretin or insulinotropic agent disclosed in WO06/059106, these agents being explicitly incorporated herein by reference as though written herein for inclusion in the present invention and claims below.

In another aspect, there is provided an anti-SA variant single variable domain in accordance with the invention, wherein the variable domain is conjugated to a drug (optionally an NCE drug), optionally wherein the selected variant is DOM7h-11-56 (SEQ ID NO: 412), DOM7h-11-57 (SEQ ID NO: 413), DOM7h-11-65 (SEQ ID NO: 414), DOM7h-11-67 (SEQ ID NO:415), DOM7h-11-68 (SEQ ID NO:416), DOM7h-11-69 (SEQ ID NO: 417), DOM7h-11-79 (SEQ ID NO:418), DOM7h-11-80 (SEQ ID NO: 419), DOM 7h-11-90 (SEQ ID NO: 420), DOM 7h-11-86 (SEQ ID NO: 421), DOM 7h-11-87 (SEQ ID NO: 422), or DOM 7h-11-88 (SEQ ID NO: 423).

In another aspect there is provided a composition comprising a variant, fusion protein or ligand of any preceding claim and a pharmaceutically acceptable diluent, carrier, excipient or vehicle.

In a further aspect, there is provided a nucleic acid comprising a nucleotide sequence encoding a variant according to the invention or a multispecific ligand or fusion protein in accordance with the invention. Suitably, there is provided a nucleic acid comprising the nucleotide sequence of a DOM7h-11 variant selected from the nucleotide sequence of DOM7h-11-56 (SEQ ID NO: 425), DOM7h-11-57 (SEQ ID NO: 426), DOM7h-11-65 (SEQ ID NO: 427), DOM7h-11-67 (SEQ ID NO:428), DOM7h-11-68 (SEQ ID NO:429), DOM7h-11-69 (SEQ ID NO: 430), DOM7h-11-79 (SEQ ID NO:431), DOM7h-11-80 (SEQ ID NO: 432), DOM 7h-11-90 (SEQ ID NO: 433), DOM 7h-11-86 (SEQ ID NO: 434), DOM 7h-11-87 (SEQ ID NO: 435), or DOM 7h-11-88 (SEQ ID NO: 436) or a nucleotide sequence that is at least 80% identical to said selected sequence.

Another aspect provides a vector comprising a nucleic acid in accordance with the invention. A further aspect provides an isolated host cell comprising a vector of the invention.

In a further aspect there is provided a method of treating or preventing a disease or disorder in a patient, comprising administering at least one dose of a variant in accordance with any aspect or embodiment of the invention to said patient.

BRIEF DESCRIPTION OF THE DRAWINGS

FIG. 1A-1B: Amino-acid sequence alignment for DOM7h-11 (SEQ ID NO: 438) variant dAbs. A "." at a particular position indicates the same amino as found in DOM7h-11 at that position. The CDRs are indicated by underlining and bold text (the first underlined sequence is CDR1, the second underlined sequence is CDR2 and the third underlined sequence is CDR3). In addition, the figure comprises the following variants: DOM 7h-11-12 (SEQ ID NO:1), DOM 7h-11-15 (SEQ ID NO:2), DOM 7h-11-18 (SEQ ID NO:3), DOM 7h-11-19 (SEQ ID NO:4), and DOM 7h-11-3 (SEQ ID NO: 5).

FIG. 2A-2D: Kinetic parameters of DOM7h-11 variants. KD units=nM; Kd units=sec$^{-1}$; Ka units=M$^{-1}$ sec$^{-1}$. The notation A e-B means A×10$^{-B}$ and C e D means C×10$^{D}$. The overall kinetic ranges in various species, as supported by the examples below, are indicated. Optional ranges are also provided for use in particular therapeutic settings (acute or chronic indications, conditions or diseases and "intermediate" for use in both chronic and acute settings). High affinity dAbs and products comprising these are useful for chronic settings. Medium affinity dAbs and products comprising these are useful for intermediate settings. Low affinity dAbs and products comprising these are useful for acute settings. The affinity in this respect is the affinity for serum albumin. Various example anti-serum dAbs and fusion proteins are listed, and these support the ranges disclosed. Many of the examples have favourable kinetics in human and one or more non-human animals (e.g., in human and Cynomolgus monkey and/or mouse). Choice of dAb or product comprising this can be tailored, according to the invention, depending on the setting (e.g., chronic or acute) to be treated therapeutically.

Figure 3A:
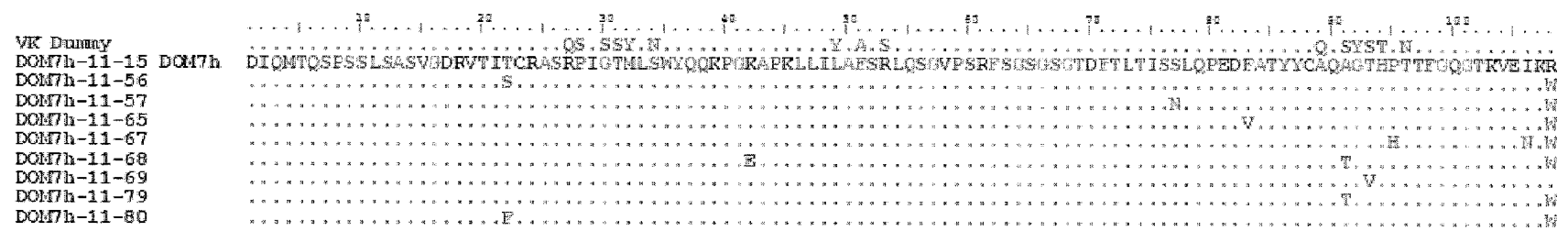
Figure 3B:
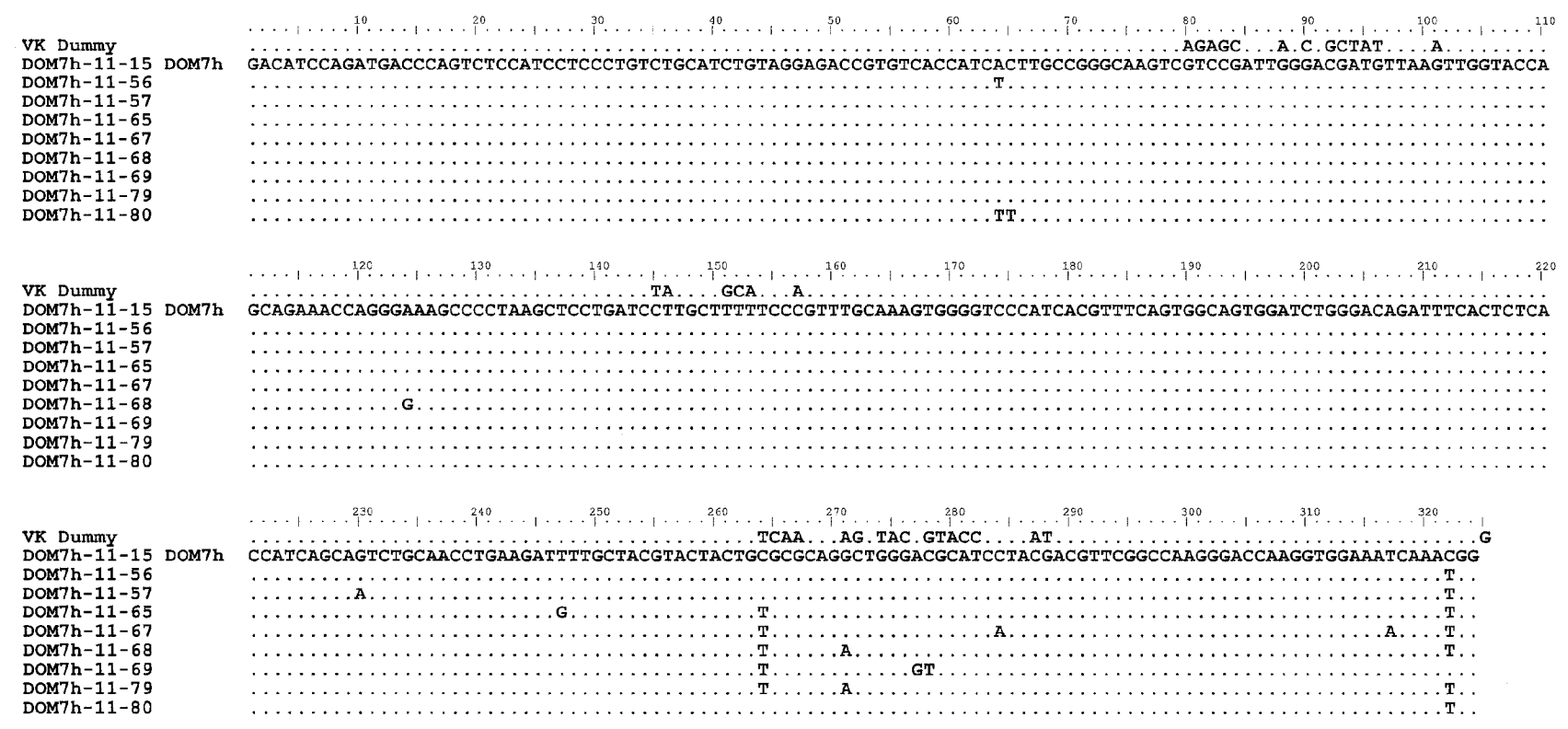

FIG. 3A-3B: Amino-acid (A) and nucleic acid (B) sequence alignment for DOM7h-11-15 (SEQ ID NO:2) variant dAbs. A "." at a particular position indicates the same amino as found in DOM7h-11-15 at that position. In addition, the figure comprises the following variants: DOM 7h-11-56 (SEQ ID NO:412), DOM 7h-11-57 (SEQ ID NO:413), DOM 7h-11-65 (SEQ ID NO:414), DOM 7h-11-67 (SEQ ID NO:415), DOM 7h-11-68 (SEQ ID NO:416), DOM 7h-11-69 (SEQ ID NO:417), DOM 7h-11-79 (SEQ ID NO:418), and DOM 7h-11-80 (SEQ ID NO: 419).

DETAILED DESCRIPTION OF THE INVENTION

Figure 1B:

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc. which are incorporated herein by reference) and chemical methods.

As used herein, the term "antagonist of Tumor Necrosis Factor Receptor 1 (TNFR1)" or "anti-TNFR1 antagonist" or the like refers to an agent (e.g., a molecule, a compound) which binds TNFR1 and can inhibit a (i.e., one or more) function of TNFR1. For example, an antagonist of TNFR1 can inhibit the binding of TNFα to TNFR1 and/or inhibit signal transduction mediated through TNFR1. Accordingly, TNFR1-mediated processes and cellular responses (e.g., TNFα-induced cell death in a standard L929 cytotoxicity assay) can be inhibited with an antagonist of TNFR1.

A "patient" is any animal, e.g., a mammal, e.g., a non-human primate (such as a baboon, rhesus monkey or Cynomolgus monkey), mouse, human, rabbit, rat, dog, cat or pig. In one embodiment, the patient is a human.

As used herein, "peptide" refers to about two to about 50 amino acids that are joined together via peptide bonds.

As used herein, "polypeptide" refers to at least about 50 amino acids that are joined together by peptide bonds. Polypeptides generally comprise tertiary structure and fold into functional domains.

As used herein an antibody refers to IgG, IgM, IgA, IgD or IgE or a fragment (such as a Fab, Fab', F(ab')$_2$, Fv, disulfide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

As used herein, "antibody format" refers to any suitable polypeptide structure in which one or more antibody variable domains can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single antibody variable domain (e.g., a dAb, $V_H$, $V_{HH}$, $V_L$), and modified versions of any of the foregoing (e.g., modified by the covalent attachment of polyethylene glycol or other suitable polymer or a humanized $V_{HH}$).

The phrase "immunoglobulin single variable domain" refers to an antibody variable domain ($V_H$, $V_{HH}$, $V_L$) that specifically binds an antigen or epitope independently of different V regions or domains. An immunoglobulin single variable domain can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" as the term is used herein. A "single immunoglobulin variable domain" is the same as an "immunoglobulin single variable domain" as the term is used herein. A "single antibody variable domain" or an "antibody single variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. The $V_{HH}$ may be humanized.

A "domain" is a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

A "lineage" refers to a series of immunoglobulin single variable domains that are derived from the same "parental" clone. For example, a lineage comprising a number of variant clones may be generated from a parental or starting immunoglobulin single variable domain by diversification, site directed mutagenesis, generation of error prone or doped libraries. Suitably binding molecules are generated in a process of affinity maturation. In the present invention, reference is made to "DOM7h-11" which is an anti-SA immunoglobulin single variable domain described in PCT/EP2010/052008 and PCT/EP2010/052007. DOM7h-11-15 is one of the DOM7h-11 lineage derived from DOM7h-11 parental clone, as described herein.

In the instant application, the term "prevention" and "preventing" involves administration of the protective composition prior to the induction of the disease or condition. "Treatment" and "treating" involves administration of the protective composition after disease or condition symptoms become manifest. "Suppression" or "suppressing" refers to administration of the composition after an inductive event, but prior to the clinical appearance of the disease or condition.

As used herein, the term "dose" refers to the quantity of ligand administered to a subject all at one time (unit dose), or in two or more administrations over a defined time interval. For example, dose can refer to the quantity of ligand (e.g., ligand comprising an immunoglobulin single variable domain that binds target antigen) administered to a subject over the course of one day (24 hours) (daily dose), two days, one week, two weeks, three weeks or one or more months (e.g., by a single administration, or by two or more administrations). The interval between doses can be any desired amount of time. The term "pharmaceutically effective" when referring to a dose means sufficient amount of the ligand, domain or pharmaceutically active agent to provide the desired effect. The amount that is "effective" will vary from subject to subject, depending on the age and general condition of the individual, the particular drug or pharmaceutically active agent and the like. Thus, it is not always possible to specify an exact "effective" amount applicable for all patients. However, an appropriate "effective" dose in any individual case may be determined by one of ordinary skill in the art using routine experimentation.

Methods for pharmacokinetic analysis and determination of ligand (e.g., single variable domain, fusion protein or multi-specific ligand) half-life will be familiar to those skilled in the art. Details may be found in Kenneth, A et al: Chemical Stability of Pharmaceuticals: A Handbook for Pharmacists and in Peters et al, Pharmacokinetc analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC). Optionally, all pharmacokinetic parameters and values quoted herein are to be read as being values in a human. Optionally, all pharmacokinetic parameters and values quoted herein are to be read as being values in a mouse or rat or Cynomolgus monkey.

Half lives (t½ alpha and t½ beta) and AUC can be determined from a curve of serum concentration of ligand against time. The WinNonlin analysis package, e.g. version 5.1 (available from Pharsight Corp., Mountain View, Calif. 94040, USA) can be used, for example, to model the curve. When two-compartment modeling is used, in a first phase (the alpha phase) the ligand is undergoing mainly distribution in the patient, with some elimination. A second phase (beta phase) is the phase when the ligand has been distributed and the serum concentration is decreasing as the ligand is cleared from the patient. The t alpha half life is the half life of the first phase and the t beta half life is the half life of the second phase. Thus, in one embodiment, in the context of the present invention, the variable domain, fusion protein or ligand has a tα half-life in the range of (or of about) 15 minutes or more. In one embodiment, the lower end of the range is (or is about) 30 minutes, 45 minutes, 1 hour, 2 hours, 3 hours, 4 hours, 5 hours, 6 hours, 7 hours, 10 hours, 11 hours or 12 hours. In addition, or alternatively, the variable domain, fusion protein or ligand according to the invention will have a tα half life in the range of up to and including 12 hours (or about 12 hours). In one embodiment, the upper end of the range is (or is about) 11, 10, 9, 8, 7, 6 or 5 hours. An example of a suitable range is (or is about) 1 to 6 hours, 2 to 5 hours or 3 to 4 hours.

In one embodiment, the present invention provides the variable domain, fusion protein or ligand according to the invention has a tβ half-life in the range of (or of about) 2.5 hours or more. In one embodiment, the lower end of the range is (or is about) 3 hours, 4 hours, 5 hours, 6 hours, 7 hours, 10 hours, 11 hours, or 12 hours. In addition, or alternatively, the tβ half-life is (or is about) up to and including 21 or 25 days. In one embodiment, the upper end of the range is (or is about) 12 hours, 24 hours, 2 days, 3 days, 5 days, 10 days, 15 days, 19 days, 20 days, 21 days or 22 days. For example, the variable domain, fusion protein or ligand according to the invention will have a tβ half life in the range 12 to 60 hours (or about 12 to 60 hours). In a further embodiment, it will be in the range 12 to 48 hours (or about 12 to 48 hours). In a further embodiment still, it will be in the range 12 to 26 hours (or about 12 to 26 hours).

As an alternative to using two-compartment modeling, the skilled person will be familiar with the use of non-compartmental modeling, which can be used to determine terminal half-lives (in this respect, the term "terminal half-life" as used herein means a terminal half-life determined using non-compartmental modeling). The WinNonlin analysis package, e.g. version 5.1 (available from Pharsight Corp., Mountain View, Calif. 94040, USA) can be used, for example, to model the curve in this way. In this instance, in one embodiment the single variable domain, fusion protein or ligand has a terminal half life of at least (or at least about) 8 hours, 10 hours, 12 hours, 15 hours, 28 hours, 20 hours, 1 day, 2 days, 3 days, 7 days, 14 days, 15 days, 16 days, 17 days, 18 days, 19 days, 20 days, 21 days, 22 days, 23 days, 24 days or 25 days. In one embodiment, the upper end of this range is (or is about) 24 hours, 48 hours, 60 hours or 72 hours or 120 hours. For example, the terminal half-life is (or is about) from 8 hours to 60 hours, or 8 hours to 48 hours or 12 to 120 hours, e.g., in man.

In addition, or alternatively to the above criteria, the variable domain, fusion protein or ligand according to the invention has an AUC value (area under the curve) in the range of (or of about) 1 mg·min/ml or more. In one embodiment, the lower end of the range is (or is about) 5, 10, 15, 20, 30, 100, 200 or 300 mg·min/ml. In addition, or alternatively, the variable domain, fusion protein or ligand according to the invention has an AUC in the range of (or of about) up to 600 mg·min/ml. In one embodiment, the upper end of the range is (or is about) 500, 400, 300, 200, 150, 100, 75 or 50 mg·min/ml. Advantageously the variable domain, fusion protein or ligand will have an AUC in (or about in) the range selected from the group consisting of the following: 15 to 150 mg·min/ml, 15 to 100 mg·min/ml, 15 to 75 mg·min/ml, and 15 to 50 mg·min/ml.

"Surface Plasmon Resonance": Competition assays can be used to determine if a specific antigen or epitope, such as human serum albumin, competes with another antigen or epitope, such as Cynomolgus serum albumin, for binding to a serum albumin binding ligand described herein, such as a specific dAb. Similarly competition assays can be used to determine if a first ligand such as dAb, competes with a second ligand such as a dAb for binding to a target antigen or epitope. The term "competes" as used herein refers to substance, such as a molecule, compound, preferably a protein, which is able to interfere to any extent with the specific binding interaction between two or more molecules. The phrase "does not competitively inhibit" means that substance, such as a molecule, compound, preferably a protein, does not interfere to any measurable or significant extent with the specific binding interaction between two or more molecules. The specific binding interaction between two or more molecules preferably includes the specific binding interaction between a single variable domain and its cognate partner or target. The interfering or competing molecule can be another single variable domain or it can be a molecule that is structurally and/or functionally similar to a cognate partner or target.

The term "binding moiety" refers to a domain that specifically binds an antigen or epitope independently of a different epitope or antigen binding domain. A binding moiety may be a domain antibody (dAb) or may be a domain which is a derivative of a non-immunoglobulin protein scaffold, e.g., a scaffold selected from the group consisting of CTLA-4, lipocalin, SpA, an adnectin, affibody, an avimer, GroEl, transferrin, GroES and fibronectin, which binds to a ligand other than the natural ligand (in the case of the present invention, the moiety binds serum albumin). See WO2008/096158, which discloses examples of protein scaffolds and methods for selecting antigen or epitope-specific binding domains from repertoires (see Examples 17 to 25). These specific disclosures of WO2008/096158 are expressly incorporated herein by reference as though explicitly written herein and for use with the present invention, and it is contemplated that any part of such disclosure can be incorporated into one or more claims herein).

In one aspect, the invention provides an anti-serum albumin (SA) immunoglobulin single variable domain variant of DOM7h-11, wherein the variant comprises at least one mutation at position 22, 42 or 91 (numbering according to Kabat) compared to DOM7h-11. In one embodiment, the variant comprises at least one mutation at position 22, 42 or 91 (numbering according to Kabat) compared to DOM7h-11-15. Suitably a variant in accordance with the invention has 1, 2, 3 or up to 8 changes compared to the amino acid sequence of DOM7h-11 or DOM7h-11-15.

In another aspect, the invention provides an anti-serum albumin (SA) immunoglobulin single variable domain variant of DOM7h-11, wherein the variant comprises at least one mutation in the framework region 3 (FW3) (amino acids 57-88) or complementarity determining region 3 (CDR3) (amino acids 89-97) compared to DOM7h-11, and wherein the variant has 1, 2, 3 or up to 8 changes compared to the amino acid sequence of DOM7h-11. In one embodiment, the variant comprises at least one mutation at these positions compared to DOM7h-11-15.

In one embodiment, the mutations at any of these positions are mutations to residues as exemplified in the Examples section herein. In another embodiment, mutations are to conservative amino acids substitutions of the exemplified residues.

Conservative amino acid substitutions are well know to the person skilled in the art and are exemplified by the following table:

| Amino Acid Substitution | | |
|---|---|---|
| Original Residues | Exemplary Substitutions | Preferred Substitutions |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |

-continued

| Amino Acid Substitution | | |
|---|---|---|
| Original Residues | Exemplary Substitutions | Preferred Substitutions |
| Leu | Norleucine, Ile, Val, Met, Ala, Phe | Ile |
| Lys | Arg, 1,4 Diamino-butyricAcid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Conservative amino acid substitutions may also relate to non-naturally occurring amino acid residues, such as peptidomimetics and other reversed or inverted forms of amino acid moieties which may be incorporated by chemical peptide synthesis.

Thermostability, or thermodynamic stability, is the quality of a substance/protein to resist (ir-)reversible unfolding upon exposure to elevated temperatures.

A measure of thermostability/thermodynamic stability can be made using Differential scanning calorimetry (DSC). DSC is a thermoanalytical technique in which the difference in the amount of energy or heat required to increase the temperature of a sample and reference are measured as a function of temperature. It can be used to study a wide range of thermal transitions in proteins and is useful for determining the melting temperatures as well as thermodynamic parameters. Briefly, the protein is heated at a constant rate of 180 degrees C./hr (at 1 mg/mL routinely in PBS) and a detectable heat capacity change associated with thermal denaturation measured. The transition midpoint ($T_m$) is determined, which is described as the temperature where 50% of the protein is in its native conformation and the other 50% is denatured. Here, DSC determines the apparent transition midpoint ($_{app}T_m$) as most of the proteins examined do not fully refold. The higher the Tm or App™, the more stable the molecule. Software packages such as was Origin® v7.0383 (Origin Lab) can be used to generate $T_m$ values.

In one embodiment of the invention, improved thermostability means an increased or higher $T_m$ compared to the parent molecule. Suitably the parent molecule is DOM7h-11 or DOM7h-11-15. Suitably "improved" thermostability means a $T_m$ value higher than the $T_m$ value of the parent molecule. Suitably "improved thermostability" means at least 54° C. or at least 55° C. In one embodiment, "improved thermostability" means at least 57° C. In another embodiment, "improved thermostability" means greater than 55° C. or greater than 57° C. Suitably $T_m$ is measured using DSC as described herein.

Improved thermostability in an immunoglobulin single variable domain is desirable as it provides enhanced stability of an immunoglobulin single variable domain or protein. Importantly, enhanced thermostability gives a measure of the likelihood of a protein being developable such that a product comprising that improved immunoglobulin single variable domain will have good stability throughout the production process and/or a suitable stability/shelf-life. Improved thermostability and exemplary methods for measuring it such as circular dichroism spectroscopy are describe, for example, in van der Sloot et al. Protein Engineering, Design and Selection, 2004, vol. 17, no. 9, p. 673-680 and Demarest et al. J. Mol. Biol. 2004, 335, 41-48.

The molecular basis for improved or higher thermostability may be a higher specific number of intra-molecule hydrogen- and ionic interactions than found in a non- or less-thermostable variant.

An immunoglobulin single variable domain that is shown to have improved thermostability may also, as a direct consequence, give a higher initial expression yield from host cell expression systems. This is because improved thermostability may arise from their being a higher number of intra-molecule interactions which may, in turn, lead to a lower level of misfolding and/or faster kinetics of folding during translation or trans-membrane transport.

In addition, a protein such as an immunoglobulin single variable domain with improved thermostability may display better overall developability as the protein is more likely to be more resistant to down-stream processes such as increased temperatures and pressure as well as extreme pHs and salt conditions when compared to an immunoglobulin single variable domain with a lower thermostability.

In one embodiment, immunoglobulin single variable domains in accordance with the invention may be used to generate dual or multi-specific compositions or fusion polypeptides. Accordingly, immunoglobulin single variable domains in accordance with the invention may be used in larger constructs. Suitable constructs include fusion proteins between an anti-SA immunoglobulin single variable domain (dAb) and a monoclonal antibody, NCE, protein or polypeptide and so forth. Accordingly, anti-SA immunoglobulin single variable domains in accordance with the invention may be used to construct multi-specific molecules, for example, bi-specific molecules such as dAb-dAb (i.e. two linked immunoglobulin single variable domains in which one is an anti-SA dAb), mAb-dAb or polypeptide-dAb constructs. In these constructs the anti-SA dAb (ALBUDAB™) component provides for half-life extension through binding to serum albumin (SA). Suitable mAb-dAbs and methods for generating these constructs are described, for example, in WO2009/068649.

Choosing an anti-SA immunoglobulin single variable domain with enhanced, improved or increased thermostability may be desirable as a starting point for a molecule that is to be made into a fusion protein as single molecules may lose thermostability properties once they are linked into a bi-specific construct. Accordingly, starting with a moiety with a higher thermostability will enable any loss in thermostability to be taken into account such that after a bi (or multi) specific construct is generated, an overall useful thermostability is maintained.

In one embodiment, the variant comprises one or more of the following kinetic characteristics:—
 (a) The variant comprises a binding site that specifically binds human SA with a dissociation constant (KD) from (or from about) 0.1 to (or to about) 10000 nM, optionally from (or from about) 1 to (or to about) 6000 nM, as determined by surface plasmon resonance;
 (b) The variant comprises a binding site that specifically binds human SA with an off-rate constant ($K_d$) from (or from about) $1.5 \times 10^{-4}$ to (or to about) 0.1 $sec^{-1}$, optionally from (or from about) $3 \times 10^{-4}$ to (or to about) 0.1 $sec^{-1}$ as determined by surface plasmon resonance;
 (c) The variant comprises a binding site that specifically binds human SA with an on-rate constant ($K_a$) from (or from about) $2 \times 10^6$ to (or to about) $1 \times 10^4$ $M^{-1} sec^{-1}$, optionally from (or from about) $1\times10^6$ to (or to about) $2\times10^4 \, M^{-1} \, sec^{-1}$ as determined by surface plasmon resonance;

(d) The variant comprises a binding site that specifically binds Cynomolgus monkey SA with a dissociation constant (KD) from (or from about) 0.1 to (or to about) 10000 nM, optionally from (or from about) 1 to (or to about) 6000 nM, as determined by surface plasmon resonance;

(e) The variant of any preceding claim, wherein the variant comprises a binding site that specifically binds Cynomolgus monkey SA with an off-rate constant ($K_d$) from (or from about) $1.5\times10^{-4}$ to (or to about) $0.1 \, sec^{-1}$, optionally from (or from about) $3\times10^{-4}$ to (or to about) $0.1 \, sec^{-1}$ asdetermined by surface plasmon resonance;

(f) The variant of any preceding claim, wherein the variant comprises a binding site that specifically binds Cynomolgus monkey SA with an on-rate constant ($K_a$) from (or from about) $2\times10^6$ to (or to about) $1\times10^4 \, M^{-1} \, sec^{-1}$, optionally from (or from about) $1\times10^6$ to (or to about) $5\times10^3 \, M^{-1} \, sec^{-1}$ as determined by surface plasmon resonance;

(g) The variant comprises a binding site that specifically binds rat SA with a dissociation constant (KD) from (or from about) 1 to (or to about) 10000 nM, optionally from (or from about) 20 to (or to about) 6000 nM, as determined by surface plasmon resonance;

(h) The variant comprises a binding site that specifically binds rat SA with an off-rate constant ($K_d$) from (or from about) $2\times10^{-3}$ to (or to about) $0.15 \, sec^{-1}$, optionally from (or from about) $9\times10^{-3}$ to (or to about) $0.14 \, sec^{-1}$ as determined by surface plasmon resonance;

(i) The variant comprises a binding site that specifically binds rat SA with an on-rate constant ($K_a$) from (or from about) $2\times10^6$ to (or to about) $1\times10^4 \, M^{-1} \, sec^{-1}$, optionally from (or from about) $1\times10^6$ to (or to about) $3\times10^4 \, M^{-1} \, sec^{-1}$ as determined by surface plasmon resonance;

(j) The variant comprises a binding site that specifically binds mouse SA with a dissociation constant (KD) from (or from about) 1 to (or to about) 10000 nM as determined by surface plasmon resonance;

(k) The variant comprises a binding site that specifically binds mouse SA with an off-rate constant ($K_d$) from (or from about) $2\times10^{-3}$ to (or to about) $0.15 \, sec^{-1}$ as determined by surface plasmon resonance; and/or (l) The variant comprises a binding site that specifically binds mouse SA with an on-rate constant ($K_a$) from (or from about) $2\times10^6$ to (or to about) $1\times10^4 \, M^{-1} \, sec^{-1}$, optionally from (or from about) $2\times10^6$ to (or to about) $1.5\times10^4 \, M^{-1} \, sec^{-1}$ as determined by surface plasmon resonance.

Optionally, the variant has

I: a KD according to (a) and (d), a $K_d$ according to (b) and (e), and a $K_a$ according to (c) and (f); or II: a KD according to (a) and (g), a $K_d$ according to (b) and (h), and a $K_a$ according to (c) and (i); or III: a KD according to (a) and (j), a $K_d$ according to (b) and (k), and a $K_a$ according to (c) and (l); or IV: kinetics according to I and II; or V: kinetics according to I and III; or VI: kinetics according to I, II and III.

The invention also provides a ligand comprising a variant of any preceding aspect or embodiment of the invention. For example, the ligand can be a dual-specific ligand (see WO04003019 for examples of dual-specific ligands). In one aspect, the invention provides a multispecific ligand comprising an anti-SA variant of any preceding aspect or embodiment of the invention and a binding moiety that specifically binds a target antigen other than SA. The binding moiety can be any binding moiety that specifically binds a target, e.g., the moiety is an antibody, antibody fragment, scFv, Fab, dAb or a binding moiety comprising a non-immunoglobulin protein scaffold. Such moieties are disclosed in detail in WO2008/096158 (see examples 17 to 25, which disclosure is incorporated herein by reference). Examples of non-immunoglobulin scaffolds are CTLA-4, lipocallin, staphylococcal protein A (spA), Affibody™, Avimers™, adnectins, GroEL and fibronectin.

In one embodiment, a linker is provided between the anti-target binding moiety and the anti-SA single variant, the linker comprising the amino acid sequence AST, optionally ASTSGPS. Alternative linkers are described in WO2007085814 (incorporated herein by reference) and WO2008/096158 (see the passage at page 135, line 12 to page 140, line 14, which disclosure and all sequences of linkers are expressly incorporated herein by reference as though explicitly written herein and for use with the present invention, and it is contemplated that any part of such disclosure can be incorporated into one or more claims herein).

In one embodiment of the multispecific ligand, the target antigen may be, or be part of, polypeptides, proteins or nucleic acids, which may be naturally occurring or synthetic. In this respect, the ligand of the invention may bind the target antigen and act as an antagonist or agonist (e.g., EPO receptor agonist). One skilled in the art will appreciate that the choice is large and varied. They may be for instance, human or animal proteins, cytokines, cytokine receptors, where cytokine receptors include receptors for cytokines, enzymes, co-factors for enzymes or DNA binding proteins. Suitable cytokines and growth factors include, but are preferably not limited to: ApoE, Apo-SAA, BDNF, Cardiotrophin-1, EGF, EGF receptor, ENA-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3 and HER 4, CD4, human chemokine receptors CXCR4 or CCR5, non-structural protein type 3 (NS3) from the hepatitis C virus, TNF-alpha, IgE, IFN-gamma, MMP-12, CEA, *H. pylori*, TB, influenza, Hepatitis E, MMP-12, internalizing receptors that are over-expressed on certain cells, such as the epidermal growth factor receptor (EGFR), ErBb2 receptor on tumor cells, an internalising cellular receptor, LDL receptor, FGF2 receptor, ErbB2 receptor, transferrin receptor, PDGF receptor, VEGF receptor, PsmAr, an extracellular matrix protein, elastin, fibronectin, laminin, a 1-antitrypsin, tissue factor protease inhibitor, PDK1, GSK1, Bad, caspase-9, Forkhead, an antigen of *Helicobacter pylori*, an antigen of *Mycobacterium*

*tuberculosis*, and an antigen of influenza virus. It will be appreciated that this list is by no means exhaustive.

In one embodiment, the multispecific ligand comprises an anti-SA dAb variant of the invention and an anti-TNFR1 binding moiety, e.g., an anti-TNFR1 dAb. Optionally, the ligand has only one anti-TNFR1 binding moiety (e.g., dAb) to reduce the chance of receptor cross-linking.

In one embodiment, the anti-TNFR1 binding moiety is DOM1h-131-206 disclosed in WO2008149148 (the amino acid sequence of which and the nucleotide sequence of which, as disclosed in that PCT application, are expressly incorporated herein by reference as though explicitly written herein and for use with the present invention, and it is contemplated that any part of such disclosure can be incorporated into one or more claims herein).

In one embodiment, the anti-TNFR1 binding moiety or dAb is any such moiety or dAb disclosed in co-pending application PCT/EP2010/052005, the disclosure of which is incorporated herein by reference. In one embodiment, the anti-TNFR1 binding moiety comprises an amino acid sequence that is at least 95% identical to the amino acid sequence of DOM1h-574-156, DOM1h-574-72, DOM1h-574-109, DOM1h-574-138, DOM1h-574-162 or DOM1h-574-180 or the amino acid sequence of any anti-TNFR1 dAb disclosed in Table 3.

In one embodiment, the ligand of the invention is a fusion protein comprising a variant of the invention fused directly or indirectly to one or more polypeptides. For example, the fusion protein can be a "drug fusion" as disclosed in WO2005/118642 (the disclosure of which is incorporated herein by reference), comprising a variant of the invention and a polypeptide drug as defined in that PCT application.

As used herein, "drug" refers to any compound (e.g., small organic molecule, nucleic acid, polypeptide) that can be administered to an individual to produce a beneficial, therapeutic or diagnostic effect through binding to and/or altering the function of a biological target molecule in the individual. The target molecule can be an endogenous target molecule encoded by the individual's genome (e.g. an enzyme, receptor, growth factor, cytokine encoded by the individual's genome) or an exogenous target molecule encoded by the genome of a pathogen (e.g. an enzyme encoded by the genome of a virus, bacterium, fungus, nematode or other pathogen). Suitable drugs for use in fusion proteins and conjugates comprising an anti-SA dAb variant of the invention are disclosed in WO2005/118642 and WO2006/059106 (the entire disclosures of which are incorporated herein by reference, and including the entire list of specific drugs as though this list were expressly written herein, and it is contemplated that such incorporation provides disclosure of specific drugs for inclusion in claims herein). For example, the drug can be glucagon-like peptide 1 (GLP-1) or a variant, interferon alpha 2b or a variant or exendin-4 or a variant.

In one embodiment, the invention provides a drug conjugate as defined and disclosed in WO2005/118642 and WO2006/059106, wherein the conjugate comprises a variant of the invention. In one example, the drug is covalently linked to the variant (e.g., the variant and the drug are expressed as part of a single polypeptide). Alternatively, in an example, the drug is non-covalently bonded or associated with the variant. The drug can be covalently or noncovalently bonded to the variant directly or indirectly (e.g., through a suitable linker and/or noncovalent binding of complementary binding partners (e.g., biotin and avidin)). When complementary binding partners are employed, one of the binding partners can be covalently bonded to the drug directly or through a suitable linker moiety, and the complementary binding partner can be covalently bonded to the variant directly or through a suitable linker moiety. When the drug is a polypeptide or peptide, the drug composition can be a fusion protein, wherein the polypeptide or peptide, drug and the polypeptide binding moiety are discrete parts (moieties) of a continuous polypeptide chain. As described herein, the polypeptide binding moieties and polypeptide drug moieties can be directly bonded to each other through a peptide bond, or linked through a suitable amino acid, or peptide or polypeptide linker.

A ligand which contains one single variable domain (monomer) variant of the invention or more than one single variable domain (multimer, fusion protein, conjugate, and dual specific ligand as defined herein) which specifically binds to serum albumin, can further comprise one or more entities selected from, but preferably not limited to a label, a tag, an additional single variable domain, a dAb, an antibody, an antibody fragment, a marker and a drug. One or more of these entities can be located at either the COOH terminus or at the N terminus or at both the N terminus and the COOH terminus of the ligand comprising the single variable domain, (either immunoglobulin or non-immunoglobulin single variable domain). One or more of these entities can be located at either the COOH terminus, or the N terminus, or both the N terminus and the COOH terminus of the single variable domain which specifically binds serum albumin of the ligand which contains one single variable domain (monomer) or more than one single variable domains (multimer, fusion protein, conjugate, and dual specific ligand as defined herein). Non-limiting examples of tags which can be positioned at one or both of these termini include a HA, his or a myc tag. The entities, including one or more tags, labels and drugs, can be bound to the ligand which contains one single variable domain (monomer) or more than one single variable domain (multimer, fusion protein, conjugate, and dual specific ligand as defined herein), which binds serum albumin, either directly or through linkers as described above.

An aspect of the invention provides a fusion product, e.g., a fusion protein or fusion with a peptide or conjugate with an NCE (new chemical entity) drug, comprising a polypeptide drug fused or conjugated (for an NCE) to any variant as described above in accordance with the present invention.

The invention provides a composition comprising a variant, fusion protein, conjugate or ligand of any aspect of the invention and a pharmaceutically acceptable diluent, carrier, excipient or vehicle.

Also encompassed herein is an isolated nucleic acid encoding any of the variants, fusion proteins, conjugates or ligands described herein, e.g., a ligand which contains one single variable domain (monomer) variant of the invention or more than one single variable domain (e.g., multimer, fusion protein, conjugate, and dual specific ligand as defined herein) variant which specifically binds to serum albumin, or which specifically binds both human serum albumin and at least one non-human serum albumin, or functionally active fragments thereof. Also encompassed herein is a vector and/or an expression vector, a host cell comprising the vector, e.g., a plant or animal cell and/or cell line transformed with a vector, a method of expressing and/or producing one or more variants, fusion proteins or ligands which contains one single variable domain (monomer) variant or more than one single variable domain variants (e.g., multimer, fusion protein, conjugate, and dual specific ligand as defined herein) which specifically binds to serum albumin, or fragment(s) thereof encoded by said vectors, including in some instances culturing the host cell so that the one or more variants, fusion proteins or ligands or fragments thereof are expressed and optionally recovering the ligand which contains one single variable domain (monomer) or more than one single variable domain (e.g., multimer, fusion protein, conjugate, and dual specific ligand as defined herein) which specifically binds to serum albumin, from the host cell culture medium. Also encompassed are methods of contacting a ligand described herein with serum albumin, including serum albumin and/or non-human serum albumin(s), and/or one or more targets other than serum albumin, where the targets include biologically active molecules, and include animal proteins, cytokines as listed above, and include methods where the contacting is in vitro as well as administering any of the variants, fusion proteins or ligands described herein to an individual host animal or cell in vivo and/or ex vivo. Preferably, administering ligands described herein which comprises a single variable domain (immunoglobulin or non-immunoglobulin) directed to serum albumin and/or non-human serum albumin (s), and one or more domains directed to one or more targets other than serum albumin, will increase the half life, including the T beta and/or terminal half life, of the anti-target ligand. Nucleic acid molecules encoding the variants, fusion proteins or single domain containing ligands or fragments thereof, including functional fragments thereof, are contemplated herein. Vectors encoding the nucleic acid molecules, including but preferably not limited to expression vectors, are contemplated herein, as are host cells from a cell line or organism containing one or more of these expression vectors. Also contemplated are methods of producing any variant, fusion protein or ligand, including, but preferably not limited to any of the aforementioned nucleic acids, vectors and host cells.

An aspect of the invention provides a nucleic acid comprising a nucleotide sequence encoding a variant according to the invention or a multispecific ligand of the invention or fusion protein of the invention.

An aspect of the invention provides a nucleic acid comprising the nucleotide sequence of a DOM7h-11 variant selected from DOM7h-11-56, DOM7h-11-57, DOM7h-11-65, DOM7h-11-67, DOM7h-11-68, DOM7h-11-69, DOM7h-11-79 and DOM7h-11-80 or a nucleotide sequence that is at least 70, 75, 80, 85, 90, 95, 96, 97, 98 or 99% identical to said selected sequence.

An aspect of the invention provides a vector comprising the nucleic acid of the invention. An aspect of the invention provides an isolated host cell comprising the vector.

Reference is made to WO2008/096158 for details of library vector systems, combining single variable domains, characterization of dual specific ligands, structure of dual specific ligands, scaffolds for use in constructing dual specific ligands, uses of anti-serum albumin dAbs and multispecific ligands and half-life-enhanced ligands, and compositions and formulations of comprising anti-serum albumin dAbs. These disclosures are incorporated herein by reference to provide guidance for use with the present invention, including for variants, ligands, fusion proteins, conjugates, nucleic acids, vectors, hosts and compositions of the present invention.

While the present invention is described with reference to DOM7h-11 variants, it will be appreciated that analogous mutations into other anti-SA immunoglobulin single variable domain lineages may be envisaged.

Sequences

TABLE 1

Amino Acid Sequences of DOM7h-11 Variant dAbs

DOM7h-11-12 (SEQ ID NO: 1)
DIQMTQSPSSLSASVGDRVTITCRASRPIGTMLSWYQQKPGKAPKLLILF
GSRLQSGVPSRFSGSGSGTDFTLTISSLQPEDFATYYCAQAGTHPTTFGQ
GTKVEIKR

TABLE 1-continued

Amino Acid Sequences of DOM7h-11 Variant dAbs

DOM7h-11-15 (SEQ ID NO: 2)
DIQMTQSPSSLSASVGDRVTITCRASRPIGTMLSWYQQKPGKAPKLLILA
FSRLQSGVPSRFSGSGSGTDFTLTISSLQPEDFATYYCAQAGTHPTTFGQ
GTKVEIKR

DOM7h-11-18 (SEQ ID NO: 3)
DIQMTQSPSSLSASVGDRVTITCRASRPIGTMLSWYQQKPGKAPKLLIWF
GSRLQSGVPSRFSGSGSGTDFTLTISSLQPEDFATYHCAQAGTHPTTFGQ
GTKVEIKR

DOM7h-11-19 (SEQ ID NO: 4)
DIQMTQSPSSLSASVGDRVTITCRASRPIGTMLSWYQQKPGKAPKLLILF
GSRLQSGVPSRFSGSGSGTDFTLTISSLQPEDFATYYCAQTGTHPTTFGQ
GTKVEIKR

DOM7h-11-3 (SEQ ID NO: 5)
DIQMTQSPSSLSASVGDRVTITCRASRPIGTTLSWYQQKPGKAPKLLILW
NSRLQSGVPSRFSGSGSGTDFTLTISSLQPEDFATYYCAQAGTHPTTFGQ
GTKVEIKR

TABLE 2

Nucleotide Sequences of DOM7h-11 Variant dAbs

DOM7h-11-12 (SEQ ID NO: 6)
GACATCCAGA TGACCCAGTC TCCATCCTCC CTGTCTGCAT
CTGTAGGAGA CCGTGTCACC ATCACTTGCC GGGCAAGTCG
TCCGATTGGG ACGATGTTAA GTTGGTACCA GCAGAAACCA
GGGAAAGCCC CTAAGCTCCT GATCTTGTTT GGTTCCCGGT
TGCAAAGTGG GGTCCCATCA CGTTTCAGTG GCAGTGGATC
TGGGACAGAT TTCACTCTCA CCATCAGCAG TCTGCAACCT
GAAGATTTTG CTACGTACTA CTGTGCGCAG GCTGGGACGC
ATCCTACGAC GTTCGGCCAA GGGACCAAGG TGGAAATCAA ACGG

DOM7h-11-15 (SEQ ID NO: 7)
GACATCCAGA TGACCCAGTC TCCATCCTCC CTGTCTGCAT
CTGTAGGAGA CCGTGTCACC ATCACTTGCC GGGCAAGTCG
TCCGATTGGG ACGATGTTAA GTTGGTACCA GCAGAAACCA
GGGAAAGCCC CTAAGCTCCT GATCCTTGCT TTTTCCCGTT
TGCAAAGTGG GGTCCCATCA CGTTTCAGTG GCAGTGGATC
TGGGACAGAT TTCACTCTCA CCATCAGCAG TCTGCAACCT
GAAGATTTTG CTACGTACTA CTGCGCGCAG GCTGGGACGC
ATCCTACGAC GTTCGGCCAA GGGACCAAGG TGGAAATCAA ACGG

DOM7h-11-18 (SEQ ID NO: 8)
GACATCCAGA TGACCCAGTC TCCATCCTCC CTGTCTGCAT
CTGTAGGAGA CCGTGTCACC ATCACTTGCC GGGCAAGTCG
TCCGATTGGG ACGATGTTAA GTTGGTACCA GCAGAAACCA
GGGAAAGCCC CAAAGCTCCT GATCTGGTTT GGTTCCCGGT
TGCAAAGTGG GGTCCCATCA CGTTTCAGTG GCAGTGGATC
TGGGACAGAT TTCACTCTCA CCATCAGCAG TCTGCAACCT
GAAGATTTTG CTACGTACCA CTGTGCGCAG GCGGGGACGC
ATCCTACGAC GTTCGGCCAA GGGACCAAGG TGGAAATCAA ACGG

DOM7h-11-19 (SEQ ID NO: 9)
GACATCCAGA TGACCCAGTC TCCATCCTCC CTGTCTGCAT
CTGTAGGAGA CCGTGTCACC ATCACTTGCC GGGCAAGTCG
TCCGATTGGG ACGATGTTAA GTTGGTACCA GCAGAAACCA
GGGAAAGCCC CTAAGCTCCT GATCTTGTTT GGTTCCCGGT
TGCAAAGTGG GGTCCCATCA CGTTTCAGTG GCAGTGGATC
TGGGACAGGAT TTCACTCTCA CCATCAGCAG TCTGCAACCT
GAAGATTTTG CTACGTACTA CTGTGCGCAG ACTGGGACGC
ATCCCACGAC GTTCGGCCAA GGGACCAAGG TGGAAATCAA ACGG

DOM7h-11-3 (SEQ ID NO: 10)
GACATCCAGA TGACCCAGTC TCCATCCTCC CTGTCTGCAT
CTGTAGGAGA CCGTGTCACC ATCACTTGCC GGGCAAGTCG
TCCGATTGGG ACGACGTTAA GTTGGTACCA GCAGAAACCA
GGGAAAGCCC CTAAGCTCCT GATCCTTTGG AATTCCCGTT
TGCAAAGTGG GGTCCCATCA CGTTTCAGTG GCAGTGGATC
TGGGACAGAT TTCACTCTCA CCATCAGCAG TCTGCAACCT
GAAGATTTTG CTACGTACTA CTGTGCGCAG GCTGGGACGC
ATCCTACGAC GTTCGGCCAA GGGACCAAGG TGGAAATCAA ACGG

TABLE 3

Amino Acid Sequences of anti-TNFR1 dAbs

>DOM1h-509 (SEQ ID NO: 11)
EVQLLESGGGLVQPGGSLRLSCAASGFTFSQYRMHWVRQAPGKSLEWVSS
IDTRGSSTYYADPVKGRFTISRDNSKNTLYLQMNSLRAEDTAVYYCAKAV
TMFSPFFDYWGQGTLVTVSS

>DOM1h-510 (SEQ ID NO: 12)
EVQLLESGGGLVQPGGSLRLSCAASGFTFADYGMRWVRQAPGKGLEWVSS
ITRTGRVTYYADSVKGRFTISRDNSKNTLYLQMNSLRAEDTAVYYCAKWR
NRHGEYLADFDYWGQGTLVTVSS

>DOM1h-543 (SEQ ID NO: 13)
EVQLLESGGGLVQPGGSLRLSCAASGFTFMRYRMHWVRQAPGKGLEWVSS
IDSNGSSTYYADSVKGRFTISRDNSKNTLYLQMNSLRAEDTAVYYCAKDR
TERSPVFDYWGQGTLVTVSS

>DOM1h-549 (SEQ ID NO: 14)
EVQLLESGGGLVQPGGSLRLSCAASGFTFVDYEMHWVRQAPGKGLEWVSS
ISESGTTTYYADSVKGRFTISRDNSKNTLYLQMNSLRAEDTAVYYCAKRR
FSASTFDYWGQGTLVTVSS

>DOM1h-574 (SEQ ID NO: 15)
EVQLLESGGGLVQPGGSLRLSCAASGFTFVKYSMGWVRQAPGKGLEWVSQ
ISNTGGHTYYADSVKGRFTISRDNSKNTLYLQMNSLRAEDTAVYYCAKYT
GHWEPFDYWGQGTLVTVSS

>DOM1h-574-1 (SEQ ID NO: 16)
EVQLLESGGGLVQPGGSLRLSCAASGFTFVKYSMGWVRQAPGKGLEWVSQ
ISNTGGHTYYADSVKGRFTISRDNSKNTLYLQMNSLRAEDTAVYYCAKYT
GRWEPYDYWGQGTLVTVSS

>DOM1h-574-2 (SEQ ID NO: 17)
EVQLLESGGGLVQPGGSLRLSCAASGFTFVKYSMGWVRQAPGKGLEWVSQ
ISNTGGHTYYADSVKGRFTISRDNSKNTLYLQMNSLRAEDTAVYYCAKYT
GRWEPFDYWGQGTLVTVSS

>DOM1h-574-7 (SEQ ID NO: 18)
EVQLLESGGGLVQPGGSLRLSCAASGFTFVKYSMGWVRQAPGKGLEWVSQ
ISNTGGHTYYADSVKGRFTISRDNSKNTLYLQMNSLRAEDTAVYYCAIYT
GRWEPFDYWGQGTLVTVSS

>DOM1h-574-8 (SEQ ID NO: 19)
EVQLLESGGGLVQPGGSLRLSCAASGFTFVKYSMGWVRQAPGKGPEWVSQ
ISNTGGHTYYADSVKGRFTISRDNSKNTLYLQMNSLRAEDTAVYYCAIYT
GRWEPFDYWGQGTLVTVSS

>DOM1h-574-9 (SEQ ID NO: 20)
EVQLLESGGGLVQPGGSLRLSCAASGFTFVKYSMGWVRQAPGKGLEWVSQ
ISNTGGHTYYADSVKGRFTISRDNSKNTLYMQMNSLRAEDTAVYYCAIYT
GRWEPFDYWGQGTLVTVSS

>DOM1h-574-10 (SEQ ID NO: 21)
EVQLLESGGGLVQPGGSLRLSCAASGFTFGKYSMGWVRQAPGKDLEWVSQ
ISNTGGHTYYADSVKGRFTISRDNSKNTLYLQMNSLRAEDTAVYYCAIYT
GRWEPFDYWGQGTLVTVSS

>DOM1h-574-11 (SEQ ID NO: 22)
EVQLLESGGGLVQPGGSLRLSCAASGFTFVKYSMGWVRQAPGKGLEWVSQ
ISNTGGHTYYADSVKGRFTISRDNSKNTLYLQMNSLRAEDTAVYYCAKYT
GRWEPFDHWGQGTLVTVSS

>DOM1h-574-12 (SEQ ID NO: 23)
EVQLLESGGGLVQPGGSLRLSCAASGFTFVKYSMGWVRQAPGKGLEWVSQ
ISNTGDHTYYADSVKGRFTISRDNSKNTLYLQMNSLRAEDTAVYYCAKYT
GRWEPFDYWGQGTLVTVSS

>DOM1h-574-13 (SEQ ID NO: 24)
EVQLLESGGGLVQPGGSLRLSCAASGFTFVKYSMGWVRQAPGKGLEWVSQ
ISNTGDRTYYADSVKGRFTISRDNSKNTLYLQMNSLRAEDTAVYYCAKYT
GRWEPFDYWGQGTLVTVSS

>DOM1h-574-14 (SEQ ID NO: 25)
EVQLLESGGGLVQPGGSLRLSCAASGFTFVKYSMGWVRQAPGKGLEWVSQ
ISNTGDRTYYADSVKGRFTISRDNSKNTLYLQMNSLRAEDTAVYYCAIYT
GRWEPFDYWGQGTLVTVSS

>DOM1h-574-15 (SEQ ID NO: 26)
EVQLLESGGGLVQPGGSLRLSCAASGFTFVKYSMGWVRQAPGKGLEWVSQ
ISNTGDHTYYADSVKGRFTISRDNSKNTLYLQMNSLRAEDTAVYYCAIYT
GRWEPFDYWGQGTLVTVSS

>DOM1h-574-16 (SEQ ID NO: 27)
EVQLLESGGGLVQPGGSLRLSCAASGFTFVKYSMGWVRQAPGKGPEWVSQ
ISNTGDRTYYADSVKGRFTISRDNSKNTLYLQMNSLRAEDTAVYYCAIYT
GRWEPFDYWGQGTLVTVSS

>DOM1h-574-17 (SEQ ID NO: 28)
EVQLLESGGGLVQPGGSLRLSCAASGFTFVKYSMGWVRQAPGKGPEWVSQ
ISNTGDHTYYADSVKGRFTISRDNSKNTLYLQMNSLRAEDTAVYYCAIYT
GRWEPFDYWGQGTLVTVSS

>DOM1h-574-18 (SEQ ID NO: 29)
EVQLLESGGGLVQPGGSLRLSCAASGFTFGKYSMGWVRQAPGKDLEWVSQ
ISNTGDRTYYADSVKGRFTISRDNSKNTLYLQMNSLRAEDTAVYYCAIYT
GRWEPFDYWGQGTLVTVSS

>DOM1h-574-19 (SEQ ID NO: 30)
EVQLLESGGGLVQPGGSLRLSCAASGFTFGKYSMGWVRQAPGKDLEWVSQ
ISNTGDHTYYADSVKGRFTISRDNSKNTLYLQMNSLRAEDTAVYYCAIYT
GRWEPFDYWGQGTLVTVSS

>DOM1h-574-25 (SEQ ID NO: 31)
EVQLLESGGGLVQPGGSLRLSCAASGFTFVKYSMGWVRQAPGKGLEWVSQ
ISNTGDRTYYADSVKGRFTISRDNSKNTLYLQMNSLRAEDTAVYYCAIYT
GRWEPFVYWGQGTLVTVSS

>DOM1h-574-26 (SEQ ID NO: 32)
EVQLLESGGGLVQPGGSLRLSCAASGFTFVKYSMGWVRQAPGKGLEWVSQ
ISNTGDRTYYADSVKGRFTISRDNSKNTLYLQMNSLRAEDTAVYYCAIYT
GRWEPFEYWGQGTLVTVSS

>DOM1h-574-27 (SEQ ID NO: 33)
EVQLLESGGGLVQPGGSLRLSCAASGFTFVKYSMGWVRQAPGKGLEWVSQ
ISNTGDRTYYADSVKGRFTISRDNSKNTLYLQMNSLRAEDTAVYYCAIYT
GRWKPFEYWGQGTLVTVSS

>DOM1h-574-28 (SEQ ID NO: 34)
EVQLLESGGGLVQPGGSLRLSCAASGFTFVKYSMGWVRQAPGKGLEWVSQ
ISNTGDRTYYADSVKGRFTISRDNSKNTLYLQMNSLRAEDTAVYYCAIYT
GRWVPFEYWGQGTLVTVSS

>DOM1h-574-29 (SEQ ID NO: 35)
EVQLLESGGGLVQPGGSLRLSCAASGFTFVKYSMGWVRQAPGKGLEWVS
QISNTGDRTYYADSVKGRFTISRDNSKNTLYLQMNSLRAEDTAVYYCAI
YTGRWRPFEYWGQGTLVTVSS

>DOM1h-574-30 (SEQ ID NO: 36)
EVQLLESGGGLVQPGGSLRLSCAASGFTFVKYSMGWVRQAPGKGLEWVS
QIANTGDRRYYADSVKGRFTISRDNSKNTLYLQMNSLRAEDTAAYYCAI
YTGRWEPFDYWGQGTLVTVSS

>DOM1h-574-31 (SEQ ID NO: 37)
EVQLLESGGGLVQPGGSLRLSCAASGFTFVKYSMGWVRQAPGKGLEWVS
QISNTADRTYYAHSVKGRFTISRDNSKNTLYLQMNSLRAEDTAVYYCAI
YTGRWEPFNYWGQGTLVTVSS

>DOM1h-574-32 (SEQ ID NO: 38)
EVQLLESGGGLVQPGGSLRLSCAASGFTFVKYSMGWVRQAPGKGLEWVS
QISNTGDRTYYADSVKGRFTISRDNSKNTLYLQMNSLRAEDTAVYYCAI
YTGRWAPFEYWGQGTLVTVSS

>DOM1h-574-33 (SEQ ID NO: 39)
EVQLLESGGGLVQPGGSLRLSCAASGFTFVKYSMGWVRQAPGKGLEWVS
QISNTGDRTYYADSVKGRFTISRDNSKNSLYLQMNSLRAEDTAVYYCAI
YTGRWVPFDNWGQGTLVTVSS

>DOM1h-574-35 (SEQ ID NO: 40)
EVQLLESGGGLVQPGGSLRLSCAASGFTFITYSMGWVRQAPGKGLEWVS
QISNTGDRTYYADSVKGRFTISRDNSKNTLYLQMNSLRAEDTAVYYCAI
YTGRWEPFQYWGQGTLVTVSS

TABLE 3-continued

Amino Acid Sequences of anti-TNFR1 dAbs

>DOM1h-574-36 (SEQ ID NO: 41)
EVQLLESGGGLVQPGGSLRLSCAASGFTFGKYSMGWVRQAPGKGLEWVS
QISNTGDRTYYADSVKGRFTISRDNSKNTLYLQMNSLRAEDTAVYYCAI
YTGRWEPFDYWGQGTLVTVSS

>DOM1h-574-37 (SEQ ID NO: 42)
EVQLLESGGGLVQPGGSLRLSCAASGFTFFKYSMGWVRQAPGKGLEWVS
QISNTGDRTYYADSVKGRFTISRDNSKNTLYLQMNSLRAEDTAVYYCAI
YTGRWEPFDYWGQGTLVTVSS

>DOM1h-574-38 (SEQ ID NO: 43)
EVQLLESGGGLVQPGGSLRLSCAASGFTFVKYSMGWVRQAPGKGLEWVS
QISDTGDRRYYDDSVKGRFTISRDNSKNTLYLQMNSLRAEDTAVYYCAI
YTGRWEPFDYWGQGTLVTVSS

>DOM1h-574-39 (SEQ ID NO: 44)
EVQLLESGGGLVQPGGSLRLSCAASGFTFVKYSMGWVRQAPGKGLEWVS
QISNTGDRRYYADAVKGRFTISRDNSKNTLYLQMNSLRAEDTAVYYCAI
YTGRWEPFDYWGQGTLVTVSS

>DOM1h-574-40 (SEQ ID NO: 45)
EVQLLESGGGLVQPGGSLRLSCAASGFTFVKYSMGWVRQAPGKGLEWVS
QISNTGDRTYYADSVKGRFTISRDNSKNTLYLQMNSLRAEDTAVYYCAI
YTGRWEPFKYWGQGTLVTVSS

>DOM1h-574-53 (SEQ ID NO: 46)
EVQLLESGGGLVQPGGSLRLSCAASGFTFSKYSMGWVRQAPGKGLEWVS
QISNTGERRYYADSVKGRFTISRDNPKNTLYLQMNSLRAEDTAVYYCAI
YTGRWEPFEYWGQGTLVTVSS

>DOM1h-574-54 (SEQ ID NO: 47)
EVQLLESGGGLVQPGGSLRLSCAASGFTFVNYSMGWVRQAPGKGLEWVS
QISNTGDRTYYADSVKGRFTISRDNSKNTLYLQMNSLRAEDTAVYYCAI
YTGRWEPYEYWGQGTLVTVTS

>DOM1h-574-65 (SEQ ID NO: 48)
EVQLLESGGGLVQPGGSLRLSCAASGFTFVKYSMGWVRQAPGKGLEWVS
QIANTGDRRYYADSVKGRFTISRDNSKNTLYLQMNSLRAEDTAVYYCAI
YTGRWEPFVYWGQGTLVTVSS

>DOM1h-574-66 (SEQ ID NO: 49)
EVQLLESGGGLVQPGGSLRLSCAASGFTFVKYSMGWVRQAPGKGLEWVS
QIANTGDRRYYADSVKGRFTISRDNSKNTLYLQMNSLRAEDTAVYYCAI
YTGRWKPFEYWGQGTLVTVSS

>DOM1h-574-67 (SEQ ID NO: 50)
EVQLLESGGGLVQPGGSLRLSCAASGFTFVKYSMGWVRQAPGKGLEWVS
QIANTGDRRYYADSVKGRFTISRDNSKNTLYLQMNSLRAEDTAVYYCAI
YTGRWVPFEYWGQGTLVTVSS

>DOM1h-574-68 (SEQ ID NO: 51)
EVQLLESGGGLVQPGGSLRLSCAASGFTFVKYSMGWVRQAPGKGLEWVS
QIANTGDRRYYADSVKGRFTISRDNSKNTLYLQMNSLRAEDTAVYYCAI
YTGRWRPFEYWGQGTLVTVSS

>DOM1h-574-69 (SEQ ID NO: 52)
EVQLLESGGGLVQPGGSLRLSCAASGFTFVKYSMGWVRQAPGKGLEWVS
QIANTGDRRYYADSVKGRFTISRDNSKNTLYLQMNSLRAEDTAVYYCAI
YTGRWAPFEYWGQGTLVTVSS

>DOM1h-574-70 (SEQ ID NO: 53)
EVQLLESGGGLVQPGGSLRLSCAASGFTFVKYSMGWVRQAPGKGLEWVS
QISNTADRTYYAHSVKGRFTISRDNSKNTLYLQMNSLRAEDTAVYYCAV
YTGRWEPFVYWGQGTLVTVSS

>DOM1h-574-71 (SEQ ID NO: 54)
EVQLLESGGGLVQPGGSLRLSCAASGFTFVKYSMGWVRQAPGKGLEWVS
QISNTADRTYYAHSVKGRFTISRDNSKNTLYLQMNSLRAEDTAVYYCAI
YTGRWKPFEYWGQGTLVTVSS

>DOM1h-574-72 (SEQ ID NO: 55)
EVQLLESGGGLVQPGGSLRLSCAASGFTFVKYSMGWVRQAPGKGLEWVS
QISNTADRTYYAHSVKGRFTISRDNSKNTLYLQMNSLRAEDTAVYYCAI
YTGRWVPFEYWGQGTLVTVSS

>DOM1h-574-73 (SEQ ID NO: 56)
EVQLLESGGGLVQPGGSLRLSCAASGFTFVKYSMGWVRQAPGKGLEWVS
QISNTADRTYYAHSVKGRFTISRDNSKNTLYLQMNSLRAEDTAVYYCAI
YTGRWRPFEYWGQGTLVTVSS

>DOM1h-574-74 (SEQ ID NO: 57)
EVQLLESGGGLVQPGGSLRLSCAASGFTFVKYSMGWVRQAPGKGLEWVS
QISNTADRTYYAHSVKGRFTISRDNSKNTLYLQMNSLRAEDTAVYYCAI
YTGRWAPFEYWGQGTLVTVSS

>DOM1h-574-75 (SEQ ID NO: 58)
EVQLLESGGGLVQPGGSLRLSCAASGFTFVKYSMGWVRQAPGKGLEWVS
QISDTGDRRYYDDSVKGRFTISRDNSKNTLYLQMNSLRAEDTAVYYCAI
YTGRWEPFVYWGQGTLVTVSS

>DOM1h-574-76 (SEQ ID NO: 59)
EVQLLESGGGLVQPGGSLRLSCAASGFTFVKYSMGWVRQAPGKGLEWVS
QISDTGDRRYYDDSVKGRFTISRDNSKNTLYLQMNSLRAEDTAVYYCAI
YTGRWKPFEYWGQGTLVTVSS

>DOM1h-574-77 (SEQ ID NO: 60)
EVQLLESGGGLVQPGGSLRLSCAASGFTFVKYSMGWVRQAPGKGLEWVS
QISDTGDRRYYDDSVKGRFTISRDNSKNTLYLQMNSLRAEDTAVYYCAI
YTGRWVPFEYWGQGTLVTVSS

>DOM1h-574-78 (SEQ ID NO: 61)
EVQLLESGGGLVQPGGSLRLSCAASGFTFVKYSMGWVRQAPGKGLEWVS
QISDTGDRRYYDDSVKGRFTISRDNSKNTLYLQMNSLRAEDTAVYYCAI
YTGRWRPFEYWGQGTLVTVSS

>DOM1h-574-79 (SEQ ID NO: 62)
EVQLLESGGGLVQPGGSLRLSCAASGFTFVKYSMGWVRQAPGKGLEWVS
QISDTGDRRYYDDSVKGRFTISRDNSKNTLYLQMNSLRAEDTAVYYCAI
YTGRWAPFEYWGQGTLVTVSS

>DOM1h-574-84 (SEQ ID NO: 63)
EVQLLESGGGLVQPGGSLRLSCAASGFTFVKYSMGWVRQAPGKGLEWVS
QISNTGDRRYYADAVKGRFTISRDNSKNTLYLQMNSLRAEDTAVYYCAI
YTGRWEPFVYWGQGTLVTVSS

>DOM1h-574-85 (SEQ ID NO: 64)
EVQLLESGGGLVQPGGSLRLSCAASGFTFVKYSMGWVRQAPGKGLEWVS
QISNTGDRRYYADAVKGRFTISRDNSKNTLYLQMNSLRAEDTAVYYCAI
YTGRWKPFEYWGQGTLVTVSS

>DOM1h-574-86 (SEQ ID NO: 65)
EVQLLESGGGLVQPGGSLRLSCAASGFTFVKYSMGWVRQAPGKGLEWVS
QISNTGDRRYYADAVKGRFTISRDNSKNTLYLQMNSLRAEDTAVYYCAI
YTGRWVPFEYWGQGTLVTVSS

>DOM1h-574-87 (SEQ ID NO: 66)
EVQLLESGGGLVQPGGSLRLSCAASGFTFVKYSMGWVRQAPGKGLEWVS
QISNTGDRRYYADAVKGRFTISRDNSKNTLYLQMNSLRAEDTAVYYCAI
YTGRWRPFEYWGQGTLVTVSS

>DOM1h-574-88 (SEQ ID NO: 67)
EVQLLESGGGLVQPGGSLRLSCAASGFTFVKYSMGWVRQAPGKGLEWVS
QISNTGDRRYYADAVKGRFTISRDNSKNTLYLQMNSLRAEDTAVYYCAI
YTGRWAPFEYWGQGTLVTVSS

>DOM1h-574-90 (SEQ ID NO: 68)
EVQLLESGGGLVQPGGSLRLSCAASGFTFLKFSMGWVRQAPGKGLEWVS
QIANTGDRRYYADSVKGRFTISRDNSKNTLYLQMNSLRAEDTAVYYCAI
YTGRWAPFEYWGQGTLVTVSS

>DOM1h-574-91 (SEQ ID NO: 69)
EVQLLESGGGLVQPGGSLRLSCAASGFTFLKYSMGWVRQAPGKGLEWVS
QISNTADRTYYAHSVKGRFTISRDNSKNTLYLQMNSLRAEDTAVYYCAI
YTGRWAPFEYWGQGTLVTVSS

>DOM1h-574-92 (SEQ ID NO: 70)
EVQLLESGGGLVQPGGSLRLSCAASGFTFFKYSMGWVRQAPGKGLEWVS
QISDTGDRRYYDDSVKGRFTISRDNSKNTLYLQMNSLRAEDTAVYYCAI
YTGRWEPFVYWGQGTLVTVSS

TABLE 3-continued

Amino Acid Sequences of anti-TNFR1 dAbs

>DOM1h-574-93 (SEQ ID NO: 71)
EVQLLESGGGLVQPGGSLRLSCAASGFTFLKYSMGWVRQAPGKGLEWVS
QISDTGDRRYYDDSVKGRFTISRDNSKNTLYLQMNSLRAEDTAVYYCAI
YTGRWEPFVYWGQGTLVTSS

>DOM1h-574-94 (SEQ ID NO: 72)
EVQLLESGGGLVQPGGSLRLSCAASGFTFVKYSMGWVRQAPGKGLEWVS
QIANTGDRRYYADSVKGRFTISRDNSKNTLYLQMNSLRAEDTAAYYCAI
YTGRWPDFDYWGQGTLVTSS

>DOM1h-574-95 (SEQ ID NO: 73)
EVQLLESGGGLVQPGGSLRLSCAASGFTFVKYSMGWVRQAPGKGLEWVS
QIANTGDRRYYADSVKGRFTISRDNSKNTLYLQMNSLRAEDTAAYYCAI
YTGRWPDFDYWGQGTLVTSS

>DOM1h-574-96 (SEQ ID NO: 74)
EVQLLESGGGLVQPGGSLRLSCAASGFTFVKYSMGWVRQAPGKGLEWVS
QISNTADRTYYAHSVKGRFTISRDNSKNTLYLQMNSLRAEDTAVYYCAI
YTGRWPDFDYWGQGTLVTSS

>DOM1h-574-97 (SEQ ID NO: 75)
EVQLLESGGGLVQPGGSLRLSCAASGFTFVKYSMGWVRQAPGKGLEWVS
QISNTADRTYYAHSVKGRFTISRDNSKNTLYLQMNSLRAEDTAVYYCAI
YTGRWPDFDYWGQGTLVTSS

>DOM1h-574-98 (SEQ ID NO: 76)
EVQLLESGGGLVQPGGSLRLSCAASGFTFVKYSMGWVRQAPGKGLEWVS
QISDTGDRRYYDDSVKGRFTISRDNSKNTLYLQMNSLRAEDTAVYYCAI
YTGRWPDFDYWGQGTLVTSS

>DOM1h-574-99 (SEQ ID NO: 77)
EVQLLESGGGLVQPGGSLRLSCAASGFTFVKYSMGWVRQAPGKGLEWVS
QISDTGDRRYYDDSVKGRFTISRDNSKNTLYLQMNSLRAEDTAVYYCAI
YTGRWPDFDYWGQGTLVTSS

>DOM1h-574-100 (SEQ ID NO: 78)
EVQLLESGGGLVQPGGSLRLSCAASGFTFVKYSMGWVRQAPGKGPEWVS
QISAWGDRTYYADSVKGRFTISRDNSKNTLYLQMNSLRAEDTAVYYCAI
YTGRWEPFDYWGQGTLVTSS

>DOM1h-574-101 (SEQ ID NO: 79)
EVQLLESGGGLVQPGGSLRLSCAASGFTFVKYSMGWVRQAPGKGPEWVS
QISDGGQRTYYADSVKGRFTISRDNSKNTLYLQMNSLRAEDTAVYYCAI
YTGRWEPFDYWGQGTLVTSS

>DOM1h-574-102 (SEQ ID NO: 80)
EVQLLESGGGLVQPGGSLRLSCAASGFTFVKYSMGWVRQAPGKGPEWVSQ
ISDSGYRTYYADSVKGRFTISRDNSKNTLYLQMNSLRAEDTAVYYCAIYT
GRWEPFDYWGQGTLVTSS

>DOM1h-574-103 (SEQ ID NO: 81)
EVQLLESGGGLVQPGGSLRLSCAASGFTFVKYSMGWVRQAPGKGPEWVSQ
ISDGGTRTYYADSVKGRFTISRDNSKNTLYLQMNSLRAEDTAVYYCAIYT
GRWEPFDYWGQGTLVTSS

>DOM1h-574-104 (SEQ ID NO: 82)
EVQLLESGGGLVQPGGSLRLSCAASGFTFVKYSMGWVRQAPGKGPEWVSQ
ISDKGTRTYYADSVKGRFTISRDNSKNTLYLQMNSLRAEDTAVYYCAIYT
GRWEPFDYWGQGTLVTSS

>DOM1h-574-105 (SEQ ID NO: 83)
EVQLLESGGGLVQPGGSLRLSCAASGFTFVKYSMGWVRQAPGKGPEWVSQ
ISETGRRTYYADSVKGRFTISRDNSKNTLYLQMNSLRAEDTAVYYCAIYT
GRWEPFDYWGQGTLVTSS

>DOM1h-574-106 (SEQ ID NO: 84)
EVQLLESGGGLVQPGGSLRLSCAASGFTFVKYSMGWVRQAPGKGLEWVSQ
INNTGSTTYYADSVKGRFTISRDNSKNTLYLQMNSLRAEDTAVYYCAIYT
GRWEPFDYWGQGTLVTSS

>DOM1h-574-107 (SEQ ID NO: 85)
EVQLLESGGGLVQPGGSLRLSCAASGFTFVKYSMGWVRQAPGKGPEWVSQ
ISNTADRTYYAHSVKGRFTISRDNSKNTLYLQMNSLRAEDTAVYYCAIYT
GRWVPFEYWGQGTLVTSS

>DOM1h-574-108 (SEQ ID NO: 86)
EVQLLESGGGLVQPGGSLRLSCAASGFTFVKYSMGWVRQAPGKGPEWVSQ
ISNTADRTYYAHSVKGRFTISRDNSKNTLYLQMNSLRAEDTAVYYCAIYT
GRWAPFEYWGQGTLVTSS

>DOM1h-574-109 (SEQ ID NO: 87)
EVQLLESGGGLVQPGGSLRLSCAASGFTFVKYSMGWVRQAPGKGLEWVSQ
ISDTADRTYYAHSVKGRFTISRDNSKNTLYLQMNSLRAEDTAVYYCAIYT
GRWVPFEYWGQGTLVTSS

>DOM1h-574-110 (SEQ ID NO: 88)
EVQLLESGGGLVQPGGSLRLSCAASGFTFVKYSMGWVRQAPGKGLEWVSQ
ISDTADRTYYAHSVKGRFTISRDNSKNTLYLQMNSLRAEDTAVYYCAIYT
GRWAPFEYWGQGTLVTSS

>DOM1h-574-111 (SEQ ID NO: 89)
EVQLLESGGGLVQPGGSLRLSCAASGFTFVKYSMGWVRQAPGKGLEWVSQ
ISDTADRTYYDDSVKGRFTISRDNSKNTLYLQMNSLRAEDTAVYYCAIYT
GRWRPFEYWGQGTLVTSS

>DOM1h-574-112 (SEQ ID NO: 90)
EVQLLESGGGLVQPGGSLRLSCAASGFTFVKYSMGWVRQAPGKGLEWVSQ
ISDTADRTYYTHSVKGRFTISRDNSKNTLYLQMNSLRAEDTAVYYCAIYT
GRWAPFEYWGQGTLVTSS

>DOM1h-574-113 (SEQ ID NO: 91)
EVQLLESGGGLVQPGGSLRLSCAASGFTFVKYSMGWVRQAPGKGLEWVSQ
ISNTADRRYYAHSVKGRFTISRDNSKNTLYLQMNSLRAEDTAVYYCAIYT
GRWAPFEYWGQGTLVTSS

>DOM1h-574-114 (SEQ ID NO: 92)
EVQLLESGGGLVQPGGSLRLSCAASGFTFVKYSMGWVRQAPGKGLEWVSQ
ILNTADRTYYDHSVKGRFTISRDNSKNTLYLQMNSLRAEDTAVYYCAIYT
GRWAPFEYWGQGTLVTSS

>DOM1h-574-115 (SEQ ID NO: 93)
EVQLLESGGGLVQPGGSLRLSCAASGFTFVKYSMGWVRQAPGKGLEWVSQ
ISNTADRTYYDHSVKGRFTISRDNSKNTLYLQMNSLRAEDTAVYYCAIYT
GRWAPFEYWGQGTLVTSS

>DOM1h-574-116 (SEQ ID NO: 94)
EVQLLESGGGLVQPGGSLRLSCAASGFTFVKYSMGWVRQAPGKGLEWVSQ
ISDTADRRYYAHSVKGRFTISRDNSKNTLYLQMNSLRAEDTAVYYCAIYT
GRWAPFEYWGQGTLVTSS

>DOM1h-574-117 (SEQ ID NO: 95)
EVQLLESGGGLVQPGGSLRLSCAASGFTFVKYSMGWVRQAPGKGLEWVSQ
ISDTADRRYYDHSVKGRFTISRDNSKNTLYLQMNSLRAEDTAVYYCAIYT
GRWAPFEYWGQGTLVTSS

>DOM1h-574-118 (SEQ ID NO: 96)
EVQLLESGGGLVQPGGSLRLSCAASGFTFVKYSMGWVRQAPGKGLEWVSQ
ISNTADRTYYAHSVKGRFTISRDNSKNTLYLQMNSLRAEDTAVYYCAVYT
GRWVSFEYWGQGTLVTSS

>DOM1h-574-119 (SEQ ID NO: 97)
EVQLLESGGGLVQPGGSLRLSCAASGFTFVKYSMGWVRQAPGKGLEWVSQ
ISNTADRTYYAHSVKGRFTISRDNSKNTLYLQMNSLRAEDTAVYYCALYT
GRWVSFEYWGQGTLVTSS

>DOM1h-574-120 (SEQ ID NO: 98)
EVQLLESGGGLVQPGGSLRLSCAASGFTFVKYSMGWVRQAPGKGLEWVSQ
ISNTADRTYYAHSVKGRFTISRDNSKNTLYLQMNSLRAEDTAVYYCAVYT
GRWVPFEYWGQGTLVTSS

>DOM1h-574-121 (SEQ ID NO: 99)
EVQLLESGGGLVQPGGSLRLSCAASGFTFVKYSMGWVRQAPGKGLEWVSQ
ISNTADRTYYAHSVKGRFTISRDNSKNTLYLQMNSLRAEDTAVYYCALYT
GRWVPFEYWGQGTLVTSS

>DOM1h-574-122 (SEQ ID NO: 100)
EVQLLESGGGLVQPGGSLRLSCAASGFTFVKYSMGWVRQAPGKGLEWVSQ
IANTADRRYYAHSVKGRFTISRDNSKNTLYLQMNSLRAEDTAVYYCAIYT
GRWAPFEYWGQGTLVTSS

TABLE 3-continued

Amino Acid Sequences of anti-TNFR1 dAbs

>DOM1h-574-123 (SEQ ID NO: 101)
EVQLLESGGGLVQPGGSLRLSCAASGFTFVKYSMGWVRQAPGKGLEWVSQ
ISNTADRRYYADAVKGRFTISRDNSKNTLYLQMNSLRAEDTAVYYCAIYT
GRWEPFVYWGQGTLVTVSS

>DOM1h-574-124 (SEQ ID NO: 102)
EVQLLESGGGLVQPGGSLRLSCAASGFTFVKYSMGWVRQAPGKGLEWVSQ
ISNTGDRRYYAHAVKGRFTISRDNSKNTLYLQMNSLRAEDTAVYYCAIYT
GRWEPFVYWGQGTLVTVSS

>DOM1h-574-125 (SEQ ID NO: 103)
EVQLLESGGGLVQPGGSLRLSCAASGFTFVKYSMGWVRQAPGKGLEWVSQ
IANTADRRYYADAVKGRFTISRDNSKNTLYLQMNSLRAEDTAVYYCAIYT
GRWEPFVYWGQGTLVTVSS

>DOM1h-574-126 (SEQ ID NO: 104)
EVQLLESGGGLVQPGGSLRLSCAASGFTFVKYSMGWVRQAPGKGLEWVSQ
IANTGDRRYYAHAVKGRFTISRDNSKNTLYLQMNSLRAEDTAVYYCAIYT
GRWEPFVYWGQGTLVTVSS

>DOM1h-574-127 (SEQ ID NO: 105)
EVQLLESGGGLVQPGGSLRLSCAASGFTFVKYSMGWVRQAPGKGLEWVSQ
ISNTADRRYYAHAVKGRFTISRDNSKNTLYLQMNSLRAEDTAVYYCAIYT
GRWEPFVYWGQGTLVTVSS

>DOM1h-574-128 (SEQ ID NO: 106)
EVQLLESGGGLVQPGGSLRLSCAASGFTFVKYSMGWVRQAPGKGLEWVSQ
IANTADRRYYAHAVKGRFTISRDNSKNTLYLQMNSLRAEDTAVYYCAIYT
GRWEPFVYWGQGTLVTVSS

>DOM1h-574-129 (SEQ ID NO: 107)
EVQLLESGGGLVQPGGSLRLSCAASGFTFVKYSMGWVRQAPGKGLEWVSQ
IVNTGDRRYYADAVKGRFTISRDNSKNTLYLQMNSLRAEDTAVYYCAIYT
GRWEPFVYWGQGTLVTVSS

>DOM1h-574-130 (SEQ ID NO: 108)
EVQLLESGGGLVQPGGSLRLSCAASGFTFVKYSMGWVRQAPGKGLEWVSQ
IANTGDRRYYADAVKGRFTISRDNSKNTLYLQMNSLRAEDTAVYYCAIYT
GRWEPFVYWGQGTLVTVSS

>DOM1h-574-131 (SEQ ID NO: 109)
EVQLLESGGGLVQPGGSLRLSCAASGFTFVKYSMGWVRQAPGKGLEWVSQ
ISDTADRTYYDHSVKGRFTISRDNSKNTLYLQMNSLRAEDTAVYYCAIYT
GRWAPFEYWGQGTLVTVSS

>DOM1h-574-132 (SEQ ID NO: 110)
EVQLLESGGGLVQPGGSLRLSCAASGFTFVKYSMGWVRQAPGKGLEWVSQ
ISDTADRTYYDHSVKGRFTISRDNSKNTLYLQMNSLRAEDTAVYYCAIYT
GRWRPFEYWGQGTLVTVSS

>DOM1h-574-133 (SEQ ID NO: 111)
EVQLLESGGGLVQPGGSLRLSCAASGFTFVKYSMGWVRQAPGKGLEWVSQ
ISDTADRTYYDHSVKGRFTISRDNSKNTLYLQMNSLRAEDTAVYYCAIYT
GRWEPFVYWGQGTLVTVSS

>DOM1h-574-134 (SEQ ID NO: 112)
EVQLLESGGGLVQPGGSLRLSCAASGFTFVKYSMGWVRQAPGKGLEWVSQ
ISDTADRTYYSHSVKGRFTISRDNSKNTLYLQMNSLRAEDTAVYYCAIYT
GRWVPFEYWGQGTLVTVSS

>DOM1h-574-135 (SEQ ID NO: 113)
EVQLLESGGGLVQPGGSLRLSCAASGFTFVKYSMGWVRQAPGKGLEWVSQ
ISDTADRTYYTHSVKGRFTISRDNSKNTLYLQMNSLRAEDTAVYYCAIYT
GRWVPFEYWGQGTLVTVSS

>DOM1h-574-137 (SEQ ID NO: 114)
EVQLLESGGGLVQPGGSLRLSCAASGFTFVKYSMGWVRQAPGKGLEWVSQ
ISDTADRTYYTDAVKGRFTISRDNSKNTLYLQMNSLRAEDTAVYYCAIYT
GRWEPFVYWGQGTLVTVSS

>DOM1h-574-138 (SEQ ID NO: 115)
EVQLLESGGGLVQPGGSLRLSCAASGFTFFKYSMGWVRQAPGKGLEWVSQ
ISDTADRTYYAHSVKGRFTISRDNSKNTLYLQMNSLRAEDTAVYYCAIYT
GRWAPFEYWGQGTLVTVSS

>DOM1h-574-139 (SEQ ID NO: 116)
EVQLLESGGGLVQPGGSLRLSCAASGFTFLKYSMGWVRQAPGKGLEWVSQ
ISDTADRTYYAHSVKGRFTISRDNSKNTLYLQMNSLRAEDTAVYYCAIYT
GRWAPFEYWGQGTLVTVSS

>DOM1h-574-140 (SEQ ID NO: 117)
EVQLLESGGGLVQPGGSLRLSCAASGFTFFKYSMGWVRQAPGKGLEWVSQ
IADTGDRRYYDDSVKGRFTISRDNSKNTLYLQMNSLRAEDTAVYYCAIYT
GRWEPFVYWGQGTLVTVSS

>DOM1h-574-141 (SEQ ID NO: 118)
EVQLLESGGGLVQPGGSLRLSCAASGFTFFKYSMGWVRQAPGKGLEWVSQ
ISDTADRRYYDDSVKGRFTISRDNSKNTLYLQMNSLRAEDTAVYYCAIYT
GRWEPFVYWGQGTLVTVSS

>DOM1h-574-142 (SEQ ID NO: 119)
EVQLLESGGGLVQPGGSLRLSCAASGFTFFKYSMGWVRQAPGKGLEWVSQ
ISDTGDRRYYDHSVKGRFTISRDNSKNTLYLQMNSLRAEDTAVYYCAIYT
GRWEPFVYWGQGTLVTVSS

>DOM1h-574-143 (SEQ ID NO: 120)
EVQLLESGGGLVQPGGSLRLSCAASGFTFFKYSMGWVRQAPGKGLEWVSQ
ISDTGDRRYYDAVKGRFTISRDNSKNTLYLQMNSLRAEDTAVYYCAIYT
GRWEPFVYWGQGTLVTVSS

>DOM1h-574-144 (SEQ ID NO: 121)
EVQLLESGGGLVQPGGSLRLSCAASGFTFFKYSMGWVRQAPGKGLEWVSQ
IADTADRRYYDDSVKGRFTISRDNSKNTLYLQMNSLRAEDTAVYYCAIYT
GRWEPFVYWGQGTLVTVSS

>DOM1h-574-145 (SEQ ID NO: 122)
EVQLLESGGGLVQPGGSLRLSCAASGFTFFKYSMGWVRQAPGKGLEWVSQ
IADTGDRRYYDHSVKGRFTISRDNSKNTLYLQMNSLRAEDTAVYYCAIYT
GRWEPFVYWGQGTLVTVSS

>DOM1h-574-146 (SEQ ID NO: 123)
EVQLLESGGGLVQPGGSLRLSCAASGFTFFKYSMGWVRQAPGKGLEWVSQ
IADTGDRRYYDDAVKGRFTISRDNSKNTLYLQMNSLRAEDTAVYYCAIYT
GRWEPFVYWGQGTLVTVSS

>DOM1h-574-147 (SEQ ID NO: 124)
EVQLLESGGGLVQPGGSLRLSCAASGFTFVKYSMGWVRQAPGKGLEWVSQ
ISDTADRTYYAHSVKGRFTISRDNSKNTLYLQMNSLRAEDTAVYYCAIYT
GRWGPFVYWGQGTLVTVSS

>DOM1h-574-148 (SEQ ID NO: 125)
EVQLLESGGGLVQPGGSLRLSCAASGFTFVKYSMGWVRQAPGKGLEWVSQ
ISDTADRTYYAHSVKGRFTISRDNSKNTLYLQMNSLRAEDTAVYYCAIYT
GRWVPFAYWGQGTLVTVSS

>DOM1h-574-149 (SEQ ID NO: 126)
EVQLLESGGGLVQPGGSLRLSCAASGFTFVKYSMGWVRQAPGKGLEWVSQ
ISDTADRTYYAHSVKGRFTISRDNSKNTLYLQMNSLRAEDTAVYYCAIYT
GRWGPFQYWGQGTLVTVSS

>DOM1h-574-150 (SEQ ID NO: 127)
EVQLLESGGGLVQPGGSLRLSCAASGFTFVKYSMGWVRQAPGKGLEWVSQ
ISDTADRTYYAHSVKGRFTISRDNSKNTLYLQMNSLRAEDTAVYYCAIYT
GRWEPFQYWGQGTLVTVSS

>DOM1h-574-151 (SEQ ID NO: 128)
EVQLLESGGGLVQPGGSLRLSCAASGFTFVKYSMGWVRQAPGKGLEWVSQ
ISDTADRTYYAHSVKGRFTISRDNSKNTLYLQMNSLRAEDTAVYYCAIYT
GRWAPFEYWGQGTLVTVSS

>DOM1h-574-152 (SEQ ID NO: 129)
EVQLLESGGGLVQPGGSLRLSCAASGFTFVKYSMGWVRQAPGKGLEWVSQ
ISDTADRTYYAHSVKGRFTISRDNSKNTLYLQMNSLRAEDTAVYYCAIYT
GRWAPFQYWGQGTLVTVSS

>DOM1h-574-153 (SEQ ID NO: 130)
EVQLLESGGGLVQPGGSLRLSCAASGFTFVKYSMGWVRQAPGKGLEWVSQ
ISDTADRTYYAHSVKGRFTISRDNSKNTLYLQMNSLRAEDTAVYYCAIYT
GRWVPFQYWGQGTLVTVSS

TABLE 3-continued

Amino Acid Sequences of anti-TNFR1 dAbs

>DOM1h-574-154 (SEQ ID NO: 131)
EVQLLESGGGLVQPGGSLRLSCAASGFTFVKYSMGWVRQAPGKGLEWVSQ
ISDTGDRRYYDHSVKGRFTISRDNSKNTLYLQMNSLRAEDTAVYYCAIYT
GRWAPFEYWGQGTLVTVSS

>DOM1h-574-155 (SEQ ID NO: 132)
EVQLLESGGGLVQPGGSLRLSCAASGFTFLKYSMGWVRQAPGKGLEWVSQ
ISDTADRTYYAHSVKGRFTISRDNSKNTLYLQMNSLRAEDTAVYYCAIYT
GRWVPFEYWGQGTLVTVSS

>DOM1h-574-156 (SEQ ID NO: 133)
EVQLLESGGGLVQPGGSLRLSCAASGFTFFKYSMGWVRQAPGKGLEWVSQ
ISDTADRTYYAHSVKGRFTISRDNSKNTLYLQMNSLRAEDTAVYYCAIYT
GRWVPFEYWGQGTLVTVSS

>DOM1h-574-157 (SEQ ID NO: 134)
EVQLLESGGGLVQPGGSLRLSCAASGFTFLKYSMGWVRQAPGKGLEWVSQ
ISDTADRTYYDHSVKGRFTISRDNSKNTLYLQMNSLRAEDTAVYYCAIYT
GRWRPFEYWGQGTLVTVSS

>DOM1h-574-158 (SEQ ID NO: 135)
EVQLLESGGGLVQPGGSLRLSCAASGFTFFKYSMGWVRQAPGKGLEWVSQ
ISDTADRTYYDHSVKGRFTISRDNSKNTLYLQMNSLRAEDTAVYYCAIYT
GRWRPFEYWGQGTLVTVSS

>DOM1h-574-159 (SEQ ID NO: 136)
EVQLLESGGGLVQPGGSLRLSCAASGFTFFKYSMGWVRQAPGKGLEWVSQ
ISDTADRTYYDHSVKGRFTISRDNSKNTLYLQMNSLRAEDTAVYYCAIYT
GRWEPFVYWGQGTLVTVSS

>DOM1h-574-160 (SEQ ID NO: 137)
EVQLLESGGGLVQPGGSLRLSCAASGFTFLKYSMGWVRQAPGKGLEWVSQ
ISDTADRTYYDHSVKGRFTISRDNSKNTLYLQMNSLRAEDTAVYYCAIYT
GRWEPFVYWGQGTLVTVSS

>DOM1h-574-161 (SEQ ID NO: 138)
EVQLLESGGGLVQPGGSLRLSCAASGFTFLKYSMGWVRQAPGKGLEWVSQ
ISDTADRTYYSHSVKGRFTISRDNSKNTLYLQMNSLRAEDTAVYYCAIYT
GRWVPFEYWGQGTLVTVSS

>DOM1h-574-162 (SEQ ID NO: 139)
EVQLLESGGGLVQPGGSLRLSCAASGFTFFKYSMGWVRQAPGKGLEWVSQ
ISDTADRTYYSHSVKGRFTISRDNSKNTLYLQMNSLRAEDTAVYYCAIYT
GRWVPFEYWGQGTLVTVSS

>DOM1h-574-163 (SEQ ID NO: 140)
EVQLLESGGGLVQPGGSLRLSCAASGFTFFKYSMGWVRQAPGKGLEWVSQ
ISDTADRTYYTHSVKGRFTISRDNSKNTLYLQMNSLRAEDTAVYYCAIYT
GRWVPFEYWGQGTLVTVSS

>DOM1h-574-164 (SEQ ID NO: 141)
EVQLLESGGGLVQPGGSLRLSCAASGFTFLKYSMGWVRQAPGKGLEWVSQ
ISDTADRTYYTHSVKGRFTISRDNSKNTLYLQMNSLRAEDTAVYYCAIYT
GRWVPFEYWGQGTLVTVSS

>DOM1h-574-165 (SEQ ID NO: 142)
EVQLLESGGGLVQPGGSLRLSCAASGFTFFKYSMGWVRQAPGKGLEWVSQ
ISDTADRTYYAHSVKGRFTISRDNSKNTLYLQMNSLRAEDTAVYYCAIYT
GRWAPFEYWGQGTLVTVSS

>DOM1h-574-166 (SEQ ID NO: 143)
EVQLLESGGGLVQPGGSLRLSCAASGFTFLKYSMGWVRQAPGKGLEWVSQ
ISDTADRTYYAHSVKGRFTISRDNSKNTLYLQMNSLRAEDTAVYYCAIYT
GRWAPFEYWGQGTLVTVSS

>DOM1h-574-167 (SEQ ID NO: 144)
EVQLLESGGGLVQPGGSLRLSCAASGFTFLKYSMGWVRQAPGKGLEWVSQ
ISDTGDRRYYDHSVKGRFTISRDNSKNTLYLQMNSLRAEDTAVYYCAIYT
GRWAPFEYWGQGTLVTVSS

>DOM1h-574-169 (SEQ ID NO: 145)
EVQLLESGGGLVQPGGSLRLSCAASGFTFVKYSMGWVRQAPGKGLEWVSQ
IADTADRTYYAHSVKGRFTISRDNSKNTLYLQMNSLRAEDTAVYYCAIYT
GRWVPFEYWGQGTLVTVSS

TABLE 3-continued

Amino Acid Sequences of anti-TNFR1 dAbs

>DOM1h-574-170 (SEQ ID NO: 146)
EVQLLESGGGLVQPGGSLRLSCAASGFTFFKYSMGWVRQAPGKGLEWVSQ
ISDTADRTYYAHAVKGRFTISRDNSKNTLYLQMNSLRAEDTAVYYCAIYT
GRWVPFEYWGQGTLVTVSS

>DOM1h-574-171 (SEQ ID NO: 147)
EVQLLESGGGLVQPGGSLRLSCAASGFTFVKYSMGWVRQAPGKGLEWVSQ
IADTADRTYYDHSVKGRFTISRDNSKNTLYLQMNSLRAEDTAVYYCAIYT
GRWVPFEYWGQGTLVTVSS

>DOM1h-574-172 (SEQ ID NO: 148)
EVQLLESGGGLVQPGGSLRLSCAASGFTFVKYSMGWVRQAPGKGLEWVSQ
IADTADRTYYDHAVKGRFTISRDNSKNTLYLQMNSLRAEDTAVYYCAIYT
GRWVPFEYWGQGTLVTVSS

>DOM1h-574-173 (SEQ ID NO: 149)
EVQLLESGGGLVQPGGSLRLSCAASGFTFVKYSMGWVRQAPGKGLEWVSQ
IADTADRRYYAHSVKGRFTISRDNSKNTLYLQMNSLRAEDTAVYYCAIYT
GRWAPFEYWGQGTLVTVSS

>DOM1h-574-174 (SEQ ID NO: 150)
EVQLLESGGGLVQPGGSLRLSCAASGFTFVKYSMGWVRQAPGKGLEWVSQ
ISDTADRRYYAHAVKGRFTISRDNSKNTLYLQMNSLRAEDTAVYYCAIYT
GRWAPFEYWGQGTLVTVSS

>DOM1h-574-175 (SEQ ID NO: 151)
EVQLLESGGGLVQPGGSLRLSCAASGFTFVKYSMGWVRQAPGKGLEWVSQ
IADTADRRYYAHAVKGRFTISRDNSKNTLYLQMNSLRAEDTAVYYCAIYT
GRWAPFEYWGQGTLVTVSS

>DOM1h-574-176 (SEQ ID NO: 152)
EVQLLESGGGLVQPGGSLRLSCAASGFTFVKYSMGWVRQAPGKGLEWVSQ
ISDTADRRYYDHAVKGRFTISRDNSKNTLYLQMNSLRAEDTAVYYCAIYT
GRWAPFEYWGQGTLVTVSS

>DOM1h-574-177 (SEQ ID NO: 153)
EVQLLESGGGLVQPGGSLRLSCAASGFTFVKYSMGWVRQAPGKGLEWVSQ
IADTADRRYYDHAVKGRFTISRDNSKNTLYLQMNSLRAEDTAVYYCAIYT
GRWAPFEYWGQGTLVTVSS

>DOM1h-574-178 (SEQ ID NO: 154)
EVQLLESGGGLVQPGGSLRLSCAASGFTFVKYSMGWVRQAPGKGLEWVSQ
IADTADRRYYDHSVKGRFTISRDNSKNTLYLQMNSLRAEDTAVYYCAIYT
GRWAPFEYWGQGTLVTVSS

>DOM1h-574-179 (SEQ ID NO: 155)
EVQLLESGGGLVQPGGSLRLSCAASGFTFFKYSMGWVRQAPGKGLEWVSQ
ISDTADRRYYDDAVKGRFTITRDNSKNTLYLQMNSLRAEDTAVYYCAIYT
GRWEPFVYWGQGTLVTVSS

>DOM1h-574-180 (SEQ ID NO: 156)
EVQLLESGGGLVQPGGSLRLSCAASGFTFVKYSMGWVRQAPGKGLEWVSQ
ISDTADRTYYAHAVKGRFTISRDNSKNTLYLQMNSLRAEDTAVYYCAIYT
GRWVPFEYWGQGTLVTVSS

>DOM1h-574-4 (SEQ ID NO: 157)
EVQLLESGGGLVQPGGSLRLSCAASGFTFVKYSMGWVRQAPGKGLEWVSQ
ISNTGGHTYYADSVKGRFTISRDNSKNTLYLQMNSLRAEDTAVYYCAKYT
GRWEPFEYWGQGTLVTVSS

>DOM1h-574-168 (SEQ ID NO: 158)
EVQLLESGGGLVQPGGSLRLSCAASGFTFFKYSMGWVRQAPGKGLEWVSQ
ISDTGDRRYYDHSVKGRFTISRDNSKNTLYLQMNSLRAEDTAVYYCAIYT
GRWAPFEYWGQGTLVTVSS

TABLE 4

Nucleotide sequences of anti-TNFR1 dAbs

>DOM1h-509 (SEQ ID NO: 159)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTCAGTATAGGA
TGCATTGGGTCCGCCAGGCTCCAGGGAAGAGTCTAGAGTGGGTCTCAAGT
ATTGATACTAGGGGTTCGTCTACATACTACGCAGACCCCGTGAAGGGCCG
GTTCACCATCTCCCGCGACAATTCCAAGAACACGCTGTATCTGCAAATGA

TABLE 4-continued

Nucleotide sequences of anti-TNFR1 dAbs

ACAGCCTGCGTGCCGAGGACACCGCGGTATATTACTGTGCGAAAGCTGTG
ACGATGTTTTCTCCTTTTTTTGACTACTGGGGTCAGGGAACCCTGGTCAC
CGTCTCGAGC

>DOM1h-510 (SEQ ID NO: 160)
GAGGTGCAGCTGTTGGAGTCTGGGGGAGGCTTGGTACAGCCTGGGGGGTC
CCTGCGTCTCTCCTGTGCAGCCTCCGGATTCACCTTTGCTGATTATGGGA
TGCGTTGGGTCCGCCAGGCTCCAGGGAAGGGTCTAGAGTGGGTCTCATCT
ATTACGCGGACTGGTCGTGTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGGCGG
AATCGGCATGGTGAGTATCTTGCTGATTTTGACTACTGGGGTCAGGGAAC
CCTGGTCACCGTCTCGAGC

>DOM1h-543 (SEQ ID NO: 161)
GAGGTGCAGCTGTTGGAGTCTGGGGGAGGCTTGGTACAGCCTGGGGGGTC
CCTGCGTCTCTCCTGTGCAGCCTCCGGATTCACCTTTATGAGGTATAGGA
TGCATTGGGTCCGCCAGGCTCCAGGGAAGGGTCTAGAGTGGGTCTCATCG
ATTGATTCTAATGGTTCTAGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAAGATCGT
ACGGAGCGTTCGCCGGTTTTTGACTACTGGGGTCAGGGAACCCTGGTCAC
CGTCTCGAGC

>DOM1h-549 (SEQ ID NO: 162)
GAGGTGCAGCTGTTGGAGTCTGGGGGAGGCTTGGTGCAGCCTGGGGGGTC
CCTGCGTCTCTCCTGTGCAGCCTCCGGATTCACCTTCAGCGATTATGAGA
TGCATTGGGTCCGCCAGGCTCCAGGGAAGGGTCTAGAGTGGGTCTCATCT
ATTAGTGAGAGTGGTACGACGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACGTCGT
TTTTCTGCTTCTACGTTTGACTACTGGGGTCAGGGAACCCTGGTCACCGT
CTCGAGC

>DOM1h-574 (SEQ ID NO: 163)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGGTCATACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATATACG
GGTCATTGGGAGCCTTTTGACTACTGGGGTCAGGGAACCCTGGTCACCGT
CTCGAGC

>DOM1h-574-1 (SEQ ID NO: 164)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGGTCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGAAA
TATACGGGTCGTTGGGAGCCTTATGACTACTGGGGTCAGGGAACCCTGG
TCACCGTCTCGAGC

>DOM1h-574-2 (SEQ ID NO: 165)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGGTCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGAAA
TATACGGGTCGTTGGGAGCCTTTTGACTACTGGGGTCAGGGAACCCTGG
TCACCGTCTCGAGC

>DOM1h-574-4 (SEQ ID NO: 166)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGGTCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGAAA
TATACGGGTCGTTGGGAGCCTTTTGAGTACTGGGGTCAGGGAACCCTGG
TCACCGTCTCGAGC

>DOM1h-574-180 (SEQ ID NO: 167)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGGATACTGCTGATCGTACATACTACGCACACGCGGTGAAGG
GCCGGTTCACCATCTCCCGCGACAATTCCAAGAACACGCTGTATCTGCA
AATGAACAGCCTGCGTGCTGAGGACACCGCGGTATATTACTGTGCGATA
TATACTGGGCGTTGGGTGCCTTTTGAGTACTGGGGTCAGGGAACCCTGG
TCACCGTCTCGAGC

>DOM1h-574-7 (SEQ ID NO: 168)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGGTCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGATA
TATACGGGTCGTTGGGAGCCTTTTGACTACTGGGGTCAGGGAACCCTGG
TCACCGTCTCGAGC

>DOM1h-574-8 (SEQ ID NO: 169)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGATGGGTCCGCCAGGCTCCAGGGAAAGGTCCAGAGTGGGTCTCA
CAGATTTCGAATACGGGTGGTCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGATA
TATACGGGTCGTTGGGAGCCTTTTGACTACTGGGGTCAGGGAACCCTGG
TCACAGTCTCGAGC

>DOM1h-574-9 (SEQ ID NO: 170)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGGTCATACATACTACGCAGACTCCGTGAAGG
GCCGGTTCACCATATCCCGCGACAATTCCAAGAACACGCTGTATATGCA
AATGAACAGCCTGCGTGCCGAGGACACCGCGGTATATTACTGTGCGATA
TATACGGGTCGTTGGGAGCCTTTTGACTACTGGGGTCAGGGAACCCTGG
TCACCGTCTCGAGC

>DOM1h-574-10 (SEQ ID NO: 171)
GAGGTGCAGCTGTTGGAGTCTGGGGGAGGCTTGGTACAGCCTGGGGGGT
CCCTGCGTCTCTCCTGTGCAGCCTCCGGATTCACCTTTGGTAAGTATTC
GATGGGGTGGGTCCGCCAGGCTCCAGGGAAGGGTCTAGAGTGGGTCTCA
CAGATTTCGAATACGGGTGGTCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGATA
TATACGGGTCGTTGGGAGCCTTTTGACTACTGGGGTCAGGGAACCCTGG
TCACCGTCTCGAGC

>DOM1h-574-11 (SEQ ID NO: 172)
GAGGTGCAGCTGTTGGAGTCAGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGGTCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGAAA
TATACGGGTCGTTGGGAGCCTTTTGACCACTGGGTCAGGGGAACCCTGG
TCACCGTCTCGAGC

>DOM1h-574-12 (SEQ ID NO: 173)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGATCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGAAA
TATACGGGTCGTTGGGAGCCTTTTGACTACTGGGGTCAGGGAACCCTGG
TCACCGTCTCGAGC

>DOM1h-574-13 (SEQ ID NO: 174)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGATCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGAAA
TATACGGGTCGTTGGGAGCCTTTTGACTACTGGGGTCAGGGAACCCTGG
TCACCGTCTCGAGC

TABLE 4-continued

Nucleotide sequences of anti-TNFR1 dAbs

>DOM1h-574-14 (SEQ ID NO: 175)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGATCGTACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGATA
TATACGGGTCGTTGGGAGCCTTTTGACTACTGGGGTCAGGGAACCCTGG
TCACCGTCTCGAGC

>DOM1h-574-15 (SEQ ID NO: 176)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGATA
TATACGGGTCGTTGGGAGCCTTTTGACTACTGGGGTCAGGGAACCCTGG
TCACCGTCTCGAGC

>DOM1h-574-16 (SEQ ID NO: 177)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGATGGGTCCGCCAGGCTCCAGGGAAAGGTCCAGAGTGGGTCTCA
CAGATTTCGAATACGGGTGATCGTACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGATA
TATACGGGTCGTTGGGAGCCTTTTGACTACTGGGGTCAGGGAACCCTGG
TCACAGTCTCGAGC

>DOM1h-574-17 (SEQ ID NO: 178)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGATGGGTCCGCCAGGCTCCAGGGAAAGGTCCAGAGTGGGTCTCA
CAGATTTCGAATACGGGTGATCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGATA
TATACGGGTCGTTGGGAGCCTTTTGACTACTGGGGTCAGGGAACCCTGG
TCACAGTCTCGAGC

>DOM1h-574-18 (SEQ ID NO: 179)
GAGGTGCAGCTGTTGGAGTCTGGGGGAGGCTTGGTACAGCCTGGGGGGT
CCCTGCGTCTCTCCTGTGCAGCCTCCGGATTCACCTTTGGTAAGTATTC
GATGGGGTGGGTCCGCCAGGCTCCAGGGAAGGATCTAGAGTGGGTCTCA
CAGATTTCGAATACGGGTGATCGTACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGATA
TATACGGGTCGTTGGGAGCCTTTTGACTACTGGGGTCAGGGAACCCTGG
TCACCGTCTCGAGC

>DOM1h-574-19 (SEQ ID NO: 180)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGATCTAGAGTGGGTCTCA
CAGATTTCGAATACGGGTGATCATACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGATA
TATACGGGTCGTTGGGAGCCTTTTGACTACTGGGGTCAGGGAACCCTGG
TCACCGTCTCGAGC

>DOM1h-574-25 (SEQ ID NO: 181)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGATCGTACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGATA
TATACGGGTCGTTGGGAGCCTTTTGTCTACTGGGGTCAGGGAACCCTGG
TCACCGTCTCGAGC

>DOM1h-574-26 (SEQ ID NO: 182)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGATCGTACATACTACGCAGACTCCGTGAAGG
GCCGGTTCACCATCTCCCGCGACAATTCCAAGAACACGCTGTATCTGCA
AATGAACAGCCTGCGTGAGGACACCGCGGTATATTACTGTGCGATA
TATACGGGTCGTTGGGAGCCTTTTGAGTACTGGGGTCAGGGAACCCTGG
TCACCGTCTCGAGC

>DOM1h-574-27 (SEQ ID NO: 183)
GAGGTGCAGCTGTTGGAGTCTGGGGGAGGCTTGGTACAGCCTGGGGGGT
CCCTGCGTCTCTCCTGTGCAGCCTCCGGATTCACCTTTGTTAAGTATTC
GATGGGGTGGGTCCGCCAGGCTCCAGGGAAGGGTCTAGAGTGGGTCTCA
CAGATTTCGAATACGGGTGATCGTACATACTACGCGGACTCCGTGAAGG
GCCGGTTCACCATCTCCCGCGACAATTCCAAGAACACGCTGTATCTGCA
AATGAACAGCCTGCGTGCTGAGGACACCGCGGTATATTACTGTGCGATA
TATACGGGTCGTTGGAAGCCTTTTGACTACTGGGGTCAGGGAACCCTGG
TCACCGTCTCGAGC

>DOM1h-574-28 (SEQ ID NO: 184)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTACATACTACGCAGACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-29 (SEQ ID NO: 185)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAGGCCTTTTGAGTACTGGGGTCAGGGAACCCTGGTCACCGT
CTCGAGC

>DOM1h-574-30 (SEQ ID NO: 186)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACGGGTGATCGTAGATACTACGCAGACTCTGTGAAGGGCCG
GTTCACCATCTCCCGCGACAATTCCAAGAACACGCTGTATCTGCAAATGA
ACAGCCTGCGTGCCGAGGACACCGCGGCATATTACTGTGCGATATATACG
GGTCGTTGGGAGCCTTTTGACTACTGGGGTCAGGGAACCCTGGTCACCGT
CTCGAGC

>DOM1h-574-31 (SEQ ID NO: 187)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTAACTACTGGGGTCAGGGAACCCTGGTCACCGT
CTCGAGC

>DOM1h-574-32 (SEQ ID NO: 188)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGCGCCTTTTGAGTACTGGGGTCAGGGAACCCTGGTCACCGT
CTCGAGC

>DOM1h-574-33 (SEQ ID NO: 189)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGTGCCTTTTGACAACTGGGGTCAGGGAACCCTGGTCACCGT
CTCGAGC

>DOM1h-574-35 (SEQ ID NO: 190)
GAGGTGCAGCTGTTGGAGTCTGGGGGAGGCTTGGTACAGCCTGGGGGGTC
CCTGCGTCTCTCCTGTGCAGCCTCCGGATTCACCTTTATTACGTATTCGA

TABLE 4-continued

Nucleotide sequences of anti-TNFR1 dAbs

TGGGGTGGGTCCGCCAGGCTCCAGGGAAGGGTCTAGAGTGGGTCTCACAG
ATTTCGAATACGGGTGATCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTCAGTACTGGGGTCAGGGAACCCTGGTCACCGT
CTCGAGC

>DOM1h-574-36 (SEQ ID NO: 191)
GAGGTGCAGCTGTTGGAGTCTGGGGGAGGCTTGGTACAGCCTGGGGGGTC
CCTGCGTCTCTCCTGTGCAGCCTCCGGATTCACCTTTGGTAAGTATTCGA
TGGGGTGGGTCCGCCAGGCTCCAGGGAAGGGTCTAGAGTGGGTCTCACAG
ATTTCGAATACGGGTGATCGTACATACTACGCGGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGACTACTGGGGTCAGGGAACCCTGGTCACCGT
CTCGAGC

>DOM1h-574-37 (SEQ ID NO: 192)
GAGGTGCAGCTGTTGGAGTCTGGGGGAGGCTTGGTACAGCCTGGGGGGTC
CCTGCGTCTCTCCTGTGCAGCCTCCGGATTCACCTTTTTTAAGTATTCGA
TGGGGTGGGTCCGCCAGGCTCCAGGGAAGGGTCTAGAGTGGGTCTCACAG
ATTTCGAATACGGGTGATCGTACATACTACGCAGACTCCGTGAAGGGCCG
GTTCACCATCTCCCGCGACAATTCCAAGAACACGCTGTATCTGCAAATGA
ACAGCCTGCGTGCCGAAGACACCGCGGTATATTACTGTGCGATATATACG
GGTCGTTGGGAGCCTTTTGACTACTGGGGTCAGGGAACCCTGGTCACCGT
CTCGAGC

>DOM1h-574-38 (SEQ ID NO: 193)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACGGGTGATCGTAGATACTACGATGACTCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGACTACTGGGGTCAGGGAACCCTGGTCACCGT
CTCGAGC

>DOM1h-574-39 (SEQ ID NO: 194)
GAGGTGCAGCTGTTGGAGTCTGGGGGAGGCTTGGTACAGCCTGGGGGGTC
CCTGCGTCTCTCCTGTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTAGATACTACGCAGACGCGGTAAGGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGACTACTGGGGTCAGGGAACCCTGGTCACCGT
CTCGAGC

>DOM1h-574-40 (SEQ ID NO: 195)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTACATACTACGGACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACG
GGTCGTTGGGAGCCTTTTAAGTACTGGGGTCAGGGAACCCTGGTCACCGT
CTCGAGC

>DOM1h-574-53 (SEQ ID NO: 196)
GAGGTGCAGCTGTTGGAGTCTGGGGGAGGCTTGGTACAGCCTGGGGGGTC
CCTGCGTCTCTCCTGTGCAGCCTCCGGATTCACCTTTAGTAAGTATTCGA
TGGGGTGGGTCCGCCAGGCTCCAGGGAAGGGTCTAGAGTGGGTCTCACAG
ATTTCGAATACGGGTGAGCGTAGATACTACGCAGACTCAGTGAAGGGCCG
GTTCACCATCTCCCGCGACAATCCCAAGAACACGCTGTATCTGCAAATGA
ACAGCCTGCGTGCCGAGGACACCGCGGTATATTACTGTGCGATATATACG
GGTCGGTGGGAGCCTTTTGAATACTGGGGTCAGGGAACCCTGGTCACCGT
CTCGAGC

>DOM1h-574-54 (SEQ ID NO: 197)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAACTATTCGA
TGGGGTGGGTCCGCCAGGCTCCAGGGAAGGGTCTAGAGTGGGTCTCACAG
ATTTCGAATACGGGTGATCGTACATACTACGGGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTATGAGTACTGGGGTCAGGGAACCCTGGTCACCGT
CACGAGC

TABLE 4-continued

Nucleotide sequences of anti-TNFR1 dAbs

>DOM1h-574-65 (SEQ ID NO: 198)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTAGATACTACGCAGACTCTGTGAAGGGCCG
GTTCACCATCTCCCGCGATAATTCCAAGAACACACTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-66 (SEQ ID NO: 199)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACGGGTGATCGTAGATACTACGCAGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAAGCCTTTTGAGTACTGGGGTCAGGGAACCCTGGTCACCGT
CTCGAGC

>DOM1h-574-67 (SEQ ID NO: 200)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACGGGTGATCGTAGATACTACGCAGACTCTGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-68 (SEQ ID NO: 201)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACGGGTGATCGTAGATACTACGCAGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAGCCTTTTGAGTACTGGGGTCAGGGAACCCTGGTCACCGT
CTCGAGC

>DOM1h-574-69 (SEQ ID NO: 202)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACGGGTGATCGTAGATACTACGCAGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGCGCCTTTTGAGTACTGGGGTCAGGGAACCCTGGTCACCGT
CTCGAGC

>DOM1h-574-70 (SEQ ID NO: 203)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATACG
GGTCGTTGGGAGCCTTTTGTCTACTGGGGTCAGGGAACCCTGGTCACCGT
CTCGAGC

>DOM1h-574-71 (SEQ ID NO: 204)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACG
GGTCGTTGGAAGCCTTTTGAGTACTGGGGTCAGGGAACCCTGGTCACCGT
CTCGAGC

TABLE 4-continued

Nucleotide sequences of anti-TNFR1 dAbs

>DOM1h-574-72 (SEQ ID NO: 205)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-73 (SEQ ID NO: 206)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGCGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAGGCCTTTTGAGTACTGGGGTCAGGGAACCCTGGTCACCGT
CTCGAGC

>DOM1h-574-74 (SEQ ID NO: 207)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-75 (SEQ ID NO: 208)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACGGGTGATCGTAGATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAGCCTTTTGTCTACTGGGGTCAGGGAACCCTGGTCACCGT
CTCGAGC

>DOM1h-574-76 (SEQ ID NO: 209)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCCCCAGGGAAGGGTCTAGAGTGGGTCTCACAG
ATTTCGGATACGGGTGATCGTAGATACTACGATGACTCTGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACG
GGTCGTTGGAAGCCTTTTGAGTACTGGGGTCAGGGAACCCTGGTCACCGT
CTCGAGC

>DOM1h-574-77 (SEQ ID NO: 210)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACGGGTGATCGTAGATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-78 (SEQ ID NO: 211)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACGGGTGATCGTAGATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAGGCCTTTTGAGTACTGGGGTCAGGGAACCCTGGTCACCGT
CTCGAGC

>DOM1h-574-79 (SEQ ID NO: 212)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACGGGTGATCGTAGATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-84 (SEQ ID NO: 213)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTAGATACTACGATGACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-85 (SEQ ID NO: 214)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTAGATACTACGACGACGCGGTGAAGGGGCG
GTTCACCATCTCCCGCGACAATTCCAAGAACACGCTGTATCTGCAAATGA
ACAGCCTGCGTGCTGAGGACACCGCGGTATATTACTGTGCGATATATACG
GGTCGTTGGAAGCCTTTTGAGTACTGGGGTCAGGGAACCCTGGTCACCGT
CTCGAGC

>DOM1h-574-86 (SEQ ID NO: 215)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCCCCAGGGAAGGGTCTAGAGTGGGTCTCACAG
ATTTCGAATACGGGTGATCGTAGATACTACGACGACGCGGTGAAGGGGCG
GTTCACCATCTCCCGCGACAATTCCAAGAACACGCTGTATCTGCAAATGA
ACAGCCTGCGTGCCGAAGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-87 (SEQ ID NO: 216)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTAGATACTACGACGACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAGGCCTTTTGAGTACTGGGGTCAGGGAACCCTGGTCACCGT
CTCGAGC

>DOM1h-574-88 (SEQ ID NO: 217)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGTGATCGTAGATACTACGACGACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-90 (SEQ ID NO: 218)
GAGGTGCAGCTGTTGGAGTCTGGGGGAGGCTTGGTACAGCCTGGGGGGTC
CCTGCGTCTCTCCTGTGCAGCCTCCGGATTCACCTTTTTGAAGTTTTCGA
TGGGGTGGGTCCGCCAGGCTCCAGGGAAGGGTCTAGAGTGGGTCTCACAG
ATTGCGAATACGGGTGATCGTAGATACTACGACAGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-91 (SEQ ID NO: 219)
GAGGTGCAGCTGTTGGAGTCTGGGGGAGGCTTGGTACAGCCTGGGGGGTC
CCTGCGTCTCTCCTGTGCAGCCTCCGGATTCACCTTTTTGAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG

TABLE 4-continued

Nucleotide sequences of anti-TNFR1 dAbs

```
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC
```

>DOM1h-574-92 (SEQ ID NO: 220)
```
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACGGGTGATCGTAGATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC
```

>DOM1h-574-93 (SEQ ID NO: 221)
```
GAGGTGCAGCTGTTGGAGTCTGGGGGAGGCTTGGTACAGCCTGGGGGGTC
CCTGCGTCTCTCCTGTGCAGCCTCCGGATTCACCTTTTTGAAGTATTCGA
TGGGGTGGGTCCGCCAGGCTCCAGGGAAGGGTCTAGAGTGGGTCTCACAG
ATTTCGGATACGGGTGATCGTAGATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC
```

>DOM1h-574-94 (SEQ ID NO: 222)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACGGGTGATCGTAGATACTACGCAGACTCTGTGAAGGGCCG
GTTCACCATCTCCCGCGACAATTCCAAGAACACGCTGTATCTGCAAATGA
ACAGCCTGCGTGCCGAGGACACCGCGGCATATTACTGTGCGATATATACG
GGTCGGTGGCCCGACTTTGACTACTGGGGTCAGGGAACCCTGGTCACCGT
CTCGAGC
```

>DOM1h-574-95 (SEQ ID NO: 223)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACGGGTGATCGTAGATACTACGCAGACTCTGTGAAGGGCCG
GTTCACCATCTCCCGCGACAATTCCAAGAACACGCTGTATCTGCAAATGA
ACAGCCTGCGTGCCGAGGACACCGCGGCATATTACTGTGCGATATATACG
GGTCGGTGGCCCGACTTTGAGTACTGGGGTCAGGGAACCCTGGTCACCGT
CTCGAGC
```

>DOM1h-574-96 (SEQ ID NO: 224)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGCCCGACTTTGACTACTGGGGTCAGGGAACCCTGGTCACCGT
CTCGAGC
```

>DOM1h-574-97 (SEQ ID NO: 225)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGCCCGACTTTGACTACTGGGGTCAGGGAACCCTGGTCACCGT
CTCGAGC
```

>DOM1h-574-98 (SEQ ID NO: 226)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACGGGTGATCGTAGATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGCCCGACTTTGACTACTGGGGTCAGGGAACCCTGGTCACCGT
CTCGAGC
```

>DOM1h-574-99 (SEQ ID NO: 227)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACGGGTGATCGTAGATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGCCCGACTTTGAGTACTGGGGTCAGGGAACCCTGGTCACCGT
CTCGAGC
```

>DOM1h-574-100 (SEQ ID NO: 228)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGATGGGTCCGCCAGGCTCCAGGGAAAGGTCCAGAGTGGGTCTCACAG
ATTTCGGCCTGGGGTGACAGGACATACTACGCAGATCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGACTACTGGGGTCAGGGAACCCTGGTCACCGT
CTCGAGC
```

>DOM1h-574-101 (SEQ ID NO: 229)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAAGGTCCAGAGTGGGTCTCACAG
ATTTCGGACGGCGGTCAGAGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGACTACTGGGGTCAGGGAACCCTGGTCACCGT
CTCGAGC
```

>DOM1h-574-102 (SEQ ID NO: 230)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGATGGGTCCGCCAGGCTCCAGGGAAAGGTCCAGAGTGGGTCTCACAG
ATTTCGGACTCCGGTTACCGCACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGACTACTGGGGTCAGGGAACCCTGGTCACCGT
CTCGAGC
```

>DOM1h-574-103 (SEQ ID NO: 231)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCCAGAGTGGGTCTCACAG
ATTTCGGACGGGGGTACGCGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGACTACTGGGGTCAGGGAACCCTGGTCACCGT
CTCGAGC
```

>DOM1h-574-104 (SEQ ID NO: 232)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGATGGGTCCGCCAGGCTCCAGGGAAAGGTCCAGAGTGGGTCTCACAG
ATTTCGGACAAGGGTACGCGCACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGACTACTGGGGTCAGGGAACCCTGGTCACCGT
CTCGAGC
```

>DOM1h-574-105 (SEQ ID NO: 233)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGATGGGTCCGCCAGGCTCCAGGGAAAGGTCCAGAGTGGGTCTCACAG
ATTTCGGAGACGGTCGCAGGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGACTACTGGGGTCAGGGAACCCTGGTCACCGT
CTCGAGC
```

>DOM1h-574-106 (SEQ ID NO: 234)
```
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAAGGTCTAGAGTGGGTCTCACAG
ATTAACAATACGGGTTCGACCACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGACTACTGGGGTCAGGGAACCCTGGTCACCGT
CTCGAGC
```

TABLE 4-continued

Nucleotide sequences of anti-TNFR1 dAbs

>DOM1h-574-107 (SEQ ID NO: 235)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCCAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-108 (SEQ ID NO: 236)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCCAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-109 (SEQ ID NO: 237)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-110 (SEQ ID NO: 238)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-111 (SEQ ID NO: 239)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAGGCCTTTTGAGTACTGGGGTCAGGGAACCCTGGTCACCGT
CTCGAGC

>DOM1h-574-112 (SEQ ID NO: 240)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACACACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-113 (SEQ ID NO: 241)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGCAGATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-114 (SEQ ID NO: 242)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTTCGAATACTGCTGATCGTACATACTACGATCACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-115 (SEQ ID NO: 243)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGATCACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-116 (SEQ ID NO: 244)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTAGATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-117 (SEQ ID NO: 245)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTAGATACTACGATCACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-118 (SEQ ID NO: 246)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGGTATATACT
GGGCGTTGGGTGTCTTTTGAGTACTGGGGTCAGGGAACCCTGGTCACCGT
CTCGAGC

>DOM1h-574-119 (SEQ ID NO: 247)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCTATATATACT
GGGCGTTGGGTGTCTTTTGAGTACTGGGGTCAGGGAACCCTGGTCACCGT
CTCGAGC

>DOM1h-574-120 (SEQ ID NO: 248)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTTACCATCTCCCGCGACAATTCCAAGAACACGCTGTATCTGCAAATGA
ACAGCCTGCGTGCCGAGGACACCGCGGTATATTACTGTGCGTATATACT
GGGCGTTGGGTGCCTTTTGAGTACTGGGGTCAGGGAACCCTGGTCACCGT
CTCGAGC

>DOM1h-574-121 (SEQ ID NO: 249)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGCTATATACT
GGGCGTTGGGTGCCTTTTGAGTACTGGGGTCAGGGAACCCTGGTCACCGT
CTCGAGC

TABLE 4-continued

Nucleotide sequences of anti-TNFR1 dAbs

>DOM1h-574-122 (SEQ ID NO: 250)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTAGATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-123 (SEQ ID NO: 251)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTAGATACTACGCAGACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-124 (SEQ ID NO: 252)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACGGGCGATCGTAGATACTACGCACACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-125 (SEQ ID NO: 253)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACTGCTGATCGTAGATACTACGCAGACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-126 (SEQ ID NO: 254)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACGGGTGATCGTAGATACTACGCACACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-127 (SEQ ID NO: 255)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGAATACTGCTGATCGTAGATACTACGCACACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-128 (SEQ ID NO: 256)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACGGCTGATCGTAGATACTACGCACACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-129 (SEQ ID NO: 257)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGTGAATACGGGTGATCGTAGATACTACGCAGACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-130 (SEQ ID NO: 258)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGAATACGGGTGATCGTAGATACTACGCAGACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-131 (SEQ ID NO: 259)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGATCACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGCGCCTTTTGAGTACTGGGTCAGGGAACCCTGGTCACCGT
CTCGAGC

>DOM1h-574-132 (SEQ ID NO: 260)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGATCACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAGGCCTTTTGAGTACTGGGTCAGGGAACCCTGGTCACCGT
CTCGAGC

>DOM1h-574-133 (SEQ ID NO: 261)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGATCACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-134 (SEQ ID NO: 262)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACTCACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-135 (SEQ ID NO: 263)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACACACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGTCAGGGAACCCTGGTCACCGT
CTCGAGC

>DOM1h-574-137 (SEQ ID NO: 264)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACACAGACGCGGTGAAGGGGCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-138 (SEQ ID NO: 265)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA

TABLE 4-continued

Nucleotide sequences of anti-TNFR1 dAbs

TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-139 (SEQ ID NO: 266)
GAGGTGCAGCTGTTGGAGTCTGGGGGAGGCTTGGTACAGCCTGGGGGGTC
CCTGCGTCTCTCCTGTGCAGCCTCCGGATTCACCTTTTTGAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-140 (SEQ ID NO: 267)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTGCGGATACGGGTGATCGTAGATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-141 (SEQ ID NO: 268)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTAGATACTACGATGACTCTGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-147 (SEQ ID NO: 274)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGGGCCTTTTGTCTACTGGGGTCAGGGAACCCTGGTCACCGT
CTCGAGC

>DOM1h-574-148 (SEQ ID NO: 275)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGTGCCTTTTGCCTACTGGGGTCAGGGAACCCTGGTCACCGT
CTCGAGC

>DOM1h-574-149 (SEQ ID NO: 276)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGGACCTTTTCAGTACTGGGGTCAGGGAACCCTGGTCACCGT
CTCGAGC

>DOM1h-574-150 (SEQ ID NO: 277)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTCAGTACTGGGGTCAGGGAACTCTGGTCACCGT
CTCGAGC

TABLE 4-continued

Nucleotide sequences of anti-TNFR1 dAbs

>DOM1h-574-151 (SEQ ID NO: 278)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGCGCCTTTTGAGTACTGGGGTCAGGGAACCCTGGTCACCGT
CTCGAGC

>DOM1h-574-152 (SEQ ID NO: 279)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGCGCCTTTTCAGTACTGGGGTCAGGGAACTCTGGTCACCGT
CTCGAGC

>DOM1h-574-153 (SEQ ID NO: 280)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGTGCCTTTTCAGTACTGGGGTCAGGGCACCCTGGTCACCGT
CTCGAGC

>DOM1h-574-154 (SEQ ID NO: 281)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACCGGTGATCGTAGATACTACGATCACTCTGTGAAGGGCCG
GTTCACTATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-155 (SEQ ID NO: 282)
GAGGTGCAGCTGTTGGAGTCTGGGGGAGGCTTGGTACAGCCTGGGGGGTC
CCTGCGTCTCTCCTGTGCAGCCTCCGGATTCACCTTTTTGAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-156 (SEQ ID NO: 283)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-157 (SEQ ID NO: 284)
GAGGTGCAGCTGTTGGAGTCTGGGGGAGGCTTGGTACAGCCTGGGGGGTC
CCTGCGTCTCTCCTGTGCAGCCTCCGGATTCACCTTTTTGAAGTATTCGA
TGGGGTGGGTCCGCCAGGCTCCAGGGAAGGGTCTAGAGTGGGTCTCACAG
ATTTCGGATACTGCTGATCGTACATACTACGATCACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAGGCCTTTTGAGTACTGGGGTCAGGGAACCCTGGTCACCGT
CTCGAGC

>DOM1h-574-158 (SEQ ID NO: 285)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTACATACTACGATCACTCCGTGAAGGGCCG

TABLE 4-continued

Nucleotide sequences of anti-TNFR1 dAbs

GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGAGGCCTTTTGAGTACTGGGGTCAGGGAACCCTGGTCACCGT
CTCGAGC

>DOM1h-574-159 (SEQ ID NO: 286)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTACATACTACGATCACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-160 (SEQ ID NO: 287)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTACATACTACGATCACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

>DOM1h-574-161 (SEQ ID NO: 288)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTACATACTACTCACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-162 (SEQ ID NO: 289)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTACATACTACTCACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-163 (SEQ ID NO: 290)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTACATACTACACACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-164 (SEQ ID NO: 291)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTACATACTACACACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-165 (SEQ ID NO: 292)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGGCGCCTTTTGAGTACTGGGGTCAGGGAACCCTGGTCACCGT
CTCGAGC

>DOM1h-574-166 (SEQ ID NO: 293)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGTTGGGCGCCTTTTGAGTACTGGGGTCAGGGAACCCTGGTCACCGT
CTCGAGC

>DOM1h-574-167 (SEQ ID NO: 294)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACCGGTGATCGTAGATACTACGATCACTCTGTGAAGGGCCG
GTTCACTATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-168 (SEQ ID NO: 295)
GAGGTGCAGCTGTTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACCGGTGATCGTAGATACTACGATCACTCTGTGAAGGGCCG
GTTCACTATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-169 (SEQ ID NO: 296)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGGATACTGCTGATCGTACATACTACGCACACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGCGCGATATATACT
GGGCGTTGGGTGCCTTTTGAGTACTGGGGTCAGGGAACCCTGGTCACCGT
CTCGAGC

>DOM1h-574-170 (SEQ ID NO: 297)
GAGGTGCAGCTGTTGGAGTCTGGGGGAGGCTTGGTACAGCCTGGGGGGTC
CCTGCGTCTCTCCTGTGCAGCCTCCGGATTCACCTTTTTTAAGTATTCGA
TGGGGTGGGTCCGCCAGGCTCCAGGGAAGGGTCTAGAGTGGGTCTCACAG
ATTTCGGATACTGCTGATCGTACATACTACGCACACGCGGTAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-171 (SEQ ID NO: 298)
GAGGTGCAGCTGTTGGAGTCTGGGGGAGGCTTGGTGCAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGGATACTGCTGATCGTACATACTACGATCACTCCGTGAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-172 (SEQ ID NO: 299)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
GTGGGGTGGGTCCGCCAGCTCCAGGGAAGGGTCTAGAGTGGGTCTCACAG
ATTGCGGATACTGCTGATCGTACATACTACGATCACGCGGTAAGGGCCG
GTTCACCATCTCCCGCGACAATTCCAAGAACACGCTGTATCTGCAAATGA
ACAGCCTGCGTGCTGAGGACACCGCGGTATATTACTGTGCGATATATACT
GGGCGTTGGGTGCCTTTTGAGTACTGGGGTCAGGGAACCCTGGTCACCGT
CTCGAGC

>DOM1h-574-173 (SEQ ID NO: 300)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGGATACTGCTGATCGTAGATACTACGCACACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

TABLE 4-continued

Nucleotide sequences of anti-TNFR1 dAbs

>DOM1h-574-174 (SEQ ID NO: 301)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTAGATACTACGCACACGCGGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-175 (SEQ ID NO: 302)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGGATACTGCTGATCGTAGATACTACGCACACGCGGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-176 (SEQ ID NO: 303)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTTCGGATACTGCTGATCGTAGATACTACGCACGCGGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-177 (SEQ ID NO: 304)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGGATACTGCTGATCGTAGATACTACGATCACGCGGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-178 (SEQ ID NO: 305)
GAGGTGCAGCTGTTGGAGTCTGGGGGAGGCTTGGTACAGCCTGGGGGGTC
CCTGCGTCTCTCCTGTGCAGCCTCCGGATTCACCTTTGTTAAGTATTCGA
TGGGGTGGGTCCGCCAGGCTCCAGGGAAGGGTCTAGAGTGGGTCTCACAG
ATTGCGGATACTGCTGATCGTAGATACTACGATCACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGATATATACG
GGTCGGTGGGCGCCTTTTGAGTACTGGGGTCAGGGAACCCTGGTCACCGT
CTCGAGC

>DOM1h-574-179 (SEQ ID NO: 306)
GAGGTGCAGCTGCTGGAGTCTGGGGGAGGCTTGGTACAGCCTGGGGGGTC
CCTGCGTCTCTCCTGTGCAGCCTCCGGATTCACCTTTTTCAAGTATTCGA
TGGGGTGGGTCCGCCAGGCTCCAGGGAAGGGTCTAGAGTGGGTCTCACAG
ATTTCGGATACTGCTGATCGTAGATACTACGATGACGCGGTGAAGGGCCG
GTTCACCATCACCCGCGACAATTCCAAGAACACGCTGTATCTGCAAATGA
ACAGCCTGCGTGCCGAGGACACCGCGGTATATTACTGTGCGATATATACG
GGTCGTTGGGAGCCTTTTGTCTACTGGGGTCAGGGAACCCTGGTCACCGT
CTCGAGC

TABLE 5

Anti-serum albumin dAb (DOM7h) fusions (used in Rat studies):-
DOM7h-14/Exendin-4 fusion DMS number 7138

Amino acid sequence (SEQ ID NO: 307)
HGEGTFTSDLSKQMEEEAVRLFIEWLKNGGPSSGAPPPSGGGGSGGGGS
GGGGSDIQMTQSPSSLSASVGDRVTITCRASQWIGSQLSWYQQKPGKAPK
LLIMWRSSLQSGVPSRFSGSGSGTDFTLTISSLQPEDFATYYCAQGAALP
RTFGQGTKVEIKR

TABLE 5-continued

Anti-serum albumin dAb (DOM7h) fusions

Nucleotide sequence (SEQ ID NO: 308)
CATGGTGAAGGAACATTTACCAGTGACTTGTCAAAACAGATGGAAGAGGA
GGCAGTGCGGTTATTTATTGAGTGGCTTAAGAACGGAGGACCAAGTAGCG
GGGCACCTCCGCCATCGGGTGGTGGAGGCGGTTCAGGCGGAGGTGGCAGC
GGCGGTGGCGGGTCGGACATCCAGATGACCCAGTCTCCATCCTCCCTGTC
TGCATCTGTAGGAGACCGTGTCACCATCACTTGCCGGGCAAGTCAGTGGA
TTGGGTCTCAGTTATCTTGGTACCAGCAGAAACCAGGGAAAGCCCCTAAG
CTCCTGATCATGTGGCGTTCCTCGTTGCAAAGTGGGGTCCCATCACGTTT
CAGTGGCAGTGGATCTGGGACAGATTTCACTCTCACCATCAGCAGTCTGC
AACCTGAAGATTTTGCTACGTACTACTGTGCTCAGGGTGCGGCGTTGCCT
AGGACGTTCGGCCAAGGGACCAAGGTGGAAATCAAACGG DOM7h-14-10/Exendin-4 fusion DMS number 7139

Amino acid sequence (SEQ ID NO: 309)
HGEGTFTSDLSKQMEEEAVRLFIEWLKNGGPSSGAPPPSGGGGSGGGGS
GGGGSDIQMTQSPSSLSASVGDRVTITCRASQWIGSQLSWYQQKPGKAPK
LLIMWRSSLQSGVPSRFSGSGSGTDFTLTISSLQPEDFATYYCAQGLRHP
KTFGQGTKVEIKR Nucleotide sequence (SEQ ID NO: 310)
CATGGTGAAGGAACATTTACCAGTGACTTGTCAAAACAGATGGAAGAGGA
GGCAGTGCGGTTATTTATTGAGTGGCTTAAGAACGGAGGACCAAGTAGCG
GGGCACCTCCGCCATCGGGTGGTGGAGGCGGTTCAGGCGGAGGTGGCAGC
GGCGGTGGCGGGTCGGACATCCAGATGACCCAGTCTCCATCCTCCCTGTC
TGCATCTGTAGGAGACCGTGTCACCATCACTTGCCGGGCAAGTCAGTGGA
TTGGGTCTCAGTTATCTTGGTACCAGCAGAAACCAGGGAAAGCCCCTAAG
CTCCTGATCATGTGGCGTTCCTCGTTGCAAAGTGGGGTCCCATCACGTTT
CAGTGGCAGTGGATCTGGGACAGATTTCACTCTCACCATCAGCAGTCTGC
AACCTGAAGATTTTGCTACGTACTACTGTGCTCAGGGTTTGAGGCATCCT
AAGACGTTCGGCCAAGGGACCAAGGTGGAAATCAAACGG DOM7h-14-18/Exendin-4 fusion DMS number 7140

Amino acid sequence (SEQ ID NO: 311)
HGEGTFTSDLSKQMEEEAVRLFIEWLKNGGPSSGAPPPSGGGGSGGGGS
GGGGSDIQMTQSPSSLSASVGDRVTITCRASQWIGSQLSWYQQKPGKAPK
LLIMWRSSLQSGVPSRFSGSGSGTDFTLTISSLQPEDFATYYCAQGLMKP
MTFGQGTKVEIKR Nucleotide sequence (SEQ ID NO: 312)
CATGGTGAAGGAACATTTACCAGTGACTTGTCAAAACAGATGGAAGAGGA
GGCAGTGCGGTTATTTATTGAGTGGCTTAAGAACGGAGGACCAAGTAGCG
GGGCACCTCCGCCATCGGGTGGTGGAGGCGGTTCAGGCGGAGGTGGCAGC
GGCGGTGGCGGGTCGGACATCCAGATGACCCAGTCTCCATCCTCCCTGTC
TGCATCTGTAGGAGACCGTGTCACCATCACTTGCCGGGCAAGTCAGTGGA
TTGGGTCTCAGTTATCTTGGTACCAGCAGAAACCAGGGAAAGCCCCTAAG
CTCCTGATCATGTGGCGTTCCTCGTTGCAAAGTGGGGTCCCATCACGTTT
CAGTGGCAGTGGATCTGGGACAGATTTCACTCTCACCATCAGCAGTCTGC
AACCTGAAGATTTTGCTACGTACTACTGTGCTCAGGGTCTTATGAAGCCT
ATGACGTTCGGCCAAGGGACCAAGGTGGAAATCAAACGG DOM7h-14-19/Exendin-4 fusion DMS number 7141

Amino acid sequence (SEQ ID NO: 313)
HGEGTFTSDLSKQMEEEAVRLFIEWLKNGGPSSGAPPPSGGGGSGGGGS
GGGGSDIQMTQSPSSLSASVGDRVTISCRASQWIGSQLSWYQQKPGEAPK
LLIMWRSSLQSGVPSRFSGSGSGTDFTLTISSLQPEDFATYYCAQGAALP
RTFGQGTKVEIKR Nucleotide sequence (SEQ ID NO: 314)
CATGGTGAAGGAACATTTACCAGTGACTTGTCAAAACAGATGGAAGAGGA
GGCAGTGCGGTTATTTATTGAGTGGCTTAAGAACGGAGGACCAAGTAGCG
GGGCACCTCCGCCATCGGGTGGTGGAGGCGGTTCAGGCGGAGGTGGCAGC
GGCGGTGGCGGGTCGGACATCCAGATGACCCAGTCTCCATCCTCCCTGTC
TGCATCTGTAGGAGACCGTGTCACCATCTCTTGCCGGGCAAGTCAGTGGA
TTGGGTCTCAGTTATCTTGGTACCAGCAGAAACCAGGGGAAGCCCCTAAG
CTCCTGATCATGTGGCGTTCCTCGTTGCAAAGTGGGGTCCCATCACGTTT
CAGTGGCAGTGGATCTGGGACAGATTTCACTCTCACCATCAGCAGTCTGC
AACCTGAAGATTTTGCTACGTACTACTGTGCTCAGGGTGCGGCGTTGCCT
AGGACGTTCGGCCAAGGGACCAAGGTGGAAATCAAACGG

TABLE 5-continued

Anti-serum albumin dAb (DOM7h) fusions

DOM7h-11/Exendin-4 fusion DMS number 7142

Amino acid sequence (SEQ ID NO: 315)
HGEGTFTSDLSKQMEEEAVRLFIEWLKNGGPSSGAPPPSGGGGGSGGGGS
GGGGSDIQMTQSPSSLSASVGDRVTITCRASRPIGTTLSWYQQKPGKAPK
LLIWFGSRLQSGVPSRFSGSGSGTDFTLTISSLQPEDFATYYCAQAGTHP
TTFGQGTKVEIKR Nucleotide sequence (SEQ ID NO: 316)
CATGGTGAAGGAACATTTACCAGTGACTTGTCAAAACAGATGGAAGAGGA
GGCAGTGCGGTTATTTATTGAGTGGCTTAAGAACGGAGGACCAAGTAGCG
GGGCACCTCCGCCATCGGGTGGTGGAGGCGGTTCAGGCGGAGGTGGCAGC
GGCGGTGGCGGGTCGGACATCCAGATGACCCAGTCTCCATCCTCCCTGTC
TGCATCTGTAGGAGACCGTGTCACCATCACTTGCCGGGCAAGTCGTCCGA
TTGGGACGACGTTAAGTTGGTACCAGCAGAAACCAGGGAAAGCCCCTAAG
CTCCTGATCTGGTTTGGTTCCCGGTTGCAAAGTGGGGTCCCATCACGTTT
CAGTGGCAGTGGATCTGGGACAGATTTCACTCTCACCATCAGCAGTCTGC
AACCTGAAGATTTTGCTACGTACTACTGTGCGCAGGCTGGGACGCATCCT
ACGACGTTCGGCCAAGGGACCAAGGTGGAAATCAAACGG

DOM7h-11-12/Exendin-4 fusion DMS number 7147

Amino acid sequence (SEQ ID NO: 317)
HGEGTFTSDLSKQMEEEAVRLFIEWLKNGGPSSGAPPPSGGGGGSGGGGS
GGGGSDIQMTQSPSSLSASVGDRVTITCRASRPIGTMLSWYQQKPGKAPK
LLILFGSRLQSGVPSRFSGSGSGTDFTLTISSLQPEDFATYYCAQAGTHP
TTFGQGTKVEIKR Nucleotide sequence (SEQ ID NO: 318)
CATGGTGAAGGAACATTTACCAGTGACTTGTCAAAACAGATGGAAGAGGA
GGCAGTGCGGTTATTTATTGAGTGGCTTAAGAACGGAGGACCAAGTAGCG
GGGCACCTCCGCCATCGGGTGGTGGAGGCGGTTCAGGCGGAGGTGGCAGC
GGCGGTGGCGGGTCGGACATCCAGATGACCCAGTCTCCATCCTCCCTGTC
TGCATCTGTAGGAGACCGTGTCACCATCACTTGCCGGGCAAGTCGTCCGA
TTGGGACGATGTTAAGTTGGTACCAGCAGAAACCAGGGAAAGCCCCTAAG
CTCCTGATCTTGTTTGGTTCCCGGTTGCAAAGTGGGGTCCCATCACGTTT
CAGTGGCAGTGGATCTGGGACAGATTTCACTCTCACCATCAGCAGTCTGC
AACCTGAAGATTTTGCTACGTACTACTGTGCGCAGGCTGGGACGCATCCT
ACGACGTTCGGCCAAGGGACCAAGGTGGAAATCAAACGG

DOM7h-11-15/Exendin-4 fusion DMS number 7143

Amino acid sequence (SEQ ID NO: 319)
HGEGTFTSDLSKQMEEEAVRLFIEWLKNGGPSSGAPPPSGGGGGSGGGGS
GGGGSDIQMTQSPSSLSASVGDRVTITCRASRPIGTMLSWYQQKPGKAPK
LLILAFSRLQSGVPSRFSGSGSGTDFTLTISSLQPEDFATYYCAQAGTHP
TTFGQGTKVEIKR Nucleotide sequence (SEQ ID NO: 320)
CATGGTGAAGGAACATTTACCAGTGACTTGTCAAAACAGATGGAAGAGGA
GGCAGTGCGGTTATTTATTGAGTGGCTTAAGAACGGAGGACCAAGTAGCG
GGGCACCTCCGCCATCGGGTGGTGGAGGCGGTTCAGGCGGAGGTGGCAGC
GGCGGTGGCGGGTCGGACATCCAGATGACCCAGTCTCCATCCTCCCTGTC
TGCATCTGTAGGAGACCGTGTCACCATCACTTGCCGGGCAAGTCGTCCGA
TTGGGACGATGTTAAGTTGGTACCAGCAGAAACCAGGGAAAGCCCCTAAG
CTCCTGATCCTTGCTTTTTCCCGTTTGCAAAGTGGGGTCCCATCACGTTT
CAGTGGCAGTGGATCTGGGACAGATTTCACTCTCACCATCAGCAGTCTGC
AACCTGAAGATTTTGCTACGTACTACTGTGCGCAGGCTGGGACGCATCCT
ACGACGTTCGGCCAAGGGACCAAGGTGGAAATCAAACGG

DOM7h14-10/G4SC-NCE fusion

Amino acid sequence (SEQ ID NO: 321) encoding
DOM7h14-10/G4SC
DIQMTQSPSSLSASVGDRVTITCRASQWIGSQLSWYQQKPGKAPKLLIMW
RSSLQSGVPSRFSGSGSGTDFTLTISSLQPEDFATYYCAQGLRHPKTFGQ
GTKVEIKRGGGGSC The C-terminal cysteine can be linked to a new
chemical entity (pharmaceutical chemical compound,
NCE), eg using maleimide linkage.

Nucleotide sequence (SEQ ID NO: 322) encoding
DOM7h14-10/G4SC
GACATCCAGATGACCCAGTCTCCATCCTCCCTGTCTGCATCTGTAGGAGA
CCGTGTCACCATCACTTGCCGGGCAAGTCAGTGGATTGGGTCTCAGTTAT
CTTGGTACCAGCAGAAACCAGGGAAAGCCCCTAAGCTCCTGATCATGTGG
CGTTCCTCGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCTCAGGGTTTGAGGCATCCTAAGACGTTCGGCCAA
GGGACCAAGGTGGAAATCAAACGGGGTGGCGGAGGGGGTTCCTGT

DOM7h14-10/TVAAPSC fusion

Amino acid sequence (SEQ ID NO: 323)
DIQMTQSPSSLSASVGDRVTITCRASQWIGSQLSWYQQKPGKAPKLLIMW
RSSLQSGVPSRFSGSGSGTDFTLTISSLQPEDFATYYCAQGLRHPKTFGQ
GTKVEIKRTVAAPSC The C-terminal cysteine can be linked to a new
chemical entity (pharmaceutical chemical compound,
NCE), eg using maleimide linkage.

Nucleotide sequence (SEQ ID NO: 324)
GACATCCAGATGACCCAGTCTCCATCCTCCCTGTCTGCATCTGTAGGAGA
CCGTGTCACCATCACTTGCCGGGCAAGTCAGTGGATTGGGTCTCAGTTAT
CTTGGTACCAGCAGAAACCAGGGAAAGCCCCTAAGCTCCTGATCATGTGG
CGTTCCTCGTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCTCAGGGTTTGAGGCATCCTAAGACGTTCGGCCAA
GGGACCAAGGTGGAAATCAAACGGACCGTCGCTGCTCCATCTTGT

(used in mouse studies):- DOM7h-11/DOM1m-21-23 fusion DMS number 5515

Amino acid sequence (SEQ ID NO: 325)
EVQLLESGGGLVQPGGSLRLSCAASGFTFNRYSMGWLRQAPGKGLEWVSR
IDSYGRGTYYEDPVKGRFSISRDNSKNTLYLQMNSLRAEDTAVYYCAKIS
QFGSNAFDYWGQGTQVTVSSASTSGPSDIQMTQSPSSLSASVGDRVTITC
RASRPIGTTLSWYQQKPGKAPKLLIWFGSRLQSGVPSRFSGSGSGTDFTL
TISSLQPEDFATYYCAQAGTHPTTFGQGTKVEIKR Amino acid plus nucleotide plus myc tag sequence
(SEQ ID NO: 326)
EVQLLESGGGLVQPGGSLRLSCAASGFTFNRYSMGWLRQAPGKGLEWVSR
IDSYGRGTYYEDPVKGRFSISRDNSKNTLYLQMNSLRAEDTAVYYCAKIS
QFGSNAFDYWGQGTQVTVSSASTSGPSDIQMTQSPSSLSASVGDRVTITC
RASRPIGTTLSWYQQKPGKAPKLLIWFGSRLQSGVPSRFSGSGSGTDFTL
TISSLQPEDFATYYCAQAGTHPTTFGQGTKVEIKRAAAEQKLISEEDLN Nucleotide sequence (SEQ ID NO: 327)
GAGGTGCAGCTGTTGGAGTCTGGGGGAGGCTTGGTACAGCCTGGGGGGTC
CCTGCGTCTCTCCTGTGCAGCCTCCGGATTCACCTTTAATAGGTATAGTA
TGGGGTGGCTCCGCCAGGCTCCAGGGAAGGGTCTAGAGTGGGTCTCACGG
ATTGATTCTTATGGTCGTGGTACATACTACGAAGACCCCGTGAAGGGCCG
GTTCAGCATCTCCCGCGACAATTCCAAGAACACGCTGTATCTGCAAATGA
ACAGCCTGCGTGCCGAGGACACCGCCGTATATTACTGTGCGAAATTTCT
CAGTTTGGGTCAAATGCGTTTGACTACTGGGGTCAGGGAACCCAGGTCAC
CGTCTCGAGCGCTAGCACCAGTGGTCCATCGGACATCCAGATGACCCAGT
CTCCATCCTCCCTGTCTGCATCTGTAGGAGACCGTGTCACCATCACTTGC
CGGGCAAGTCGTCCGATTGGGACGACGTTAAGTTGGTACCAGCAGAAACC
AGGGAAAGCCCCTAAGCTCCTGATCTGGTTTGGTTCCCGGTTGCAAAGTG
GGGTCCCATCACGTTTCAGTGGCAGTGGATCTGGGACAGATTTCACTCTC
ACCATCAGCAGTCTGCAACCTGAAGATTTTGCTACGTACTACTGTGCGCA
GGCTGGGACGCATCCTACGACGTTCGGCCAAGGGACCAAGGTGGAAATCA
AACGG Nucleotide plus myc tag sequence (SEQ ID NO: 328)
GAGGTGCAGCTGTTGGAGTCTGGGGGAGGCTTGGTACAGCCTGGGGGGTC
CCTGCGTCTCTCCTGTGCAGCCTCCGGATTCACCTTTAATAGGTATAGTA
TGGGGTGGCTCCGCCAGGCTCCAGGGAAGGGTCTAGAGTGGGTCTCACGG
ATTGATTCTTATGGTCGTGGTACATACTACGAAGACCCCGTGAAGGGCCG
GTTCAGCATCTCCCGCGACAATTCCAAGAACACGCTGTATCTGCAAATGA
ACAGCCTGCGTGCCGAGGACACCGCCGTATATTACTGTGCGAAATTTCT
CAGTTTGGGTCAAATGCGTTTGACTACTGGGGTCAGGGAACCCAGGTCAC
CGTCTCGAGCGCTAGCACCAGTGGTCCATCGGACATCCAGATGACCCAGT
CTCCATCCTCCCTGTCTGCATCTGTAGGAGACCGTGTCACCATCACTTGC
CGGGCAAGTCGTCCGATTGGGACGACGTTAAGTTGGTACCAGCAGAAACC
AGGGAAAGCCCCTAAGCTCCTGATCTGGTTTGGTTCCCGGTTGCAAAGTG
GGGTCCCATCACGTTTCAGTGGCAGTGGATCTGGGACAGATTTCACTCTC
ACCATCAGCAGTCTGCAACCTGAAGATTTTGCTACGTACTACTGTGCGCA
GGCTGGGACGCATCCTACGACGTTCGGCCAAGGGACCAAGGTGGAAATCA
AACGGGCGGCCGCAGAACAAAAACTCATCTCAGAAGAGGATCTGAATTAA

TABLE 5-continued

Anti-serum albumin dAb (DOM7h) fusions

DOM7h-11-12/DOM1m-21-23 fusion DMS number 5516

Amino acid sequence (SEQ ID NO: 329)
EVQLLESGGGLVQPGGSLRLSCAASGFTFNRYSMGWLRQAPGKGLEWVSR
IDSYGRGTYYEDPVKGRFSISRDNSKNTLYLQMNSLRAEDTAVYYCAKIS
QFGSNAFDYWGQGTQVTVSSASTSGPSDIQMTQSPSSLSASVGDRVTITC
RASRPIGTMLSWYQQKPGKAPKLLILFGSRLQSGVPSRFSGSGSGTDFTL
TISSLQPEDFATYYCAQAGTHPTTFGQGTKVEIKR Amino acid plus nucleotide plus myc tag sequence
(SEQ ID NO: 330)
EVQLLESGGGLVQPGGSLRLSCAASGFTFNRYSMGWLRQAPGKGLEWVSR
IDSYGRGTYYEDPVKGRFSISRDNSKNTLYLQMNSLRAEDTAVYYCAKIS
QFGSNAFDYWGQGTQVTVSSASTSGPSDIQMTQSPSSLSASVGDRVTITC
RASRPIGTMLSWYQQKPGKAPKLLILFGSRLQSGVPSRFSGSGSGTDFTL
TISSLQPEDFATYYCAQAGTHPTTFGQGTKVEIKRAAAEQKLISEEDLN Nucleotide sequence (SEQ ID NO: 331)
GAGGTGCAGCTGTTGGAGTCTGGGGGAGGCTTGGTACAGCCTGGGGGGTC
CCTGCGTCTCTCCTGTGCAGCCTCCGGATTCACCTTTAATAGGTATAGTA
TGGGGTGGCTCCGCCAGGCTCCAGGGAAGGGTCTAGAGTGGGTCTCACGG
ATTGATTCTTATGGTCGTGGTACATACTACGAAGACCCCGTGAAGGGCCG
GTTCAGCATCTCCCGCGACAATTCCAAGAACACGCTGTATCTGCAAATGA
ACAGCCTGCGTGCCGAGGACACCGCCGTATATTACTGTGCGAAAATTTCT
CAGTTTGGGTCAAATGCGTTTGACTACTGGGGTCAGGGAACCCAGGTCAC
CGTCTCGAGCGCTAGCACCAGTGGTCCATCGGACATCCAGATGACCCAGT
CTCCATCCTCCCTGTCTGCATCTGTAGGAGACCGTGTCACCATCACTTGC
CGGGCAAGTCGTCCGATTGGGACGATGTTAAGTTGGTACCAGCAGAAACC
AGGGAAAGCCCCTAAGCTCCTGATCTTGTTTGGTTCCCGGTTGCAAAGTG
GGGTCCCATCACGTTTCAGTGGCAGTGGATCTGGGACAGATTTCACTCTC
ACCATCAGCAGTCTGCAACCTGAAGATTTTGCTACGTACTACTGCGCGCA
GGCTGGGACGCATCCTACGACGTTCGGCCAAGGGACCAAGGTGGAAATCA
AACGG Nucleotide plus myc tag sequence (SEQ ID NO: 332)
GAGGTGCAGCTGTTGGAGTCTGGGGGAGGCTTGGTACAGCCTGGGGGGTC
CCTGCGTCTCTCCTGTGCAGCCTCCGGATTCACCTTTAATAGGTATAGTA
TGGGGTGGCTCCGCCAGGCTCCAGGGAAGGGTCTAGAGTGGGTCTCACGG
ATTGATTCTTATGGTCGTGGTACATACTACGAAGACCCCGTGAAGGGCCG
GTTCAGCATCTCCCGCGACAATTCCAAGAACACGCTGTATCTGCAAATGA
ACAGCCTGCGTGCCGAGGACACCGCCGTATATTACTGTGCGAAAATTTCT
CAGTTTGGGTCAAATGCGTTTGACTACTGGGGTCAGGGAACCCAGGTCAC
CGTCTCGAGCGCTAGCACCAGTGGTCCATCGGACATCCAGATGACCCAGT
CTCCATCCTCCCTGTCTGCATCTGTAGGAGACCGTGTCACCATCACTTGC
CGGGCAAGTCGTCCGATTGGGACGATGTTAAGTTGGTACCAGCAGAAACC
AGGGAAAGCCCCTAAGCTCCTGATCTTGTTTGGTTCCCGGTTGCAAAGTG
GGGTCCCATCACGTTTCAGTGGCAGTGGATCTGGGACAGATTTCACTCTC
ACCATCAGCAGTCTGCAACCTGAAGATTTTGCTACGTACTACTGCGCGCA
GGCTGGGACGCATCCTACGACGTTCGGCCAAGGGACCAAGGTGGAAATCA
AACGGGCGGCCGCAGAACAAAAACTCATCTCAGAAGAGGATCTGAATTAA DOM7h-11-15/DOM1m-21-23 fusion DMS number 5517

Amino acid sequence (SEQ ID NO: 333)
EVQLLESGGGLVQPGGSLRLSCAASGFTFNRYSMGWLRQAPGKGLEWVSR
IDSYGRGTYYEDPVKGRFSISRDNSKNTLYLQMNSLRAEDTAVYYCAKIS
QFGSNAFDYWGQGTQVTVSSASTSGPSDIQMTQSPSSLSASVGDRVTITC
RASRPIGTMLSWYQQKPGKAPKLLILAFSRLQSGVPSRFSGSGSGTDFTL
TISSLQPEDFATYYCAQAGTHPTTFGQGTKVEIKR Amino acid plus nucleotide plus myc tag sequence
(SEQ ID NO: 334)
EVQLLESGGGLVQPGGSLRLSCAASGFTFNRYSMGWLRQAPGKGLEWVSR
IDSYGRGTYYEDPVKGRFSISRDNSKNTLYLQMNSLRAEDTAVYYCAKIS
QFGSNAFDYWGQGTQVTVSSASTSGPSDIQMTQSPSSLSASVGDRVTITC
RASRPIGTMLSWYQQKPGKAPKLLILAFSRLQSGVPSRFSGSGSGTDFTL
TISSLQPEDFATYYCAQAGTHPTTFGQGTKVEIKRAAAEQKLISEEDLN Nucleotide sequence (SEQ ID NO: 335)
GAGGTGCAGCTGTTGGAGTCTGGGGGAGGCTTGGTACAGCCTGGGGGGTC
CCTGCGTCTCTCCTGTGCAGCCTCCGGATTCACCTTTAATAGGTATAGTA
TGGGGTGGCTCCGCCAGGCTCCAGGGAAGGGTCTAGAGTGGGTCTCACGG
ATTGATTCTTATGGTCGTGGTACATACTACGAAGACCCCGTGAAGGGCCG
GTTCAGCATCTCCCGCGACAATTCCAAGAACACGCTGTATCTGCAAATGA
ACAGCCTGCGTGCCGAGGACACCGCCGTATATTACTGTGCGAAAATTTCT
CAGTTTGGGTCAAATGCGTTTGACTACTGGGGTCAGGGAACCCAGGTCAC
CGTCTCGAGCGCTAGCACCAGTGGTCCATCGGACATCCAGATGACCCAGT
CTCCATCCTCCCTGTCTGCATCTGTAGGAGACCGTGTCACCATCACTTGC
CGGGCAAGTCGTCCGATTGGGACGATGTTAAGTTGGTACCAGCAGAAACC
AGGGAAAGCCCCTAAGCTCCTGATCTTGCTTTTTCCCGTTTGCAAAGTG
GGGTCCCATCACGTTTCAGTGGCAGTGGATCTGGGACAGATTTCACTCTC
ACCATCAGCAGTCTGCAACCTGAAGATTTTGCTACGTACTACTGCGCGCA
GGCTGGGACGCATCCTACGACGTTCGGCCAAGGGACCAAGGTGGAAATCA
AACGG Nucleotide plus myc tag sequence (SEQ ID NO: 336)
GAGGTGCAGCTGTTGGAGTCTGGGGGAGGCTTGGTACAGCCTGGGGGGTC
CCTGCGTCTCTCCTGTGCAGCCTCCGGATTCACCTTTAATAGGTATAGTA
TGGGGTGGCTCCGCCAGGCTCCAGGGAAGGGTCTAGAGTGGGTCTCACGG
ATTGATTCTTATGGTCGTGGTACATACTACGAAGACCCCGTGAAGGGCCG
GTTCAGCATCTCCCGCGACAATTCCAAGAACACGCTGTATCTGCAAATGA
ACAGCCTGCGTGCCGAGGACACCGCCGTATATTACTGTGCGAAAATTTCT
CAGTTTGGGTCAAATGCGTTTGACTACTGGGGTCAGGGAACCCAGGTCAC
CGTCTCGAGCGCTAGCACCAGTGGTCCATCGGACATCCAGATGACCCAGT
CTCCATCCTCCCTGTCTGCATCTGTAGGAGACCGTGTCACCATCACTTGC
CGGGCAAGTCGTCCGATTGGGACGATGTTAAGTTGGTACCAGCAGAAACC
AGGGAAAGCCCCTAAGCTCCTGATCTTGCTTTTTCCCGTTTGCAAAGTG
GGGTCCCATCACGTTTCAGTGGCAGTGGATCTGGGACAGATTTCACTCTC
ACCATCAGCAGTCTGCAACCTGAAGATTTTGCTACGTACTACTGCGCGCA
GGCTGGGACGCATCCTACGACGTTCGGCCAAGGGACCAAGGTGGAAATCA
AACGGGCGGCCGCAGAACAAAAACTCATCTCAGAAGAGGATCTGAATTAA Where a myc-tagged molecule is indicated in this table, this was the version used in PK studies in the examples. Where no myc-tagged sequences are given, the PK studies in the examples were not done with myc-tagged material, ie, the studies were done with the non-tagged constructs shown.

EXEMPLIFICATION

All numbering in the experimental section is according to Kabat (Kabat, E.A. National Institutes of Health (US) & Columbia University. Sequences of proteins of immunological interest, edn 5 (US Dept. Of Health and Human Services Public Health Service, National Institutes of Health, Bethesda, Md., 1991)).

Derivation of DOM7h-11 variants is described.

Example 1

Vk Affinity Maturation

Selections:
HSA (Human Serum Albumin) and RSA (Rat Serum Albumin) antigens were obtained from Sigma (essentially fatty acid free, ~99% (agarose gel electrophoresis), lyophilized powder Cat. No. A3782 and A6414 respectively)

Biotinylated products of above two antigens were made by using EZ Link Sulfo-NHS-SS-Biotin (Pierce, Cat. No. 21331). Free biotin reagent was removed by passing the samples twice through PD10 desalting column followed by overnight dialysis against 1000× excess volume of PBS at 4° C. Resulting product was tested by mass spec and 1-2 biotins per molecule were observed.

Affinity Maturation Libraries:

Both error-prone and CDR libraries were created using DOM7h-11 and DOM7h-14 parental dAbs (see WO2008/096158 for the sequences of DOM7h-11 and DOM7h-14). The CDR libraries were generated in the pDOM4 vector and the error prone libraries were generated in the pDOM33 vector (to allow for selection with or without protease treatment). Vector pDOM4, is a derivative of the Fd phage vector in which the gene III signal peptide sequence is replaced with the yeast glycolipid anchored surface protein (GAS) signal peptide. It also contains a c-myc tag between the leader sequence and gene III, which puts the gene III back in frame. This leader sequence functions well both in phage display vectors but also in other prokaryotic expression vectors and can be universally used. pDOM33 is a modified version of the pDOM4 vector where the c-myc tag has been removed which renders the dAb-phage fusion resistant to the protease trypsin. This allows the use of trypsin within the phage selection to select for dAbs that are more protease stable (see WO2008149143).

For error-prone maturation libraries, plasmid DNA encoding the dAb to be matured was amplified by PCR, using the GENEMORPH® II RANDOM MUTAGENESIS KIT (random, unique mutagenesis kit, Stratagene). The product was digested with Sal I and Not I and used in a ligation reaction with cut phage vector pDOM33. For the CDR libraries, PCR reactions were performed using degenerate oligonucleotides containing NNK or NNS codons to diversify the required positions in the dAb to be affinity matured. Assembly PCR was then used to generate a full length diversified insert. The insert was digested with Sal I and Not I and used in a ligation reaction with pDOM4 for mutagenesis of multiple residues and pDOM5 for mutagenesis of single residues. The pDOM5 vector is a pUC119-based expression vector where protein expression is driven by the LacZ promoter. A GAS1 leader sequence (see WO 2005/093074) ensures secretion of isolated, soluble dAbs into the periplasm and culture supernatant of E. coli. dAbs are cloned SalI/NotI in this vector, which appends a myc tag at the C-terminus of the dAb. This protocol using SalI and Not I results in inclusion of an ST amino acid sequence at the N-terminus.

The ligation produced by either method was then used to transform E. coli strain TB1 by electroporation and the transformed cells plated on 2×TY agar containing 15 µg/ml tetracycline, yielding library sizes of >5×10$^7$ clones.

The error-prone libraries had the following average mutation rate and size: DOM7h-11 (2.5 mutations per dAb), size: 6.1×10$^8$, DOM7h-14 (2.9 mutations per dAb), size: 5.4×10$^8$.

Each CDR library has four amino acid diversity. Two libraries were generated for each of CDRs 1 and 3, and one library for CDR2. The positions diversified within each library are as follows (amino acids based on VK dummy DPK9 sequence):

|  | Library size | |
| --- | --- | --- |
|  | DOM7h-11 | DOM7h-14 |
| 1—Q27, S28, S30, S31 (CDR1) | 8.8 × 10$^7$ | 5.8 × 10$^7$ |
| 2—S30, S31, Y32, N34 (CDR1) | 4.6 × 10$^8$ | 4.2 × 10$^8$ |
| 3—Y49, A50, A51, S53 (CDR2) | 3.9 × 10$^8$ | 2.4 × 10$^8$ |
| 4—Q89, S91, Y92, S93 (CDR3) | 1.8 × 10$^8$ | 2.5 × 10$^8$ |
| 5—Y92, Y93, T94, N96 (CDR3) | 4.0 × 10$^8$ | 3.3 × 10$^8$ |

Example 2

Selection Strategies

1) Three phage selection strategies were adopted for Vκ ALBUDAB™ (anti-serum albumin dAb) affinity maturation: Selections against HSA only:
   Three rounds of selection against HSA were carried out. The error prone libraries and each CDR library were selected as an individual pool in all rounds. The first round of selection was performed against HSA passively coated onto an immunotube at 1 mg/ml. Round 2 was performed against 100 nM HSA and round 3 against 10 nM (CDR selections) or 20 or 100 nM (Error prone selections) HSA, both as soluble selections followed by a fourth round of selection with the error prone libraries against 1.5 nM HSA as a soluble selection. The error prone libraries were eluted with 0.1M glycine pH 2.0 before neutralisation with 1M Tris pH 8.0 and the CDR libraries were eluted with 1 mg/ml trypsin before infection into log phase TG1 cells. The third round of each selection was subcloned into pDOM5 for screening. Soluble selections used biotinylated HSA.

2) Trypsin selections against HSA:
   In order to select dAbs with increased protease resistance compared to the parental clone and with potentially improved biophysical properties, trypsin was used in phage selections (see WO2008149143). Four rounds of selection were preformed against HSA. The first round of selection of error prone libraries was performed against passively coated HSA at 1 mg/ml without trypsin; the second round against passively coated HSA at 1 mg/ml with 20 µg/ml trypsin for 1 hour at 37° C.; the third round selection was performed by soluble selection using biotinylated HSA against 100 nM HSA with 20 µg/ml or 100 µg/ml trypsin for 1 hour at 37° C. The final round of selection was performed by soluble selection using biotinylated HSA against 100 nM HSA with 100 µg/ml trypsin overnight at 37° C.

3) Cross-over selections against HSA (round 1) and RSA (rounds 2-4): The first round selection was carried out against 1 mg/ml passively coated HSA or 1 µM HSA (soluble selection), followed by a further three rounds of soluble selections against biotinylated RSA at concentrations of 1 µM for round 1, 100 nm for round 2 and 20 nM, 10 nM or 1 nM for round 3.

Screening Strategy and Affinity Determination:

In each case after selection a pool of phage DNA from the appropriate round of selection is prepared using a QIAfilter midiprep kit (Qiagen), the DNA is digested using the restriction enzymes SalI and NotI and the enriched V genes are ligated into the corresponding sites in pDOM5 the soluble expression vector which expresses the dAb with a myc tag (see PCT/EP2008/067789). The ligated DNA is used to electro-transform E. coli HB 2151 cells which are then grown overnight on agar plates containing the antibiotic carbenicillin. The resulting colonies are individually assessed for antigen binding. In each case at least 96 clones were tested for binding to HSA, CSA (Cynomolgus monkey Serum Albumin), MSA (mouse serum albumin) and RSA by BIACORE™ (surface plasmon resonance). MSA antigen was obtained from Sigma (essentially fatty acid free, ~99% (agarose gel electrophoresis), lyophilized powder Cat. No. A3559) and CSA was purified from Cynomolgus serum albumin using prometic blue resin (Amersham). Soluble dAb fragments were produced in bacterial culture in ONEX culture media (Novagen) overnight at 37° C. in 96 well plates. The culture supernatant containing soluble dAb was centrifuged and analysed by BIACORE™ for binding to high density HSA, CSA, MSA and RSA CM5 chips. Clones were found to bind to all these species of serum albumin by off-rate screening. The clones were sequenced revealing unique dAb sequences. The minimum identity to parent (at the amino acid level) of the clones selected was 97.2% (DOM7h-11-3: 97.2%, DOM7h-11-12: 98.2%, DOM7h11-15: 96.3%, DOM7h-11-18: 98.2%, DOM7h-11-19: 97.2%)

The minimum identity to parent (at the amino acid level) of the clones selected was 96.3% (DOM7h-14-10: 96.3%, DOM7h-14-18: 96.3%, DOM7h-14-19: 98.2%, DOM7h-14-28: 99.1%, DOM7h-14-36: 97.2%)

Unique dAbs were expressed as bacterial supernatants in 2.5 L shake flasks in Onex media at 30° C. for 48 hrs at 250 rpm. dAbs were purified from the culture media by absorption to protein L agarose followed by elution with 10 mM glycine pH2.0. Binding to HSA, CSA, MSA and RSA by BIACORE™ was confirmed using purified protein at 3 concentrations 1 µM, 500 nM and 50 nM. To determine the binding affinity ($K_D$) of the ALBUDABS™ to each serum albumin; purified dAbs were analysed by BIACORE™ over albumin concentration range from 5000 nM to 39 nM (5000 nM, 2500 nM, 1250 nM, 625 nM, 312 nM, 156 nM, 78 nM, 39 nM).

All DOM7h-14 derived variants are cross-reactive to mouse, rat, human and cyno serum albumin. DOM7h-14-10 has improved affinity to rat, cyno and human serum albumin compared to parent. DOM7h-14-28 has an improved affinity to RSA. DOM7h-14-36 has an improved affinity to RSA, CSA and MSA.

DOM7h-11-3 has improved affinity to CSA and HSA. DOM7h-11-12 has improved affinity to RSA, MSA and HSA. DOM7h-11-15 has improved affinity to RSA, MSA, CSA and HSA. DOM7h-11-18 and DOM7h-11-19 have improved affinity to RSA, MSA and HSA.

TABLE 6

| ALBUDAB ™ | Affinity ($K_D$) to SA (nM) | Kd | Ka |
|---|---|---|---|
| Rat | | | |
| DOM7h-14 | 60 | 2.095E−01 | 4.00E+06 |
| DOM7h-14-10 | 4 | 9.640E−03 | 4.57E+06 |
| DOM7h-14-18 | 410 | 2.275E−01 | 5.60E+05 |
| DOM 7h-14-19 | 890 | 2.870E−01 | 3.20E+05 |
| DOM 7h-14-28 | 45 (140) | 7.0E−02 (1.141e−1) | 2.10E+06 (8.3e5) |
| DOM 7h-14-36 | 30 (6120) | 2.9E−02 (5.54e−2) | 1.55E+06 (9e3) |
| DOM 7h-11 | 2100 | 1.00E−01 | 4.80E+04 |
| DOM 7h-11-3 | 10000 (88000) | (7.18e−1) | (8.11e3) |
| DOM 7h-11-12 | 200 | 5.22E−01 | 2.76E+06 |
| DOM 7h-11-15 | 20 | 2.10E−02 | 1.10E+06 |
| DOM 7h-11-18 | 80 (29000) | 6.0E−02 (3.7e−1) | 1.64E+06 (1.3e4) |
| DOM 7h-11-19 | 28 (17000) | 9.1e−02 (1.4e−1) | 9.80E+05 (8.1e3) |
| Cyno | | | |
| DOM 7h-14 | 66 | 9.65E−02 | 1.50E+06 |
| DOM 7h-14-10 | 9 | 1.15E−02 | 1.60E+06 |
| DOM 7h-14-18 | 180 | 1.05E−01 | 6.30E+5 |
| DOM 7h-14-19 | 225 | 1.56E−01 | 7.00E+05 |
| DOM 7h-14-28 | 66 (136) | 1.3E−01 (1.34e−1) | 2.50E+06 (9.8e5) |
| DOM 7h-14-36 | 35 (7830) | 1.9E−02 (1.1e−1) | 9.80E+06 (1.43e4) |
| DOM 7h-11 | 1000 | 6.82E−01 | 8.00E+05 |
| DOM 7h-11-3 | 670 (200) | 9.6E−02 (1.5e−1) | 2.90E+05 (7.26e5) |
| DOM 7h-11-12 | ≥6000 | | |
| DOM 7h-11-15 | 3 | 5.57E−03 | 5.80E+06 |
| DOM 7h-11-18 | 10000 (65000) | 1.36 (4.8e−1) | 2.25E+05 (7.3e3) |
| DOM 7h-11-19 | ≥10000 (375000) | (6.2e−1) | (1.7e3) |
| Mouse | | | |
| DOM 7h-14 | 12 | 4.82E−02 | 4.10E+06 |
| DOM 7h-14-10 | 30 | 3.41E−02 | 1.29E+06 |
| DOM 7h-14-18 | 65 | 9.24E−02 | 2.28E+06 |
| DOM 7h-14-19 | 60 | 5.76E−02 | 1.16E+06 |
| DOM 7h-14-28 | 26 (31) | 3.4E−02 (7.15e−2) | 1.60E+06 (2.28e6) |
| DOM 7h-14-36 | 35 (33) | 2.3E−02 (7.06e−2) | 8.70E+05 (2.11e6) |
| DOM 7h-11 | 5000 | 9.00E−01 | |
| DOM 7h-11-3 | ≥10000 (36000) | (6.12e−1) | (1.67e4) |
| DOM 7h-11-12 | 130 | 1.89E−01 | 1.53E+06 |
| DOM 7h-11-15 | 10 | 9.40E−03 | 1.10E+06 |
| DOM 7h-11-18 | 150 (1600) | 2.4E−02 (6.23e−2) | 4.40E+05 (4e4) |
| DOM 7h-11-19 | 100 (18000) | 3.7E−02 (8.8e−2) | 1.40E+06 (4.9e3) |
| Human | | | |
| DOM 7h-14 | 33 | 4.17E−02 | 1.43E+06 |
| DOM 7h-14-10 | 12 | 1.39E−02 | 1.50E+06 |
| DOM 7h-14-18 | 280 | 3.39E−02 | 1.89E+05 |
| DOM 7h-14-19 | 70 | 5.25E−02 | 8.26E+05 |
| DOM 7h-14-28 | 30 (8260) | 3.3E−02 (5.6e−2) | 1.24E+06 (6.78e3) |
| DOM 7h-14-36 | 28 (1260) | 2.4E−02 (6.7e−2) | 1.23E+06 (5.4e4) |
| DOM 7h-11 | 2800 | 6.41E−01 | 7.00E+05 |
| DOM 7h-11-3 | 32 (130) | 1.6E−02 (2.35e−2) | 6.50E+05 (1.86e5) |
| DOM 7h-11-12 | 350 | 4.13E−01 | 1.26E+06 |
| DOM 7h-11-15 | 1 | 1.84E−03 | 2.00E+06 |
| DOM 7h-11-18 | 36 (32000) | 5.1E−02 (2.7e−1) | 3.40E+06 (8.39e3) |
| DOM 7h-11-19 | 65 (38000) | 1.1E−01 (2.09e−1) | 1.80E+06 (5.4e3) |

* values in brackets were derived from a second, independent SPR experiment.

Example 3

Origins of Key DOM7h-11 Lineage Clones

DOM7h-11-3: From affinity maturation performed against HSA using the CDR2 library (Y49, A50, A51, S53), round 3 output 10 nM HSA.

DOM7h-11-12: From affinity maturation performed against HSA using the error prone library, round 3 outputs (100 nM, HSA) with 100 ug/ml trypsin.

DOM7h-11-15: From cross-over selections performed against HSA as round 1 followed by additional 3 rounds of selections against RSA using the CDR2 library (Y49, A50, A51, S53) at round 3 selection with 1 nM of RSA.

DOM7h-11-18 From cross-over selections performed against HSA as round 1 followed by additional 3 rounds of selections against RSA using the error prone library, round 3 output at 20 nM of RSA DOM7h-11-19 From cross-over selections performed against HSA as round 1 followed by additional 3 rounds of selections against RSA using the error prone library, round 3 output at 5 nM of RSA

TABLE 7

CDR sequences (according to Kabat; ref. as above)

| ALBUDAB ™ | CDR1 | CDR2 | CDR3 |
|---|---|---|---|
| DPK9 Vk dummy | SQSISSYLN (SEQ ID NO: 337) | YAASSLQS (SEQ ID NO: 338) | QQSYSTPNT (SEQ ID NO: 339) |
| DOM7h-11 | SRPIGTTLS (SEQ ID NO: 340) | WFGSRLQS (SEQ ID NO: 341) | AQAGTHPTT (SEQ ID NO: 342) |
| DOM7h-11-12 | SRPIGTMLS (SEQ ID NO: 343) | LFGSRLQS (SEQ ID NO: 344) | AQAGTHPTT (SEQ ID NO: 345) |
| DOM 7h-11-15 | SRPIGTMLS (SEQ ID NO: 346) | LAFSRLQS (SEQ ID NO: 347) | AQAGTHPTT (SEQ ID NO: 348) |
| DOM 7h-11-18 | SRPIGTMLS (SEQ ID NO: 349) | WFGSRLQS (SEQ ID NO: 350) | AQAGTHPTT (SEQ ID NO: 351) |
| DOM 7h-11-19 | SRPIGTMLS (SEQ ID NO: 352) | LFGSRLQS (SEQ ID NO: 353) | AQTGTHPTT (SEQ ID NO: 354) |
| DOM 7h-11-3 | SRPIGTTLS (SEQ ID NO: 355) | LWFSRLQS (SEQ ID NO: 356) | AQAGTHPTT (SEQ ID NO: 357) |

Example 4

Origins of Key DOM7h-14 Lineage Clones

DOM7h-14-19: From affinity maturation performed against HSA using the error prone library, round 3 outputs (100 nM, HSA) with 100 ug/ml trypsin.

DOM7h-14-10, DOM7h-14-18, DOM7h-14-28, DOM7h-14-36: From affinity maturation performed against HSA using CDR3 library (Y92, Y93, T94, N96), round 3 output.

TABLE 8

CDR sequences (according to Kabat; ref. as above)

| ALBUDAB ™ | CDR1 | CDR2 | CDR3 |
|---|---|---|---|
| DPK9 Vk dummy | SQSISSYLN (SEQ ID NO: 337) | YAASSLQS (SEQ ID NO: 338) | QQSYSTPNT (SEQ ID NO: 339) |
| DOM 7h-14 | SQWIGSQLS (SEQ ID NO: 358) | MWRSSLQS (SEQ ID NO: 359) | AQGAALPRT (SEQ ID NO: 360) |
| DOM 7h-14-10 | SQWIGSQLS (SEQ ID NO: 361) | MWRSSLQS (SEQ ID NO: 362) | AQGLRHPKT (SEQ ID NO: 363) |
| DOM 7h-14-18 | SQWIGSQLS (SEQ ID NO: 364) | MWRSSLQS (SEQ ID NO: 365) | AQGLMKPMT (SEQ ID NO: 366) |
| DOM 7h-14-19 | SQWIGSQLS (SEQ ID NO: 367) | MWRSSLQS (SEQ ID NO: 368) | AQGAALPRT (SEQ ID NO: 369) |
| DOM 7h-14-28 | SQWIGSQLS (SEQ ID NO: 370) | MWRSSLQS (SEQ ID NO: 371) | AQGAALPKT (SEQ ID NO: 372) |
| DOM 7h-14-36 | SQWIGSQLS (SEQ ID NO: 373) | MWRSSLQS (SEQ ID NO: 374) | AQGFKKPRT (SEQ ID NO: 375) |

Example 5

Expression and Biophysical Characterisation

The routine bacterial expression level in 2.5 L shake flasks was determined following culture in Onex media at 30° C. for 48 hrs at 250 rpm. The biophysical characteristics were determined by SEC MALLS and DSC.

SEC MALLS (size exclusion chromatography with multi-angle-LASER-light-scattering) is a non-invasive technique for the characterizing of macromolecules in solution. Briefly, proteins (at concentration of 1 mg/mL in buffer Dulbecco's PBS at 0.5 ml/min are separated according to their hydrodynamic properties by size exclusion chromatography (column: TSK3000 from TOSOH Biosciences; 5200 from Pharmacia). Following separation, the propensity of the protein to scatter light is measured using a multi-angle-LASER-light-scattering (MALLS) detector. The intensity of the scattered light while protein passes through the detector is measured as a function of angle. This measurement taken together with the protein concentration determined using the refractive index (RI) detector allows calculation of the molar mass using appropriate equations (integral part of the analysis software Astra v.5.3.4.12).

DSC (Differential Scanning calorimetry): briefly, the protein is heated at a constant rate of 180° C./hrs (at 1 mg/mL in PBS) and a detectable heat change associated with thermal denaturation measured. The transition midpoint ($_{app}T_m$) is determined, which is described as the temperature where 50% of the protein is in its native conformation and the other 50% is denatured. Here, DSC determined the apparent transition midpoint (App™) as most of the proteins examined do not fully refold. The higher the Tm, the more stable the molecule. Unfolding curves were analysed by non-2-state equations. The software package used was Origin® v7.0383.

TABLE 9

| ALBUDAB ™ | Biophysical parameters | |
|---|---|---|
| | SEC MALLS | DSC Tm(° C.) |
| DOM7h-14 | M | 60 |
| DOM 7h-14-10 | M | 59 |
| DOM 7h-14-18 | M | 58 |
| DOM 7h-14-19 | M | 59 |
| DOM 7h-14-28 | M | 58.3/60.2 |
| DOM 7h-14-36 | M | 59.2 |
| DOM 7h-11 | M | 66.9-72.2 |
| DOM 7h-11-3 | M (95%)* | 66.6/70.5 |
| DOM 7h-11-12 | M (<2% D) | 71.7 |
| DOM 7h-11-15 | M (<5% D) | 58.5-60.5 |
| DOM 7h-11-18 | M (98%) | 58.9/65.8 |
| DOM 7h-11-19 | M | 71.8/76.6 |

*in one other trial, monomer was primarily seen by SEC MALLS, although lower than 95%

Expression levels for all clones in Table 9 were observed in the range from 15 to 119 mg/L in E coli.

For DOM7h-14 and DOM7h-11 variants, favorable biophysical parameters (monomeric in solution as determined by SEC MALLs and App™ of >55° C. as determined by DSC) and expression levels were maintained during affinity maturation. Monomeric state is advantageous because it avoids dimerisation and the risk of products that may cross-link targets such as cell-surface receptors.

Example 6

Determination of Serum Half Life in Rat, Mouse and Cynomolgus Monkey

ALBUDAB™ DOM7h-14-10, DOM7h-14-18, DOM7h-14-19, DOM7h-11, DOM7h11-12 and DOM7h-11-15 were cloned into the pDOM5 vector. For each ALBUDAB™, 20-50 mg quantities were expressed in E. coli and purified from bacterial culture supernatant using protein L affinity resin and eluted with 100 mM glycine pH2. The proteins were concentrated to greater than 1 mg/ml, buffer exchanged into PBS and endotoxin depleted using Q spin columns (Vivascience). For Rat pharmacokinetic (PK) analysis, ALBUDAB™ were dosed as single i.v injections at 2.5 mg/kg using 3 rats per compound. Serum samples were taken at 0.16, 1, 4, 12, 24, 48, 72, 120, 168 hrs. Analysis of serum levels was by anti-myc ELISA as per the method described below.

For Mouse PK, DOM7h-11, DOM7h11-12 and DOM7h-11-15 were dosed as single i.v injections at 2.5 mg/kg per dose group of 3 subjects and serum samples taken at 10 mins; 1 h; 8 h; 24 h; 48 h; 72 h; 96 h. Analysis of serum levels was by anti-myc ELISA as per the method described below.

For Cynomolgus monkey PK DOM7h-14-10 and DOM7h-11-15 were dosed as single i.v injections at 2.5 mg/kg into 3 female Cynomolgus monkeys per dose group and serum samples taken at 0.083, 0.25, 0.5, 1, 2, 4, 8, 24, 48, 96, 144, 192, 288, 336, 504 hrs. Analysis of serum levels was by anti-myc ELISA as per the method described below.

Anti-myc ELISA Method

The ALBUDAB™ concentration in serum was measured by anti-myc ELISA. Briefly, goat anti-myc polyclonal antibody (1:500; Abcam, catalogue number ab9132) was coated overnight onto Nunc 96-well Maxisorp plates and blocked with 5% BSA/PBS+1% tween. Serum samples were added at a range of dilutions alongside a standard at known concentrations. Bound myc-tagged ALBUDAB™ was then detected using a rabbit polyclonal anti-Vk (1:1000; in-house reagent, bleeds were pooled and protein A purified before use) followed by an anti-rabbit IgG HRP antibody (1:10,000; Sigma, catalogue number A2074). Plates were washed between each stage of the assay with 3xPBS+0.1% Tween20 followed by 3xPBS. TMB (SureBlue TMB 1-Component Microwell Peroxidase Substrate, KPL, catalogue number 52-00-00) was added after the last wash and was allowed to develop. This was stopped with 1M HCl and the signal was then measured using absorbance at 450 nm.

From the raw ELISA data, the concentration of unknown samples was established by interpolation against the standard curve taking into account dilution factors. The mean concentration result from each time point was determined from replicate values and entered into WinNonLin analysis package (eg version 5.1 (available from Pharsight Corp., Mountain View, Calif. 94040, USA). The data was fitted using a non-compartmental model, where PK parameters were estimated by the software to give terminal half-lives. Dosing information and time points were selected to reflect the terminal phase of each PK profile.

TABLE 10

Single ALBUDAB ™ PK

| Species | ALBUDAB ™ | Albumin $K_D$ (nM) | PK parameters | | | |
|---|---|---|---|---|---|---|
| | | | AUC h x μg/ml | CL ml/h/kg | t½ h | Vz ml/kg |
| Rat | DOM7h-14* | 60 | | | | |
| | DOM7h-14-10 | 4 | 2134.6 | 1.2 | 42.1 | 71.2 |
| | DOM7h-14-18 | 410 | 617.3 | 4.1 | 38.4 | 228.1 |
| | DOM 7h-14-19 | 890 | 632.6 | 4.1 | 36.3 | 213.3 |
| | DOM 7h-11 | 2100 | 320.1 | 7.8 | 23.3 | 263.9 |
| | DOM 7h-11-12 | 200 | 398.7 | 6.4 | 35.5 | 321.2 |
| | DOM 7h-11-15 | 20 | 843.4 | 3.0 | 30.3 | 130.7 |
| mouse | DOM 7h-11 | 5000 | 304.7 | 8.2 | 18.3 | 216.8 |
| | DOM 7h-11-12 | 130 | 646.6 | 3.9 | 43.9 | 244.8 |
| | DOM 7h-11-15 | 10 | 499.2 | 5.0 | 33.7 | 243.4 |
| Cyno | DOM 7h-14* | 66 | | | 217.5 | |
| | DOM 7h-14-10 | 9 | 6174.6 | 0.4 | 200.8 | 117.8 |
| | DOM 7h-11* | 3300 | | | 135.1 | |
| | DOM 7h-11-15 | 3 | 4195 | 0.6 | 198.1 | 170.3 |

*Historical data

Pharmacokinetic parameters derived from rat, mouse and cynomolgus monkey studies were fitted using a non-compartmental model. Key: AUC: Area under the curve from dosing time extrapolated to infinity; CL: clearance; t1/2: is the time during which the blood concentration is halved; Vz: volume of distribution based on the terminal phase. DOM7h-11 12 and DOM7h-11-15 have an improved AUC and t1/2 in rat and mouse compared to parent. DOM7h-11-15 also has an improved AUC and t1/2 in cyno compared to parent. This improvement in AUC/t1/2 correlates with an improved in vitro KD to serum albumin.

Example 7

ALBUDAB™ IFN Fusions

Cloning and Expression

As well as single ALBUDABs™, the affinity matured Vk ALBUDABs™ were linked to Interferon alpha 2b (IFNα$_2$b) to determine whether a useful PK of the ALBUDAB™ was maintained as a fusion protein.

Interferon alpha 2b amino acid sequence:
(SEQ ID NO: 376)
CDLPQTHSLGSRRTLMLLAQMRRISLFSCLKDRHDFGFPQEEFGNQFQ

KAETIPVLHEMIQQIFNLFSTKDSSAAWDETLLLDKFYTELYQQLNDLE

ACVIQGVGVTETPLMKEDSILAVRKYFQRITLYLKEKKYSPCAWEVVR

AEIMRSFSLSTNLQESLRSKE

Interferon alpha 2b nucleotide sequence:
(SEQ ID NO: 377)
TGTGATCTGCCTCAAACCCACAGCCTGGGTAGCAGGAGGACCTTGATG

CTCCTGGCACAGATGAGGAGAATCTCTCTTTTCTCCTGCTTGAAGGACA

GACATGACTTTGGATTTCCCCAGGAGGAGTTTGGCAACCAGTTCCAAAA

GGCTGAAACCATCCCTGTCCTCCATGAGATGATCCAGCAGATCTTCAA

TCTCTTCAGCACAAAGGACTCATCTGCTGCTTGGGATGAGACCCTCCT

AGACAAATTCTACACTGAACTCTACCAGCAGCTGAATGACCTGGAAGC

CTGTGTGATACAGGGGGTGGGGGTGACAGAGACTCCCCTGATGAAGG

AGGACTCCATTCTGGCTGTGAGGAAATACTTCCAAAGAATCACTCTCT

ATCTGAAAGAGAAGAAATACAGCCCTTGTGCCTGGGAGGTTGTCAGA

GCAGAAATCATGAGATCTTTTTCTTTGTCAACAAACTTGCAAGAAAGTT

TAAGAAGTAAGGAA

IFNα2b was linked to the ALBUDAB™ via a TVAAPS (SEQ ID NO: 437) linker region (see WO2007085814). The constructs were cloned by SOE-PCR (single overlap extension according to the method of Horton et al. Gene, 77, p 61 (1989)). PCR amplification of the ALBUDAB™ and IFN sequences were carried out separately using primers with a ~15 base pair overlap at the TVAAPS (SEQ ID NO: 437) linker region. The primers used are as follows:—

```
IFNα2b SOE fragment 5'
                    (SEQ ID NO: 378)
GCCCGGATCCACCGGCTGTGATCTG IFNα2b SOE fragment 3'
                    (SEQ ID NO: 379)
GGAGGATGGAGACTGGGTCATCTGGATGTC Vk SOE fragment 5'
                    (SEQ ID NO: 380)
GACATCCAGATGACCCAGTCTCCATCCTCC Vk SOE fragment 3' to
also introduce a myc tag
                    (SEQ ID NO: 381)
GCGCAAGCTTTTATTAATTCAGATCCTCTTC
TGAGATGAGTTTTTGTTCTGCGGCCGCCCGT
TTGATTTCCACCTTGGTCCC
```

The fragments were purified separately and subsequently assembled in a SOE (single overlap extension PCR extension) reaction using only the flanking primers.

```
IFNα2b SOE fragment 5'
                    (SEQ ID NO: 382)
GCCCGGATCCACCGGCTGTGATCTG Vk SOE fragment 3' to
also introduce a myc tag
                    (SEQ ID NO: 383)
GCGCAAGCTTTTATTAATTCAGATCCTCTTC
TGAGATGAGTTTTTGTTCTGCGGCCGCCCGT
TTGATTTCCACCTTGGTCCC
```

The assembled PCR product was digested using the restriction enzymes BamHI and HindIII and the gene ligated into the corresponding sites in the pDOM50, a mammalian expression vector which is a pTT5 derivative with an N-terminal V-J2-C mouse IgG secretory leader sequence to facilitate expression into the cell media.

```
Leader sequence (amino acid):
                    (SEQ ID NO: 384)
METDTLLLWVLLLWVPGSTG Leader sequence (nucleotide):
                    (SEQ ID NO: 385)
ATGGAGACCGACACCCTGCTGCTGTGGGTGCTGCTGCTGTGGGTGCCC

GGATCCACCGGGC
```

Plasmid DNA was prepared using QIAfilter megaprep (Qiagen). 1 µg DNA/ml was transfected with 293-Fectin into HEK293E cells and grown in serum free media. The protein is expressed in culture for 5 days and purified from culture supernatant using protein L affinity resin and eluted with 100 mM glycine pH2. The proteins were concentrated to greater than 1 mg/ml, buffer exchanged into PBS and endotoxin depleted using Q spin columns (Vivascience).

Affinity Determination and Biophysical Characterisation:

To determine the binding affinity ($K_D$) of the AlbudAb-IFNα2b fusion proteins to each serum albumin; purified fusion proteins were analysed by BIACORE™ over albumin (immobilised by primary-amine coupling onto CM5 chips; BIACORE™) using fusion protein concentrations from 5000 nM to 39 nM (5000 nM, 2500 nM, 1250 nM, 625 nM, 312 nM, 156 nM, 78 nM, 39 nM) in HBS-EP BIACORE™ buffer.

TABLE 12

| | | Affinity to SA | | |
|---|---|---|---|---|
| ALBUDAB™ | Fusion | Affinity to SA (nM) | Kd | Ka |
| | | Rat | | |
| DOM7h-14 | IFNα2b | 350 | 4.500E−02 | 1.28E+05 |
| DOM7h-14-10 | IFNα2b | 16 | 4.970E−03 | 5.90E+05 |
| DOM7h-14-18 | IFNα2b | 780 | 2.127E−01 | 5.80E+05 |
| DOM 7h-14-19 | IFNα2b | 1900 | 1.206E−01 | 7.96E+04 |
| DOM 7h-11 | IFNα2b | 6000 | 7.500E−01 | nd |
| DOM 7h-11-12 | IFNα2b | 1700 | 3.100E−01 | 1.30E+05 |
| DOM 7h-11-15 | IFNα2b | 200 | 1.660E−02 | 1.50E+05 |
| | | Cyno | | |
| DOM 7h-14 | IFNα2b | 60 | 1.32E−02 | 5.0E+05 |
| DOM 7h-14-10 | IFNα2b | 19 | 7.05E−03 | 4.50E+05 |
| DOM 7h-14-18 | IFNα2b | no binding | no binding | no binding |
| DOM 7h-14-19 | IFNα2b | 520 | 8.47E−02 | 2.73E+05 |
| DOM 7h-11 | IFNα2b | 3300 | 3.59E−01 | 1.20E+05 |
| DOM 7h-11-12 | IFNα2b | 630 | 3.45E−01 | 7.00E+05 |
| DOM 7h-11-15 | IFNα2b | 15 | 4.86E−03 | 3.60E+05 |
| | | Mouse | | |
| DOM 7h-14 | IFNα2b | 240 | 3.21E−02 | 1.50E+06 |
| DOM 7h-14-10 | IFNα2b | 60 | 3.45E−02 | 6.86E+05 |
| DOM 7h-14-18 | IFNα2b | 180 | 1.50E−01 | 9.84E+05 |

TABLE 12-continued

Affinity to SA

| ALBUDAB ™ | Fusion | Affinity to SA (nM) | Kd | Ka |
|---|---|---|---|---|
| DOM 7h-14-19 | IFNα2b | 490 | 4.03E−02 | 1.19E+05 |
| DOM 7h-11 | IFNα2b | 6000 | 1.55E−01 | nd |
| DOM 7h-11-12 | IFNα2b | 150 | 9.49E−02 | 6.30E+05 |
| DOM 7h-11-15 | IFNα2b | 28 | 6.69E−03 | 2

Pharmacokinetic parameters derived from rat and mouse studies were fitted using a non-compartmental model. Key: AUC: Area under the curve from dosing time extrapolated to infinity; CL: clearance; t1/2: is the time during which the blood concentration is halved; Vz: volume of distribution based on the terminal phase.

IFNα2b—AlbudAbs were tested in rat and mouse. For all IFNα2b-DOM7h-11 variant fusion proteins in both rat and mouse, t1/2 is improved compared to parent. The improvement in t1/2 correlates with the improved in vitro $K_D$ to serum albumin. For IFNα2b-DOM7h-14-10 variants, the improvement in in vitro $K_D$ to serum albumin also correlated to an improvement in t1/2 in rat.

All IFNα2b-AlbudAb fusion proteins exhibit a 5 to 10-fold decrease in the binding to RSA compared to the single ALBUDAB™. This effect is more pronounced (i.e. 10-fold) for the DOM7h-14 series than the DOM7h-11 series (only 5-fold decrease).

Example 8

Further ALBUDAB™ Fusions with Proteins, Peptides and NCEs

Various ALBUDABs™ fused to other chemical entities namely domain antibodies (dAbs), peptides and NCEs were tested. The results are shown in table 15.

HEK293E cells at $1.75 \times 10^6$ cells/ml using 333 ul of 293 fectin (Invitrogen) and 250 ug of DNA per flask and expression was at 30° C. for 5 days. The supernatant was harvested by centrifugation and purification was by affinity purification on protein L. Protein was batch bound to the resin, packed on a column and washed with 10 column volumes of PBS. Protein was eluted with 50 ml of 0.1M glycine pH2 and neutralised with Tris pH8. Protein of the expected size was identified on an SDS-PAGE gel.

NCE ALBUDAB™ Fusions:

A new chemical entity (NCE) ALBUDAB™ fusion was tested. The NCE, a small molecule ADAMTS-4 inhibitor was synthesised with a PEG linker (PEG 4 linker (ie 4 PEG molecules before the maleimide) and a maleimide group for conjugation to the ALBUDAB™. Conjugation of the NCE to the ALBUDAB™ is via an engineered cystine residue at amino acid position R108C, or following a 5 amino acid (GGGGSC (SEQ ID NO:439)) or 6 amino acid (TVAAPSC (SEQ ID NO:440)) spacer engineered at the end of the ALBUDAB™. Briefly, the ALBUDAB™ was reduced with TCEP (Pierce, Catalogue Number 77720), desalted using a PD10 column (GE healthcare) into 25 mM Bis-Tris, 5 mM EDTA, 10% (v/v) glycerol pH6.5. A 5 fold molar excess of maleimide activated NCE was added in DMSO not to exceed

TABLE 15

| Species | ALBUDAB ™ | Fusion | Albumin $K_D$ (nM) | PK parameters | | | |
|---|---|---|---|---|---|---|---|
| | | | | AUC h x ug/ml | CL ml/h/kg | t½ h | Vz ml/kg |
| Rat | DOM7h-14 | Exendin-4 | 2400 | 18 | 57.1 | 11 | 901.9 |
| | DOM7h-14-10 | Exendin-4 | 19 | 43.6 | 23.1 | 22.1 | 740.3 |
| | DOM7h-14-18 | Exendin-4 | 16000 | 16.9 | 75.7 | 9.4 | 1002.5 |
| | DOM7h-14-19 | Exendin-4 | 17000 | 31.4 | 32.5 | 11.9 | 556.7 |
| | DOM7h-11 | Exendin-4 | 24000 | 6.1 | 168 | 7.1 | 1684.1 |
| | DOM7h-11-12 | Exendin-4 | 1400 | 24.2 | 59.9 | 13 | 1068.7 |
| | DOM7h-11-15 | Exendin-4 | 130 | 36.3 | 27.6 | 19.3 | 765.7 |
| | DOM7h14-10 | NCE-GGGGSC | 62 | | | | |
| | DOM7h14-10 | NCE-TVAAPSC | 35 | | | | |
| Human | DOM7h-14 | NCE | 204 | | | | |
| Mouse | DOM7h-11 | DOM1m-21-23 | | 234 | 10.7 | 4.7 | 72.5 |
| | DOM7h-11-12 | DOM1m-21-23 | | 755 | 3.3 | 18 | 86.2 |
| | DOM7h-11-15 | DOM1m-21-23 | | 1008 | 2.5 | 17.4 | 62.4 |

Key: DOM1m-21-23 is an anti-TNFR1 dAb, Exendin-4 is a peptide (a GLP-1 agonist) of 39 amino acids length. NCE, NCE-GGGGSC and NCE-TVAAPSC are described below.

Previously, the use of genetic fusions with an albumin-binding dAb (ALBUDAB™) to extend the PK half-life of anti-TNFR1 dAbs in vivo was described (see, eg, WO04003019, WO2006038027, WO2008149148). Reference is made to the protocols in these PCT applications. In the table above, DOM1m-21-23 is an anti-mouse TNFR1 dAb.

To produce genetic fusions of exendin-4 or with DOM7h-14 (or other ALBUDAB™) which binds serum albumin, the exendin-4-linker-AlbudAb sequence was cloned into the pTT-5 vector (obtainable from CNRC, Canada). In each case the exendin-4 was at the 5' end of the construct and the dAb at the 3' end. The linker was a $(G_4S)_3$ linker. Endotoxin-free DNA was prepared in *E. coli* using alkaline lysis (using the endotoxin-free plasmid Giga kit, obtainable from Qiagen Calif.) and used to transfect HEK293E cells (obtainable from CNRC, Canada). Transfection was into 250 ml/flask of 10% (V/V) final concentration. The reaction was incubated over night at room temperature and dialysed extensively into 20 mM Tris pH7.4

PEG Linker:

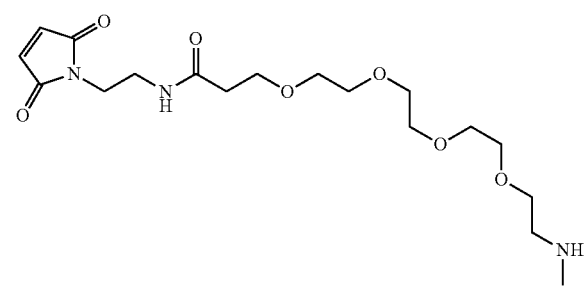 [SMILES: CNCCOCCOCCOCCOCCC(=O)NCCN1C(=O)C=CC1=O]

Sequences:

DOM7h-14 R108C:

(SEQ ID NO: 386)
DIQMTQSPSSLSASVGDRVTITCRASQWIGSQLSWYQQKPGKAPKLLIM
WRSSLQSGVPSRFSGSGSGTDFTLTISSLQPEDFATYYCAQGLRHPKT
FGQGTKVEIKC

Nucleotide:

(SEQ ID NO: 387)
GACATCCAGATGACCCAGTCTCCATCCTCCCTGTCTGCATCTGTAGGAG
ACCGTGTCACCATCACTTGCCGGGCAAGTCAGTGGATTGGGTCTCAGTT
ATCTTGGTACCAGCAGAAACCAGGGAAAGCCCCTAAGCTCCTGATCAT
GTGGCGTTCCTCGTTGCAAAGTGGGGTCCCATCACGTTTCAGTGGCAG
TGGATCTGGGACAGATTTCACTCTCACCATCAGCAGTCTGCAACCTGA
AGATTTTGCTACGTACTACTGTGCTCAGGGTTTGAGGCATCCTAAGACG
TTCGGCCAAGGGACCAAGGTGGAAATCAAATGC

See Table 5 for the sequences of DOM7h-14-10/TVAAPSC and DOM7h-14-10/GGGGSC (ie, DOM7h-14-10/G4SC). NCE-AlbudAbs DOM7h-14-10 GGGGSC and DOM7h14-10 TVAAPSC, exhibit a 5 to 10 fold decrease in in vitro affinity ($K_D$) to RSA as determined by BIACORE™ when fused to the chemical entity. PK data are not available for these molecules yet.

dAb-Albudab fusion: the 2 DOM7h-11 ALBUDABs™ with the highest affinity to RSA experience a 2-fold decrease in affinity to RSA as on BIACORE™ when fused to a therapeutic domain antibody (DOM1m-21-23) compared to the unfused ALBUDAB™. The DOM7h-11 clone shows a micromolar $K_D$ when fused (2.8 uM) as well as when unfused (~5 uM).

Exendin 4-AlbudAb fusion: the effect of fusing the ALBUDABs™ to a peptide on the binding ability to RSA is about 10-fold, apart from DOM7h-14-10, which only shows a 4-fold decrease in binding. The effect, however, is more pronounced for the DOM7h-14 series (except DOM7h-14-10) than it appears to be for the DOM7h-11 series.

For all the above data, the T1/2 of the fusion increased with improved affinity to the species' SA.

Generally, ALBUDAB™-therapeutics are classified as being therapeutically amenable (for treatment and/or prophylaxis of diseases, conditions or indications) when the ALBUDAB™-drug fusions show an affinity range ($K_D$) of from 0.1 nM to 10 mM for serum albumin binding.

The therapeutic ranges of ALBUDABs™ and ALBUDAB™ fusions (Protein-ALBUDABs™ for example IFNa2b-DOM7h-14-10; Peptide—ALBUDABs™ for example Exendin-4-DOM7h-14-10; dAb—ALBUDABs™ for example DOM1 m21-23-DOM7h11-15; NCE—ALBUDAB™ for example ADAMTS-4-DOM7h-14-10) are described as follows: Affinity ($K_D$) ranges that are useful for therapy of chronic or acute conditions, diseases or indications are shown. Also shown are affinity ranges marked as "intermediate". ALBUDABs™ and fusions in this range have utility for chronic or acute diseases, conditions or indications. In this way, the affinity of the ALBUDAB™ or fusion for serum albumin can be tailored or chosen according to the disease, condition or indication to be addressed. As described above, the invention provides ALBUDABs™ with affinities that allow for each ALBUDAB™ to be categorised as "high affinity", "medium affinity" or "low affinity", thus enabling the skilled person to select the appropriate ALBUDAB™ of the invention according to the therapy at hand. See FIG. 2.

Example 9

DOM7h-11-15$^{S12P}$ Sequences

Amino Acid Sequence of DOM7h-11-15$^{S12P}$ (SEQ ID NO: 388)
DIQMTQSPSSLPASVGDRVTITCRASRPIGTMLSWYQQKPGKAPKLL
ILAFSRLQSGVPSRFSGSGSGTDFTLTISSLQPEDFATYYCAQAGTHP
TTFGQGTKVEIKR An aspect of the invention provides a nucleic acid comprising the nucleotide sequence of DOM7h-11-15$^{S12P}$ or a nucleotide sequence that is at least 80% identical to said selected sequence. DOM7h-11-15$^{S12P}$ was produced using the following nucleic acid sequence (the underlined C denotes the change (versus the nucleic acid encoding DOM7h-11-15) leading to a proline at position 12):—

(SEQ ID NO: 389)
GACATCCAGATGACCCAGTCTCCATCCTCCCTGCCTGCATCTGTAGGAG
ACCGTGTCACCATCACTTGCCGGGCAAGTCGTCCGATTGGGACGATGTT
AAGTTGGTACCAGCAGAAACCAGGGAAAGCCCCTAAGCTCCTGATCCT
TGCTTTTTCCCGTTTGCAAAGTGGGGTCCCATCACGTTTCAGTGGCAGT
GGATCTGGGACAGATTTCACTCTCACCATCAGCAGTCTGCAACCTGAAG
ATTTTGCTACGTACTACTGCGCGCAGGCTGGGACGCATCCTACGACGT
TCGGCCAAGGGACCAAGGTGGAAATCAAACGG

DOM7h-11-15$^{S12P}$ was constructed by using DOM7h-11-15 as a template in a PCR where a primer was used to introduce the S12P mutation. The primer sequence is:—

(SEQ ID NO: 390)
GCAACAGCGTCGACGGACATCCAGATGACCCAGTCTCCATCCTCCCTG
CCTGCATCTGTAGG.

An alternative aspect of the invention provides a nucleic acid comprising the nucleotide sequence of SEQ ID NO: 389 or a nucleotide sequence that is at least 80% identical to said selected sequence. In one embodiment, DOM7h-11-15$^{S12P}$ is encoded by, and expressed from, a vector that contains a linker region and a C-terminal sequence encoding a protein or peptide drug or a single variable domain or other antibody fragment to make the in-line protein fusion product. The linker, in one embodiment, comprises the amino acid sequence TVA, e.g., TVAAPS (SEQ ID NO: 437). Other aspects of the invention are a vector comprising the nucleic acid; and an isolated host cell comprising the vector. The invention also provides a method of treating or preventing a disease or disorder in a patient, comprising administering at least one dose of DOM7h-11-15$^{S12P}$ to said patient.

Example 10

DOM 7h-11-15 Variants i) Vk Affinity Maturation
Selections:
HSA (Human Serum Albumin) and RSA (Rat Serum Albumin) antigens and biotinylated products were obtained as described in Example 1.
Affinity Maturation Libraries:
Both error prone and doped libraries were created using DOM7h-11-15 parental dAb (see SEQ ID NO: 2) as a template with arginine at position 108 mutated to tryptophan (DOM7h-11-15 R108W (DOM7h-11-55)) allowing use of trypsin for phage selection. The libraries were generated in the pDOM33 vector.

For the doped CDR libraries, primary PCR reactions were performed using doped oligonucleotides containing biased degenerated codons to diversify the required positions in the dAb. Generation of doped libraries is described, for example, in Balint and Larrick, Gene, 137, 109-118 (1993). Primers were designed in order to change only the first two nucleotides from each degenerated codon so that the parental nucleotides were present in 85% of cases and in 5% of cases all other possible nucleotides were present. Six codons per CDR were targeted for being mutated simultaneously with 15% probability per nucleotide in the codon to be different than the parental nucleotide. Assembly PCR was then used to generate a full length diversified insert. The inserts were digested with Sal I and Not I and used in a ligation reaction with pDOM33. The ligation of libraries were then used to transform *E. coli* strain TB1 by electroporation and the transformed cells plated on 2xTY agar containing 15 µg/ml tetracycline.

There were three doped libraries, one per each CDR and the mutation rate and libraries sizes were as follows:
CDR1 library—1.6 amino acid mutation per dAb with library size of $1.4 \times 10^8$
CDR2 library—1.7 amino acid mutation per dAb with library size of $2 \times 10^8$
CDR3 library—2 amino acid mutation per dAb with library size of $1.1 \times 10^8$ ii) Selection Strategies:
Selections Against HSA
Two rounds of selection against HSA were carried out. Each CDR library was selected as an individual pool in all rounds. Both rounds of selections were performed in solution against biotinylated HSA at 10 nM concentration. Libraries were eluted with 0.1M glycine pH 2.0 before neutralization with 1M Tris pH 8.0 and before infection into log phase TG1 cells. The second round of each selection was subcloned into pDOM5 for screening.

Cross Over Selection
Two rounds of selection against biotinylated SA in solution were carried out. The first round was performed against HSA at 10 nM concentration and the second round against RSA at 100 nm concentration. Each CDR library was selected as an individual pool in all rounds. Libraries were eluted with 0.1M glycine pH 2.0 before neutralization with 1M Tris pH 8.0 and before infection into log phase TG1 cells. The second round of each selection was subcloned into pDOM5 for screening.

ii) Screening Strategy and Affinity Determination
In each case after selection a pool of phage DNA from the appropriate round of selection was prepared using a QIAfilter midiprep kit (Qiagen), the DNA is digested using the restriction enzymes SalI and NotI and the enriched V genes are ligated into the corresponding sites in pDOM5 the soluble expression vector which expresses the dAb with a myc tag (see PCT/EP2008/067789). The ligated DNA is used to transform chemically competent *E. coli* HB 2151 cells which are then grown overnight on agar plates containing the antibiotic carbenicillin. The resulting colonies are individually assessed for antigen binding. For each selection output, 93 clones were tested for binding to HSA, and RSA by BIACORE™ (surface plasmon resonance). Soluble dAb fragments were produced in bacterial culture in ONEX culture media (Novagen) overnight at 37° C. in 96 well plates. The culture supernatant containing soluble dAb was centrifuged and analysed by BIACORE™ for binding to high density HSA, and RSA CM5 chips. Clones which were found to bind equally or better than parental clone to both these species of serum albumin by off-rate screening were sequenced revealing unique dAb sequences.

Unique dAbs were expressed as bacterial supernatants in 0.5 L shake flasks in Onex media at 30° C. for 48 hrs at 250 rpm. dAbs were purified from the culture media by absorption to protein L streamline followed by elution with 0.1M glycine pH2.0. To determine the binding affinity ($K_D$) of the ALBUD-ABs™ to Human, Rat, Mouse and Cynomolgus serum albumin; purified dAbs were analysed by BIACORE™ over albumin concentration range from 500 nM to 3.9 nM (500 nM, 250 nM, 125 nM, 31.25 nM, 15.625 nM, 7.8125 nM, 3.90625 nM).

MSA antigen was obtained from Sigma (essentially fatty acid free, ~99% (agarose gel electrophoresis), lyophilized powder Cat. No. A3559) and CSA was purified from Cynomolgus serum albumin using prometic blue resin (Amersham). The affinities to all tested serum albumin species of key clones is presented in Table 16.

In these assays, myc-tagged molecules were used in PK studies.

TABLE 16

A to D

| | ka (1/Ms) | kd (Ms) | KA (1/M) | KD (nM) |
|---|---|---|---|---|
| A | | RSA | | |
| DOM7h-11-15 | | | | 21.0 |
| DOM7h-11-56 | | | | 23.4 |
| DOM7h-11-57 | 5.66E+05 | 1.93E−02 | 3.42E+07 | 29.2 |
| DOM7h-11-65 | 7.80E+05 | 2.04E−02 | 4.06E+07 | 24.6 |
| DOM7h-11-67 | 1.33E+06 | 1.46E−02 | 8.60E+07 | 11.6 |
| DOM7h-11-68 | | | | 25.3 |
| DOM7h-11-69 | | | | 27.1 |
| DOM7h-11-79 | | | | 11.1 |
| DOM7h-11-80 | | | | 24.1 |
| B | | HSA | | |
| DOM7h-11-15 | | | | 1.4 |
| DOM7h-11-56 | | | | 1.6 |
| DOM7h-11-57 | 1.22E+06 | 1.97E−03 | 5.52E+08 | 1.8 |
| DOM7h-11-65 | 1.30E+06 | 2.22E−03 | 5.52E+08 | 1.8 |
| DOM7h-11-67 | 1.75E+06 | 1.65E−03 | 1.12E+09 | 0.9 |
| DOM7h-11-68 | | | | 33.5 |
| DOM7h-11-69 | | | | 3.2 |
| DOM7h-11-79 | | | | 5.9 |
| DOM7h-11-80 | | | | 2.1 |
| C | | CSA | | |
| DOM7h-11-15 | | | | 5.3 |
| DOM7h-11-56 | | | | 5.2 |
| DOM7h-11-57 | 1.34E+06 | 7.23E−03 | 1.63E+08 | 6.1 |

TABLE 16-continued

A to D

|  | ka (1/Ms) | kd (Ms) | KA (1/M) | KD (nM) |
|---|---|---|---|---|
| DOM7h-11-65 | 1.19E+06 | 7.96E−03 | 6.35E+07 | 15.7 |
| DOM7h-11-67 | 2.03E+06 | 5.34E−03 | 3.69E+08 | 2.7 |
| DOM7h-11-68 |  |  |  | 37.9 |
| DOM7h-11-69 |  |  |  | 5.9 |
| DOM7h-11-79 |  |  |  | 11.7 |
| DOM7h-11-80 |  |  |  | 5.5 |

| D | MSA |
|---|---|
| DOM7h-11-15 | 10.3 |
| DOM7h-11-56 | 7.6 |
| DOM7h-11-57 | 10.9 |
| DOM7h-11-65 | 9.4 |
| DOM7h-11-67 | 6.7 |
| DOM7h-11-68 | 15.5 |
| DOM7h-11-69 | 10.0 |
| DOM7h-11-79 | 6.9 |
| DOM7h-11-80 | 10.9 |

All DOM7h-11-15 variants are cross-reactive to rat, human, cyno and mouse serum albumin. (dissociation constant (KD); off-rate constant ($K_d$); on-rate constant ($K_a$)).

iv) Expression and Biophysical Characterisation:

Bacterial expression and expression by SECMALLS and DSC was carried out as described above in Example 5.

TABLE 17

Biophysical parameters

| ALBUDAB ™ | DSC Tm (° C.) | SEC MALLS | Average Expression level (mg/l) |
|---|---|---|---|
| DOM7h-11-15 (R108W) | 53.9 | T/D, Monomer | 21 |
| DOM7h-11-56 | 56.1 | Trimer, Monomer | 10 |
| DOM7h-11-57 | 58.2 | Monomer | 15 |
| DOM7h-11-65 | 61.2 | Monomer | 40 |
| DOM7h-11-67 | 57.2 | Monomer | 36 |
| DOM7h-11-68 | 55.9 | Monomer | 12 |
| DOM7h-11-69 | 57.8 | Monomer | 22 |
| DOM7h-11-79 | 55.1 | T/D, D/M, Monomer | 16 |
| DOM7h-11-80 | 56.2 | Monomer | 11 |

T/D and D/M indicates an equilibrium between trimer and dimer or dimer and monomer, respectively, as detected by SEC-MALLS.

All the DOM7h-11-15 variants presented in the Table 2 have favorable biophysical parameters (monomeric in solution as determined by SEC MALLs and App™ of >55° C. as determined by DSC) and expression levels were mostly maintained during affinity maturation. Thermostability is advantageous because it may improve the shelf life of the drug fused to ALBUDAB™ with higher melting temperature when compared to ALBUDAB™ with low Tm.

v) CDR3 and Framework 3 Sequences of Most Thermostable Clones

The essential differences in properties of the most thermostable ALBUDABs™ (App™ of >57° C.) are due to single amino acid mutations in CDR 3 or framework 3 (mutations due to polymerase error) of these clones when compared to parental clone DOM7h-11-15. Sequences of framework 3 or CDR 3 containing favorable mutations are presented in Tables 18 and 19. Amino acids that distinguish thermostable ALBUDABs™ from parent are in bold.

Full amino acid and nucleotide sequences of parent and all thermostable variants of DOM7h-11-15 (Tm of >55° C.) are listed in the sequences section (sequence 1-18). Most of the clones has arginine at position 108 mutated to tryptophan which was done to enable trypsin driven selection if necessary (knocking trypsin recognition site out). Mutation of isoleucine to asparagine at position 106 in DOM7h-11-67 was also included.

Other clones (see DOM 7h-11-87, DOM 7h-11-90, DOM 7h-11-86) were derived in which position 108 was back mutated to arginine (W108R) and, optionally, position 106 was back mutated to isoleucine. The sequences of these clones are listed below.

Binding to SA is summarized in the following tables:

HSA

|  | ka (1/Ms) | kd (Ms) | KA (1/M) | KD (M) |
|---|---|---|---|---|
| DOM7h-11-90 | 4.69E+05 | 8.70E−05 | 5.27E+07 | 2.02E−08 |
| DOM7h-11-86 | 7.90E+05 | 8.83E−05 | 9.51E+07 | 1.07E−08 |
| DOM7h-11-87 | 1.17E+06 | 1.04E−04 | 1.37E+08 | 7.39E−09 |
| DOM7h-11-88 | 1.14E+06 | 8.12E−05 | 1.51E+08 | 6.71E−09 |

RSA

|  | ka (1/Ms) | kd (Ms) | KA (1/M) | KD (M) |
|---|---|---|---|---|
| DOM7h-11-90 | 3.76E+05 | 3.66E−04 | 1.91E+07 | 5.36E−08 |
| DOM7h-11-86 | 5.60E+05 | 3.87E−04 | 2.80E+07 | 3.78E−08 |
| DOM7h-11-87 | 8.30E+05 | 1.90E−04 | 5.77E+07 | 1.76E−08 |
| DOM7h-11-88 | 8.46E+05 | 2.03E−04 | 5.96E+07 | 1.69E−08 |

CSA

|  | ka (1/Ms) | kd (Ms) | KA (1/M) | KD (M) |
|---|---|---|---|---|
| DOM7h-11-90 | 7.47E+05 | 1.31E−04 | 1.01E+08 | 9.99E−09 |
| DOM7h-11-86 | 8.33E+05 | 1.43E−04 | 1.08E+08 | 1.34E−08 |
| DOM7h-11-87 | 1.37E+06 | 1.23E−04 | 2.47E+08 | 4.21E−09 |
| DOM7h-11-66 | 1.49E+06 | 1.27E−04 | 2.76E+08 | 3.65E−09 |

Table Showing Biophysical Properties

| ALBUDAB ™ | Average expression level mg/L | Thermal stability Tm (° C.) | Solution state |
|---|---|---|---|
| DOM7h-11-90 (DOM7h-11-57 W108R/N106I) | 4 | 60 | Monomer |
| DOM7h-11-86 (DOM7h-11-65 W108R/N106I) | 17 | 61.5 | Monomer |
| DOM7h-11-87 (DOM7h-11-67 W108R/N106I) | 17 | 57.2 | Monomer |
| DOM7h-11-88 (DOM7h-11-67 W108R) | 16 | 57 | Monomer |

TABLE 18

Amino acids that distinguish thermostable ALBUDABs ™ from parent are in bold. All numbering is with reference to Kabat.

Amino acid sequences

| ALBUDAB ™ | Framework 3 (amino acid residues 57 to 88) | CDR 3 (amino acid residues 89-97) |
|---|---|---|
| DOM7h-11-15 | GVPSRFSGSGSGTDFTLTISSL QPEDFATYYC (SEQ ID NO: 391) | AQAGTHPTT (SEQ ID NO: 392) |

TABLE 18-continued

Amino acids that distinguish thermostable ALBUDABs ™ from parent are in bold. All numbering is with reference to Kabat.

Amino acid sequences

| ALBUDAB ™ | Framework 3 (amino acid residues 57 to 88) | CDR 3 (amino acid residues 89-97) |
|---|---|---|
| DOM7h-11-57 | GVPSRFSGSGSGTDFTLTISNLQPEDFATYYC (SEQ ID NO: 393) | AQAGTHPTT (SEQ ID NO: 394) |
| DOM7h-11-65 | GVPSRFSGSGSGTDFTLTISSLQPEDVATYYC (SEQ ID NO: 395) | AQAGTHPTT (SEQ ID NO: 396) |
| DOM7h-11-67 | GVPSRFSGSGSGTDFTLTISSLQPEDFATYYC (SEQ ID NO: 397) | AQAGTHHTT (SEQ ID NO: 398) |
| DOM7h-11-69 | GVPSRFSGSGSGTDFTLTISSLQPEDFATYYC (SEQ ID NO: 399) | AQAGVHPTT (SEQ ID NO: 400) |

TABLE 19

Nucleotide sequences

| ALBUDAB ™ | Framework 3 | CDR 3 |
|---|---|---|
| DOM7h-11-15 | GGGGTCCCATCACGTTTCAGTGGCAGTGGATCTGGGACAGATTTCACTCTCACCATCAGCAGTCTGCAACCTGAAGATTTTGCTACGTACTACTGC (SEQ ID NO: 401) | GCGCAGGCTGGGACGCATCCTACGACG (SEQ ID NO: 402) |
| DOM7h-11-57 | GGGGTCCCATCACGTTTCAGTGGCAGTGGATCTGGGACAGATTTCACTCTCACCATCAGCAATCTGCAACCTGAAGATTTTGCTACGTACTACTGC (SEQ ID NO: 403) | GCGCAGGCTGGGACGCATCCTACGACG (SEQ ID NO: 404) |
| DOM7h-11-65 | GGGGTCCCATCACGTTTCAGTGGCAGTGGATCTGGGACAGATTTCACTCTCACCATCAGCAGTCTGCAACCTGAAGATGTTGCTACGTACTACTGT (SEQ ID NO: 405) | GCGCAGGCTGGGACGCATCCTACGACG (SEQ ID NO: 406) |
| DOM7h-11-67 | GGGGTCCCATCACGTTTCAGTGGCAGTGGATCTGGGACAGATTTCACTCTCACCATCAGCAGTCTGCAACCTGAAGATTTTGCTACGTACTACTGT (SEQ ID NO: 407) | GCGCAGGCTGGGACGCATCATACGACG (SEQ ID NO: 408) |
| DOM7h-11-69 | GGGGTCCCATCACGTTTCAGTGGCAGTGGATCTGGGACAGATTTCACTCTCACCATCAGCAGTCTGCAACCTGAAGATTTTGCTACGTACTACTGT (SEQ ID NO: 409) | GCGCAGGCTGGGGTGCATCCTACGACG (SEQ ID NO: 410) | the Mutations to DOM 7h-11-15 Identified are as Follows:

| ALBUDAB ™ | Mutation compared to DOM 7h-11-15 |
|---|---|
| DOM7h-11-56 | T22S, R108W |
| DOM7h-11-57 | S77N, R108W |
| DOM7h-11-65 | F83V, R108W |
| DOM7h-11-67 | P95H, I106N, R108W |
| DOM7h-11-68 | K42E, A91T, R108W |
| DOM7h-11-69 | T93V |
| DOM7h-11-79 | A91T, R108W |
| DOM7h-11-80 | T22F, R108W |

Sequences of DOM7h-11-15 Variants

Amino acid sequences
DOM7h-11-15 R108W (DOM7h-11-55)
(SEQ ID NO: 411)
DIQMTQSPSSLSASVGDRVTITCRASRPIGTMLSWYQQKPGKAPKLLIL

AFSRLQSGVPSRFSGSGSGTDFTLTISSLQPEDFATYYCAQAGTHPTTF

GQGTKVEIKW

DOM7h-11-56
(SEQ ID NO: 412)
DIQMTQSPSSLSASVGDRVTISCRASRPIGTMLSWYQQKPGKAPKLLIL

AFSRLQSGVPSRFSGSGSGTDFTLTISSLQPEDFATYYCAQAGTHPTTF

GQGTKVEIKW

DOM7h-11-57
(SEQ ID NO: 413)
DIQMTQSPSSLSASVGDRVTITCRASRPIGTMLSWYQQKPGKAPKLLIL

AFSRLQSGVPSRFSGSGSGTDFTLTISNLQPEDFATYYCAQAGTHPTTF

GQGTKVEIKW

DOM7h-11-65
(SEQ ID NO: 414)
DIQMTQSPSSLSASVGDRVTITCRASRPIGTMLSWYQQKPGKAPKLLIL

AFSRLQSGVPSRFSGSGSGTDFTLTISSLQPEDVATYYCAQAGTHPTTF

GQGTKVEIKW

DOM7h-11-67
(SEQ ID NO: 415)
DIQMTQSPSSLSASVGDRVTITCRASRPIGTMLSWYQQKPGKAPKLLIL

AFSRLQSGVPSRFSGSGSGTDFTLTISSLQPEDFATYYCAQAGTHHTTF

GQGTKVENKW

DOM7h-11-68
(SEQ ID NO: 416)
DIQMTQSPSSLSASVGDRVTITCRASRPIGTMLSWYQQKPGEAPKLLIL

AFSRLQSGVPSRFSGSGSGTDFTLTISSLQPEDFATYYCAQTGTHPTTF

GQGTKVEIKW

DOM7h-11-69
(SEQ ID NO: 417)
DIQMTQSPSSLSASVGDRVTITCRASRPIGTMLSWYQQKPGKAPKLLIL

AFSRLQSGVPSRFSGSGSGTDFTLTISSLQPEDFATYYCAQAGVHPTTF

GQGTKVEIKR

DOM7h-11-79
(SEQ ID NO: 418)
DIQMTQSPSSLSASVGDRVTITCRASRPIGTMLSWYQQKPGKAPKLLIL

AFSRLQSGVPSRFSGSGSGTDFTLTISSLQPEDFATYYCAQTGTHPTTF

GQGTKVEIKW

-continued

DOM7h-11-80
(SEQ ID NO: 419)
DIQMTQSPSSLSASVGDRVTIFCRASRPIGTMLSWYQQKPGKAPKLLIL
AFSRLQSGVPSRFSGSGSGTDFTLTISSLQPEDFATYYCAQAGTHPTTF
GQGTKVEIKW

>DOM7h-11-90
(SEQ ID NO: 420)
DIQMTQSPSSLSASVGDRVTITCRASRPIGTMLSWYQQKPGKAPKLLIL
AFSRLQSGVPSRFSGSGSGTDFTLTISNLQPEDFATYYCAQAGTHPTTF
GQGTKVEIKR

>DOM7h-11-86
(SEQ ID NO: 421)
DIQMTQSPSSLSASVGDRVTITCRASRPIGTMLSWYQQKPGKAPKLLIL
AFSRLQSGVPSRFSGSGSGTDFTLTISSLQPEDVATYYCAQAGTHPTTF
GQGTKVEIKR

>DOM7h-11-87
(SEQ ID NO: 422)
DIQMTQSPSSLSASVGDRVTITCRASRPIGTMLSWYQQKPGKAPKLLIL
AFSRLQSGVPSRFSGSGSGTDFTLTISSLQPEDFATYYCAQAGTHHTTF
GQGTKVEIKR

DOM7h-11-88
(SEQ ID NO: 423)
DIQMTQSPSSLSASVGDRVTITCRASRPIGTMLSWYQQKPGKAPKLLIL
AFSRLQSGVPSRFSGSGSGTDFTLTISSLQPEDFATYYCAQAGTHHTTF
GQGTKVENKR

Nucleotide sequences
DOM7h-11-15 R108W (DOM7h-11-55)
(SEQ ID NO: 424)
GACATCCAGATGACCCAGTCTCCATCCTCCCTGTCTGCATCTGTAGGAG
ACCGTGTCACCATCACTTGCCGGGCAAGTCGTCCGATTGGGACGATGTT
AAGTTGGTACCAGCAGAAACCAGGGAAAGCCCCTAAGCTCCTGATCCTT
GCTTTTTCCCGTTTGCAAAGTGGGGTCCCATCACGTTTCAGTGGCAGTG
GATCTGGGACAGATTCACTCTCACCATCAGCAGTCTGCAACCTGAAGA
TTTTGCTACGTACTACTGCGCGCAGGCTGGGACGCATCCTACGACGTTC
GGCCAAGGGACCAAGGTGGAAATCAAATGG DOM7h-11-56
(SEQ ID NO: 425)
GACATCCAGATGACCCAGTCTCCATCCTCCCTGTCTGCATCTGTAGGAG
ACCGTGTCACCATCTCTTGCCGGGCAAGTCGTCCGATTGGGACGATGTT
AAGTTGGTACCAGCAGAAACCAGGGAAAGCCCCTAAGCTCCTGATCCTT
GCTTTTTCCCGTTTGCAAAGTGGGGTCCCATCACGTTTCAGTGGCAGTG
GATCTGGGACAGATTTCACTCTCACCATCAGCAGTCTGCAACCTGAAGA
TTTTGCTACGTACTACTGCGCGCAGGCTGGGACGCATCCTACGACGTTC
GGCCAAGGGACCAAGGTGGAAATCAAATGG DOM7h-11-57
(SEQ ID NO: 426)
GACATCCAGATGACCCAGTCTCCATCCTCCCTGTCTGCATCTGTAGGAG
ACCGTGTCACCATCACTTGCCGGGCAAGTCGTCCGATTGGGACGATGTT
AAGTTGGTACCAGCAGAAACCAGGGAAAGCCCCTAAGCTCCTGATCCTT
GCTTTTTCCCGTTTGCAAAGTGGGGTCCCATCACGTTTCAGTGGCAGTG
GATCTGGGACAGATTTCACTCTCACCATCAGCAATCTGCAACCTGAAGA
TTTTGCTACGTACTACTGCGCGCAGGCTGGGACGCATCCTACGACGTTC
GGCCAAGGGACCAAGGTGGAAATCAAATGG DOM7h-11-65
(SEQ ID NO: 427)
GACATCCAGATGACCCAGTCTCCATCCTCCCTGTCTGCATCTGTAGGAG
ACCGTGTCACCATCACTTGCCGGGCAAGTCGTCCGATTGGGACGATGTT
AAGTTGGTACCAGCAGAAACCAGGGAAAGCCCCTAAGCTCCTGATCCTT
GCTTTTTCCCGTTTGCAAAGTGGGGTCCCATCACGTTTCAGTGGCAGTG
GATCTGGGACAGATTTCACTCTCACCATCAGCAGTCTGCAACCTGAAGA
TGTTGCTACGTACTACTGTGCGCAGGCTGGGACGCATCCTACGACGTTC
GGCCAAGGGACCAAGGTGGAAATCAAATGG DOM7h-11-67
(SEQ ID NO: 428)
GACATCCAGATGACCCAGTCTCCATCCTCCCTGTCTGCATCTGTAGGAG
ACCGTGTCACCATCACTTGCCGGGCAAGTCGTCCGATTGGGACGATGTT
AAGTTGGTACCAGCAGAAACCAGGGAAAGCCCCTAAGCTCCTGATCCTT
GCTTTTTCCCGTTTGCAAAGTGGGGTCCCATCACGTTTCAGTGGCAGTG
GATCTGGGACAGATTCACTCTCACCATCAGCAGTCTGCAACCTGAAGA
TTTTGCTACGTACTACTGTGCGCAGGCTGGGACGCATCATACGACGTTC
GGCCAAGGGACCAAGGTGGAAAACAAATGG DOM7h-11-68
(SEQ ID NO: 429)
GACATCCAGATGACCCAGTCTCCATCCTCCCTGTCTGCATCTGTAGGAG
ACCGTGTCACCATCACTTGCCGGGCAAGTCGTCCGATTGGGACGATGTT
AAGTTGGTACCAGCAGAAACCAGGGGAAGCCCCTAAGCTCCTGATCCTT
GCTTTTTCCCGTTTGCAAAGTGGGGTCCCATCACGTTTCAGTGGCAGTG
GATCTGGGACAGATTCACTCTCACCATCAGCAGTCTGCAACCTGAAGA
TTTTGCTACGTACTACTGTGCGCAGACTGGGACGCATCCTACGACGTTC
GGCCAAGGGACCAAGGTGGAAATCAAATGG DOM7h-11-69
(SEQ ID NO: 430)
GACATCCAGATGACCCAGTCTCCATCCTCCCTGTCTGCATCTGTAGGAG
ACCGTGTCACCATCACTTGCCGGGCAAGTCGTCCGATTGGGACGATGTT
AAGTTGGTACCAGCAGAAACCAGGGAAAGCCCCTAAGCTCCTGATCCTT
GCTTTTTCCCGTTTGCAAAGTGGGGTCCCATCACGTTTCAGTGGCAGTG
GATCTGGGACAGATTTCACTCTCACCATCAGCAGTCTGCAACCTGAAGA
TTTTGCTACGTACTACTGTGCGCAGGCTGGGGTGCATCCTACGACGTTC
GGCCAAGGGACCAAGGTGGAAATCAAACGG DOM7h-11-79
(SEQ ID NO: 431)
GACATCCAGATGACCCAGTCTCCATCCTCCCTGTCTGCATCTGTAGGAG
ACCGTGTCACCATCACTTGCCGGGCAAGTCGTCCGATTGGGACGATGTT
AAGTTGGTACCAGCAGAAACCAGGGAAAGCCCCTAAGCTCCTGATCCTT
GCTTTTTCCCGTTTGCAAAGTGGGGTCCCATCACGTTTCAGTGGCAGTG -continued

GATCTGGGACAGATTTCACTCTCACCATCAGCAGTCTGCAACCTGAAGA

TTTTGCTACGTACTACTGTGCGCAGACTGGGACGCATCCTACGACGTTC

GGCCAAGGGACCAAGGTGGAAATCAAATGG

DOM7h-11-80
(SEQ ID NO: 432)
GACATCCAGATGACCCAGTCTCCATCCTCCCTGTCTGCATCTGTAGGAG

ACCGTGTCACCATCTTTTGCCGGGCAAGTCGTCCGATTGGGACGATGTT

AAGTTGGTACCAGCAGAAACCAGGGAAAGCCCCTAAGCTCCTGATCCTT

GCTTTTTCCCGTTTGCAAAGTGGGGTCCCATCACGTTTCAGTGGCAGTG

GATCTGGGACAGATTTCACTCTCACCATCAGCAGTCTGCAACCTGAAGA

TTTTGCTACGTACTACTGCGCGCAGGCTGGGACGCATCCTACGACGTTC

GGCCAAGGGACCAAGGTGGAAATCAAATGG

>DOM7h-11-90
(SEQ ID NO: 433)
GACATCCAGATGACCCAGTCTCCATCCTCCCTGTCTGCATCTGTAGGAG

ACCGTGTCACCATCACTTGCCGGGCAAGTCGTCCGATTGGGACGATGTT

AAGTTGGTACCAGCAGAAACCAGGGAAAGCCCCTAAGCTCCTGATCCTT

GCTTTTTCCCGTTTGCAAAGTGGGGTCCCATCACGTTTCAGTGGCAGTG

GATCTGGGACAGATTTCACTCTCACCATCAGCAATCTGCAACCTGAAGA

TTTTGCTACGTACTACTGCGCGCAGGCTGGGACGCATCCTACGACGTT

CGGCCAAGGGACCAAGGTGGAAATCAAACGG

>DOM7h-11-86
(SEQ ID NO: 434)
GACATCCAGATGACCCAGTCTCCATCCTCCCTGTCTGCATCTGTAGGAG

ACCGTGTCACCATCACTTGCCGGGCAAGTCGTCCGATTGGGACGATGTT

AAGTTGGTACCAGCAGAAACCAGGGAAAGCCCCTAAGCTCCTGATCCTT

GCTTTTTCCCGTTTGCAAAGTGGGGTCCCATCACGTTTCAGTGGCAGTG

GATCTGGGACAGATTTCACTCTCACCATCAGCAGTCTGCAACCTGAAGA

TGTTGCTACGTACTACTGTGCGCAGGCTGGGACGCATCCTACGACGTTC

GGCCAAGGGACCAAGGTGGAAATCAAACGG

>DOM7h-11-87
(SEQ ID NO: 435)
GACATCCAGATGACCCAGTCTCCATCCTCCCTGTCTGCATCTGTAGGAG

ACCGTGTCACCATCACTTGCCGGGCAAGTCGTCCGATTGGGACGATGTT

AAGTTGGTACCAGCAGAAACCAGGGAAAGCCCCTAAGCTCCTGATCCTT

GCTTTTTCCCGTTTGCAAAGTGGGGTCCCATCACGTTTCAGTGGCAGTG

GATCTGGGACAGATTTCACTCTCACCATCAGCAGTCTGCAACCTGAAGA

TTTTGCTACGTACTACTGTGCGCAGGCTGGGACGCATCATACGACGTTC

GGCCAAGGGACCAAGGTGGAAATCAAACGG

DOM7h-11-88
(SEQ ID NO: 436)
GACATCCAGATGACCCAGTCTCCATCCTCCCTGTCTGCATCTGTAGGAG

ACCGTGTCACCATCACTTGCCGGGCAAGTCGTCCGATTGGGACGATGTT

AAGTTGGTACCAGCAGAAACCAGGGAAAGCCCCTAAGCTCCTGATCCTT

GCTTTTTCCCGTTTGCAAAGTGGGGTCCCATCACGTTTCAGTGGCAGTG

GATCTGGGACAGATTTCACTCTCACCATCAGCAGTCTGCAACCTGAAGA

TTTTGCTACGTACTACTGTGCGCAGGCTGGGACGCATCATACGACGTTC

GGCCAAGGGACCAAGGTGGAAAACAAACGG

TABLE OF SEQUENCES

| | SEQ ID No | |
|---|---|---|
| Description | Amino acids | Nucleotide |
| DOM7h-11-12 amino acid | 1 | 6 |
| DOM7h-11-15 amino acid | 2 | 7 |
| DOM7h-11-18 amino acid | 3 | 8 |
| DOM7h-11-19 amino acid | 4 | 9 |
| DOM7h-11-3 nucleotide | 5 | 10 |
| Sequences of anti-TNFR1 dAbs | 11 to 158 | 159 to 306 |
| DOM7h-14/Exendin-4 fusion DMS number 7138 | 307 | 308 |
| DOM7h-14-10/Exendin-4 fusion DMS number 7139 | 309 | 310 |
| DOM7h-14-18/Exendin-4 fusion DMS number 7140 | 311 | 312 |
| DOM7h-14-19/Exendin-4 fusion DMS number 7141 | 313 | 314 |
| DOM7h-11/Exendin-4 fusion DMS number 7142 | 315 | 316 |
| DOM7h-11-12/Exendin-4 fusion DMS number 7147 | 317 | 318 |
| DOM7h-11-15/Exendin-4 fusion DMS number 7143 | 319 | 320 |
| DOM7h14-10/G4SC-NCE fusion | 321 | 322 |
| DOM7h14-10/TVAAPSC fusion | 323 | 324 |
| DOM7h-11/DOM1m-21-23 fusion DMS number 5515 | 325 | 327 |
| DOM7h-11/DOM1m-21-23 fusion DMS number 5515 plus myc tag | 326 | 328 |
| DOM7h-11-12/DOM1m-21-23 fusion DMS number 5516 | 329 | 331 |
| DOM7h-11-12/DOM1m-21-23 fusion DMS number 5516 plus myc tag | 330 | 332 |
| DOM7h-11-15/DOM1m-21-23 fusion DMS number 5517 | 333 | 335 |
| DOM7h-11-15/DOM1m-21-23 fusion DMS number 5517 plus myc tag | 334 | 336 |
| DPK9 Vk dummy CDRs | 337-339 | |
| DOM7h-11 CDRs | 340-342 | |
| DOM7h-11-12 CDRs | 343-345 | |
| DOM 7h-11-15 CDRs | 346-348 | |
| DOM 7h-11-18 CDRs | 349-351 | |
| DOM 7h-11-19 CDRs | 352-354 | |
| DOM 7h-11-3 CDRs | 355-357 | |
| DOM 7h-14 CDRs | 358-360 | |
| DOM 7h-14-10 CDRs | 361-363 | |
| DOM 7h-14-18 CDRs | 364-366 | |
| DOM 7h-14-19 CDRs | 367-369 | |
| DOM 7h-14-28 CDRs | 370-372 | |
| DOM 7h-14-36 | 373-375 | |

TABLE OF SEQUENCES

| Description | SEQ ID No Amino acids | SEQ ID No Nucleotide |
|---|---|---|
| CDRs | | |
| Interferon alpha 2b | 376 | 377 |
| IFNα2b SOE fragment 5' | | 378 |
| IFNα2b SOE fragment 3' | | 379 |
| Vk SOE fragment 5' | | 380 |
| Vk SOE fragment 3' to also introduce a myc tag | | 381 |
| IFNα2b SOE fragment 5' | | 382 |
| Vk SOE fragment 3' to also introduce a myc tag | | 383 |
| Leader sequence | 384 | 385 |
| DOM7h-14 R108C | 386 | 387 |
| DOM7h-11-15$^{S12P}$ | 388 | 389 |
| primer sequence | | 390 |
| FR3 and CDR3 sequences | 391 to 400 | 401 to 410 |

TABLE OF SEQUENCES

| Description | SEQ ID No Amino acids | SEQ ID No Nucleotide |
|---|---|---|
| for thermostable variants | | |
| DOM7h-11-15 R108W | 411 | 424 |
| DOM7h-11-56 | 412 | 425 |
| DOM7h-11-57 | 413 | 426 |
| DOM7h-11-65 | 414 | 427 |
| DOM7h-11-67 | 415 | 428 |
| DOM7h-11-68 | 416 | 429 |
| DOM7h-11-69 | 417 | 430 |
| DOM7h-11-79 | 418 | 431 |
| DOM7h-11-80 | 419 | 432 |
| DOM7h-11-90 | 420 | 433 |
| DOM7h-11-86 | 421 | 434 |
| DOM7h-11-87 | 422 | 435 |
| DOM7h-11-88 | 423 | 436 |
| Linker sequence | 437 | |
| DOM7h-11 | 438 | |

---

The invention claimed is:

1. An anti-serum albumin (SA) immunoglobulin single variable domain comprising an amino acid sequence selected from the group consisting of: SEQ ID NO: 412 (DOM7h-11-56), SEQ ID NO: 413 (DOM7h-11-57), SEQ ID NO: 414 (DOM7h-11-65), SEQ ID NO: 415 (DOM7h-11-67), SEQ ID NO: 416 (DOM7h-11-68), SEQ ID NO: 417 (DOM7h-11-69), SEQ ID NO:418 (DOM7h-11-79), SEQ ID NO:419 (DOM7h-11-80), SEQ ID NO:420 (DOM7h-11-90), SEQ ID NO:421 (DOM7h-11-86), SEQ ID NO:422 (DOM7h-11-87), and SEQ ID NO:423 (DOM7h-11-88).

2. A multispecific ligand comprising the anti-SA immunoglobulin single variable domain of claim 1, and a binding moiety that specifically binds a target antigen other than SA.

3. The anti-SA immunoglobulin single variable domain of claim 1, wherein the variable domain is conjugated to a new chemical entity (NCE) drug.

4. A fusion protein comprising a polypeptide or peptide drug fused to the anti-SA immunoglobulin single variable domain according to claim 1, wherein the fusion protein comprises a linker selected from the group consisting of: SEQ ID NO: 437 (TVAAPS) and TVA between the single variable domain and the drug.

5. A composition comprising the anti-SA immunoglobulin single variable domain of claim 1, and a pharmaceutically acceptable diluent, carrier, excipient or vehicle.

6. A composition comprising the fusion protein of claim 4, and a pharmaceutically acceptable diluent, carrier, excipient or vehicle.

7. A composition comprising the multispecific ligand of claim 2, and a pharmaceutically acceptable diluent, carrier, excipient or vehicle.

8. An anti-SA immunoglobulin single variable domain comprising SEQ ID NO:421 (DOM7h-11-86).

9. An anti-SA immunoglobulin single variable domain comprising SEQ ID NO:420 (DOM7h-11-90).

* * * * *

SEQUENCE LISTING

```
<160> NUMBER OF SEQ ID NOS: 440

<210> SEQ ID NO 1
<211> LENGTH: 108
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
                20                  25                  30

Leu Ser Trp Tyr Gln Gln Lys Pro Gly Lys Ala Pro Lys Leu Leu Ile
            35                  40                  45

Leu Phe Gly Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His Pro Thr
                85                  90                  95

Thr Phe Gly Gln Gly Thr Lys Val Glu Ile Lys Arg
            100                 105

<210> SEQ ID NO 2
<211> LENGTH: 108
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
                20                  25                  30

Leu Ser Trp Tyr Gln Gln Lys Pro Gly Lys Ala Pro Lys Leu Leu Ile
            35                  40                  45

Leu Ala Phe Ser Arg Leu Gln Ser Gly Val Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Ala Gly His Pro Thr
                 85                  90                  95

Thr Phe Gly Gln Gly Thr Lys Val Glu Ile Lys Arg
                100                 105
```

<210> SEQ ID NO 3
<211> LENGTH: 108
<212> TYPE: PRT
<213> ORGANISM: Homo sapiens

<400> SEQUENCE: 3

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Arg Pro Ile Gly Thr Met
                 20                  25                  30

Leu Ser Trp Tyr Gln Gln Lys Pro Gly Lys Ala Pro Lys Leu Leu Ile
                 35                  40                  45

Trp Phe Gly Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr His Cys Ala Gln Ala Gly His Pro Thr
                 85                  90                  95

Thr Phe Gly Gln Gly Thr Lys Val Glu Ile Lys Arg
                100                 105
```

<210> SEQ ID NO 4
<211> LENGTH: 108
<212> TYPE: PRT
<213> ORGANISM: Homo sapiens

<400> SEQUENCE: 4

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Arg Pro Ile Gly Thr Met
                 20                  25                  30

Leu Ser Trp Tyr Gln Gln Lys Pro Gly Lys Ala Pro Lys Leu Leu Ile
                 35                  40                  45

Leu Phe Gly Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Thr Gly His Pro Thr
                 85                  90                  95

Thr Phe Gly Gln Gly Thr Lys Val Glu Ile Lys Arg
                100                 105
```

<210> SEQ ID NO 5
<211> LENGTH: 108
<212> TYPE: PRT
<213> ORGANISM: Homo sapiens

<400> SEQUENCE: 5

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Arg Pro Ile Gly Thr Thr
```

```
                  20                  25                  30

Leu Ser Trp Tyr Gln Gln Lys Pro Gly Lys Ala Pro Lys Leu Leu Ile
         35                  40                  45

Leu Trp Asn Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Ala Gly Thr His Pro Thr
                 85                  90                  95

Thr Phe Gly Gln Gly Thr Lys Val Glu Ile Lys Arg
             100                 105
```

```
<210> SEQ ID NO 6
<211> LENGTH: 324
<212> TYPE: DNA
<213> ORGANISM: Artificial Sequence
<220> FEATURE:
<223> OTHER INFORMATION: Nucleotide

<400> SEQUENCE: 6
gacatccaga tgacccagtc tccatcctcc ctgtctgcat ctgtaggaga ccgtgtcacc      60
atcacttgcc gggcaagtcg tccgattggg acgatgttaa gttggtacca gcagaaacca     120
gggaaagccc ctaagctcct gatcttgttt ggttcccggt tgcaaagtgg ggtcccatca     180
cgtttcagtg gcagtggatc tgggacagat ttcactctca ccatcagcag tctgcaacct     240
gaagattttg ctacgtacta ctgtgcgcag gctgggacgc atcctacgac gttcggccaa     300
gggaccaagg tggaaatcaa acgg                                            324
```

```
<210> SEQ ID NO 7
<211> LENGTH: 324
<212> TYPE: DNA
<213> ORGANISM: Artificial Sequence
<220> FEATURE:
<223> OTHER INFORMATION: Nucleotide

<400> SEQUENCE: 7
gacatccaga tgacccagtc tccatcctcc ctgtctgcat ctgtaggaga ccgtgtcacc      60
atcacttgcc gggcaagtcg tccgattggg acgatgttaa gttggtacca gcagaaacca     120
gggaaagccc ctaagctcct gatccttgct ttttcccgtt tgcaaagtgg ggtcccatca     180
cgtttcagtg gcagtggatc tgggacagat ttcactctca ccatcagcag tctgcaacct     240
gaagattttg ctgcgtacta ctgcgcgcag gctgggacgc atcctacgac gttcggccaa     300
gggaccaagg tggaaatcaa acgg                                            324
```

```
<210> SEQ ID NO 8
<211> LENGTH: 324
<212> TYPE: DNA
<213> ORGANISM: Artificial Sequence
<220> FEATURE:
<223> OTHER INFORMATION: Nucleotide

<400> SEQUENCE: 8
gacatccaga tgacccagtc tccatcctcc ctgtctgcat ctgtaggaga ccgtgtcacc      60
atcacttgcc gggcaagtcg tccgattggg acgatgttaa gttggtacca gcagaaacca     120
gggaaagccc ctaagctcct gatcttgttt ggttcccggt tgcaaagtgg ggtcccatca     180
cgtttcagtg gcagtggatc tgggacggat ttcactctca ccatcagcag tctgcaacct     240
```

```
gaagattttg ctacgtacta ctgtgcgcag actgggacgc atcccacgac gttcggccaa    300
gggaccaagg tggaaatcaa acgg                                            324
```

<210> SEQ ID NO 9
<211> LENGTH: 324
<212> TYPE: DNA
<213> ORGANISM: Artificial Sequence
<220> FEATURE:
<223> OTHER INFORMATION: Nucleotide

<400> SEQUENCE: 9

```
gacatccaga tgacccagtc tccatcctcc ctgtctgcat ctgtaggaga ccgtgtcacc     60
atcacttgcc gggcaagtcg tccgattggg acgacgttaa gttggtacca gcagaaacca    120
gggaaagccc ctaagctcct gatcctttgg aattcccgtt tgcaaagtgg ggtcccatca    180
cgtttcagtg gcagtggatc tgggacagat ttcactctca ccatcagcag tctgcaacct    240
gaagattttg ctacgtacta ctgtgcgcag gctgggacgc atcctacgac gttcggccaa    300
gggaccaagg tggaaatcaa acgg                                            324
```

<210> SEQ ID NO 10
<211> LENGTH: 324
<212> TYPE: DNA
<213> ORGANISM: Artificial Sequence
<220> FEATURE:
<223> OTHER INFORMATION: Nucleotide

<400> SEQUENCE: 10

```
gacatccaga tgacccagtc tccatcctcc ctgtctgcat ctgtaggaga ccgtgtcacc     60
atcacttgcc gggcaagtcg tccgattggg acgacgttaa gttggtacca gcagaaacca    120
gggaaagccc ctaagctcct gatcctttgg aattcccgtt tgcaaagtgg ggtcccatca    180
cgtttcagtg gcagtggatc tgggacagat ttcactctca ccatcagcag tctgcaacct    240
gaagattttg ctacgtacta ctgtgcgcag gctgggacgc atcctacgac gttcggccaa    300
gggaccaagg tggaaatcaa acgg                                            324
```

<210> SEQ ID NO 11
<211> LENGTH: 120
<212> TYPE: PRT
<213> ORGANISM: Homo sapiens

<400> SEQUENCE: 11

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Gln Tyr
             20                  25                  30

Arg Met His Trp Val Arg Gln Ala Pro Gly Lys Ser Leu Glu Trp Val
         35                  40                  45

Ser Ser Ile Asp Thr Arg Gly Ser Ser Thr Tyr Tyr Ala Asp Pro Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Val Thr Met Phe Ser Pro Phe Phe Asp Tyr Trp Gly Gln
            100                 105                 110

Gly Thr Leu Val Thr Val Ser Ser
        115                 120
```

<210> SEQ ID NO 12
<211> LENGTH: 123
<212> TYPE: PRT
<213> ORGANISM: Homo sapiens

<400> SEQUENCE: 12

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Asp Tyr
            20                  25                  30

Gly Met Arg Trp Val Arg Gln Ala Pro Gly Lys Gly Leu Glu Trp Val
        35                  40                  45

Ser Ser Ile Thr Arg Thr Gly Arg Val Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Trp Arg Asn Arg His Gly Glu Tyr Leu Ala Asp Phe Asp Tyr
            100                 105                 110

Trp Gly Gln Gly Thr Leu Val Thr Val Ser Ser
        115                 120
```

<210> SEQ ID NO 13
<211> LENGTH: 120
<212> TYPE: PRT
<213> ORGANISM: Homo sapiens

<400> SEQUENCE: 13

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Met Arg Tyr
            20                  25                  30

Arg Met His Trp Val Arg Gln Ala Pro Gly Lys Gly Leu Glu Trp Val
        35                  40                  45

Ser Ser Ile Asp Ser Asn Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Arg Thr Glu Arg Ser Pro Val Phe Asp Tyr Trp Gly Gln
            100                 105                 110

Gly Thr Leu Val Thr Val Ser Ser
        115                 120
```

<210> SEQ ID NO 14
<211> LENGTH: 119
<212> TYPE: PRT
<213> ORGANISM: Homo sapiens

<400> SEQUENCE: 14

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Asp Tyr
            20                  25                  30
```

Glu Met His Trp Val Arg Gln Ala Pro Gly Lys Gly Leu Glu Trp Val
         35                  40                  45

Ser Ser Ile Ser Glu Ser Gly Thr Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Arg Arg Phe Ser Ala Ser Thr Phe Asp Tyr Trp Gly Gln Gly
            100                 105                 110

Thr Leu Val Thr Val Ser Ser
            115

<210> SEQ ID NO 15
<211> LENGTH: 119
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Gly His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Tyr Thr Gly His Trp Glu Pro Phe Asp Tyr Trp Gly Gln Gly
            100                 105                 110

Thr Leu Val Thr Val Ser Ser
            115

<210> SEQ ID NO 16
<211> LENGTH: 119
<212> TYPE: PRT
<213> ORGANISM: Homo sapiens

<400> SEQUENCE: 16

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Gly His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Tyr Thr Gly Arg Trp Glu Pro Tyr Asp Tyr Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Arg Trp Glu Pro Phe Asp Tyr Trp Gly Gln Gly
            100                 105                 110

Thr Leu Val Thr Val Ser Ser
        115

<210> SEQ ID NO 18
<211> LENGTH: 119
<212> TYPE: PRT
<213> ORGANISM: Homo sapiens

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 19
<211> LENGTH: 119
<212> TYPE: PRT
<213> ORGANISM: Homo sapiens

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr

```
                 20                  25                  30

Ser Met Gly Trp Val Arg Gln Ala Pro Gly Lys Gly Pro Glu Trp Val
            35                  40                  45

Ser Gln Ile Ser Asn Thr Gly Gly His Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 20
<211> LENGTH: 119
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
            35                  40                  45

Ser Gln Ile Ser Asn Thr Gly Gly His Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Met Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 21
<211> LENGTH: 119
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Lys Tyr
            20                  25                  30

Ser Met Gly Trp Val Arg Gln Ala Pro Gly Lys Asp Leu Glu Trp Val
            35                  40                  45

Ser Gln Ile Ser Asn Thr Gly Gly His Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
```

```
                    100                 105                 110

Thr Leu Val Thr Val Ser Ser
        115

<210> SEQ ID NO 22
<211> LENGTH: 119
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Lys Tyr
            20                  25                  30

Ser Met Gly Trp Val Arg Gln Ala Pro Gly Lys Asp Leu Glu Trp Val
        35                  40                  45

Ser Gln Ile Ser Asn Thr Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 23
<211> LENGTH: 119
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Arg Trp Glu Pro Phe Asp Tyr Trp Gly Gln Gly
            100                 105                 110

Thr Leu Val Thr Val Ser Ser
        115

<210> SEQ ID NO 24
<211> LENGTH: 119
<212> TYPE: PRT
<213> ORGANISM: Homo sapiens

<400> SEQUENCE: 24

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Arg Trp Glu Pro Phe Asp Tyr Trp Gly Gln Gly
            100                 105                 110

Thr Leu Val Thr Val Ser Ser
            115

<210> SEQ ID NO 25
<211> LENGTH: 119
<212> TYPE: PRT
<213> ORGANISM: Homo sapiens

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
            115

<210> SEQ ID NO 26
<211> LENGTH: 119
<212> TYPE: PRT
<213> ORGANISM: Homo sapiens

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp His Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 27
<211> LENGTH: 119
<212> TYPE: PRT
<213> ORGANISM: Homo sapiens

<400> SEQUENCE: 27

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 28
<211> LENGTH: 119
<212> TYPE: PRT
<213> ORGANISM: Homo sapiens

<400> SEQUENCE: 28

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Asn Thr Gly Asp His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 29
<211> LENGTH: 119
<212> TYPE: PRT
<213> ORGANISM: Homo sapiens

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Lys Tyr
            20                  25                  30

Ser Met Gly Trp Val Arg Gln Ala Pro Gly Lys Asp Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
            115

<210> SEQ ID NO 30
<211> LENGTH: 119
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Lys Tyr
            20                  25                  30

Ser Met Gly Trp Val Arg Gln Ala Pro Gly Lys Asp Leu Glu Trp Val
        35                  40                  45

Ser Gln Ile Ser Asn Thr Gly Asp His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
            115

<210> SEQ ID NO 31
<211> LENGTH: 119
<212> TYPE: PRT
<213> ORGANISM: Homo sapiens

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

-continued

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 32
<211> LENGTH: 119
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Glu Tyr Trp Gly Gln Gly
            100                 105                 110

Thr Leu Val Thr Val Ser Ser
        115

<210> SEQ ID NO 33
<211> LENGTH: 119
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Lys Pro Phe Glu Tyr Trp Gly Gln Gly
            100                 105                 110

Thr Leu Val Thr Val Ser Ser
        115

<210> SEQ ID NO 34
<211> LENGTH: 119
<212> TYPE: PRT
<213> ORGANISM: Homo sapiens

```
<400> SEQUENCE: 34

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Asp Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
                100                 105                 110

Thr Leu Val Thr Val Ser Ser
            115

<210> SEQ ID NO 35
<211> LENGTH: 119
<212> TYPE: PRT
<213> ORGANISM: Homo sapiens

<400> SEQUENCE: 35

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Asp Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Arg Pro Phe Glu Tyr Trp Gly Gln Gly
                100                 105                 110

Thr Leu Val Thr Val Ser Ser
            115

<210> SEQ ID NO 36
<211> LENGTH: 119
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ala Asn Thr Gly Asp Arg Arg Tyr Tyr Ala Asp Ser Val
     50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Ala Tyr Tyr Cys
                    85                  90                  95

Ala Ile Tyr Thr Gly Arg Trp Glu Pro Phe Asp Tyr Trp Gly Gln Gly
                100                 105                 110

Thr Leu Val Thr Val Ser Ser
            115

<210> SEQ ID NO 37
<211> LENGTH: 119
<212> TYPE: PRT
<213> ORGANISM: Homo sapiens

<400> SEQUENCE: 37

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Leu Glu Trp Val
            35                  40                  45

Ser Gln Ile Ser Asn Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ile Tyr Thr Gly Arg Trp Glu Pro Phe Asn Tyr Trp Gly Gln Gly
                100                 105                 110

Thr Leu Val Thr Val Ser Ser
            115

<210> SEQ ID NO 38
<211> LENGTH: 119
<212> TYPE: PRT
<213> ORGANISM: Homo sapiens

<400> SEQUENCE: 38

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Leu Glu Trp Val
            35                  40                  45

Ser Gln Ile Ser Asn Thr Gly Asp Arg Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ile Tyr Thr Gly Arg Trp Ala Pro Phe Glu Tyr Trp Gly Gln Gly
                100                 105                 110

Thr Leu Val Thr Val Ser Ser
            115

<210> SEQ ID NO 39
<211> LENGTH: 119
<212> TYPE: PRT
```

<213> ORGANISM: Homo sapiens

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Asp Asn Trp Gly Gln Gly
            100                 105                 110

Thr Leu Val Thr Val Ser Ser
        115

<210> SEQ ID NO 40
<211> LENGTH: 119
<212> TYPE: PRT
<213> ORGANISM: Homo sapiens

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Thr Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Gln Tyr Trp Gly Gln Gly
            100                 105                 110

Thr Leu Val Thr Val Ser Ser
        115

<210> SEQ ID NO 41
<211> LENGTH: 119
<212> TYPE: PRT
<213> ORGANISM: Homo sapiens

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 42
<211> LENGTH: 119
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Asp Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 43
<211> LENGTH: 119
<212> TYPE: PRT
<213> ORGANISM: Homo sapiens

<400> SEQUENCE: 43

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Gly Asp Arg Arg Tyr Tyr Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 44
```

<211> LENGTH: 119
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 45
<211> LENGTH: 119
<212> TYPE: PRT
<213> ORGANISM: Homo sapiens

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Lys Tyr Trp Gly Gln Gly
            100                 105                 110

Thr Leu Val Thr Val Ser Ser
        115

<210> SEQ ID NO 46
<211> LENGTH: 119
<212> TYPE: PRT
<213> ORGANISM: Homo sapiens

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ser Met Gly Trp Val Arg Gln Ala Pro Gly Lys Gly Leu Glu Trp Val
        35                  40                  45

```
Ser Gln Ile Ser Asn Thr Gly Glu Arg Arg Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Glu Tyr Trp Gly Gln Gly
            100                 105                 110

Thr Leu Val Thr Val Ser Ser
            115

<210> SEQ ID NO 47
<211> LENGTH: 119
<212> TYPE: PRT
<213> ORGANISM: Homo sapiens

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Asn Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Tyr Glu Tyr Trp Gly Gln Gly
            100                 105                 110

Thr Leu Val Thr Val Thr Ser
            115

<210> SEQ ID NO 48
<211> LENGTH: 119
<212> TYPE: PRT
<213> ORGANISM: Homo sapiens

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
            115
```

<210> SEQ ID NO 49
<211> LENGTH: 119
<212> TYPE: PRT
<213> ORGANISM: Homo sapiens

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Lys Pro Phe Glu Tyr Trp Gly Gln Gly
            100                 105                 110

Thr Leu Val Thr Val Ser Ser
            115

<210> SEQ ID NO 50
<211> LENGTH: 119
<212> TYPE: PRT
<213> ORGANISM: Homo sapiens

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
            115

<210> SEQ ID NO 51
<211> LENGTH: 119
<212> TYPE: PRT
<213> ORGANISM: Homo sapiens

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val

```
                      35                  40                  45

Ser Gln Ile Ala Asn Thr Gly Asp Arg Arg Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Arg Pro Phe Glu Tyr Trp Gly Gln Gly
            100                 105                 110

Thr Leu Val Thr Val Ser Ser
            115

<210> SEQ ID NO 52
<211> LENGTH: 119
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115

<210> SEQ ID NO 53
<211> LENGTH: 119
<212> TYPE: PRT
<213> ORGANISM: Homo sapiens

<400> SEQUENCE: 53

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Tyr Thr Gly Arg Trp Glu Pro Phe Val Tyr Trp Gly Gln Gly
            100                 105                 110

Thr Leu Val Thr Val Ser Ser
```

<210> SEQ ID NO 54
<211> LENGTH: 119
<212> TYPE: PRT
<213> ORGANISM: Homo sapiens

<400> SEQUENCE: 54

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Val Lys Tyr
             20                  25                  30
Ser Met Gly Trp Val Arg Gln Ala Pro Gly Lys Gly Leu Glu Trp Val
         35                  40                  45
Ser Gln Ile Ser Asn Thr Ala Asp Arg Thr Tyr Tyr Ala His Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ile Tyr Thr Gly Arg Trp Lys Pro Phe Glu Tyr Trp Gly Gln Gly
            100                 105                 110
Thr Leu Val Thr Val Ser Ser
        115
```

<210> SEQ ID NO 55
<211> LENGTH: 119
<212> TYPE: PRT
<213> ORGANISM: Homo sapiens

<400> SEQUENCE: 55

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Val Lys Tyr
             20                  25                  30
Ser Met Gly Trp Val Arg Gln Ala Pro Gly Lys Gly Leu Glu Trp Val
         35                  40                  45
Ser Gln Ile Ser Asn Thr Ala Asp Arg Thr Tyr Tyr Ala His Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ile Tyr Thr Gly Arg Trp Val Pro Phe Glu Tyr Trp Gly Gln Gly
            100                 105                 110
Thr Leu Val Thr Val Ser Ser
        115
```

<210> SEQ ID NO 56
<211> LENGTH: 119
<212> TYPE: PRT
<213> ORGANISM: Homo sapiens

<400> SEQUENCE: 56

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Val Lys Tyr
             20                  25                  30
```

```
Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
                100                 105                 110

Thr Leu Val Thr Val Ser Ser
        115

<210> SEQ ID NO 57
<211> LENGTH: 119
<212> TYPE: PRT
<213> ORGANISM: Homo sapiens

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
                100                 105                 110

Thr Leu Val Thr Val Ser Ser
        115

<210> SEQ ID NO 58
<211> LENGTH: 119
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
                100                 105                 110
```

```
Thr Leu Val Thr Val Ser Ser
        115

<210> SEQ ID NO 59
<211> LENGTH: 119
<212> TYPE: PRT
<213> ORGANISM: Homo sapiens

<400> SEQUENCE: 59

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Lys Pro Phe Glu Tyr Trp Gly Gln Gly
            100                 105                 110

Thr Leu Val Thr Val Ser Ser
        115

<210> SEQ ID NO 60
<211> LENGTH: 119
<212> TYPE: PRT
<213> ORGANISM: Homo sapiens

<400> SEQUENCE: 60

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 61
<211> LENGTH: 119
<212> TYPE: PRT
<213> ORGANISM: Homo sapiens

<400> SEQUENCE: 61

Glu Val Gln Leu Leu Glu Ser Gly Gly Gly Leu Val Gln Pro Gly Gly
 1               5                  10                  15
```

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
                100                 105                 110

Thr Leu Val Thr Val Ser Ser
            115

<210> SEQ ID NO 62
<211> LENGTH: 119
<212> TYPE: PRT
<213> ORGANISM: Homo sapiens

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
                100                 105                 110

Thr Leu Val Thr Val Ser Ser
            115

<210> SEQ ID NO 63
<211> LENGTH: 119
<212> TYPE: PRT
<213> ORGANISM: Homo sapiens

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110
Thr Leu Val Thr Val Ser Ser
        115

<210> SEQ ID NO 64
<211> LENGTH: 119
<212> TYPE: PRT
<213> ORGANISM: Homo sapiens

<400> SEQUENCE: 64

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Arg Tyr Tyr Ala Asp Ala Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Pro Phe Glu Tyr Trp Gly Gln Gly
            100                 105                 110

Thr Leu Val Thr Val Ser Ser
        115

<210> SEQ ID NO 65
<211> LENGTH: 119
<212> TYPE: PRT
<213> ORGANISM: Homo sapiens

<400> SEQUENCE: 65

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Arg Tyr Tyr Ala Asp Ala Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 66
<211> LENGTH: 119
<212> TYPE: PRT
<213> ORGANISM: Homo sapiens

<400> SEQUENCE: 66

Glu Val Gln Leu Leu Glu Ser Gly Gly Gly Leu Val Gln Pro Gly Gly

```
                1               5                  10                 15
Ser Leu Arg Leu Ser Cys Ala Ala Ser Gly Phe Thr Phe Val Lys Tyr
                20                 25                 30

Ser Met Gly Trp Val Arg Gln Ala Pro Gly Lys Gly Leu Glu Trp Val
                35                 40                 45

Ser Gln Ile Ser Asn Thr Gly Asp Arg Arg Tyr Tyr Ala Asp Ala Val
                50                 55                 60

Lys Gly Arg Phe Thr Ile Ser Arg Asp Asn Ser Lys Asn Thr Leu Tyr
 65                70                 75                 80

Leu Gln Met Asn Ser Leu Arg Ala Glu Asp Thr Ala Val Tyr Tyr Cys
                85                 90                 95

Ala Ile Tyr Thr Gly Arg Trp Arg Pro Phe Glu Tyr Trp Gly Gln Gly
                100                105                110

Thr Leu Val Thr Val Ser Ser
                115
```

<210> SEQ ID NO 67
<211> LENGTH: 119
<212> TYPE: PRT
<213> ORGANISM: Homo sapiens

<400> SEQUENCE: 67

```
Glu Val Gln Leu Leu Glu Ser Gly Gly Gly Leu Val Gln Pro Gly Gly
 1               5                  10                 15

Ser Leu Arg Leu Ser Cys Ala Ala Ser Gly Phe Thr Phe Val Lys Tyr
                20                 25                 30

Ser Met Gly Trp Val Arg Gln Ala Pro Gly Lys Gly Leu Glu Trp Val
                35                 40                 45

Ser Gln Ile Ser Asn Thr Gly Asp Arg Arg Tyr Tyr Ala Asp Ala Val
                50                 55                 60

Lys Gly Arg Phe Thr Ile Ser Arg Asp Asn Ser Lys Asn Thr Leu Tyr
 65                70                 75                 80

Leu Gln Met Asn Ser Leu Arg Ala Glu Asp Thr Ala Val Tyr Tyr Cys
                85                 90                 95

Ala Ile Tyr Thr Gly Arg Trp Ala Pro Phe Glu Tyr Trp Gly Gln Gly
                100                105                110

Thr Leu Val Thr Val Ser Ser
                115
```

<210> SEQ ID NO 68
<211> LENGTH: 119
<212> TYPE: PRT
<213> ORGANISM: Homo sapiens

<400> SEQUENCE: 68

```
Glu Val Gln Leu Leu Glu Ser Gly Gly Gly Leu Val Gln Pro Gly Gly
 1               5                  10                 15

Ser Leu Arg Leu Ser Cys Ala Ala Ser Gly Phe Thr Phe Leu Lys Phe
                20                 25                 30

Ser Met Gly Trp Val Arg Gln Ala Pro Gly Lys Gly Leu Glu Trp Val
                35                 40                 45

Ser Gln Ile Ala Asn Thr Gly Asp Arg Arg Tyr Tyr Ala Asp Ser Val
                50                 55                 60

Lys Gly Arg Phe Thr Ile Ser Arg Asp Asn Ser Lys Asn Thr Leu Tyr
 65                70                 75                 80

Leu Gln Met Asn Ser Leu Arg Ala Glu Asp Thr Ala Val Tyr Tyr Cys
```

```
                    85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115

<210> SEQ ID NO 69
<211> LENGTH: 119
<212> TYPE: PRT
<213> ORGANISM: Homo sapiens

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115

<210> SEQ ID NO 70
<211> LENGTH: 119
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
            115

<210> SEQ ID NO 71
<211> LENGTH: 119
<212> TYPE: PRT
<213> ORGANISM: Homo sapiens

<400> SEQUENCE: 71
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
            115

<210> SEQ ID NO 72
<211> LENGTH: 119
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Ile Tyr Thr Gly Arg Trp Pro Asp Phe Asp Tyr Trp Gly Gln Gly
            100                 105                 110

Thr Leu Val Thr Val Ser Ser
            115

<210> SEQ ID NO 73
<211> LENGTH: 119
<212> TYPE: PRT
<213> ORGANISM: Homo sapiens

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

-continued

Leu Gln Met Asn Ser Leu Arg Ala Glu Asp Thr Ala Ala Tyr Tyr Cys
                85                  90                  95

Ala Ile Tyr Thr Gly Arg Trp Pro Asp Phe Glu Tyr Trp Gly Gln Gly
            100                 105                 110

Thr Leu Val Thr Val Ser Ser
        115

<210> SEQ ID NO 74
<211> LENGTH: 119
<212> TYPE: PRT
<213> ORGANISM: Homo sapiens

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Pro Asp Phe Asp Tyr Trp Gly Gln Gly
            100                 105                 110

Thr Leu Val Thr Val Ser Ser
        115

<210> SEQ ID NO 75
<211> LENGTH: 119
<212> TYPE: PRT
<213> ORGANISM: Homo sapiens

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Pro Asp Phe Glu Tyr Trp Gly Gln Gly
            100                 105                 110

Thr Leu Val Thr Val Ser Ser
        115

<210> SEQ ID NO 76
<211> LENGTH: 119
<212> TYPE: PRT
<213> ORGANISM: Homo sapiens

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Tyr Thr Gly Arg Trp Pro Asp Phe Asp Tyr Trp Gly Gln Gly
            100                 105                 110

Thr Leu Val Thr Val Ser Ser
        115

<210> SEQ ID NO 77
<211> LENGTH: 119
<212> TYPE: PRT
<213> ORGANISM: Homo sapiens

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Tyr Thr Gly Arg Trp Pro Asp Phe Glu Tyr Trp Gly Gln Gly
            100                 105                 110

Thr Leu Val Thr Val Ser Ser
        115

<210> SEQ ID NO 78
<211> LENGTH: 119
<212> TYPE: PRT
<213> ORGANISM: Homo sapiens

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Ala Trp Gly Asp Arg Thr Tyr Tyr Ala Asp Ser Val
50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
            100                 105                 110

Thr Leu Val Thr Val Ser Ser
            115
```

<210> SEQ ID NO 79
<211> LENGTH: 119
<212> TYPE: PRT
<213> ORGANISM: Homo sapiens

<400> SEQUENCE: 79

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Pro Glu Trp Val
         35                  40                  45

Ser Gln Ile Ser Asp Gly Gly Gln Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
            100                 105                 110

Thr Leu Val Thr Val Ser Ser
            115
```

<210> SEQ ID NO 80
<211> LENGTH: 119
<212> TYPE: PRT
<213> ORGANISM: Homo sapiens

<400> SEQUENCE: 80

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Pro Glu Trp Val
         35                  40                  45

Ser Gln Ile Ser Asp Ser Gly Tyr Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
            100                 105                 110

Thr Leu Val Thr Val Ser Ser
            115
```

<210> SEQ ID NO 81
<211> LENGTH: 119

<212> TYPE: PRT
<213> ORGANISM: Homo sapiens

<400> SEQUENCE: 81

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Asp Gly Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115
```

<210> SEQ ID NO 82
<211> LENGTH: 119
<212> TYPE: PRT
<213> ORGANISM: Homo sapiens

<400> SEQUENCE: 82

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Asp Lys Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115
```

<210> SEQ ID NO 83
<211> LENGTH: 119
<212> TYPE: PRT
<213> ORGANISM: Homo sapiens

<400> SEQUENCE: 83

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Glu Thr Gly Arg Arg Thr Tyr Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
                100                 105                 110

Thr Leu Val Thr Val Ser Ser
            115

<210> SEQ ID NO 84
<211> LENGTH: 119
<212> TYPE: PRT
<213> ORGANISM: Homo sapiens

<400> SEQUENCE: 84

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Asn Asn Thr Gly Ser Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
                100                 105                 110

Thr Leu Val Thr Val Ser Ser
            115

<210> SEQ ID NO 85
<211> LENGTH: 119
<212> TYPE: PRT
<213> ORGANISM: Homo sapiens

<400> SEQUENCE: 85

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Pro Glu Trp Val
         35                  40                  45

Ser Gln Ile Ser Asn Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
                100                 105                 110

Thr Leu Val Thr Val Ser Ser
            115
```

-continued

<210> SEQ ID NO 86
<211> LENGTH: 119
<212> TYPE: PRT
<213> ORGANISM: Homo sapiens

<400> SEQUENCE: 86

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115
```

<210> SEQ ID NO 87
<211> LENGTH: 119
<212> TYPE: PRT
<213> ORGANISM: Homo sapiens

<400> SEQUENCE: 87

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115
```

<210> SEQ ID NO 88
<211> LENGTH: 119
<212> TYPE: PRT
<213> ORGANISM: Homo sapiens

<400> SEQUENCE: 88

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45
```

```
Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115

<210> SEQ ID NO 89
<211> LENGTH: 119
<212> TYPE: PRT
<213> ORGANISM: Homo sapiens

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
            100                 105                 110

Thr Leu Val Thr Val Ser Ser
            115

<210> SEQ ID NO 90
<211> LENGTH: 119
<212> TYPE: PRT
<213> ORGANISM: Homo sapiens

<400> SEQUENCE: 90

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Thr His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115
```

<210> SEQ ID NO 91
<211> LENGTH: 119
<212> TYPE: PRT
<213> ORGANISM: Homo sapiens

<400> SEQUENCE: 91

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Arg Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115
```

<210> SEQ ID NO 92
<211> LENGTH: 119
<212> TYPE: PRT
<213> ORGANISM: Homo sapiens

<400> SEQUENCE: 92

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Leu Asn Thr Ala Asp Arg Thr Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115
```

<210> SEQ ID NO 93
<211> LENGTH: 119
<212> TYPE: PRT
<213> ORGANISM: Homo sapiens

<400> SEQUENCE: 93

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30
```

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Asp His Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
             100                 105                 110

Thr Leu Val Thr Val Ser Ser
        115

<210> SEQ ID NO 94
<211> LENGTH: 119
<212> TYPE: PRT
<213> ORGANISM: Homo sapiens

<400> SEQUENCE: 94

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Arg Tyr Tyr Ala His Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
             100                 105                 110

Thr Leu Val Thr Val Ser Ser
        115

<210> SEQ ID NO 95
<211> LENGTH: 119
<212> TYPE: PRT
<213> ORGANISM: Homo sapiens

<400> SEQUENCE: 95

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Arg Tyr Tyr Asp His Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
             100                 105                 110

```
Thr Leu Val Thr Val Ser Ser
        115

<210> SEQ ID NO 96
<211> LENGTH: 119
<212> TYPE: PRT
<213> ORGANISM: Homo sapiens

<400> SEQUENCE: 96

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Tyr Thr Gly Arg Trp Val Ser Phe Glu Tyr Trp Gly Gln Gly
            100                 105                 110

Thr Leu Val Thr Val Ser Ser
        115

<210> SEQ ID NO 97
<211> LENGTH: 119
<212> TYPE: PRT
<213> ORGANISM: Homo sapiens

<400> SEQUENCE: 97

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Tyr Thr Gly Arg Trp Val Ser Phe Glu Tyr Trp Gly Gln Gly
            100                 105                 110

Thr Leu Val Thr Val Ser Ser
        115

<210> SEQ ID NO 98
<211> LENGTH: 119
<212> TYPE: PRT
<213> ORGANISM: Homo sapiens

<400> SEQUENCE: 98

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
```

```
                    20                  25                  30
Ser Met Gly Trp Val Arg Gln Ala Pro Gly Lys Gly Leu Glu Trp Val
                35                  40                  45

Ser Gln Ile Ser Asn Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Val Tyr Thr Gly Arg Trp Val Pro Phe Glu Tyr Trp Gly Gln Gly
                100                 105                 110

Thr Leu Val Thr Val Ser Ser
            115
```

<210> SEQ ID NO 99
<211> LENGTH: 119
<212> TYPE: PRT
<213> ORGANISM: Homo sapiens

<400> SEQUENCE: 99

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Leu Glu Trp Val
                35                  40                  45

Ser Gln Ile Ser Asn Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Leu Tyr Thr Gly Arg Trp Val Pro Phe Glu Tyr Trp Gly Gln Gly
                100                 105                 110

Thr Leu Val Thr Val Ser Ser
            115
```

<210> SEQ ID NO 100
<211> LENGTH: 119
<212> TYPE: PRT
<213> ORGANISM: Homo sapiens

<400> SEQUENCE: 100

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Leu Glu Trp Val
                35                  40                  45

Ser Gln Ile Ala Asn Thr Ala Asp Arg Arg Tyr Tyr Ala His Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
```

Thr Leu Val Thr Val Ser Ser
        115

<210> SEQ ID NO 101
<211> LENGTH: 119
<212> TYPE: PRT
<213> ORGANISM: Homo sapiens

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 102
<211> LENGTH: 119
<212> TYPE: PRT
<213> ORGANISM: Homo sapiens

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Arg Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 103
<211> LENGTH: 119
<212> TYPE: PRT
<213> ORGANISM: Homo sapiens

<400> SEQUENCE: 103

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Ala Asp Arg Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
                100                 105                 110

Thr Leu Val Thr Val Ser Ser
            115
```

```
<210> SEQ ID NO 104
<211> LENGTH: 119
<212> TYPE: PRT
<213> ORGANISM: Homo sapiens

<400> SEQUENCE: 104
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
                100                 105                 110

Thr Leu Val Thr Val Ser Ser
            115
```

```
<210> SEQ ID NO 105
<211> LENGTH: 119
<212> TYPE: PRT
<213> ORGANISM: Homo sapiens

<400> SEQUENCE: 105
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Arg Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Ile Tyr Thr Gly Arg Trp Glu Pro Phe Val Tyr Trp Gly Gln Gly
            100                 105                 110

Thr Leu Val Thr Val Ser Ser
        115
```

<210> SEQ ID NO 106
<211> LENGTH: 119
<212> TYPE: PRT
<213> ORGANISM: Homo sapiens

<400> SEQUENCE: 106

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Ala Asp Arg Arg Tyr Tyr Ala His Ala Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115
```

<210> SEQ ID NO 107
<211> LENGTH: 119
<212> TYPE: PRT
<213> ORGANISM: Homo sapiens

<400> SEQUENCE: 107

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Val Asn Thr Gly Asp Arg Arg Tyr Tyr Ala Asp Ala Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115
```

<210> SEQ ID NO 108
<211> LENGTH: 119
<212> TYPE: PRT
<213> ORGANISM: Homo sapiens

<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala Asp Ala Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
            115

<210> SEQ ID NO 109
<211> LENGTH: 119
<212> TYPE: PRT
<213> ORGANISM: Homo sapiens

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Asp His Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115

<210> SEQ ID NO 110
<211> LENGTH: 119
<212> TYPE: PRT
<213> ORGANISM: Homo sapiens

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Asp His Ser Val
50                  55                  60

Lys Gly Arg Phe Thr Ile Ser Arg Asp Asn Ser Lys Asn Thr Leu Tyr
65                  70                  75                  80

-continued

```
Leu Gln Met Asn Ser Leu Arg Ala Glu Asp Thr Ala Val Tyr Tyr Cys
                 85                  90                  95

Ala Ile Tyr Thr Gly Arg Trp Arg Pro Phe Glu Tyr Trp Gly Gln Gly
            100                 105                 110

Thr Leu Val Thr Val Ser Ser
        115

<210> SEQ ID NO 111
<211> LENGTH: 119
<212> TYPE: PRT
<213> ORGANISM: Homo sapiens

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Asp His Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 112
<211> LENGTH: 119
<212> TYPE: PRT
<213> ORGANISM: Homo sapiens

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ser His Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 113
<211> LENGTH: 119
<212> TYPE: PRT
<213> ORGANISM: Homo sapiens
```

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Thr His Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 114
<211> LENGTH: 119
<212> TYPE: PRT
<213> ORGANISM: Homo sapiens

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Thr Asp Ala Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 115
<211> LENGTH: 119
<212> TYPE: PRT
<213> ORGANISM: Homo sapiens

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
50                  55                  60

Lys Gly Arg Phe Thr Ile Ser Arg Asp Asn Ser Lys Asn Thr Leu Tyr

```
                    65                  70                  75                  80
Leu Gln Met Asn Ser Leu Arg Ala Glu Asp Thr Ala Val Tyr Tyr Cys
                85                  90                  95
Ala Ile Tyr Thr Gly Arg Trp Ala Pro Phe Glu Tyr Trp Gly Gln Gly
            100                 105                 110
Thr Leu Val Thr Val Ser Ser
        115

<210> SEQ ID NO 116
<211> LENGTH: 119
<212> TYPE: PRT
<213> ORGANISM: Homo sapiens

<400> SEQUENCE: 116

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Leu Lys Tyr
             20                  25                  30
Ser Met Gly Trp Val Arg Gln Ala Pro Gly Lys Gly Leu Glu Trp Val
         35                  40                  45
Ser Gln Ile Ser Asp Thr Ala Asp Arg Thr Tyr Tyr Ala His Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Ile Tyr Thr Gly Arg Trp Ala Pro Phe Glu Tyr Trp Gly Gln Gly
            100                 105                 110
Thr Leu Val Thr Val Ser Ser
        115

<210> SEQ ID NO 117
<211> LENGTH: 119
<212> TYPE: PRT
<213> ORGANISM: Homo sapiens

<400> SEQUENCE: 117

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Phe Lys Tyr
             20                  25                  30
Ser Met Gly Trp Val Arg Gln Ala Pro Gly Lys Gly Leu Glu Trp Val
         35                  40                  45
Ser Gln Ile Ala Asp Thr Gly Asp Arg Arg Tyr Tyr Asp Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Ile Tyr Thr Gly Arg Trp Glu Pro Phe Val Tyr Trp Gly Gln Gly
            100                 105                 110
Thr Leu Val Thr Val Ser Ser
        115

<210> SEQ ID NO 118
<211> LENGTH: 119
<212> TYPE: PRT
```

<213> ORGANISM: Homo sapiens

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
            115

<210> SEQ ID NO 119
<211> LENGTH: 119
<212> TYPE: PRT
<213> ORGANISM: Homo sapiens

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
            115

<210> SEQ ID NO 120
<211> LENGTH: 119
<212> TYPE: PRT
<213> ORGANISM: Homo sapiens

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 121
<211> LENGTH: 119
<212> TYPE: PRT
<213> ORGANISM: Homo sapiens

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Ala Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 122
<211> LENGTH: 119
<212> TYPE: PRT
<213> ORGANISM: Homo sapiens

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Gly Asp Arg Arg Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 123

```
<211> LENGTH: 119
<212> TYPE: PRT
<213> ORGANISM: Homo sapiens

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Gly Asp Arg Tyr Tyr Asp Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 124
<211> LENGTH: 119
<212> TYPE: PRT
<213> ORGANISM: Homo sapiens

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Gly Pro Phe Val Tyr Trp Gly Gln Gly
            100                 105                 110

Thr Leu Val Thr Val Ser Ser
        115

<210> SEQ ID NO 125
<211> LENGTH: 119
<212> TYPE: PRT
<213> ORGANISM: Homo sapiens

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45
```

-continued

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Ala Tyr Trp Gly Gln Gly
            100                 105                 110

Thr Leu Val Thr Val Ser Ser
        115

<210> SEQ ID NO 126
<211> LENGTH: 119
<212> TYPE: PRT
<213> ORGANISM: Homo sapiens

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Gly Pro Phe Gln Tyr Trp Gly Gln Gly
            100                 105                 110

Thr Leu Val Thr Val Ser Ser
        115

<210> SEQ ID NO 127
<211> LENGTH: 119
<212> TYPE: PRT
<213> ORGANISM: Homo sapiens

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Gln Tyr Trp Gly Gln Gly
            100                 105                 110

Thr Leu Val Thr Val Ser Ser
        115

<210> SEQ ID NO 128
<211> LENGTH: 119
<212> TYPE: PRT
<213> ORGANISM: Homo sapiens

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 129
<211> LENGTH: 119
<212> TYPE: PRT
<213> ORGANISM: Homo sapiens

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Gln Tyr Trp Gly Gln Gly
            100                 105                 110

Thr Leu Val Thr Val Ser Ser
        115

<210> SEQ ID NO 130
<211> LENGTH: 119
<212> TYPE: PRT
<213> ORGANISM: Homo sapiens

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val

```
                35                  40                  45
Ser Gln Ile Ser Asp Thr Ala Asp Arg Thr Tyr Tyr Ala His Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ile Tyr Thr Gly Arg Trp Val Pro Phe Gln Tyr Trp Gly Gln Gly
                100                 105                 110
Thr Leu Val Thr Val Ser Ser
            115

<210> SEQ ID NO 131
<211> LENGTH: 119
<212> TYPE: PRT
<213> ORGANISM: Homo sapiens

<400> SEQUENCE: 131

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Val Lys Tyr
            20                  25                  30
Ser Met Gly Trp Val Arg Gln Ala Pro Gly Lys Gly Leu Glu Trp Val
        35                  40                  45
Ser Gln Ile Ser Asp Thr Gly Asp Arg Arg Tyr Tyr Asp His Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ile Tyr Thr Gly Arg Trp Ala Pro Phe Glu Tyr Trp Gly Gln Gly
                100                 105                 110
Thr Leu Val Thr Val Ser Ser
            115

<210> SEQ ID NO 132
<211> LENGTH: 119
<212> TYPE: PRT
<213> ORGANISM: Homo sapiens

<400> SEQUENCE: 132

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Leu Lys Tyr
            20                  25                  30
Ser Met Gly Trp Val Arg Gln Ala Pro Gly Lys Gly Leu Glu Trp Val
        35                  40                  45
Ser Gln Ile Ser Asp Thr Ala Asp Arg Thr Tyr Tyr Ala His Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ile Tyr Thr Gly Arg Trp Val Pro Phe Glu Tyr Trp Gly Gln Gly
                100                 105                 110
Thr Leu Val Thr Val Ser Ser
```

<210> SEQ ID NO 133
<211> LENGTH: 119
<212> TYPE: PRT
<213> ORGANISM: Homo sapiens

<400> SEQUENCE: 133

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 134
<211> LENGTH: 119
<212> TYPE: PRT
<213> ORGANISM: Homo sapiens

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
            100                 105                 110

Thr Leu Val Thr Val Ser Ser
        115

<210> SEQ ID NO 135
<211> LENGTH: 119
<212> TYPE: PRT
<213> ORGANISM: Homo sapiens

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

```
Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Asp His Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Arg Pro Phe Glu Tyr Trp Gly Gln Gly
                100                 105                 110

Thr Leu Val Thr Val Ser Ser
        115

<210> SEQ ID NO 136
<211> LENGTH: 119
<212> TYPE: PRT
<213> ORGANISM: Homo sapiens

<400> SEQUENCE: 136

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Lys Tyr
             20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Asp His Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
                100                 105                 110

Thr Leu Val Thr Val Ser Ser
        115

<210> SEQ ID NO 137
<211> LENGTH: 119
<212> TYPE: PRT
<213> ORGANISM: Homo sapiens

<400> SEQUENCE: 137

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Leu Lys Tyr
             20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Asp His Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
                100                 105                 110
```

Thr Leu Val Thr Val Ser Ser
        115

<210> SEQ ID NO 138
<211> LENGTH: 119
<212> TYPE: PRT
<213> ORGANISM: Homo sapiens

<400> SEQUENCE: 138

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Leu Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ser His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 139
<211> LENGTH: 119
<212> TYPE: PRT
<213> ORGANISM: Homo sapiens

<400> SEQUENCE: 139

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ser His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 140
<211> LENGTH: 119
<212> TYPE: PRT
<213> ORGANISM: Homo sapiens

<400> SEQUENCE: 140

Glu Val Gln Leu Leu Glu Ser Gly Gly Gly Leu Val Gln Pro Gly Gly
 1               5                  10                  15

```
Ser Leu Arg Leu Ser Cys Ala Ala Ser Gly Phe Thr Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Thr His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
            115

<210> SEQ ID NO 141
<211> LENGTH: 119
<212> TYPE: PRT
<213> ORGANISM: Homo sapiens

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Thr His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
            115

<210> SEQ ID NO 142
<211> LENGTH: 119
<212> TYPE: PRT
<213> ORGANISM: Homo sapiens

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 143
<211> LENGTH: 119
<212> TYPE: PRT
<213> ORGANISM: Homo sapiens

<400> SEQUENCE: 143

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Leu Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 144
<211> LENGTH: 119
<212> TYPE: PRT
<213> ORGANISM: Homo sapiens

<400> SEQUENCE: 144

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Leu Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Gly Asp Arg Arg Tyr Tyr Asp His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 145
<211> LENGTH: 119
<212> TYPE: PRT
<213> ORGANISM: Homo sapiens

<400> SEQUENCE: 145

Glu Val Gln Leu Leu Glu Ser Gly Gly Gly Leu Val Gln Pro Gly Gly

```
                1               5                   10                  15
Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Leu Glu Trp Val
                35                  40                  45

Ser Gln Ile Ala Asp Thr Ala Asp Arg Thr Tyr Tyr Ala His Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
                100                 105                 110

Thr Leu Val Thr Val Ser Ser
                115

<210> SEQ ID NO 146
<211> LENGTH: 119
<212> TYPE: PRT
<213> ORGANISM: Homo sapiens

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
                20                  25                  30

Ser Met Gly Trp Val Arg Gln Ala Pro Gly Lys Gly Leu Glu Trp Val
                35                  40                  45

Ser Gln Ile Ser Asp Thr Ala Asp Arg Thr Tyr Tyr Ala His Ala Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
                100                 105                 110

Thr Leu Val Thr Val Ser Ser
                115

<210> SEQ ID NO 147
<211> LENGTH: 119
<212> TYPE: PRT
<213> ORGANISM: Homo sapiens

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Leu Glu Trp Val
                35                  40                  45

Ser Gln Ile Ala Asp Thr Ala Asp Arg Thr Tyr Tyr Asp His Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Ile Tyr Thr Gly Arg Trp Val Pro Phe Glu Tyr Trp Gly Gln Gly
            100                 105                 110

Thr Leu Val Thr Val Ser Ser
            115

<210> SEQ ID NO 148
<211> LENGTH: 119
<212> TYPE: PRT
<213> ORGANISM: Homo sapiens

<400> SEQUENCE: 148

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Ala Asp Arg Thr Tyr Tyr Asp His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
            115

<210> SEQ ID NO 149
<211> LENGTH: 119
<212> TYPE: PRT
<213> ORGANISM: Homo sapiens

<400> SEQUENCE: 149

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Ala Asp Arg Arg Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115

<210> SEQ ID NO 150
<211> LENGTH: 119
<212> TYPE: PRT
<213> ORGANISM: Homo sapiens

<400> SEQUENCE: 150
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Arg Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
                100                 105                 110

Thr Leu Val Thr Val Ser Ser
            115

<210> SEQ ID NO 151
<211> LENGTH: 119
<212> TYPE: PRT
<213> ORGANISM: Homo sapiens

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Ala Asp Arg Arg Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
                100                 105                 110

Thr Leu Val Thr Val Ser Ser
            115

<210> SEQ ID NO 152
<211> LENGTH: 119
<212> TYPE: PRT
<213> ORGANISM: Homo sapiens

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Arg Tyr Tyr Asp His Ala Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115
```

<210> SEQ ID NO 153
<211> LENGTH: 119
<212> TYPE: PRT
<213> ORGANISM: Homo sapiens

<400> SEQUENCE: 153

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Ala Asp Arg Arg Tyr Tyr Asp His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115
```

<210> SEQ ID NO 154
<211> LENGTH: 119
<212> TYPE: PRT
<213> ORGANISM: Homo sapiens

<400> SEQUENCE: 154

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Ala Asp Arg Arg Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115
```

<210> SEQ ID NO 155
<211> LENGTH: 119
<212> TYPE: PRT
<213> ORGANISM: Homo sapiens

<400> SEQUENCE: 155

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Tyr Tyr Asp Asp Ala Val
50                  55                  60

Lys Gly Arg Phe Thr Ile Thr Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 156
<211> LENGTH: 119
<212> TYPE: PRT
<213> ORGANISM: Homo sapiens

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ala Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Tyr Thr Gly Arg Trp Pro Phe Glu Tyr Trp Gly Gln Gly
            100                 105                 110

Thr Leu Val Thr Val Ser Ser
        115

<210> SEQ ID NO 157
<211> LENGTH: 119
<212> TYPE: PRT
<213> ORGANISM: Homo sapiens

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Gly His Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Arg Trp Glu Pro Phe Glu Tyr Trp Gly Gln Gly
            100                 105                 110

Thr Leu Val Thr Val Ser Ser
            115

<210> SEQ ID NO 158
<211> LENGTH: 119
<212> TYPE: PRT
<213> ORGANISM: Homo sapiens

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115

<210> SEQ ID NO 159
<211> LENGTH: 360
<212> TYPE: DNA
<213> ORGANISM: Artificial Sequence
<220> FEATURE:
<223> OTHER INFORMATION: Nucleotide

<400> SEQUENCE: 159
gaggtgcagc tgttggagtc tgggggaggc ttggtacagc ctgggggtc cctgcgtctc      60 tcctgtgcag cctccggatt cacctttagt cagtatagga tgcattgggt ccgccaggct    120
ccagggaaga gtctagagtg ggtctcaagt attgatacta ggggttcgtc tacatactac    180
gcagaccccg tgaagggccg gttcaccatc tcccgcgaca attccaagaa cacgctgtat    240
ctgcaaatga acagcctgcg tgccgaggac accgcggtat attactgtgc gaaagctgtg    300
acgatgtttt ctccttttt tgactactgg ggtcaggaa ccctggtcac cgtctcgagc      360

<210> SEQ ID NO 160
<211> LENGTH: 369
<212> TYPE: DNA
<213> ORGANISM: Artificial Sequence
<220> FEATURE:
<223> OTHER INFORMATION: Nucleotide

<400> SEQUENCE: 160
gaggtgcagc tgttggagtc tgggggaggc ttggtacagc ctgggggtc cctgcgtctc      60 tcctgtgcag cctccggatt cacctttgct gattatggga tgcgttgggt ccgccaggct    120

```
ccagggaagg gtctagagtg ggtctcatct attacgcgga ctggtcgtgt tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatggcgg    300
aatcggcatg gtgagtatct tgctgatttt gactactggg gtcagggaac cctggtcacc    360
gtctcgagc                                                             369
```

```
<210> SEQ ID NO 161
<211> LENGTH: 360
<212> TYPE: DNA
<213> ORGANISM: Artificial Sequence
<220> FEATURE:
<223> OTHER INFORMATION: Nucleotide

<400> SEQUENCE: 161
gaggtgcagc tgttggagtc tgggggaggc ttggtacagc ctggggggtc cctgcgtctc    60
tcctgtgcag cctccggatt cacctttatg aggtatagga tgcattgggt ccgccaggct    120
ccagggaagg gtctagagtg ggtctcatcg attgattcta atggttctag tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatcgt    300
acggagcgtt cgccggtttt tgactactgg ggtcagggaa ccctggtcac cgtctcgagc    360
```

```
<210> SEQ ID NO 162
<211> LENGTH: 357
<212> TYPE: DNA
<213> ORGANISM: Artificial Sequence
<220> FEATURE:
<223> OTHER INFORMATION: Nucleotide

<400> SEQUENCE: 162
gaggtgcagc tgttggagtc tgggggaggc ttggtgcagc ctggggggtc cctgcgtctc    60
tcctgtgcag cctccggatt cacctttgtt gattatgaga tgcattgggt ccgccaggct    120
ccagggaagg gtctagagtg ggtctcatct attagtgaga gtggtacgac gacatactac    180
gcagactccg tgaagggccg gttcaccatc tcccgcgaca attccaagaa cacgctgtat    240
ctgcaaatga acagcctgcg tgccgaggac accgcggtat attactgtgc gaaacgtcgt    300
ttttctgctt ctacgtttga ctactggggt caggaacccc tggtcaccgt ctcgagc      357
```

```
<210> SEQ ID NO 163
<211> LENGTH: 357
<212> TYPE: DNA
<213> ORGANISM: Artificial Sequence
<220> FEATURE:
<223> OTHER INFORMATION: Nucleotide

<400> SEQUENCE: 163
gaggtgcagc tgttggagtc tgggggaggc ttggtacagc ctggggggtc cctgcgtctc    60
tcctgtgcag cctccggatt cacctttgtt aagtattcga tggggtgggt ccgccaggct    120
ccagggaagg gtctagagtg ggtctcacag atttcgaata cgggtggtca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatacg    300
ggtcattggg agccttttga ctactggggt caggaacccc tggtcaccgt ctcgagc      357
```

```
<210> SEQ ID NO 164
```

<211> LENGTH: 357
<212> TYPE: DNA
<213> ORGANISM: Artificial Sequence
<220> FEATURE:
<223> OTHER INFORMATION: Nucleotide

<400> SEQUENCE: 164

| | | | | | |
|---|---|---|---|---|---|
| gaggtgcagc | tgttggagtc | tgggggaggc | ttggtacagc | ctgggggtc | cctgcgtctc | 60 |
| tcctgtgcag | cctccggatt | cacctttgtt | aagtattcga | tggggtgggt | ccgccaggct | 120 |
| ccagggaagg | gtctagagtg | ggtctcacag | atttcgaata | cgggtggtca | tacatactac | 180 |
| gcagactccg | tgaagggccg | gttcaccatc | tcccgcgaca | attccaagaa | cacgctgtat | 240 |
| ctgcaaatga | acagcctgcg | tgccgaggac | accgcggtat | attactgtgc | gaaatatacg | 300 |
| ggtcgttggg | agccttatga | ctactggggt | cagggaaccc | tggtcaccgt | ctcgagc | 357 |

<210> SEQ ID NO 165
<211> LENGTH: 357
<212> TYPE: DNA
<213> ORGANISM: Artificial Sequence
<220> FEATURE:
<223> OTHER INFORMATION: Nucleotide

<400> SEQUENCE: 165

| | | | | | |
|---|---|---|---|---|---|
| gaggtgcagc | tgttggagtc | tgggggaggc | ttggtacagc | ctgggggtc | cctgcgtctc | 60 |
| tcctgtgcag | cctccggatt | cacctttgtt | aagtattcga | tggggtgggt | ccgccaggct | 120 |
| ccagggaagg | gtctagagtg | ggtctcacag | atttcgaata | cgggtggtca | tacatactac | 180 |
| gcagactccg | tgaagggccg | gttcaccatc | tcccgcgaca | attccaagaa | cacgctgtat | 240 |
| ctgcaaatga | acagcctgcg | tgccgaggac | accgcggtat | attactgtgc | gaaatatacg | 300 |
| ggtcgttggg | agcctttga | ctactggggt | cagggaaccc | tggtcaccgt | ctcgagc | 357 |

<210> SEQ ID NO 166
<211> LENGTH: 357
<212> TYPE: DNA
<213> ORGANISM: Artificial Sequence
<220> FEATURE:
<223> OTHER INFORMATION: Nucleotide

<400> SEQUENCE: 166

| | | | | | |
|---|---|---|---|---|---|
| gaggtgcagc | tgttggagtc | tgggggaggc | ttggtacagc | ctgggggtc | cctgcgtctc | 60 |
| tcctgtgcag | cctccggatt | cacctttgtt | aagtattcga | tggggtgggt | ccgccaggct | 120 |
| ccagggaagg | gtctagagtg | ggtctcacag | atttcgaata | cgggtggtca | tacatactac | 180 |
| gcagactccg | tgaagggccg | gttcaccatc | tcccgcgaca | attccaagaa | cacgctgtat | 240 |
| ctgcaaatga | acagcctgcg | tgccgaggac | accgcggtat | attactgtgc | gaaatatacg | 300 |
| ggtcgttggg | agcctttga | gtactggggt | cagggaaccc | tggtcaccgt | ctcgagc | 357 |

<210> SEQ ID NO 167
<211> LENGTH: 357
<212> TYPE: DNA
<213> ORGANISM: Artificial Sequence
<220> FEATURE:
<223> OTHER INFORMATION: Nucleotide

<400> SEQUENCE: 167

| | | | | | |
|---|---|---|---|---|---|
| gaggtgcagc | tgttggagtc | tgggggaggc | ttggtacagc | ctgggggtc | cctgcgtctc | 60 |
| tcctgtgcag | cctccggatt | cacctttgtt | aagtattcga | tggggtgggt | ccgccaggct | 120 |
| ccagggaagg | gtctagagtg | ggtctcacag | atttcggata | ctgctgatcg | tacatactac | 180 |

```
gcacacgcgg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357
```

<210> SEQ ID NO 168
<211> LENGTH: 357
<212> TYPE: DNA
<213> ORGANISM: Artificial Sequence
<220> FEATURE:
<223> OTHER INFORMATION: Nucleotide

<400> SEQUENCE: 168

```
gaggtgcagc tgttggagtc tgggggaggc ttggtacagc ctgggggtc cctgcgtctc     60 tcctgtgcag cctccggatt cacctttgtt aagtattcga tggggtgggt ccgccaggct   120
ccagggaagg gtctagagtg gtctcacag atttcgaata cgggtggtca tacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcaccgt ctcgagc     357
```

<210> SEQ ID NO 169
<211> LENGTH: 357
<212> TYPE: DNA
<213> ORGANISM: Artificial Sequence
<220> FEATURE:
<223> OTHER INFORMATION: Nucleotide

<400> SEQUENCE: 169

```
gaggtgcagc tgttggagtc tgggggaggc ttggtacagc ctgggggtc cctgcgtctc     60 tcctgtgcag cctccggatt cacctttgtt aagtattcga tgggatgggt ccgccaggct   120
ccagggaaag gtccagagtg gtctcacag atttcgaata cgggtggtca tacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcacagt ctcgagc     357
```

<210> SEQ ID NO 170
<211> LENGTH: 357
<212> TYPE: DNA
<213> ORGANISM: Artificial Sequence
<220> FEATURE:
<223> OTHER INFORMATION: Nucleotide

<400> SEQUENCE: 170

```
gaggtgcagc tgttggagtc tgggggaggc ttggtacagc ctgggggtc cctgcgtctc     60 tcctgtgcag cctccggatt cacctttgtt aagtattcga tggggtgggt ccgccaggct   120
ccagggaagg gtctagagtg gtctcacag atttcgaata cgggtggtca tacatactac   180
gcagactccg tgaagggccg gttcaccata tcccgcgaca attccaagaa cacgctgtat   240
atgcaaatga acagcctgcg tgccgaggac accgcggtat attactgtgc gatatatacg   300
ggtcgttggg agccttttga ctactggggt cagggaaccc tggtcaccgt ctcgagc     357
```

<210> SEQ ID NO 171
<211> LENGTH: 357
<212> TYPE: DNA
<213> ORGANISM: Artificial Sequence
<220> FEATURE:

<223> OTHER INFORMATION: Nucleotide

<400> SEQUENCE: 171

```
gaggtgcagc tgttggagtc tgggggaggc ttggtacagc ctggggggtc cctgcgtctc     60
tcctgtgcag cctccggatt cacctttggt aagtattcga tggggtgggt ccgccaggct    120
ccagggaagg atctagagtg ggtctcacag atttcgaata cgggtggtca tacatactac    180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt caggaaccc tggtcaccgt ctcgagc        357
```

<210> SEQ ID NO 172
<211> LENGTH: 357
<212> TYPE: DNA
<213> ORGANISM: Artificial Sequence
<220> FEATURE:
<223> OTHER INFORMATION: Nucleotide

<400> SEQUENCE: 172

```
gaggtgcagc tgttggagtc aggggggaggc ttggtacagc ctggggggtc cctgcgtctc    60
tcctgtgcag cctccggatt cacctttgtt aagtattcga tggggtgggt ccgccaggct    120
ccagggaagg gtctagagtg ggtctcacag atttcgaata cgggtggtca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatacg    300
ggtcgttggg agccttttga ccactggggt caggggaccc tggtcaccgt ctcgagc       357
```

<210> SEQ ID NO 173
<211> LENGTH: 357
<212> TYPE: DNA
<213> ORGANISM: Artificial Sequence
<220> FEATURE:
<223> OTHER INFORMATION: Nucleotide

<400> SEQUENCE: 173

```
gaggtgcagc tgttggagtc tgggggaggc ttggtacagc ctggggggtc cctgcgtctc     60
tcctgtgcag cctccggatt cacctttgtt aagtattcga tggggtgggt ccgccaggct    120
ccagggaagg gtctagagtg ggtctcacag atttcgaata cgggtgatca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatacg    300
ggtcgttggg agccttttga ctactggggt caggaaccc tggtcaccgt ctcgagc        357
```

<210> SEQ ID NO 174
<211> LENGTH: 357
<212> TYPE: DNA
<213> ORGANISM: Artificial Sequence
<220> FEATURE:
<223> OTHER INFORMATION: Nucleotide

<400> SEQUENCE: 174

```
gaggtgcagc tgttggagtc tgggggaggc ttggtacagc ctggggggtc cctgcgtctc     60
tcctgtgcag cctccggatt cacctttgtt aagtattcga tggggtgggt ccgccaggct    120
ccagggaagg gtctagagtg ggtctcacag atttcgaata cgggtgatcg tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatacg    300
```

```
ggtcgttggg agccttttga ctactggggt cagggaaccc tggtcaccgt ctcgagc      357
```

<210> SEQ ID NO 175
<211> LENGTH: 357
<212> TYPE: DNA
<213> ORGANISM: Artificial Sequence
<220> FEATURE:
<223> OTHER INFORMATION: Nucleotide

<400> SEQUENCE: 175

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg ggtctcacag atttcgaata cgggtgatcg tacatactac    180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc      357
```

<210> SEQ ID NO 176
<211> LENGTH: 357
<212> TYPE: DNA
<213> ORGANISM: Artificial Sequence
<220> FEATURE:
<223> OTHER INFORMATION: Nucleotide

<400> SEQUENCE: 176

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg ggtctcacag atttcgaata cgggtgatca tacatactac    180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc      357
```

<210> SEQ ID NO 177
<211> LENGTH: 357
<212> TYPE: DNA
<213> ORGANISM: Artificial Sequence
<220> FEATURE:
<223> OTHER INFORMATION: Nucleotide

<400> SEQUENCE: 177

```
gaggtgcagc tgttggagtc tgggggaggc ttggtacagc ctgggggtc cctgcgtctc      60
tcctgtgcag cctccggatt cacctttgtt aagtattcga tgggatgggt ccgccaggct    120
ccagggaaag gtccagagtg ggtctcacag atttcgaata cgggtgatcg tacatactac    180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcacagt ctcgagc      357
```

<210> SEQ ID NO 178
<211> LENGTH: 357
<212> TYPE: DNA
<213> ORGANISM: Artificial Sequence
<220> FEATURE:
<223> OTHER INFORMATION: Nucleotide

<400> SEQUENCE: 178

```
gaggtgcagc tgttggagtc tggggggaggc ttggtacagc ctggggggtc cctgcgtctc    60
tcctgtgcag cctccggatt cacctttgtt aagtattcga tgggatgggt ccgccaggct   120
ccagggaaag gtccagagtg ggtctcacag atttcgaata cgggtgatca tacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcacagt ctcgagc     357
```

```
<210> SEQ ID NO 179
<211> LENGTH: 357
<212> TYPE: DNA
<213> ORGANISM: Artificial Sequence
<220> FEATURE:
<223> OTHER INFORMATION: Nucleotide

<400> SEQUENCE: 179
```

```
gaggtgcagc tgttggagtc tggggggaggc ttggtacagc ctggggggtc cctgcgtctc    60
tcctgtgcag cctccggatt cacctttggt aagtattcga tggggtgggt ccgccaggct   120
ccagggaagg atctagagtg ggtctcacag atttcgaata cgggtgatcg tacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcaccgt ctcgagc     357
```

```
<210> SEQ ID NO 180
<211> LENGTH: 357
<212> TYPE: DNA
<213> ORGANISM: Artificial Sequence
<220> FEATURE:
<223> OTHER INFORMATION: Nucleotide

<400> SEQUENCE: 180
```

```
gaggtgcagc tgttggagtc tggggggaggc ttggtacagc ctggggggtc cctgcgtctc    60
tcctgtgcag cctccggatt cacctttggt aagtattcga tggggtgggt ccgccaggct   120
ccagggaagg atctagagtg ggtctcacag atttcgaata cgggtgatca tacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcaccgt ctcgagc     357
```

```
<210> SEQ ID NO 181
<211> LENGTH: 357
<212> TYPE: DNA
<213> ORGANISM: Artificial Sequence
<220> FEATURE:
<223> OTHER INFORMATION: Nucleotide

<400> SEQUENCE: 181
```

```
gaggtgcagc tgttggagtc tggggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcgaata cgggtgatcg tacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc     357
```

<210> SEQ ID NO 182
<211> LENGTH: 357
<212> TYPE: DNA
<213> ORGANISM: Artificial Sequence
<220> FEATURE:
<223> OTHER INFORMATION: Nucleotide

<400> SEQUENCE: 182

```
gaggtgcagc tgttggagtc tgggggaggc ttggtacagc ctgggggggtc cctgcgtctc      60
tcctgtgcag cctccggatt cacctttgtt aagtattcga tggggtgggt ccgccaggct     120
ccagggaagg gtctagagtg ggtctcacag atttcgaata cgggtgatcg tacatactac     180
gcagactccg tgaagggccg gttcaccatc tcccgcgaca attccaagaa cacgctgtat     240
ctgcaaatga acagcctgcg tgctgaggac accgcggtat attactgtgc gatatatacg     300
ggtcgttggg agccttttga gtactggggt caggaaccc tggtcaccgt ctcgagc         357
```

<210> SEQ ID NO 183
<211> LENGTH: 357
<212> TYPE: DNA
<213> ORGANISM: Artificial Sequence
<220> FEATURE:
<223> OTHER INFORMATION: Nucleotide

<400> SEQUENCE: 183

```
gaggtgcagc tgttggagtc tgggggaggc ttggtacagc ctgggggggtc cctgcgtctc      60
tcctgtgcag cctccggatt cacctttgtt aagtattcga tggggtgggt ccgccaggct     120
ccagggaagg gtctagagtg ggtctcacag atttcgaata cgggtgatcg tacatactac     180
gcggactccg tgaagggccg gttcaccatc tcccgcgaca attccaagaa cacgctgtat     240
ctgcaaatga acagcctgcg tgctgaggac accgcggtat attactgtgc gatatatacg     300
ggtcgttgga agccttttga gtactggggt caggaaccc tggtcaccgt ctcgagc         357
```

<210> SEQ ID NO 184
<211> LENGTH: 357
<212> TYPE: DNA
<213> ORGANISM: Artificial Sequence
<220> FEATURE:
<223> OTHER INFORMATION: Nucleotide

<400> SEQUENCE: 184

```
gaggtgcagc tgttggagtc tgggggaggc ttggtacagc ctgggggggtc cctgcgtctc      60
tcctgtgcag cctccggatt cacctttgtt aagtattcga tggggtgggt ccgccaggct     120
ccagggaagg gtctagagtg ggtctcacag atttcgaata cgggtgatcg tacatactac     180
gcagactccg tgaagggccg gttcaccatc tcccgcgaca attccaagaa cacgctgtat     240
ctgcaaatga acagcctgcg tgctgaggac accgcggtat attactgtgc gatatatact     300
gggcgttggg tgccttttga gtactggggt caggaaccc tggtcaccgt ctcgagc         357
```

<210> SEQ ID NO 185
<211> LENGTH: 357
<212> TYPE: DNA
<213> ORGANISM: Artificial Sequence
<220> FEATURE:
<223> OTHER INFORMATION: Nucleotide

<400> SEQUENCE: 185

```
gaggtgcagc tgttggagtc tgggggaggc ttggtacagc ctgggggggtc cctgcgtctc      60
tcctgtgcag cctccggatt cacctttgtt aagtattcga tggggtgggt ccgccaggct     120
```

| | |
|---|---|
| ccagggaagg gtctagagtg gtctcacag atttcgaata cgggtgatcg tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcgttgga ggccttttga gtactggggt cagggaaccc tggtcaccgt ctcgagc | 357 |

<210> SEQ ID NO 186
<211> LENGTH: 357
<212> TYPE: DNA
<213> ORGANISM: Artificial Sequence
<220> FEATURE:
<223> OTHER INFORMATION: Nucleotide

<400> SEQUENCE: 186

| | |
|---|---|
| gaggtgcagc tgttggagtc tgggggaggc ttggtacagc ctgggggggtc cctgcgtctc | 60 |
| tcctgtgcag cctccggatt caccttttgtt aagtattcga tggggtgggt ccgccaggct | 120 |
| ccagggaagg gtctagagtg gtctcacag attgcgaata cgggtgatcg tagatactac | 180 |
| gcagactctg tgaagggccg gttcaccatc tcccgcgaca attccaagaa cacgctgtat | 240 |
| ctgcaaatga acagcctgcg tgccgaggac accgcggcat attactgtgc gatatatacg | 300 |
| ggtcgttggg agccttttga ctactggggt cagggaaccc tggtcaccgt ctcgagc | 357 |

<210> SEQ ID NO 187
<211> LENGTH: 357
<212> TYPE: DNA
<213> ORGANISM: Artificial Sequence
<220> FEATURE:
<223> OTHER INFORMATION: Nucleotide

<400> SEQUENCE: 187

| | |
|---|---|
| gaggtgcagc tgttggagtc tgggggaggc ttggtacagc ctgggggggtc cctgcgtctc | 60 |
| tcctgtgcag cctccggatt caccttttgtt aagtattcga tggggtgggt ccgccaggct | 120 |
| ccagggaagg gtctagagtg gtctcacag atttcgaata ctgctgatcg tacatactac | 180 |
| gcacactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcgttggg agcctttttaa ctactggggt cagggaaccc tggtcaccgt ctcgagc | 357 |

<210> SEQ ID NO 188
<211> LENGTH: 357
<212> TYPE: DNA
<213> ORGANISM: Artificial Sequence
<220> FEATURE:
<223> OTHER INFORMATION: Nucleotide

<400> SEQUENCE: 188

| | |
|---|---|
| gaggtgcagc tgttggagtc tgggggaggc ttggtacagc ctgggggggtc cctgcgtctc | 60 |
| tcctgtgcag cctccggatt caccttttgtt aagtattcga tggggtgggt ccgccaggct | 120 |
| ccagggaagg gtctagagtg gtctcacag atttcgaata cgggtgatcg tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcggtggg cgccttttga gtactggggt cagggaaccc tggtcaccgt ctcgagc | 357 |

<210> SEQ ID NO 189
<211> LENGTH: 357
<212> TYPE: DNA
<213> ORGANISM: Artificial Sequence

```
<220> FEATURE:
<223> OTHER INFORMATION: Nucleotide

<400> SEQUENCE: 189
gaggtgcagc tgttggagtc tgggggaggc ttggtacagc ctgggggtc cctgcgtctc      60 tcctgtgcag cctccggatt caccttttgtt aagtattcga tggggtgggt ccgccaggct   120
ccagggaagg gtctagagtg ggtctcacag atttcgaata cgggtgatcg tacatactac   180
gcagactccg tgaagggccg gttcaccatc tcccgcgaca attccaagaa ctcgctgtat   240
ctgcaaatga acagcctgcg tgccgaggac accgcggtat attactgtgc gatatatacg   300
ggtcgttggg tgccttttga caactggggt cagggaaccc tggtcaccgt ctcgagc      357

<210> SEQ ID NO 190
<211> LENGTH: 357
<212> TYPE: DNA
<213> ORGANISM: Artificial Sequence
<220> FEATURE:
<223> OTHER INFORMATION: Nucleotide

<400> SEQUENCE: 190
gaggtgcagc tgttggagtc tgggggaggc ttggtacagc ctgggggtc cctgcgtctc      60 tcctgtgcag cctccggatt cacctttatt acgtattcga tggggtgggt ccgccaggct   120
ccagggaagg gtctagagtg ggtctcacag atttcgaata cgggtgatcg tacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttca gtactggggt cagggaaccc tggtcaccgt ctcgagc      357

<210> SEQ ID NO 191
<211> LENGTH: 357
<212> TYPE: DNA
<213> ORGANISM: Artificial Sequence
<220> FEATURE:
<223> OTHER INFORMATION: Nucleotide

<400> SEQUENCE: 191
gaggtgcagc tgttggagtc tgggggaggc ttggtacagc ctgggggtc cctgcgtctc      60 tcctgtgcag cctccggatt caccttttggt aagtattcga tggggtgggt ccgccaggct  120
ccagggaagg gtctagagtg ggtctcacag atttcgaata cgggtgatcg tacatactac   180
gcggactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcaccgt ctcgagc      357

<210> SEQ ID NO 192
<211> LENGTH: 357
<212> TYPE: DNA
<213> ORGANISM: Artificial Sequence
<220> FEATURE:
<223> OTHER INFORMATION: Nucleotide

<400> SEQUENCE: 192
gaggtgcagc tgttggagtc tgggggaggc ttggtacagc ctgggggtc cctgcgtctc      60 tcctgtgcag cctccggatt caccttttttt aagtattcga tggggtgggt ccgccaggct  120
ccagggaagg gtctagagtg ggtctcacag atttcgaata cgggtgatcg tacatactac   180
gcagactccg tgaagggccg gttcaccatc tcccgcgaca attccaagaa cacgctgtat   240
```
ctgcaaatga acagcctgcg tgccgaagac accgcggtat attactgtgc gatatatacg    300
ggtcgttggg agccttttga ctactggggt cagggaaccc tggtcaccgt ctcgagc       357

<210> SEQ ID NO 193
<211> LENGTH: 357
<212> TYPE: DNA
<213> ORGANISM: Artificial Sequence
<220> FEATURE:
<223> OTHER INFORMATION: Nucleotide

<400> SEQUENCE: 193
gaggtgcagc tgttggagtc tgggggaggc ttggtacagc ctgggggtc cctgcgtctc     60 tcctgtgcag cctccggatt cacctttgtt aagtattcga tggggtgggt ccgccaggct    120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357

<210> SEQ ID NO 194
<211> LENGTH: 357
<212> TYPE: DNA
<213> ORGANISM: Artificial Sequence
<220> FEATURE:
<223> OTHER INFORMATION: Nucleotide

<400> SEQUENCE: 194
gaggtgcagc tgttggagtc tgggggaggc ttggtacagc ctgggggtc cctgcgtctc     60 tcctgtgcag cctccggatt cacctttgtt aagtattcga tggggtgggt ccgccaggct    120
ccagggaagg gtctagagtg ggtctcacag atttcgaata cgggtgatcg tagatactac    180
gcagacgcgg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357

<210> SEQ ID NO 195
<211> LENGTH: 357
<212> TYPE: DNA
<213> ORGANISM: Artificial Sequence
<220> FEATURE:
<223> OTHER INFORMATION: Nucleotide

<400> SEQUENCE: 195
gaggtgcagc tgttggagtc tgggggaggc ttggtacagc ctgggggtc cctgcgtctc     60 tcctgtgcag cctccggatt cacctttgtt aagtattcga tggggtgggt ccgccaggct    120
ccagggaagg gtctagagtg ggtctcacag atttcgaata cgggtgatcg tacatactac    180
gcagactccg tgaagggccg gttcaccatc tcccgcgaca attccaagaa cacgctgtat    240
ctgcaaatga acagcctgcg tgctgaggac accgcggtat attactgtgc gatatatacg    300
ggtcgttggg agcctttta gtactggggt cagggaaccc tggtcaccgt ctcgagc        357

<210> SEQ ID NO 196
<211> LENGTH: 357
<212> TYPE: DNA
<213> ORGANISM: Artificial Sequence
<220> FEATURE:
<223> OTHER INFORMATION: Nucleotide

<400> SEQUENCE: 196

| gaggtgcagc tgttggagtc tggggaggc ttggtacagc ctgggggtc cctgcgtctc | 60 |
| tcctgtgcag cctccggatt cacctttagt aagtattcga tggggtgggt ccgccaggct | 120 |
| ccagggaagg gtctagagtg gtctcacag atttcgaata cgggtgagcg tagatactac | 180 |
| gcagactcag tgaagggccg gttcaccatc tcccgcgaca atcccaagaa cacgctgtat | 240 |
| ctgcaaatga acagcctgcg tgccgaggac accgcggtat attactgtgc gatatatacg | 300 |
| ggtcggtggg agccttttga atactgggt cagggaaccc tggtcaccgt ctcgagc | 357 |

<210> SEQ ID NO 197
<211> LENGTH: 357
<212> TYPE: DNA
<213> ORGANISM: Artificial Sequence
<220> FEATURE:
<223> OTHER INFORMATION: Nucleotide

<400> SEQUENCE: 197

| gaggtgcagc tgttggagtc tggggaggc ttggtacagc ctgggggtc cctgcgtctc | 60 |
| tcctgtgcag cctccggatt cacctttgtt aactattcga tggggtgggt ccgccaggct | 120 |
| ccagggaagg gtctagagtg gtctcacag atttcgaata cgggtgatcg tacatactac | 180 |
| gcggactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcgttggg agccttatga gtactgggt cagggaaccc tggtcaccgt cacgagc | 357 |

<210> SEQ ID NO 198
<211> LENGTH: 357
<212> TYPE: DNA
<213> ORGANISM: Artificial Sequence
<220> FEATURE:
<223> OTHER INFORMATION: Nucleotide

<400> SEQUENCE: 198

| gaggtgcagc tgttggagtc tggggaggc ttggtacagc ctgggggtc cctgcgtctc | 60 |
| tcctgtgcag cctccggatt cacctttgtt aagtattcga tggggtgggt ccgccaggct | 120 |
| ccagggaagg gtctagagtg gtctcacag attgcgaata cgggtgatcg tagatactac | 180 |
| gcagactctg tgaagggccg gttcaccatc tcccgcgata attccaagaa cacactgtat | 240 |
| ctgcaaatga acagcctgcg tgccgaggac accgcggtat attactgtgc gatatatacg | 300 |
| ggtcgttggg agccttttgt ctactgggt cagggaaccc tggtcaccgt ctcgagc | 357 |

<210> SEQ ID NO 199
<211> LENGTH: 357
<212> TYPE: DNA
<213> ORGANISM: Artificial Sequence
<220> FEATURE:
<223> OTHER INFORMATION: Nucleotide

<400> SEQUENCE: 199

| gaggtgcagc tgttggagtc tggggaggc ttggtacagc ctgggggtc cctgcgtctc | 60 |
| tcctgtgcag cctccggatt cacctttgtt aagtattcga tggggtgggt ccgccaggct | 120 |
| ccagggaagg gtctagagtg gtctcacag attgcgaata cgggtgatcg tagatactac | 180 |
| gcagactctg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcgttgga agccttttga gtactgggt cagggaaccc tggtcaccgt ctcgagc | 357 |

<210> SEQ ID NO 200
<211> LENGTH: 357
<212> TYPE: DNA
<213> ORGANISM: Artificial Sequence
<220> FEATURE:
<223> OTHER INFORMATION: Nucleotide

<400> SEQUENCE: 200

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
ccagggaagg gtctagagtg ggtctcacag attgcgaata cgggtgatcg tagatactac   180
gcagactctg tgaagggccg gttcaccatc tcccgcgaca attccaagaa cacgctgtat   240
ctgcaaatga acagcctgcg tgctgaggac accgcggtat attactgtgc gatatatact   300
gggcgttggg tgccttttga gtactggggt cagggaaccc tggtcaccgt ctcgagc      357
```

<210> SEQ ID NO 201
<211> LENGTH: 357
<212> TYPE: DNA
<213> ORGANISM: Artificial Sequence
<220> FEATURE:
<223> OTHER INFORMATION: Nucleotide

<400> SEQUENCE: 201

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
ccagggaagg gtctagagtg ggtctcacag attgcgaata cgggtgatcg tagatactac   180
gcagactctg tgaagggccg gttcaccatc tcccgcgaca attccaagaa cacgctgtat   240
ctgcaaatga acagcctgcg tgccgaggac accgcggtat attactgtgc gatatatacg   300
ggtcgttgga ggccttttga gtactggggt cagggaaccc tggtcaccgt ctcgagc      357
```

<210> SEQ ID NO 202
<211> LENGTH: 357
<212> TYPE: DNA
<213> ORGANISM: Artificial Sequence
<220> FEATURE:
<223> OTHER INFORMATION: Nucleotide

<400> SEQUENCE: 202

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
ccagggaagg gtctagagtg ggtctcacag attgcgaata cgggtgatcg tagatactac   180
gcagactctg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 203
<211> LENGTH: 357
<212> TYPE: DNA
<213> ORGANISM: Artificial Sequence
<220> FEATURE:
<223> OTHER INFORMATION: Nucleotide

<400> SEQUENCE: 203

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
```

```
ccagggaagg gtctagagtg ggtctcacag atttcgaata ctgctgatcg tacatactac      180
gcacactccg tgaagggccg gttcaccatc tcccgcgaca attccaagaa cacgctgtat      240
ctgcaaatga acagcctgcg tgccgaggac accgcggtat attactgtgc ggtatatacg      300
ggtcgttggg agccttttgt ctactggggt cagggaaccc tggtcaccgt ctcgagc         357
```

<210> SEQ ID NO 204
<211> LENGTH: 357
<212> TYPE: DNA
<213> ORGANISM: Artificial Sequence
<220> FEATURE:
<223> OTHER INFORMATION: Nucleotide

<400> SEQUENCE: 204

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcgaata ctgctgatcg tacatactac     180
gcacactccg tgaagggccg gttcaccatc tcccgcgaca attccaagaa cacgctgtat     240
ctgcaaatga acagcctgcg tgctgaggac accgcggtat attactgtgc gatatatacg     300
ggtcgttgga agccttttga gtactggggt cagggaaccc tggtcaccgt ctcgagc        357
```

<210> SEQ ID NO 205
<211> LENGTH: 357
<212> TYPE: DNA
<213> ORGANISM: Artificial Sequence
<220> FEATURE:
<223> OTHER INFORMATION: Nucleotide

<400> SEQUENCE: 205

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcgaata ctgctgatcg tacatactac     180
gcacactccg tgaagggccg gttcaccatc tcccgcgaca attccaagaa cacgctgtat     240
ctgcaaatga acagcctgcg tgctgaggac accgcggtat attactgtgc gatatatact     300
gggcgttggg tgccttttga gtactggggt cagggaaccc tggtcaccgt ctcgagc        357
```

<210> SEQ ID NO 206
<211> LENGTH: 357
<212> TYPE: DNA
<213> ORGANISM: Artificial Sequence
<220> FEATURE:
<223> OTHER INFORMATION: Nucleotide

<400> SEQUENCE: 206

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcgaata ctgctgatcg tacatactac     180
gcacactccg tgaagggccg gttcaccatc tcccgcgaca attccaagaa cacgctgtat     240
ctgcaaatga acagcctgcg tgccgaggac accgcggtat attactgtgc gatatatacg     300
ggtcgttgga ggccttttga gtactggggt cagggaaccc tggtcaccgt ctcgagc        357
```

<210> SEQ ID NO 207
<211> LENGTH: 357
<212> TYPE: DNA

```
<213> ORGANISM: Artificial Sequence
<220> FEATURE:
<223> OTHER INFORMATION: Nucleotide

<400> SEQUENCE: 207
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg ggtctcacag atttcgaata ctgctgatcg tacatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357

<210> SEQ ID NO 208
<211> LENGTH: 357
<212> TYPE: DNA
<213> ORGANISM: Artificial Sequence
<220> FEATURE:
<223> OTHER INFORMATION: Nucleotide

<400> SEQUENCE: 208
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357

<210> SEQ ID NO 209
<211> LENGTH: 357
<212> TYPE: DNA
<213> ORGANISM: Artificial Sequence
<220> FEATURE:
<223> OTHER INFORMATION: Nucleotide

<400> SEQUENCE: 209
gaggtgcagc tgttggagtc tgggggaggc ttggtacagc ctgggggtc cctgcgtctc      60 tcctgtgcag cctccggatt cacctttgtt aagtattcga tggggtgggt ccgccaggcc    120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgctgaggac accgcggtat attactgtgc gatatatacg    300
ggtcgttgga agccttttga gtactggggt cagggaaccc tggtcaccgt ctcgagc       357

<210> SEQ ID NO 210
<211> LENGTH: 357
<212> TYPE: DNA
<213> ORGANISM: Artificial Sequence
<220> FEATURE:
<223> OTHER INFORMATION: Nucleotide

<400> SEQUENCE: 210
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg ggtctcacag atttcggata cgggtgatcg tagatactac    180
gatgactctg tgaagggccg gttcaccatc tcccgcgaca attccaagaa cacgctgtat    240
```

```
ctgcaaatga acagcctgcg tgccgaggac accgcggtat attactgtgc gatatatact    300
gggcgttggg tgccttttga gtactggggt cagggaaccc tggtcaccgt ctcgagc       357
```

<210> SEQ ID NO 211
<211> LENGTH: 357
<212> TYPE: DNA
<213> ORGANISM: Artificial Sequence
<220> FEATURE:
<223> OTHER INFORMATION: Nucleotide

<400> SEQUENCE: 211

```
gaggtgcagc tgttggagtc tgggggaggc ttggtacagc ctgggggtc cctgcgtctc     60 tcctgtgcag cctccggatt cacctttgtt aagtattcga tggggtgggt ccgccaggct    120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttgga ggccttttga gtactggggt cagggaaccc tggtcaccgt ctcgagc       357
```

<210> SEQ ID NO 212
<211> LENGTH: 357
<212> TYPE: DNA
<213> ORGANISM: Artificial Sequence
<220> FEATURE:
<223> OTHER INFORMATION: Nucleotide

<400> SEQUENCE: 212

```
gaggtgcagc tgttggagtc tgggggaggc ttggtacagc ctgggggtc cctgcgtctc     60 tcctgtgcag cctccggatt cacctttgtt aagtattcga tggggtgggt ccgccaggct    120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357
```

<210> SEQ ID NO 213
<211> LENGTH: 357
<212> TYPE: DNA
<213> ORGANISM: Artificial Sequence
<220> FEATURE:
<223> OTHER INFORMATION: Nucleotide

<400> SEQUENCE: 213

```
gaggtgcagc tgttggagtc tgggggaggc ttggtacagc ctgggggtc cctgcgtctc     60 tcctgtgcag cctccggatt caccttttgtt aagtattcga tggggtgggt ccgccaggct   120
ccagggaagg gtctagagtg ggtctcacag atttcgaata cgggtgatcg tagatactac    180
gcagacgcgg tgaaggggcg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 214
<211> LENGTH: 357
<212> TYPE: DNA
<213> ORGANISM: Artificial Sequence
<220> FEATURE:
<223> OTHER INFORMATION: Nucleotide

<400> SEQUENCE: 214

```
gaggtgcagc tgttggagtc tgggggaggc ttggtacagc ctgggggtc cctgcgtctc    60
tcctgtgcag cctccggatt caccttttgtt aagtattcga tggggtgggt ccgccaggct   120
ccagggaagg gtctagagtg gtctcacag atttcgaata cgggtgatcg tagatactac    180
gcagacgcgg tgaaggggcg gttcaccatc tcccgcgaca attccaagaa cacgctgtat   240
ctgcaaatga acagcctgcg tgctgaggac accgcggtat attactgtgc gatatatacg   300
ggtcgttgga agccttttga gtactggggt cagggaaccc tggtcaccgt ctcgagc      357
```

<210> SEQ ID NO 215
<211> LENGTH: 357
<212> TYPE: DNA
<213> ORGANISM: Artificial Sequence
<220> FEATURE:
<223> OTHER INFORMATION: Nucleotide

<400> SEQUENCE: 215

```
gaggtgcagc tgttggagtc tgggggaggc ttggtacagc ctgggggtc cctgcgtctc    60
tcctgtgcag cctccggatt caccttttgtt aagtattcga tggggtgggt ccgccaggcc   120
ccagggaagg gtctagagtg gtctcacag atttcgaata cgggtgatcg tagatactac    180
gcagacgcgg tgaaggggcg gttcaccatc tcccgcgaca attccaagaa cacgctgtat   240
ctgcaaatga acagcctgcg tgccgaagac accgcggtat attactgtgc gatatatact   300
gggcgttggg tgccttttga gtactggggt cagggaaccc tggtcaccgt ctcgagc      357
```

<210> SEQ ID NO 216
<211> LENGTH: 357
<212> TYPE: DNA
<213> ORGANISM: Artificial Sequence
<220> FEATURE:
<223> OTHER INFORMATION: Nucleotide

<400> SEQUENCE: 216

```
gaggtgcagc tgttggagtc tgggggaggc ttggtacagc ctgggggtc cctgcgtctc    60
tcctgtgcag cctccggatt caccttttgtt aagtattcga tggggtgggt ccgccaggct   120
ccagggaagg gtctagagtg gtctcacag atttcgaata cgggtgatcg tagatactac    180
gcagacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcgttgga ggccttttga gtactggggt cagggaaccc tggtcaccgt ctcgagc      357
```

<210> SEQ ID NO 217
<211> LENGTH: 357
<212> TYPE: DNA
<213> ORGANISM: Artificial Sequence
<220> FEATURE:
<223> OTHER INFORMATION: Nucleotide

<400> SEQUENCE: 217

```
gaggtgcagc tgttggagtc tgggggaggc ttggtacagc ctgggggtc cctgcgtctc    60
tcctgtgcag cctccggatt caccttttgtt aagtattcga tggggtgggt ccgccaggct   120
ccagggaagg gtctagagtg gtctcacag atttcgaata cgggtgatcg tagatactac    180
gcagacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 218
<211> LENGTH: 357
<212> TYPE: DNA
<213> ORGANISM: Artificial Sequence
<220> FEATURE:
<223> OTHER INFORMATION: Nucleotide

<400> SEQUENCE: 218

```
gaggtgcagc tgttggagtc tgggggaggc ttggtacagc ctgggggtc cctgcgtctc      60
tcctgtgcag cctccggatt cacctttttg aagttttcga tggggtgggt ccgccaggct    120
ccagggaagg gtctagagtg gtctcacag attgcgaata cggtgatcg tagatactac      180
gcagactctg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357
```

<210> SEQ ID NO 219
<211> LENGTH: 357
<212> TYPE: DNA
<213> ORGANISM: Artificial Sequence
<220> FEATURE:
<223> OTHER INFORMATION: Nucleotide

<400> SEQUENCE: 219

```
gaggtgcagc tgttggagtc tgggggaggc ttggtacagc ctgggggtc cctgcgtctc      60
tcctgtgcag cctccggatt cacctttttg aagtattcga tggggtgggt ccgccaggct    120
ccagggaagg gtctagagtg gtctcacag atttcgaata ctgctgatcg tacatactac     180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357
```

<210> SEQ ID NO 220
<211> LENGTH: 357
<212> TYPE: DNA
<213> ORGANISM: Artificial Sequence
<220> FEATURE:
<223> OTHER INFORMATION: Nucleotide

<400> SEQUENCE: 220

```
gaggtgcagc tgttggagtc tgggggaggc ttggtacagc ctgggggtc cctgcgtctc      60
tcctgtgcag cctccggatt caccttttc aagtattcga tggggtgggt ccgccaggct     120
ccagggaagg gtctagagtg gtctcacag atttcggata cggtgatcg tagatactac      180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 221
<211> LENGTH: 357
<212> TYPE: DNA
<213> ORGANISM: Artificial Sequence
<220> FEATURE:
<223> OTHER INFORMATION: Nucleotide

<400> SEQUENCE: 221

```
gaggtgcagc tgttggagtc tgggggaggc ttggtacagc ctgggggtc cctgcgtctc      60
```

```
tcctgtgcag cctccggatt cacctttttg aagtattcga tggggtgggt ccgccaggct      120
ccagggaagg gtctagagtg gtctcacag  atttcggata cgggtgatcg tagatactac      180
gatgactctg tgaagggccg gttcaccatc tcccgcgaca attccaagaa cacgctgtat      240
ctgcaaatga acagcctgcg tgccgaggac accgcggtat attactgtgc gatatatacg      300
ggtcgttggg agccttttgt ctactggggt cagggaaccc tggtcaccgt ctcgagc         357
```

<210> SEQ ID NO 222
<211> LENGTH: 357
<212> TYPE: DNA
<213> ORGANISM: Artificial Sequence
<220> FEATURE:
<223> OTHER INFORMATION: Nucleotide

<400> SEQUENCE: 222

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct      120
ccagggaagg gtctagagtg gtctcacag  attgcgaata cgggtgatcg tagatactac      180
gcagactctg tgaagggccg gttcaccatc tcccgcgaca attccaagaa cacgctgtat      240
ctgcaaatga acagcctgcg tgccgaggac accgcggcat attactgtgc gatatatacg      300
ggtcggtggc ccgactttga ctactggggt cagggaaccc tggtcaccgt ctcgagc         357
```

<210> SEQ ID NO 223
<211> LENGTH: 357
<212> TYPE: DNA
<213> ORGANISM: Artificial Sequence
<220> FEATURE:
<223> OTHER INFORMATION: Nucleotide

<400> SEQUENCE: 223

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct      120
ccagggaagg gtctagagtg gtctcacag  attgcgaata cgggtgatcg tagatactac      180
gcagactctg tgaagggccg gttcaccatc tcccgcgaca attccaagaa cacgctgtat      240
ctgcaaatga acagcctgcg tgccgaggac accgcggcat attactgtgc gatatatacg      300
ggtcggtggc ccgactttga gtactggggt cagggaaccc tggtcaccgt ctcgagc         357
```

<210> SEQ ID NO 224
<211> LENGTH: 357
<212> TYPE: DNA
<213> ORGANISM: Artificial Sequence
<220> FEATURE:
<223> OTHER INFORMATION: Nucleotide sequences of anti-TNFR1 dAbs

<400> SEQUENCE: 224

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct      120
ccagggaagg gtctagagtg gtctcacag  atttcgaata ctgctgatcg tacatactac      180
gcacactccg tgaagggccg gttcaccatc tcccgcgaca attccaagaa cacgctgtat      240
ctgcaaatga acagcctgcg tgccgaggac accgcggtat attactgtgc gatatatacg      300
ggtcggtggc ccgactttga ctactggggt cagggaaccc tggtcaccgt ctcgagc         357
```

<210> SEQ ID NO 225
<211> LENGTH: 357

```
<212> TYPE: DNA
<213> ORGANISM: Artificial Sequence
<220> FEATURE:
<223> OTHER INFORMATION: Nucleotide

<400> SEQUENCE: 225
gaggtgcagc tgttggagtc tgggggaggc ttggtacagc ctgggggtc cctgcgtctc      60 tcctgtgcag cctccggatt cacctttgtt aagtattcga tggggtgggt ccgccaggct     120
ccagggaagg gtctagagtg ggtctcacag atttcgaata ctgctgatcg tacatactac    180
gcacactccg tgaagggccg gttcaccatc tcccgcgaca attccaagaa cacgctgtat     240
ctgcaaatga acagcctgcg tgccgaggac accgcggtat attactgtgc gatatatacg    300
ggtcggtggc ccgactttga gtactggggt cagggaaccc tggtcaccgt ctcgagc       357

<210> SEQ ID NO 226
<211> LENGTH: 357
<212> TYPE: DNA
<213> ORGANISM: Artificial Sequence
<220> FEATURE:
<223> OTHER INFORMATION: Nucleotide

<400> SEQUENCE: 226
gaggtgcagc tgttggagtc tgggggaggc ttggtacagc ctgggggtc cctgcgtctc      60 tcctgtgcag cctccggatt cacctttgtt aagtattcga tggggtgggt ccgccaggct     120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcggtggc ccgactttga ctactggggt cagggaaccc tggtcaccgt ctcgagc       357

<210> SEQ ID NO 227
<211> LENGTH: 357
<212> TYPE: DNA
<213> ORGANISM: Artificial Sequence
<220> FEATURE:
<223> OTHER INFORMATION: Nucleotide

<400> SEQUENCE: 227
gaggtgcagc tgttggagtc tgggggaggc ttggtacagc ctgggggtc cctgcgtctc      60 tcctgtgcag cctccggatt cacctttgtt aagtattcga tggggtgggt ccgccaggct     120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcggtggc ccgactttga gtactggggt cagggaaccc tggtcaccgt ctcgagc       357

<210> SEQ ID NO 228
<211> LENGTH: 357
<212> TYPE: DNA
<213> ORGANISM: Artificial Sequence
<220> FEATURE:
<223> OTHER INFORMATION: Nucleotide

<400> SEQUENCE: 228
gaggtgcagc tgttggagtc tgggggaggc ttggtacagc ctgggggtc cctgcgtctc      60 tcctgtgcag cctccggatt cacctttgtt aagtattcga tgggatgggt ccgccaggct    120
ccagggaaag gtccagagtg ggtctcacag atttcggcct ggggtgacag gacatactac    180
```

```
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 229
<211> LENGTH: 357
<212> TYPE: DNA
<213> ORGANISM: Artificial Sequence
<220> FEATURE:
<223> OTHER INFORMATION: Nucleotide

<400> SEQUENCE: 229

```
gaggtgcagc tgttggagtc tgggggaggc ttggtacagc ctggggggtc cctgcgtctc     60
tcctgtgcag cctccggatt cacctttgtt aagtattcga tggggtgggt ccgccaggct    120
ccagggaaag gtccagagtg gtctcacag atttcggacg cggtcagag acatactac       180 gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 230
<211> LENGTH: 357
<212> TYPE: DNA
<213> ORGANISM: Artificial Sequence
<220> FEATURE:
<223> OTHER INFORMATION: Nucleotide

<400> SEQUENCE: 230

```
gaggtgcagc tgttggagtc tgggggaggc ttggtacagc ctggggggtc cctgcgtctc     60
tcctgtgcag cctccggatt cacctttgtt aagtattcga tgggatgggt ccgccaggct    120
ccagggaaag gtccagagtg gtctcacag atttcggact ccggttaccg cacatactac    180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 231
<211> LENGTH: 357
<212> TYPE: DNA
<213> ORGANISM: Artificial Sequence
<220> FEATURE:
<223> OTHER INFORMATION: Nucleotide

<400> SEQUENCE: 231

```
gaggtgcagc tgttggagtc tgggggaggc ttggtacagc ctggggggtc cctgcgtctc     60
tcctgtgcag cctccggatt cacctttgtt aagtattcga tggggtgggt ccgccaggct    120
ccagggaagg gtccagagtg gtctcacag atttcggacg gggtacgcg gacatactac     180 gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 232
<211> LENGTH: 357
<212> TYPE: DNA
<213> ORGANISM: Artificial Sequence
<220> FEATURE:
<223> OTHER INFORMATION: Nucleotide

<400> SEQUENCE: 232

```
gaggtgcagc tgttggagtc tgggggaggc ttggtacagc ctgggggtc cctgcgtctc    60
tcctgtgcag cctccggatt cacctttgtt aagtattcga tgggatgggt ccgccaggct   120
ccagggaaag gtccagagtg gtctcacag atttcggaca agggtacgcg cacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcaccgt ctcgagc     357
```

<210> SEQ ID NO 233
<211> LENGTH: 357
<212> TYPE: DNA
<213> ORGANISM: Artificial Sequence
<220> FEATURE:
<223> OTHER INFORMATION: Nucleotide

<400> SEQUENCE: 233

```
gaggtgcagc tgttggagtc tgggggaggc ttggtacagc ctgggggtc cctgcgtctc    60
tcctgtgcag cctccggatt cacctttgtt aagtattcga tgggatgggt ccgccaggct   120
ccagggaaag gtccagagtg gtctcacag atttcggaga ccggtcgcag gacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcaccgt ctcgagc     357
```

<210> SEQ ID NO 234
<211> LENGTH: 357
<212> TYPE: DNA
<213> ORGANISM: Artificial Sequence
<220> FEATURE:
<223> OTHER INFORMATION: Nucleotide

<400> SEQUENCE: 234

```
gaggtgcagc tgttggagtc tgggggaggc ttggtacagc ctgggggtc cctgcgtctc    60
tcctgtgcag cctccggatt cacctttgtt aagtattcga tggggtgggt ccgccaggct   120
ccagggaagg gtctagagtg gtctcacag attaacaata cggggttcgac cacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcaccgt ctcgagc     357
```

<210> SEQ ID NO 235
<211> LENGTH: 357
<212> TYPE: DNA
<213> ORGANISM: Artificial Sequence
<220> FEATURE:
<223> OTHER INFORMATION: Nucleotide sequences of anti-TNFR1 dAbs

<400> SEQUENCE: 235

```
gaggtgcagc tgttggagtc tgggggaggc ttggtacagc ctgggggtc cctgcgtctc    60
tcctgtgcag cctccggatt cacctttgtt aagtattcga tggggtgggt ccgccaggct   120
ccagggaagg gtccagagtg gtctcacag atttcgaata ctgctgatcg tacatactac   180
gcacactccg tgaagggccg gttcaccatc tcccgcgaca attccaagaa cacgctgtat   240
ctgcaaatga acagcctgcg tgctgaggac accgcggtat attactgtgc gatatatact   300
```

```
gggcgttggg tgccttttga gtactggggt cagggaaccc tggtcaccgt ctcgagc      357
```

<210> SEQ ID NO 236
<211> LENGTH: 357
<212> TYPE: DNA
<213> ORGANISM: Artificial Sequence
<220> FEATURE:
<223> OTHER INFORMATION: Nucleotide

<400> SEQUENCE: 236

```
gaggtgcagc tgttggagtc tgggggaggc ttggtacagc ctgggggtc cctgcgtctc     60
tcctgtgcag cctccggatt cacctttgtt aagtattcga tggggtgggt ccgccaggct   120
ccagggaagg gtccagagtg gtctcacag atttcgaata ctgctgatcg tacatactac    180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 237
<211> LENGTH: 357
<212> TYPE: DNA
<213> ORGANISM: Artificial Sequence
<220> FEATURE:
<223> OTHER INFORMATION: Nucleotide

<400> SEQUENCE: 237

```
gaggtgcagc tgttggagtc tgggggaggc ttggtacagc ctgggggtc cctgcgtctc     60
tcctgtgcag cctccggatt cacctttgtt aagtattcga tggggtgggt ccgccaggct   120
ccagggaagg gtctagagtg gtctcacag atttcggata ctgctgatcg tacatactac    180
gcacactccg tgaagggccg gttcaccatc tcccgcgaca attccaagaa cacgctgtat   240
ctgcaaatga acagcctgcg tgctgaggac accgcggtat attactgtgc gatatatact   300
gggcgttggg tgccttttga gtactggggt cagggaaccc tggtcaccgt ctcgagc      357
```

<210> SEQ ID NO 238
<211> LENGTH: 357
<212> TYPE: DNA
<213> ORGANISM: Artificial Sequence
<220> FEATURE:
<223> OTHER INFORMATION: Nucleotide

<400> SEQUENCE: 238

```
gaggtgcagc tgttggagtc tgggggaggc ttggtacagc ctgggggtc cctgcgtctc     60
tcctgtgcag cctccggatt cacctttgtt aagtattcga tggggtgggt ccgccaggct   120
ccagggaagg gtctagagtg gtctcacag atttcggata ctgctgatcg tacatactac    180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 239
<211> LENGTH: 357
<212> TYPE: DNA
<213> ORGANISM: Artificial Sequence
<220> FEATURE:
<223> OTHER INFORMATION: Nucleotide

<400> SEQUENCE: 239

```
gaggtgcagc tgttggagtc tgggggaggc ttggtacagc ctgggggtc cctgcgtctc     60
```

```
tcctgtgcag cctccggatt cacctttgtt aagtattcga tggggtgggt ccgccaggct    120
ccagggaagg gtctagagtg ggtctcacag atttcggata ctgctgatcg tacatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttgga ggccttttga gtactggggt cagggaaccc tggtcaccgt ctcgagc      357
```

<210> SEQ ID NO 240
<211> LENGTH: 357
<212> TYPE: DNA
<213> ORGANISM: Artificial Sequence
<220> FEATURE:
<223> OTHER INFORMATION: Nucleotide

<400> SEQUENCE: 240

```
gaggtgcagc tgttggagtc tgggggaggc ttggtacagc ctgggggtc cctgcgtctc    60 tcctgtgcag cctccggatt cacctttgtt aagtattcga tggggtgggt ccgccaggct    120
ccagggaagg gtctagagtg ggtctcacag atttcggata ctgctgatcg tacatactac    180
acacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc      357
```

<210> SEQ ID NO 241
<211> LENGTH: 357
<212> TYPE: DNA
<213> ORGANISM: Artificial Sequence
<220> FEATURE:
<223> OTHER INFORMATION: Nucleotide

<400> SEQUENCE: 241

```
gaggtgcagc tgttggagtc tgggggaggc ttggtacagc ctgggggtc cctgcgtctc    60 tcctgtgcag cctccggatt cacctttgtt aagtattcga tggggtgggt ccgccaggct    120
ccagggaagg gtctagagtg ggtctcacag atttcgaata ctgctgatcg cagatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc      357
```

<210> SEQ ID NO 242
<211> LENGTH: 357
<212> TYPE: DNA
<213> ORGANISM: Artificial Sequence
<220> FEATURE:
<223> OTHER INFORMATION: Nucleotide

<400> SEQUENCE: 242

```
gaggtgcagc tgttggagtc tgggggaggc ttggtacagc ctgggggtc cctgcgtctc    60 tcctgtgcag cctccggatt cacctttgtt aagtattcga tggggtgggt ccgccaggct    120
ccagggaagg gtctagagtg ggtctcacag attttgaata ctgctgatcg tacatactac    180
gatcactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc      357
```

<210> SEQ ID NO 243

```
<211> LENGTH: 357
<212> TYPE: DNA
<213> ORGANISM: Artificial Sequence
<220> FEATURE:
<223> OTHER INFORMATION: Nucleotide

<400> SEQUENCE: 243
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcgaata ctgctgatcg tacatactac   180
gatcactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357

<210> SEQ ID NO 244
<211> LENGTH: 357
<212> TYPE: DNA
<213> ORGANISM: Artificial Sequence
<220> FEATURE:
<223> OTHER INFORMATION: Nucleotide

<400> SEQUENCE: 244
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcggata ctgctgatcg tagatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357

<210> SEQ ID NO 245
<211> LENGTH: 357
<212> TYPE: DNA
<213> ORGANISM: Artificial Sequence
<220> FEATURE:
<223> OTHER INFORMATION: Nucleotide

<400> SEQUENCE: 245
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcggata ctgctgatcg tagatactac   180
gatcactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357

<210> SEQ ID NO 246
<211> LENGTH: 357
<212> TYPE: DNA
<213> ORGANISM: Artificial Sequence
<220> FEATURE:
<223> OTHER INFORMATION: Nucleotide

<400> SEQUENCE: 246
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcgaata ctgctgatcg tacatactac   180
```
gcacactccg tgaagggccg gttcaccatc tcccgcgaca attccaagaa cacgctgtat    240
ctgcaaatga acagcctgcg tgccgaggac accgcggtat attactgtgc ggtatatact    300
gggcgttggg tgtcttttga gtactggggt cagggaaccc tggtcaccgt ctcgagc       357

<210> SEQ ID NO 247
<211> LENGTH: 357
<212> TYPE: DNA
<213> ORGANISM: Artificial Sequence
<220> FEATURE:
<223> OTHER INFORMATION: Nucleotide

<400> SEQUENCE: 247
gaggtgcagc tgttggagtc tgggggaggc ttggtacagc ctgggggtc cctgcgtctc     60 tcctgtgcag cctccggatt caccttttgtt aagtattcga tggggtgggt ccgccaggct   120
ccagggaagg gtctagagtg ggtctcacag atttcgaata ctgctgatcg tacatactac    180
gcacactccg tgaagggccg gttcaccatc tcccgcgaca attccaagaa cacgctgtat    240
ctgcaaatga acagcctgcg tgccgaggac accgcggtat attactgtgc gctatatact    300
gggcgttggg tgtcttttga gtactggggt cagggaaccc tggtcaccgt ctcgagc       357

<210> SEQ ID NO 248
<211> LENGTH: 357
<212> TYPE: DNA
<213> ORGANISM: Artificial Sequence
<220> FEATURE:
<223> OTHER INFORMATION: Nucleotide

<400> SEQUENCE: 248
gaggtgcagc tgttggagtc tgggggaggc ttggtacagc ctgggggtc cctgcgtctc     60 tcctgtgcag cctccggatt caccttttgtt aagtattcga tggggtgggt ccgccaggct   120
ccagggaagg gtctagagtg ggtctcacag atttcgaata ctgctgatcg tacatactac    180
gcacactccg tgaagggccg gtttaccatc tcccgcgaca attccaagaa cacgctgtat    240
ctgcaaatga acagcctgcg tgccgaggac accgcggtat attactgtgc ggtatatact    300
gggcgttggg tgccttttga gtactggggt cagggaaccc tggtcaccgt ctcgagc       357

<210> SEQ ID NO 249
<211> LENGTH: 357
<212> TYPE: DNA
<213> ORGANISM: Artificial Sequence
<220> FEATURE:
<223> OTHER INFORMATION: Nucleotide

<400> SEQUENCE: 249
gaggtgcagc tgttggagtc tgggggaggc ttggtacagc ctgggggtc cctgcgtctc     60 tcctgtgcag cctccggatt caccttttgtt aagtattcga tggggtgggt ccgccaggct   120
ccagggaagg gtctagagtg ggtctcacag atttcgaata ctgctgatcg tacatactac    180
gcacactccg tgaagggccg gttcaccatc tcccgcgaca attccaagaa cacgctgtat    240
ctgcaaatga acagcctgcg tgccgaggac accgcggtat attactgtgc gctatatact    300
gggcgttggg tgccttttga gtactggggt cagggaaccc tggtcaccgt ctcgagc       357

<210> SEQ ID NO 250
<211> LENGTH: 357
<212> TYPE: DNA
<213> ORGANISM: Artificial Sequence
<220> FEATURE:

```
<223> OTHER INFORMATION: Nucleotide

<400> SEQUENCE: 250
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag attgcgaata ctgctgatcg tagatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt caggaaccc tggtcaccgt ctcgagc      357

<210> SEQ ID NO 251
<211> LENGTH: 357
<212> TYPE: DNA
<213> ORGANISM: Artificial Sequence
<220> FEATURE:
<223> OTHER INFORMATION: Nucleotide

<400> SEQUENCE: 251
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcgaata ctgctgatcg tagatactac   180 gcagacgcgcg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt caggaaccc tggtcaccgt ctcgagc      357

<210> SEQ ID NO 252
<211> LENGTH: 357
<212> TYPE: DNA
<213> ORGANISM: Artificial Sequence
<220> FEATURE:
<223> OTHER INFORMATION: Nucleotide

<400> SEQUENCE: 252
gaggtgcagc tgttggagtc tgggggaggc ttggtacagc ctggggggtc cctgcgtctc    60
tcctgtgcgg cctccggatt cacctttgtt aagtattcga tggggtgggt ccgccaggct   120
ccagggaagg gtctagagtg ggtctcacag atttcgaata cgggcgatcg tagatactac   180 gcacacgcgcg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc      357

<210> SEQ ID NO 253
<211> LENGTH: 357
<212> TYPE: DNA
<213> ORGANISM: Artificial Sequence
<220> FEATURE:
<223> OTHER INFORMATION: Nucleotide

<400> SEQUENCE: 253
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag attgcgaata ctgctgatcg tagatactac   180 gcagacgcgcg tgaagggccg gttcaccatc tcccgcgaca attccaagaa cacgctgtat   240
ctgcaaatga acagcctgcg tgccgaggac accgcggtat attactgtgc gatatatacg   300
```
ggtcgttggg agcctttgt ctactggggt cagggaaccc tggtcaccgt ctcgagc         357

<210> SEQ ID NO 254
<211> LENGTH: 357
<212> TYPE: DNA
<213> ORGANISM: Artificial Sequence
<220> FEATURE:
<223> OTHER INFORMATION: Nucleotide

<400> SEQUENCE: 254
gaggtgcagc tgttggagtc tgggggaggc ttggtacagc ctgggggtc cctgcgtctc       60 tcctgtgcag cctccggatt cacctttgtt aagtattcga tggggtgggt ccgccaggct      120
ccagggaagg gtctagagtg ggtctcacag attgcgaata cggtgatcg tagatactac       180 gcacacgcgg tgaaggggcg gttcaccatc tcccgcgaca attccaagaa cacgctgtat      240
ctgcaaatga acagcctgcg tgccgaggac accgcggtat attactgtgc gatatatacg      300
ggtcgttggg agcctttgt ctactggggt cagggaaccc tggtcaccgt ctcgagc         357

<210> SEQ ID NO 255
<211> LENGTH: 357
<212> TYPE: DNA
<213> ORGANISM: Artificial Sequence
<220> FEATURE:
<223> OTHER INFORMATION: Nucleotide

<400> SEQUENCE: 255
gaggtgcagc tgttggagtc tgggggaggc ttggtacagc ctgggggtc cctgcgtctc       60 tcctgtgcag cctccggatt cacctttgtt aagtattcga tggggtgggt ccgccaggct      120
ccagggaagg gtctagagtg ggtctcacag atttcgaata ctgctgatcg tagatactac      180
gcacacgcgg tgaaggggcg gttcaccatc tcccgcgaca attccaagaa cacgctgtat      240
ctgcaaatga acagcctgcg tgccgaggac accgcggtat attactgtgc gatatatacg      300
ggtcgttggg agcctttgt ctactggggt cagggaaccc tggtcaccgt ctcgagc         357

<210> SEQ ID NO 256
<211> LENGTH: 357
<212> TYPE: DNA
<213> ORGANISM: Artificial Sequence
<220> FEATURE:
<223> OTHER INFORMATION: Nucleotide

<400> SEQUENCE: 256
gaggtgcagc tgttggagtc tgggggaggc ttggtacagc ctgggggtc cctgcgtctc       60 tcctgtgcag cctccggatt cacctttgtt aagtattcga tggggtgggt ccgccaggct      120
ccagggaagg gtctagagtg ggtctcacag attgcgaata cggctgatcg tagatactac      180
gcacacgcgg tgaaggggcg gttcaccatc tcccgcgaca attccaagaa cacgctgtat      240
ctgcaaatga acagcctgcg tgccgaggac accgcggtat attactgtgc gatatatacg      300
ggtcgttggg agcctttgt ctactggggt cagggaaccc tggtcaccgt ctcgagc         357

<210> SEQ ID NO 257
<211> LENGTH: 357
<212> TYPE: DNA
<213> ORGANISM: Artificial Sequence
<220> FEATURE:
<223> OTHER INFORMATION: Nucleotide

<400> SEQUENCE: 257

```
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag attgtgaata cgggtgatcg tagatactac   180
gcagacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc      357
```

<210> SEQ ID NO 258
<211> LENGTH: 357
<212> TYPE: DNA
<213> ORGANISM: Artificial Sequence
<220> FEATURE:
<223> OTHER INFORMATION: Nucleotide

<400> SEQUENCE: 258

```
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag attgcgaata cgggtgatcg tagatactac   180
gcagacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc      357
```

<210> SEQ ID NO 259
<211> LENGTH: 357
<212> TYPE: DNA
<213> ORGANISM: Artificial Sequence
<220> FEATURE:
<223> OTHER INFORMATION: Nucleotide

<400> SEQUENCE: 259

```
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcggata ctgctgatcg tacatactac   180
gatcactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 260
<211> LENGTH: 357
<212> TYPE: DNA
<213> ORGANISM: Artificial Sequence
<220> FEATURE:
<223> OTHER INFORMATION: Nucleotide

<400> SEQUENCE: 260

```
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcggata ctgctgatcg tacatactac   180
gatcactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttgga ggccttttga gtactggggt cagggaaccc tggtcaccgt ctcgagc      357
```

```
<210> SEQ ID NO 261
<211> LENGTH: 357
<212> TYPE: DNA
<213> ORGANISM: Artificial Sequence
<220> FEATURE:
<223> OTHER INFORMATION: Nucleotide

<400> SEQUENCE: 261
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcggata ctgctgatcg tacatactac     180
gatcactccg tgaagggccg gttcaccatc tcccgcgaca attccaagaa cacgctgtat     240
ctgcaaatga acagcctgcg tgccgaggac accgcggtat attactgtgc gatatatacg     300
ggtcgttggg agccttttgt ctactggggt caggaaccc tggtcaccgt ctcgagc        357

<210> SEQ ID NO 262
<211> LENGTH: 357
<212> TYPE: DNA
<213> ORGANISM: Artificial Sequence
<220> FEATURE:
<223> OTHER INFORMATION: Nucleotide

<400> SEQUENCE: 262
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcggata ctgctgatcg tacatactac     180
tcacactccg tgaagggccg gttcaccatc tcccgcgaca attccaagaa cacgctgtat     240
ctgcaaatga acagcctgcg tgctgaggac accgcggtat attactgtgc gatatatact     300
gggcgttggg tgccttttga gtactggggt cagggaaccc tggtcaccgt ctcgagc        357

<210> SEQ ID NO 263
<211> LENGTH: 357
<212> TYPE: DNA
<213> ORGANISM: Artificial Sequence
<220> FEATURE:
<223> OTHER INFORMATION: Nucleotide

<400> SEQUENCE: 263
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcggata ctgctgatcg tacatactac     180
acacactccg tgaagggccg gttcaccatc tcccgcgaca attccaagaa cacgctgtat     240
ctgcaaatga acagcctgcg tgctgaggac accgcggtat attactgtgc gatatatact     300
gggcgttggg tgccttttga gtactggggt cagggaaccc tggtcaccgt ctcgagc        357

<210> SEQ ID NO 264
<211> LENGTH: 357
<212> TYPE: DNA
<213> ORGANISM: Artificial Sequence
<220> FEATURE:
<223> OTHER INFORMATION: Nucleotide

<400> SEQUENCE: 264
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
```

```
ccagggaagg gtctagagtg ggtctcacag atttcggata ctgctgatcg tacatactac    180
acagacgcgg tgaaggggcg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 265
<211> LENGTH: 357
<212> TYPE: DNA
<213> ORGANISM: Artificial Sequence
<220> FEATURE:
<223> OTHER INFORMATION: Nucleotide

<400> SEQUENCE: 265

```
gaggtgcagc tgttggagtc tgggggaggc ttggtacagc ctgggggtc cctgcgtctc     60 tcctgtgcag cctccggatt caccttttc aagtattcga tggggtgggt ccgccaggct    120
ccagggaagg gtctagagtg ggtctcacag atttcggata ctgctgatcg tacatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357
```

<210> SEQ ID NO 266
<211> LENGTH: 357
<212> TYPE: DNA
<213> ORGANISM: Artificial Sequence
<220> FEATURE:
<223> OTHER INFORMATION: Nucleotide

<400> SEQUENCE: 266

```
gaggtgcagc tgttggagtc tgggggaggc ttggtacagc ctgggggtc cctgcgtctc     60 tcctgtgcag cctccggatt cacctttttg aagtattcga tggggtgggt ccgccaggct    120
ccagggaagg gtctagagtg ggtctcacag atttcggata ctgctgatcg tacatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357
```

<210> SEQ ID NO 267
<211> LENGTH: 357
<212> TYPE: DNA
<213> ORGANISM: Artificial Sequence
<220> FEATURE:
<223> OTHER INFORMATION: Nucleotide

<400> SEQUENCE: 267

```
gaggtgcagc tgttggagtc tgggggaggc ttggtacagc ctgggggtc cctgcgtctc     60 tcctgtgcag cctccggatt caccttttc aagtattcga tggggtgggt ccgccaggct    120
ccagggaagg gtctagagtg ggtctcacag attgcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 268
<211> LENGTH: 357
<212> TYPE: DNA
<213> ORGANISM: Artificial Sequence

```
<220> FEATURE:
<223> OTHER INFORMATION: Nucleotide

<400> SEQUENCE: 268
gaggtgcagc tgttggagtc tgggggaggc ttggtacagc ctgggggtc cctgcgtctc      60
tcctgtgcag cctccggatt cacctttttc aagtattcga tggggtgggt ccgccaggct    120
ccagggaagg gtctagagtg ggtctcacag atttcggata ctgctgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357

<210> SEQ ID NO 269
<211> LENGTH: 357
<212> TYPE: DNA
<213> ORGANISM: Artificial Sequence
<220> FEATURE:
<223> OTHER INFORMATION: Nucleotide sequences of anti-TNFR1 dAbs

<400> SEQUENCE: 269
gaggtgcagc tgttggagtc tgggggaggc ttggtacagc ctgggggtc cctgcgcctc      60
tcctgtgcag cctccggatt cacctttttc aagtattcga tggggtgggt ccgccaggct    120
ccagggaagg gtctagagtg ggtctcacag atttcggata cgggtgatcg tagatactac    180
gatcactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg aaccttttgt ctactggggt cagggaaccc tggtcaccgt ctcgagc       357

<210> SEQ ID NO 270
<211> LENGTH: 357
<212> TYPE: DNA
<213> ORGANISM: Artificial Sequence
<220> FEATURE:
<223> OTHER INFORMATION: Nucleotide

<400> SEQUENCE: 270
gaggtgcagc tgttggagtc tgggggaggc ttggtacagc ctgggggtc cctgcgtctc      60
tcctgtgcag cctccggatt cacctttttc aagtattcga tggggtgggt ccgccaggct    120
ccagggaagg gtctagagtg ggtctcacag atttcggata cgggtgatcg tagatactac    180
gatgacgcgg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357

<210> SEQ ID NO 271
<211> LENGTH: 357
<212> TYPE: DNA
<213> ORGANISM: Artificial Sequence
<220> FEATURE:
<223> OTHER INFORMATION: Nucleotide

<400> SEQUENCE: 271
gaggtgcagc tgttggagtc tgggggaggc ttggtacagc ctgggggtc cctgcgtctc      60
tcctgtgcag cctccggatt cacctttttc aagtattcga tggggtgggt ccgccaggct    120
ccagggaagg gtctagagtg ggtctcacag attgcggata ctgctgatcg tagatactac    180
gatgactctg tgaagggccg gttcaccatc tcccgcgaca attccaagaa cacgctgtat    240
```
ctgcaaatga acagcctgcg tgccgaggac accgcggtat attactgtgc gatatatacg    300
ggtcgttggg agccttttgt ctactggggt cagggaaccc tggtcaccgt ctcgagc       357

<210> SEQ ID NO 272
<211> LENGTH: 357
<212> TYPE: DNA
<213> ORGANISM: Artificial Sequence
<220> FEATURE:
<223> OTHER INFORMATION: Nucleotide

<400> SEQUENCE: 272
gaggtgcagc tgttggagtc tggggggaggc ttggtacagc ctgggggtc cctgcgtctc    60 tcctgtgcag cctccggatt cacctttttc aagtattcga tggggtgggt ccgccaggct    120
ccagggaagg gtctagagtg gtctcacag attgcggata cgggtgatcg tagatactac    180
gatcactctg tgaagggccg gttcactatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357

<210> SEQ ID NO 273
<211> LENGTH: 357
<212> TYPE: DNA
<213> ORGANISM: Artificial Sequence
<220> FEATURE:
<223> OTHER INFORMATION: Nucleotide

<400> SEQUENCE: 273
gaggtgcagc tgttggagtc tggggggaggc ttggtacagc ctgggggtc cctgcgtctc    60 tcctgtgcag cctccggatt cacctttttc aagtattcga tggggtgggt ccgccaggct    120
ccagggaagg gtctagagtg gtctcacag attgcggata cgggtgatcg tagatactac    180
gatgacgcgg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357

<210> SEQ ID NO 274
<211> LENGTH: 357
<212> TYPE: DNA
<213> ORGANISM: Artificial Sequence
<220> FEATURE:
<223> OTHER INFORMATION: Nucleotide

<400> SEQUENCE: 274
gaggtgcagc tgttggagtc tggggggaggc ttggtacagc ctgggggtc cctgcgtctc    60 tcctgtgcag cctccggatt caccttttgtt aagtattcga tggggtgggt ccgccaggct    120
ccagggaagg gtctagagtg gtctcacag atttcggata ctgctgatcg tacatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg ggccttttgt ctactggggt cagggaaccc tggtcaccgt ctcgagc       357

<210> SEQ ID NO 275
<211> LENGTH: 357
<212> TYPE: DNA
<213> ORGANISM: Artificial Sequence
<220> FEATURE:
<223> OTHER INFORMATION: Nucleotide

<400> SEQUENCE: 275

```
gaggtgcagc tgttggagtc tggggagc ttggtacagc ctgggggtc cctgcgtctc    60 tcctgtgcag cctccggatt cacctttgtt aagtattcga tggggtgggt ccgccaggct  120
ccagggaagg gtctagagtg ggtctcacag atttcggata ctgctgatcg tacatactac  180
gcacactccg tgaagggccg gttcaccatc tcccgcgaca attccaagaa cacgctgtat  240
ctgcaaatga acagcctgcg tgccgaggac accgcggtat attactgtgc gatatatacg  300
ggtcgttggg tgccttttgc ctactggggt cagggaaccc tggtcaccgt ctcgagc    357
```

<210> SEQ ID NO 276
<211> LENGTH: 357
<212> TYPE: DNA
<213> ORGANISM: Artificial Sequence
<220> FEATURE:
<223> OTHER INFORMATION: Nucleotide

<400> SEQUENCE: 276

```
gaggtgcagc tgttggagtc tggggagc ttggtacagc ctgggggtc cctgcgtctc    60 tcctgtgcag cctccggatt cacctttgtt aagtattcga tggggtgggt ccgccaggct  120
ccagggaagg gtctagagtg ggtctcacag atttcggata ctgctgatcg tacatactac  180
gcacactccg tgaagggccg gttcaccatc tcccgcgaca attccaagaa cacgctgtat  240
ctgcaaatga acagcctgcg tgccgaggac accgcggtat attactgtgc gatatatacg  300
ggtcgttggg gaccttttca gtactggggt cagggaaccc tggtcaccgt ctcgagc    357
```

<210> SEQ ID NO 277
<211> LENGTH: 357
<212> TYPE: DNA
<213> ORGANISM: Artificial Sequence
<220> FEATURE:
<223> OTHER INFORMATION: Nucleotide

<400> SEQUENCE: 277

```
gaggtgcagc tgttggagtc tggggagc ttggtacagc ctgggggtc cctgcgtctc    60 tcctgtgcag cctccggatt cacctttgtt aagtattcga tggggtgggt ccgccaggct  120
ccagggaagg gtctagagtg ggtctcacag atttcggata ctgctgatcg tacatactac  180
gcacactccg tgaagggccg gttcaccatc tcccgcgaca attccaagaa cacgctgtat  240
ctgcaaatga acagcctgcg tgccgaggac accgcggtat attactgtgc gatatatacg  300
ggtcgttggg agccttttca gtactggggt cagggaactc tggtcaccgt ctcgagc    357
```

<210> SEQ ID NO 278
<211> LENGTH: 357
<212> TYPE: DNA
<213> ORGANISM: Artificial Sequence
<220> FEATURE:
<223> OTHER INFORMATION: Nucleotide

<400> SEQUENCE: 278

```
gaggtgcagc tgttggagtc tggggagc ttggtacagc ctgggggtc cctgcgtctc    60 tcctgtgcag cctccggatt cacctttgtt aagtattcga tggggtgggt ccgccaggct  120
ccagggaagg gtctagagtg ggtctcacag atttcggata ctgctgatcg tacatactac  180
gcacactccg tgaagggccg gttcaccatc tcccgcgaca attccaagaa cacgctgtat  240
ctgcaaatga acagcctgcg tgccgaggac accgcggtat attactgtgc gatatatacg  300
ggtcgttggg cgccttttga gtactggggt cagggaaccc tggtcaccgt ctcgagc    357
```

<210> SEQ ID NO 279
<211> LENGTH: 357
<212> TYPE: DNA
<213> ORGANISM: Artificial Sequence
<220> FEATURE:
<223> OTHER INFORMATION: Nucleotide

<400> SEQUENCE: 279
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg ggtctcacag atttcggata ctgctgatcg tacatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg cgccttttca gtactggggt caggaactc tggtcaccgt ctcgagc        357

<210> SEQ ID NO 280
<211> LENGTH: 357
<212> TYPE: DNA
<213> ORGANISM: Artificial Sequence
<220> FEATURE:
<223> OTHER INFORMATION: Nucleotide

<400> SEQUENCE: 280
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg ggtctcacag atttcggata ctgctgatcg tacatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg tgccttttca gtactggggt caggcacccc tggtcaccgt ctcgagc       357

<210> SEQ ID NO 281
<211> LENGTH: 357
<212> TYPE: DNA
<213> ORGANISM: Artificial Sequence
<220> FEATURE:
<223> OTHER INFORMATION: Nucleotide

<400> SEQUENCE: 281
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg ggtctcacag atttcggata ccggtgatcg tagatactac    180
gatcactctg tgaagggccg gttcactatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357

<210> SEQ ID NO 282
<211> LENGTH: 357
<212> TYPE: DNA
<213> ORGANISM: Artificial Sequence
<220> FEATURE:
<223> OTHER INFORMATION: Nucleotide

<400> SEQUENCE: 282
gaggtgcagc tgttggagtc tgggggaggc ttggtacagc ctgggggtc cctgcgtctc      60 tcctgtgcag cctccggatt cacctttttg aagtattcga tggggtgggt ccgccaggct    120

```
ccagggaagg gtctagagtg ggtctcacag atttcggata ctgctgatcg tacatactac      180
gcacactccg tgaagggccg gttcaccatc tcccgcgaca attccaagaa cacgctgtat      240
ctgcaaatga acagcctgcg tgctgaggac accgcggtat attactgtgc gatatatact      300
gggcgttggg tgccttttga gtactggggt cagggaaccc tggtcaccgt ctcgagc         357

<210> SEQ ID NO 283
<211> LENGTH: 357
<212> TYPE: DNA
<213> ORGANISM: Artificial Sequence
<220> FEATURE:
<223> OTHER INFORMATION: Nucleotide

<400> SEQUENCE: 283
gaggtgcagc tgttggagtc tgggggaggc ttggtacagc ctgggggtc cctgcgtctc       60 tcctgtgcag cctccggatt cacctttttc aagtattcga tggggtgggt ccgccaggct     120
ccagggaagg gtctagagtg ggtctcacag atttcggata ctgctgatcg tacatactac     180
gcacactccg tgaagggccg gttcaccatc tcccgcgaca attccaagaa cacgctgtat     240
ctgcaaatga acagcctgcg tgctgaggac accgcggtat attactgtgc gatatatact     300
gggcgttggg tgccttttga gtactggggt cagggaaccc tggtcaccgt ctcgagc        357

<210> SEQ ID NO 284
<211> LENGTH: 357
<212> TYPE: DNA
<213> ORGANISM: Artificial Sequence
<220> FEATURE:
<223> OTHER INFORMATION: Nucleotide

<400> SEQUENCE: 284
gaggtgcagc tgttggagtc tgggggaggc ttggtacagc ctgggggtc cctgcgtctc       60 tcctgtgcag cctccggatt cacctttttg aagtattcga tggggtgggt ccgccaggct     120
ccagggaagg gtctagagtg ggtctcacag atttcggata ctgctgatcg tacatactac     180
gatcactccg tgaagggccg gttcaccatc tcccgcgaca attccaagaa cacgctgtat     240
ctgcaaatga acagcctgcg tgccgaggac accgcggtat attactgtgc gatatatacg     300
ggtcgttgga ggccttttga gtactggggt cagggaaccc tggtcaccgt ctcgagc        357

<210> SEQ ID NO 285
<211> LENGTH: 357
<212> TYPE: DNA
<213> ORGANISM: Artificial Sequence
<220> FEATURE:
<223> OTHER INFORMATION: Nucleotide

<400> SEQUENCE: 285
gaggtgcagc tgttggagtc tgggggaggc ttggtacagc ctgggggtc cctgcgtctc       60 tcctgtgcag cctccggatt cacctttttc aagtattcga tggggtgggt ccgccaggct     120
ccagggaagg gtctagagtg ggtctcacag atttcggata ctgctgatcg tacatactac     180
gatcactccg tgaagggccg gttcaccatc tcccgcgaca attccaagaa cacgctgtat     240
ctgcaaatga acagcctgcg tgccgaggac accgcggtat attactgtgc gatatatacg     300
ggtcgttgga ggccttttga gtactggggt cagggaaccc tggtcaccgt ctcgagc        357

<210> SEQ ID NO 286
<211> LENGTH: 357
<212> TYPE: DNA
```

<213> ORGANISM: Artificial Sequence
<220> FEATURE:
<223> OTHER INFORMATION: Nucleotide

<400> SEQUENCE: 286

```
gaggtgcagc tgttggagtc tggggggaggc ttggtacagc ctggggggtc cctgcgtctc    60
tcctgtgcag cctccggatt cacctttttc aagtattcga tggggtgggt ccgccaggct   120
ccagggaagg gtctagagtg gtctcacag atttcggata ctgctgatcg tacatactac    180
gatcactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc      357
```

<210> SEQ ID NO 287
<211> LENGTH: 357
<212> TYPE: DNA
<213> ORGANISM: Artificial Sequence
<220> FEATURE:
<223> OTHER INFORMATION: Nucleotide

<400> SEQUENCE: 287

```
gaggtgcagc tgttggagtc tggggggaggc ttggtacagc ctggggggtc cctgcgtctc    60
tcctgtgcag cctccggatt ccctttttg aagtattcga tggggtgggt ccgccaggct   120
ccagggaagg gtctagagtg gtctcacag atttcggata ctgctgatcg tacatactac    180
gatcactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc      357
```

<210> SEQ ID NO 288
<211> LENGTH: 357
<212> TYPE: DNA
<213> ORGANISM: Artificial Sequence
<220> FEATURE:
<223> OTHER INFORMATION: Nucleotide

<400> SEQUENCE: 288

```
gaggtgcagc tgttggagtc tggggggaggc ttggtacagc ctggggggtc cctgcgtctc    60
tcctgtgcag cctccggatt ccctttttg aagtattcga tggggtgggt ccgccaggct   120
ccagggaagg gtctagagtg gtctcacag atttcggata ctgctgatcg tacatactac    180
tcacactccg tgaagggccg gttcaccatc tcccgcgaca attccaagaa cacgctgtat   240
ctgcaaatga acagcctgcg tgctgaggac accgcggtat attactgtgc gatatatact   300
gggcgttggg tgccttttga gtactggggt cagggaaccc tggtcaccgt ctcgagc      357
```

<210> SEQ ID NO 289
<211> LENGTH: 357
<212> TYPE: DNA
<213> ORGANISM: Artificial Sequence
<220> FEATURE:
<223> OTHER INFORMATION: Nucleotide

<400> SEQUENCE: 289

```
gaggtgcagc tgttggagtc tggggggaggc ttggtacagc ctggggggtc cctgcgtctc    60
tcctgtgcag cctccggatt cacctttttc aagtattcga tggggtgggt ccgccaggct   120
ccagggaagg gtctagagtg gtctcacag atttcggata ctgctgatcg tacatactac    180
tcacactccg tgaagggccg gttcaccatc tcccgcgaca attccaagaa cacgctgtat   240
```
ctgcaaatga acagcctgcg tgctgaggac accgcggtat attactgtgc gatatatact    300
gggcgttggg tgccttttga gtactggggt cagggaaccc tggtcaccgt ctcgagc       357

<210> SEQ ID NO 290
<211> LENGTH: 357
<212> TYPE: DNA
<213> ORGANISM: Artificial Sequence
<220> FEATURE:
<223> OTHER INFORMATION: Nucleotide

<400> SEQUENCE: 290
gaggtgcagc tgttggagtc tgggggaggc ttggtacagc ctggggggtc cctgcgtctc    60
tcctgtgcag cctccggatt cacctttttc aagtattcga tggggtgggt ccgccaggct    120
ccagggaagg gtctagagtg gtctcacag atttcggata ctgctgatcg tacatactac     180
acacactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357

<210> SEQ ID NO 291
<211> LENGTH: 357
<212> TYPE: DNA
<213> ORGANISM: Artificial Sequence
<220> FEATURE:
<223> OTHER INFORMATION: Nucleotide

<400> SEQUENCE: 291
gaggtgcagc tgttggagtc tgggggaggc ttggtacagc ctggggggtc cctgcgtctc    60
tcctgtgcag cctccggatt caccttttg aagtattcga tggggtgggt ccgccaggct     120
ccagggaagg gtctagagtg gtctcacag atttcggata ctgctgatcg tacatactac     180
acacactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357

<210> SEQ ID NO 292
<211> LENGTH: 357
<212> TYPE: DNA
<213> ORGANISM: Artificial Sequence
<220> FEATURE:
<223> OTHER INFORMATION: Nucleotide

<400> SEQUENCE: 292
gaggtgcagc tgttggagtc tgggggaggc ttggtacagc ctggggggtc cctgcgtctc    60
tcctgtgcag cctccggatt cacctttttc aagtattcga tggggtgggt ccgccaggct    120
ccagggaagg gtctagagtg gtctcacag atttcggata ctgctgatcg tacatactac     180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg cgccttttga gtactggggt cagggaaccc tggtcaccgt ctcgagc       357

<210> SEQ ID NO 293
<211> LENGTH: 357
<212> TYPE: DNA
<213> ORGANISM: Artificial Sequence
<220> FEATURE:
<223> OTHER INFORMATION: Nucleotide

<400> SEQUENCE: 293

```
gaggtgcagc tgttggagtc tgggggaggc ttggtacagc ctgggggtc cctgcgtctc    60
tcctgtgcag cctccggatt cacctttttg aagtattcga tggggtgggt ccgccaggct   120
ccagggaagg gtctagagtg gtctcacag atttcggata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg cgccttttga gtactggggt cagggaaccc tggtcaccgt ctcgagc      357
```

<210> SEQ ID NO 294
<211> LENGTH: 357
<212> TYPE: DNA
<213> ORGANISM: Artificial Sequence
<220> FEATURE:
<223> OTHER INFORMATION: Nucleotide

<400> SEQUENCE: 294

```
gaggtgcagc tgttggagtc tgggggaggc ttggtacagc ctgggggtc cctgcgtctc    60
tcctgtgcag cctccggatt cacctttttc aagtattcga tggggtgggt ccgccaggct   120
ccagggaagg gtctagagtg gtctcacag atttcggata ccggtgatcg tagatactac   180
gatcactctg tgaagggccg gttcactatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 295
<211> LENGTH: 357
<212> TYPE: DNA
<213> ORGANISM: Artificial Sequence
<220> FEATURE:
<223> OTHER INFORMATION: Nucleotide

<400> SEQUENCE: 295

```
gaggtgcagc tgttggagtc tgggggaggc ttggtacagc ctgggggtc cctgcgtctc    60
tcctgtgcag cctccggatt caccttttgtt aagtattcga tggggtgggt ccgccaggct  120
ccagggaagg gtctagagtg gtctcacag attgcggata ctgctgatcg tacatactac   180
gcacactccg tgaagggccg gttcaccatc tcccgcgaca attccaagaa cacgctgtat   240
ctgcaaatga acagcctgcg tgctgaggac accgcggtat attactgcgc gatatatact   300
gggcgttggg tgccttttga gtactggggt cagggaaccc tggtcaccgt ctcgagc      357
```

<210> SEQ ID NO 296
<211> LENGTH: 357
<212> TYPE: DNA
<213> ORGANISM: Artificial Sequence
<220> FEATURE:
<223> OTHER INFORMATION: Nucleotide

<400> SEQUENCE: 296

```
gaggtgcagc tgttggagtc tgggggaggc ttggtacagc ctgggggtc cctgcgtctc    60
tcctgtgcag cctccggatt cacctttttt aagtattcga tggggtgggt ccgccaggct   120
ccagggaagg gtctagagtg gtctcacag atttcggata ctgctgatcg tacatactac   180
gcacacgcgg tgaagggccg gttcaccatc tcccgcgaca attccaagaa cacgctgtat   240
ctgcaaatga acagcctgcg tgctgaggac accgcggtat attactgtgc gatatatact   300
gggcgttggg tgccttttga gtactggggt cagggaaccc tggtcaccgt ctcgagc      357
```

<210> SEQ ID NO 297
<211> LENGTH: 357
<212> TYPE: DNA
<213> ORGANISM: Artificial Sequence
<220> FEATURE:
<223> OTHER INFORMATION: Nucleotide

<400> SEQUENCE: 297

```
gaggtgcagc tgttggagtc tgggggaggc ttggtacagc ctgggggtc cctgcgtctc      60
tcctgtgcag cctccggatt cacctttttt aagtattcga tggggtgggt ccgccaggct    120
ccagggaagg gtctagagtg gtctcacag atttcggata ctgctgatcg tacatactac     180
gcacacgcgg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357
```

<210> SEQ ID NO 298
<211> LENGTH: 357
<212> TYPE: DNA
<213> ORGANISM: Artificial Sequence
<220> FEATURE:
<223> OTHER INFORMATION: Nucleotide

<400> SEQUENCE: 298

```
gaggtgcagc tgttggagtc tgggggaggc ttggtgcagc ctgggggtc cctgcgtctc      60
tcctgtgcag cctccggatt caccttgtt aagtattcga tggggtgggt ccgccaggct    120
ccagggaagg gtctagagtg gtctcacag attgcggata ctgctgatcg tacatactac     180
gatcactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357
```

<210> SEQ ID NO 299
<211> LENGTH: 357
<212> TYPE: DNA
<213> ORGANISM: Artificial Sequence
<220> FEATURE:
<223> OTHER INFORMATION: Nucleotide

<400> SEQUENCE: 299

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg gtctcacag attgcggata ctgctgatcg tacatactac     180
gatcacgcgg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357
```

<210> SEQ ID NO 300
<211> LENGTH: 357
<212> TYPE: DNA
<213> ORGANISM: Artificial Sequence
<220> FEATURE:
<223> OTHER INFORMATION: Nucleotide

<400> SEQUENCE: 300

```
gaggtgcagc tgttggagtc tgggggaggc ttggtacagc ctgggggtc cctgcgtctc      60
```

```
tcctgtgcag cctccggatt cacctttgtt aagtattcga tggggtgggt ccgccaggct    120
ccagggaagg gtctagagtg ggtctcacag attgcggata ctgctgatcg tagatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357
```

<210> SEQ ID NO 301
<211> LENGTH: 357
<212> TYPE: DNA
<213> ORGANISM: Artificial Sequence
<220> FEATURE:
<223> OTHER INFORMATION: Nucleotide

<400> SEQUENCE: 301

```
gaggtgcagc tgttggagtc tgggggaggc ttggtacagc ctggggggtc cctgcgtctc     60
tcctgtgcag cctccggatt cacctttgtt aagtattcga tggggtgggt ccgccaggct    120
ccagggaagg gtctagagtg ggtctcacag atttcggata ctgctgatcg tagatactac    180
gcacacgcgg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357
```

<210> SEQ ID NO 302
<211> LENGTH: 357
<212> TYPE: DNA
<213> ORGANISM: Artificial Sequence
<220> FEATURE:
<223> OTHER INFORMATION: Nucleotide

<400> SEQUENCE: 302

```
gaggtgcagc tgttggagtc tgggggaggc ttggtacagc ctggggggtc cctgcgtctc     60
tcctgtgcag cctccggatt cacctttgtt aagtattcga tggggtgggt ccgccaggct    120
ccagggaagg gtctagagtg ggtctcacag attgcggata ctgctgatcg tagatactac    180
gcacacgcgg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357
```

<210> SEQ ID NO 303
<211> LENGTH: 357
<212> TYPE: DNA
<213> ORGANISM: Artificial Sequence
<220> FEATURE:
<223> OTHER INFORMATION: Nucleotide

<400> SEQUENCE: 303

```
gaggtgcagc tgttggagtc tgggggaggc ttggtacagc ctggggggtc cctgcgtctc     60
tcctgtgcag cctccggatt cacctttgtt aagtattcga tggggtgggt ccgccaggct    120
ccagggaagg gtctagagtg ggtctcacag atttcggata ctgctgatcg tagatactac    180
gatcacgcgg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357
```

<210> SEQ ID NO 304
<211> LENGTH: 357

<210> SEQ ID NO 304
<211> LENGTH: 357
<212> TYPE: DNA
<213> ORGANISM: Artificial Sequence
<220> FEATURE:
<223> OTHER INFORMATION: Nucleotide

<400> SEQUENCE: 304

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag attgcggata ctgctgatcg tagatactac     180
gatcacgcgg tgaagggccg gttcaccatc tcccgcgaca attccaagaa cacgctgtat     240
ctgcaaatga acagcctgcg tgccgaggac accgcggtat attactgtgc gatatatacg     300
ggtcggtggg cgccttttga gtactggggt caggggaccc tggtcaccgt ctcgagc        357
```

<210> SEQ ID NO 305
<211> LENGTH: 357
<212> TYPE: DNA
<213> ORGANISM: Artificial Sequence
<220> FEATURE:
<223> OTHER INFORMATION: Nucleotide

<400> SEQUENCE: 305

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag attgcggata ctgctgatcg tagatactac     180
gatcactccg tgaagggccg gttcaccatc tcccgcgaca attccaagaa cacgctgtat     240
ctgcaaatga acagcctgcg tgccgaggac accgcggtat attactgtgc gatatatacg     300
ggtcggtggg cgccttttga gtactggggt cagggaaccc tggtcaccgt ctcgagc        357
```

<210> SEQ ID NO 306
<211> LENGTH: 357
<212> TYPE: DNA
<213> ORGANISM: Artificial Sequence
<220> FEATURE:
<223> OTHER INFORMATION: Nucleotide

<400> SEQUENCE: 306

```
gaggtgcagc tgctggagtc tgggggaggc ttggtacagc ctggggggtc cctgcgtctc      60
tcctgtgcag cctccggatt caccttttc aagtattcga tggggtgggt ccgccaggct      120
ccagggaagg gtctagagtg ggtctcacag atttcggata ctgctgatcg tagatactac     180
gatgacgcgg tgaagggccg gttcaccatc acccgcgaca attccaagaa cacgctgtat     240
ctgcaaatga acagcctgcg tgccgaggac accgcggtat attactgtgc gatatatacg     300
ggtcgttggg agccttttgt ctactggggt cagggaaccc tggtcaccgt ctcgagc        357
```

<210> SEQ ID NO 307
<211> LENGTH: 163
<212> TYPE: PRT
<213> ORGANISM: Mouse

<400> SEQUENCE: 307

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Gly Ser Gly Gly Gly
        35                  40                  45

Gly Ser Gly Gly Gly Ser Asp Ile Gln Met Thr Gln Ser Pro Ser
            50                  55                  60

Ser Leu Ser Ala Ser Val Gly Asp Arg Val Thr Ile Thr Cys Arg Ala
 65                  70                  75                  80

Ser Gln Trp Ile Gly Ser Gln Leu Ser Trp Tyr Gln Gln Lys Pro Gly
                 85                  90                  95

Lys Ala Pro Lys Leu Leu Ile Met Trp Arg Ser Ser Leu Gln Ser Gly
            100                 105                 110

Val Pro Ser Arg Phe Ser Gly Ser Gly Ser Gly Thr Asp Phe Thr Leu
            115                 120                 125

Thr Ile Ser Ser Leu Gln Pro Glu Asp Phe Ala Thr Tyr Tyr Cys Ala
            130                 135                 140

Gln Gly Ala Ala Leu Pro Arg Thr Phe Gly Gln Gly Thr Lys Val Glu
145                 150                 155                 160

Ile Lys Arg

<210> SEQ ID NO 308
<211> LENGTH: 489
<212> TYPE: DNA
<213> ORGANISM: Artificial Sequence
<220> FEATURE:
<223> OTHER INFORMATION: Nucleotide

<400> SEQUENCE: 308
catggtgaag gaacatttac cagtgacttg tcaaaacaga tggaagagga ggcagtgcgg        60
ttatttattg agtggcttaa gaacggagga ccaagtagcg gggcacctcc gccatcgggt       120
ggtggaggcg gttcaggcgg aggtggcagc ggcggtggcg ggtcggacat ccagatgacc       180
cagtctccat cctccctgtc tgcatctgta ggagaccgtg tcaccatcac ttgccgggca       240
agtcagtgga ttgggtctca gttatcttgg taccagcaga accagggaa agcccctaag       300 ctcctgatca tgtggcgttc ctcgttgcaa agtggggtcc catcacgttt cagtggcagt       360
ggatctggga cagatttcac tctcaccatc agcagtctgc aacctgaaga ttttgctacg       420
tactactgtg ctcagggtgc ggcgttgcct aggacgttcg gccaagggac caaggtggaa       480
atcaaacgg                                                               489

<210> SEQ ID NO 309
<211> LENGTH: 163
<212> TYPE: PRT
<213> ORGANISM: Homo sapiens

<400> SEQUENCE: 309

His Gly Glu Gly Thr Phe Thr Ser Asp Leu Ser Lys Gln Met Glu Glu
  1                   5                  10                  15

Glu Ala Val Arg Leu Phe Ile Glu Trp Leu Lys Asn Gly Gly Pro Ser
             20                  25                  30

Ser Gly Ala Pro Pro Pro Ser Gly Gly Gly Gly Ser Gly Gly Gly
         35                  40                  45

Gly Ser Gly Gly Gly Gly Ser Asp Ile Gln Met Thr Gln Ser Pro Ser
             50                  55                  60

Ser Leu Ser Ala Ser Val Gly Asp Arg Val Thr Ile Thr Cys Arg Ala
 65                  70                  75                  80

Ser Gln Trp Ile Gly Ser Gln Leu Ser Trp Tyr Gln Gln Lys Pro Gly
                 85                  90                  95

Lys Ala Pro Lys Leu Leu Ile Met Trp Arg Ser Ser Leu Gln Ser Gly

Val Pro Ser Arg Phe Ser Gly Ser Gly Ser Gly Thr Asp Phe Thr Leu
            115                 120                 125

Thr Ile Ser Ser Leu Gln Pro Glu Asp Phe Ala Thr Tyr Tyr Cys Ala
        130                 135                 140

Gln Gly Leu Arg His Pro Lys Thr Phe Gly Gln Gly Thr Lys Val Glu
145                 150                 155                 160

Ile Lys Arg

<210> SEQ ID NO 310
<211> LENGTH: 489
<212> TYPE: DNA
<213> ORGANISM: Artificial Sequence
<220> FEATURE:
<223> OTHER INFORMATION: Nucleotide

<400> SEQUENCE: 310
catggtgaag gaacatttac cagtgacttg tcaaaacaga tggaagagga ggcagtgcgg      60
ttatttattg agtggcttaa aacggagga ccaagtagcg gggcacctcc gccatcgggt     120
ggtggaggcg gttcaggcgg aggtggcagc ggcggtggcg ggtcggacat ccagatgacc     180
cagtctccat cctccctgtc tgcatctgta ggagaccgtg tcaccatcac ttgccgggca     240
agtcagtgga ttgggtctca gttatcttgg taccagcaga aaccagggaa agcccctaag     300
ctcctgatca tgtggcgttc ctcgttgcaa agtggggtcc catcacgttt cagtggcagt     360
ggatctggga cagatttcac tctcaccatc agcagtctgc aacctgaaga ttttgctacg     420
tactactgtg ctcagggttt gaggcatcct aagacgttcg gccaagggac caaggtggaa     480
atcaaacgg                                                             489

<210> SEQ ID NO 311
<211> LENGTH: 163
<212> TYPE: PRT
<213> ORGANISM: Homo sapiens

<400> SEQUENCE: 311

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser Gly Gly Gly Gly Ser Gly Gly Gly
         35                  40                  45

Gly Ser Gly Gly Gly Gly Ser Asp Ile Gln Met Thr Gln Ser Pro Ser
 50                  55                  60

Ser Leu Ser Ala Ser Val Gly Asp Arg Val Thr Ile Thr Cys Arg Ala
65                  70                  75                  80

Ser Gln Trp Ile Gly Ser Gln Leu Ser Trp Tyr Gln Gln Lys Pro Gly
             85                  90                  95

Lys Ala Pro Lys Leu Leu Ile Met Trp Arg Ser Ser Leu Gln Ser Gly
            100                 105                 110

Val Pro Ser Arg Phe Ser Gly Ser Gly Ser Gly Thr Asp Phe Thr Leu
            115                 120                 125

Thr Ile Ser Ser Leu Gln Pro Glu Asp Phe Ala Thr Tyr Tyr Cys Ala
        130                 135                 140

Gln Gly Leu Met Lys Pro Met Thr Phe Gly Gln Gly Thr Lys Val Glu
145                 150                 155                 160

Ile Lys Arg

<210> SEQ ID NO 312
<211> LENGTH: 489
<212> TYPE: DNA
<213> ORGANISM: Artificial Sequence
<220> FEATURE:
<223> OTHER INFORMATION: Nucleotide

<400> SEQUENCE: 312

```
catggtgaag gaacatttac cagtgacttg tcaaaacaga tggaagagga ggcagtgcgg      60
ttatttattg agtggcttaa gaacggagga ccaagtagcg gggcacctcc gccatcgggt     120
ggtggaggcg gttcaggcgg aggtggcagc ggcggtggcg ggtcggacat ccagatgacc     180
cagtctccat cctccctgtc tgcatctgta ggagaccgtg tcaccatcac ttgccgggca     240
agtcagtgga ttgggtctca gttatcttgg taccagcaga accagggaaa gcccctaag     300
ctcctgatca tgtggcgttc ctcgttgcaa agtggggtcc catcacgttt cagtggcagt     360
ggatctggga cagatttcac tctcaccatc agcagtctgc aacctgaaga ttttgctacg     420
tactactgtg ctcagggtct tatgaagcct atgacgttcg gccaagggac caaggtggaa     480
atcaaacgg                                                             489
```

<210> SEQ ID NO 313
<211> LENGTH: 163
<212> TYPE: PRT
<213> ORGANISM: Homo sapiens

<400> SEQUENCE: 313

```
His Gly Glu Gly Thr Phe Thr Ser Asp Leu Ser Lys Gln Met Glu Glu
 1               5                  10                  15
Glu Ala Val Arg Leu Phe Ile Glu Trp Leu Lys Asn Gly Gly Pro Ser
             20                  25                  30
Ser Gly Ala Pro Pro Pro Ser Gly Gly Gly Gly Ser Gly Gly Gly
         35                  40                  45
Gly Ser Gly Gly Gly Gly Ser Asp Ile Gln Met Thr Gln Ser Pro Ser
     50                  55                  60
Ser Leu Ser Ala Ser Val Gly Asp Arg Val Thr Ile Ser Cys Arg Ala
 65                  70                  75                  80
Ser Gln Trp Ile Gly Ser Gln Leu Ser Trp Tyr Gln Gln Lys Pro Gly
                 85                  90                  95
Glu Ala Pro Lys Leu Leu Ile Met Trp Arg Ser Ser Leu Gln Ser Gly
            100                 105                 110
Val Pro Ser Arg Phe Ser Gly Ser Gly Ser Gly Thr Asp Phe Thr Leu
        115                 120                 125
Thr Ile Ser Ser Leu Gln Pro Glu Asp Phe Ala Thr Tyr Tyr Cys Ala
    130                 135                 140
Gln Gly Ala Ala Leu Pro Arg Thr Phe Gly Gln Gly Thr Lys Val Glu
145                 150                 155                 160
Ile Lys Arg
```

<210> SEQ ID NO 314
<211> LENGTH: 489
<212> TYPE: DNA
<213> ORGANISM: Artificial Sequence
<220> FEATURE:
<223> OTHER INFORMATION: Nucleotide

<400> SEQUENCE: 314

-continued

```
catggtgaag gaacatttac cagtgacttg tcaaaacaga tggaagagga ggcagtgcgg      60
ttatttattg agtggcttaa gaacggagga ccaagtagcg gggcacctcc gccatcgggt     120
ggtggaggcg gttcaggcgg aggtggcagc ggcggtggcg ggtcggacat ccagatgacc     180
cagtctccat cctccctgtc tgcatctgta ggagaccgtg tcaccatctc ttgccgggca     240
agtcagtgga ttgggtctca gttatcttgg taccagcaga accagggga agcccctaag      300 ctcctgatca tgtggcgttc ctcgttgcaa agtggggtcc catcacgttt cagtggcagt     360
ggatctggga cagatttcac tctcaccatc agcagtctgc aacctgaaga ttttgctacg     420
tactactgtg ctcagggtgc ggcgttgcct aggacgttcg gccaagggac caaggtggaa     480
atcaaacgg                                                             489
```

<210> SEQ ID NO 315
<211> LENGTH: 163
<212> TYPE: PRT
<213> ORGANISM: Homo sapiens

<400> SEQUENCE: 315

```
His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Ser Gly Gly Gly Gly Ser Gly Gly
         35                  40                  45

Gly Ser Gly Gly Gly Ser Asp Ile Gln Met Thr Gln Ser Pro Ser
 50                  55                  60

Ser Leu Ser Ala Ser Val Gly Asp Arg Val Thr Ile Thr Cys Arg Ala
 65                  70                  75                  80

Ser Arg Pro Ile Gly Thr Thr Leu Ser Trp Tyr Gln Gln Lys Pro Gly
             85                  90                  95

Lys Ala Pro Lys Leu Leu Ile Trp Phe Gly Ser Arg Leu Gln Ser Gly
            100                 105                 110

Val Pro Ser Arg Phe Ser Gly Ser Gly Ser Gly Thr Asp Phe Thr Leu
            115                 120                 125

Thr Ile Ser Ser Leu Gln Pro Glu Asp Phe Ala Thr Tyr Tyr Cys Ala
        130                 135                 140

Gln Ala Gly Thr His Pro Thr Thr Phe Gly Gln Gly Thr Lys Val Glu
145                 150                 155                 160

Ile Lys Arg
```

<210> SEQ ID NO 316
<211> LENGTH: 489
<212> TYPE: DNA
<213> ORGANISM: Artificial Sequence
<220> FEATURE:
<223> OTHER INFORMATION: Nucleotide

<400> SEQUENCE: 316

```
catggtgaag gaacatttac cagtgacttg tcaaaacaga tggaagagga ggcagtgcgg      60
ttatttattg agtggcttaa gaacggagga ccaagtagcg gggcacctcc gccatcgggt     120
ggtggaggcg gttcaggcgg aggtggcagc ggcggtggcg ggtcggacat ccagatgacc     180
cagtctccat cctccctgtc tgcatctgta ggagaccgtg tcaccatcac ttgccgggca     240
agtcgtccga ttgggacgac gttaagttgg taccagcaga accagggaa agcccctaag      300
```

```
ctcctgatct ggtttggttc ccggttgcaa agtggggtcc catcacgttt cagtggcagt      360
ggatctggga cagatttcac tctcaccatc agcagtctgc aacctgaaga ttttgctacg      420
tactactgtg cgcaggctgg gacgcatcct acgacgttcg gccagggac caaggtggaa       480 atcaaacgg                                                              489
```

<210> SEQ ID NO 317
<211> LENGTH: 163
<212> TYPE: PRT
<213> ORGANISM: Homo sapiens

<400> SEQUENCE: 317

```
His Gly Glu Gly Thr Phe Thr Ser Asp Leu Ser Lys Gln Met Glu Glu
  1               5                  10                  15
Glu Ala Val Arg Leu Phe Ile Glu Trp Leu Lys Asn Gly Gly Pro Ser
                 20                  25                  30
Ser Gly Ala Pro Pro Ser Gly Gly Gly Gly Ser Gly Gly Gly
             35                  40                  45
Gly Ser Gly Gly Gly Ser Asp Ile Gln Met Thr Gln Ser Pro Ser
 50                  55                  60
Ser Leu Ser Ala Ser Val Gly Asp Arg Val Thr Ile Thr Cys Arg Ala
 65                  70                  75                  80
Ser Arg Pro Ile Gly Thr Met Leu Ser Trp Tyr Gln Gln Lys Pro Gly
                 85                  90                  95
Lys Ala Pro Lys Leu Leu Ile Leu Phe Gly Ser Arg Leu Gln Ser Gly
                100                 105                 110
Val Pro Ser Arg Phe Ser Gly Ser Gly Ser Gly Thr Asp Phe Thr Leu
                115                 120                 125
Thr Ile Ser Ser Leu Gln Pro Glu Asp Phe Ala Thr Tyr Tyr Cys Ala
                130                 135                 140
Gln Ala Gly Thr His Pro Thr Thr Phe Gly Gln Gly Thr Lys Val Glu
145                 150                 155                 160
Ile Lys Arg
```

<210> SEQ ID NO 318
<211> LENGTH: 489
<212> TYPE: DNA
<213> ORGANISM: Artificial Sequence
<220> FEATURE:
<223> OTHER INFORMATION: Nucleotide

<400> SEQUENCE: 318

```
catggtgaag gaacatttac cagtgacttg tcaaaacaga tggaagagga ggcagtgcgg      60
ttatttattg agtggcttaa gaacggagga ccaagtagcg gggcacctcc gccatcgggt      120
ggtggaggcg gttcaggcgg aggtggcagc ggcggtggcg gtcggacat ccagatgacc       180 cagtctccat cctccctgtc tgcatctgta ggagaccgtg tcaccatcac ttgccgggca      240
agtcgtccga ttgggacgat gttaagttgg taccagcaga aaccagggaa agcccctaag     300
ctcctgatct tgtttggttc ccggttgcaa agtggggtcc catcacgttt cagtggcagt     360
ggatctggga cagatttcac tctcaccatc agcagtctgc aacctgaaga ttttgctacg     420
tactactgtg cgcaggctgg gacgcatcct acgacgttcg gccagggac caaggtggaa      480 atcaaacgg                                                              489
```

<210> SEQ ID NO 319
<211> LENGTH: 163

<212> TYPE: PRT
<213> ORGANISM: Homo sapiens

<400> SEQUENCE: 319

```
His Gly Glu Gly Thr Phe Thr Ser Asp Leu Ser Lys Gln Met Glu Glu
 1               5                  10                  15
Glu Ala Val Arg Leu Phe Ile Glu Trp Leu Lys Asn Gly Gly Pro Ser
            20                  25                  30
Ser Gly Ala Pro Pro Pro Ser Gly Gly Gly Gly Ser Gly Gly Gly
        35                  40                  45
Gly Ser Gly Gly Gly Gly Ser Asp Ile Gln Met Thr Gln Ser Pro Ser
    50                  55                  60
Ser Leu Ser Ala Ser Val Gly Asp Arg Val Thr Ile Thr Cys Arg Ala
65                  70                  75                  80
Ser Arg Pro Ile Gly Thr Met Leu Ser Trp Tyr Gln Gln Lys Pro Gly
                85                  90                  95
Lys Ala Pro Lys Leu Leu Ile Leu Ala Phe Ser Arg Leu Gln Ser Gly
            100                 105                 110
Val Pro Ser Arg Phe Ser Gly Ser Gly Ser Gly Thr Asp Phe Thr Leu
        115                 120                 125
Thr Ile Ser Ser Leu Gln Pro Glu Asp Phe Ala Thr Tyr Tyr Cys Ala
    130                 135                 140
Gln Ala Gly Thr His Pro Thr Thr Phe Gly Gln Gly Thr Lys Val Glu
145                 150                 155                 160
Ile Lys Arg
```

<210> SEQ ID NO 320
<211> LENGTH: 489
<212> TYPE: DNA
<213> ORGANISM: Artificial Sequence
<220> FEATURE:
<223> OTHER INFORMATION: Nucleotide

<400> SEQUENCE: 320

```
catggtgaag gaacatttac cagtgacttg tcaaaacaga tggaagagga ggcagtgcgg      60
ttatttattg agtggcttaa gaacggagga ccaagtagcg gggcacctcc gccatcgggt     120
ggtggaggcg gttcaggcgg aggtggcagc ggcggtggcg ggtcggacat ccagatgacc     180
cagtctccat cctccctgtc tgcatctgta ggagaccgtg tcaccatcac ttgccgggca     240
agtcgtccga ttgggacgat gttaagttgg taccagcaga aaccagggaa agcccctaag     300
ctcctgatcc ttgcttttc ccgtttgcaa agtggggtcc catcacgttt cagtggcagt     360
ggatctggga cagatttcac tctcaccatc agcagtctgc aacctgaaga ttttgctacg     420
tactactgcg cgcaggctgg gacgcatcct acgacgttcg gccaagggac caaggtggaa     480
atcaaacgg                                                            489
```

<210> SEQ ID NO 321
<211> LENGTH: 114
<212> TYPE: PRT
<213> ORGANISM: Homo sapiens

<400> SEQUENCE: 321

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Trp Ile Gly Ser Gln
            20                  25                  30
```

```
Leu Ser Trp Tyr Gln Gln Lys Pro Gly Lys Ala Pro Lys Leu Leu Ile
         35                  40                  45

Met Trp Arg Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Phe Gly Gln Gly Thr Lys Val Glu Ile Lys Arg Gly Gly Gly Gly
            100                 105                 110

Ser Cys
```

```
<210> SEQ ID NO 322
<211> LENGTH: 345
<212> TYPE: DNA
<213> ORGANISM: Artificial Sequence
<220> FEATURE:
<223> OTHER INFORMATION: Nucleotide

<400> SEQUENCE: 322
gacatccaga tgacccagtc tccatcctcc ctgtctgcat ctgtaggaga ccgtgtcacc    60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat ttcactctca ccatcagcag tctgcaacct   240
gaagattttg ctacgtacta ctgtgctcag ggtttgaggc atcctaagac gttcggccaa   300
gggaccaagg tggaaatcaa acggggtggc ggaggggtt cctgt                    345
```

```
<210> SEQ ID NO 323
<211> LENGTH: 115
<212> TYPE: PRT
<213> ORGANISM: Homo sapiens

<400> SEQUENCE: 323

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Ser Gln
                 20                  25                  30

Leu Ser Trp Tyr Gln Gln Lys Pro Gly Lys Ala Pro Lys Leu Leu Ile
         35                  40                  45

Met Trp Arg Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Phe Gly Gln Gly Thr Lys Val Glu Ile Lys Arg Thr Val Ala Ala
            100                 105                 110

Pro Ser Cys
        115
```

```
<210> SEQ ID NO 324
<211> LENGTH: 345
<212> TYPE: DNA
<213> ORGANISM: Artificial Sequence
<220> FEATURE:
<223> OTHER INFORMATION: Nucleotide
```

-continued

```
<400> SEQUENCE: 324
gacatccaga tgacccagtc tccatcctcc ctgtctgcat ctgtaggaga ccgtgtcacc      60
atcacttgcc gggcaagtca gtggattggg tctcagttat cttggtacca gcagaaacca    120
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgaggc atcctaagac gttcggccaa    300
gggaccaagg tggaaatcaa acggaccgtc gctgctccat cttgt                    345

<210> SEQ ID NO 325
<211> LENGTH: 235
<212> TYPE: PRT
<213> ORGANISM: Mouse

<400> SEQUENCE: 325

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
        115                 120                 125

Ile Gln Met Thr Gln Ser Pro Ser Ser Leu Ser Ala Ser Val Gly Asp
    130                 135                 140

Arg Val Thr Ile Thr Cys Arg Ala Ser Arg Pro Ile Gly Thr Thr Leu
145                 150                 155                 160

Ser Trp Tyr Gln Gln Lys Pro Gly Lys Ala Pro Lys Leu Leu Ile Trp
                165                 170                 175

Phe Gly Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Ala Gln Ala Gly Thr His Pro Thr Thr
    210                 215                 220

Phe Gly Gln Gly Thr Lys Val Glu Ile Lys Arg
225                 230                 235

<210> SEQ ID NO 326
<211> LENGTH: 249
<212> TYPE: PRT
<213> ORGANISM: Artificial Sequence
<220> FEATURE:
<223> OTHER INFORMATION: Amino acid plus nucleotide plus myc tag
      sequence

<400> SEQUENCE: 326

Glu Val Gln Leu Leu Glu Ser Gly Gly Gly Leu Val Gln Pro Gly Gly
```

```
              1               5              10              15
            Ser Leu Arg Leu Ser Cys Ala Ala Ser Gly Phe Thr Phe Asn Arg Tyr
                            20                  25                  30

Ser Met Gly Trp Leu Arg Gln Ala Pro Gly Lys Gly Leu Glu Trp Val
                            35                  40                  45

Ser Arg Ile Asp Ser Tyr Gly Arg Gly Thr Tyr Tyr Glu Asp Pro Val
                            50                  55                  60

Lys Gly Arg Phe Ser Ile Ser Arg Asp Asn Ser Lys Asn Thr Leu Tyr
             65                 70                  75                  80

Leu Gln Met Asn Ser Leu Arg Ala Glu Asp Thr Ala Val Tyr Tyr Cys
                                85                  90                  95

Ala Lys Ile Ser Gln Phe Gly Ser Asn Ala Phe Asp Tyr Trp Gly Gln
                            100                 105                 110

Gly Thr Gln Val Thr Val Ser Ser Ala Ser Thr Ser Gly Pro Ser Asp
                            115                 120                 125

Ile Gln Met Thr Gln Ser Pro Ser Ser Leu Ser Ala Ser Val Gly Asp
                            130                 135                 140

Arg Val Thr Ile Thr Cys Arg Ala Ser Arg Pro Ile Gly Thr Thr Leu
            145                 150                 155                 160

Ser Trp Tyr Gln Gln Lys Pro Gly Lys Ala Pro Lys Leu Leu Ile Trp
                                165                 170                 175

Phe Gly Ser Arg Leu Gln Ser Gly Val Pro Ser Arg Phe Ser Gly Ser
                            180                 185                 190

Gly Ser Gly Thr Asp Phe Thr Leu Thr Ile Ser Ser Leu Gln Pro Glu
                            195                 200                 205

Asp Phe Ala Thr Tyr Tyr Cys Ala Gln Ala Gly Thr His Pro Thr Thr
                            210                 215                 220

Phe Gly Gln Gly Thr Lys Val Glu Ile Lys Arg Ala Ala Ala Glu Gln
            225                 230                 235                 240

Lys Leu Ile Ser Glu Glu Asp Leu Asn
                            245

<210> SEQ ID NO 327
<211> LENGTH: 705
<212> TYPE: DNA
<213> ORGANISM: Artificial Sequence
<220> FEATURE:
<223> OTHER INFORMATION: Nucleotide

<400> SEQUENCE: 327
gaggtgcagc tgttggagtc tgggggaggc ttggtacagc ctgggggtc cctgcgtctc      60 tcctgtgcag cctccggatt cacctttaat aggtatagta tggggtggct ccgccaggct    120
ccagggaagg gtctagagtg gtctcacgg attgattctt atggtcgtgg tacatactac     180
gaagaccccg tgaagggccg gttcagcatc tcccgcgaca attccaagaa cacgctgtat    240
ctgcaaatga acagcctgcg tgccgaggac accgccgtat attactgtgc gaaaatttct   300
cagtttgggt caaatgcgtt tgactactgg ggtcaggaa cccaggtcac cgtctcgagc    360
gctagcacca gtggtccatc ggacatccag atgacccagt ctccatcctc cctgtctgca    420
tctgtaggag accgtgtcac catcacttgc cgggcaagtc gtccgattgg acgacgtta    480 agttggtacc agcagaaacc agggaaagcc cctaagctcc tgatctggtt tggttcccgg    540
ttgcaaagtg gggtcccatc acgtttcagt ggcagtggat ctgggacaga tttcactctc   600
accatcagca gtctgcaacc tgaagatttt gctacgtact actgtgcgca ggctgggacg    660
```
catcctacga cgttcggcca agggaccaag gtggaaatca aacgg 705

<210> SEQ ID NO 328
<211> LENGTH: 750
<212> TYPE: DNA
<213> ORGANISM: Artificial Sequence
<220> FEATURE:
<223> OTHER INFORMATION: Nucleotide plus myc tag sequence

<400> SEQUENCE: 328

```
gaggtgcagc tgttggagtc tgggggaggc ttggtacagc ctggggggtc cctgcgtctc    60
tcctgtgcag cctccggatt cacctttaat aggtatagta tggggtggct ccgccaggct   120
ccagggaagg gtctagagtg gtctcacgg attgattctt atggtcgtgg tacatactac   180
gaagaccccg tgaagggccg gttcagcatc tcccgcgaca attccaagaa cacgctgtat   240
ctgcaaatga acagcctgcg tgccgaggac accgccgtat attactgtgc gaaaatttct   300
cagtttgggt caaatgcgtt tgactactgg ggtcagggaa cccaggtcac cgtctcgagc   360
gctagcacca gtggtccatc ggacatccag atgacccagt ctccatcctc cctgtctgca   420
tctgtaggag accgtgtcac catcacttgc cgggcaagtc gtccgattgg gacgacgtta   480
agttggtacc agcagaaacc agggaaagcc cctaagctcc tgatctggtt tggttccccgg   540
ttgcaaagtg gggtcccatc acgtttcagt ggcagtggat ctgggacaga tttcactctc   600
accatcagca gtctgcaacc tgaagatttt gctacgtact actgtgcgca ggctgggacg   660
catcctacga cgttcggcca agggaccaag gtggaaatca aacgggcggc cgcagaacaa   720
aaactcatct cagaagagga tctgaattaa                                      750
```

<210> SEQ ID NO 329
<211> LENGTH: 235
<212> TYPE: PRT
<213> ORGANISM: Homo sapiens

<400> SEQUENCE: 329

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asn Arg Tyr
             20                  25                  30

Ser Met Gly Trp Leu Arg Gln Ala Pro Gly Lys Gly Leu Glu Trp Val
         35                  40                  45

Ser Arg Ile Asp Ser Tyr Gly Arg Gly Thr Tyr Tyr Glu Asp Pro Val
     50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
        115                 120                 125

Ile Gln Met Thr Gln Ser Pro Ser Ser Leu Ser Ala Ser Val Gly Asp
    130                 135                 140

Arg Val Thr Ile Thr Cys Arg Ala Ser Arg Pro Ile Gly Thr Met Leu
145                 150                 155                 160

Ser Trp Tyr Gln Gln Lys Pro Gly Lys Ala Pro Lys Leu Leu Ile Leu
                165                 170                 175
```

```
Phe Gly Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Ala Gln Ala Gly Thr His Pro Thr Thr
        210                 215                 220

Phe Gly Gln Gly Thr Lys Val Glu Ile Lys Arg
225                 230                 235
```

<210> SEQ ID NO 330
<211> LENGTH: 249
<212> TYPE: PRT
<213> ORGANISM: Artificial Sequence
<220> FEATURE:
<223> OTHER INFORMATION: Amino acid plus nucleotide plus myc tag
      sequence

<400> SEQUENCE: 330

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
        115                 120                 125

Ile Gln Met Thr Gln Ser Pro Ser Ser Leu Ser Ala Ser Val Gly Asp
    130                 135                 140

Arg Val Thr Ile Thr Cys Arg Ala Ser Arg Pro Ile Gly Thr Met Leu
145                 150                 155                 160

Ser Trp Tyr Gln Gln Lys Pro Gly Lys Ala Pro Lys Leu Leu Ile Leu
                165                 170                 175

Phe Gly Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Ala Gln Ala Gly Thr His Pro Thr Thr
        210                 215                 220

Phe Gly Gln Gly Thr Lys Val Glu Ile Lys Arg Ala Ala Ala Glu Gln
225                 230                 235                 240

Lys Leu Ile Ser Glu Glu Asp Leu Asn
                245
```

<210> SEQ ID NO 331
<211> LENGTH: 705
<212> TYPE: DNA
<213> ORGANISM: Artificial Sequence
<220> FEATURE:
<223> OTHER INFORMATION: Nucleotide plus myc tag sequence

<400> SEQUENCE: 331

```
gaggtgcagc tgttggagtc tgggggaggc ttggtacagc ctgggggtc cctgcgtctc       60
tcctgtgcag cctccggatt cacctttaat aggtatagta tggggtggct ccgccaggct     120
ccagggaagg gtctagagtg ggtctcacgg attgattctt atggtcgtgg tacatactac     180
gaagaccccg tgaagggccg gttcagcatc tcccgcgaca attccaagaa cacgctgtat     240
ctgcaaatga acagcctgcg tgccgaggac accgccgtat attactgtgc gaaaatttct     300
cagtttgggt caaatgcgtt tgactactgg ggtcagggaa cccaggtcac cgtctcgagc     360
gctagcacca gtggtccatc ggacatccag atgacccagt ctccatcctc cctgtctgca     420
tctgtaggag accgtgtcac catcacttgc cgggcaagtc gtccgattgg gacgatgtta     480
agttggtacc agcagaaacc agggaaagcc cctaagctcc tgatcttgtt tggttcccgg     540
ttgcaaagtg gggtcccatc acgtttcagt ggcagtggat ctgggacaga tttcactctc     600
accatcagca gtctgcaacc tgaagatttt gctacgtact actgtgcgca ggctgggacg     660
catcctacga cgttcggcca agggaccaag gtggaaatca aacgg                      705
```

<210> SEQ ID NO 332
<211> LENGTH: 750
<212> TYPE: DNA
<213> ORGANISM: Artificial Sequence
<220> FEATURE:
<223> OTHER INFORMATION: Nucleotide plus myc tag sequence

<400> SEQUENCE: 332

```
gaggtgcagc tgttggagtc tgggggaggc ttggtacagc ctgggggtc cctgcgtctc       60
tcctgtgcag cctccggatt cacctttaat aggtatagta tggggtggct ccgccaggct     120
ccagggaagg gtctagagtg ggtctcacgg attgattctt atggtcgtgg tacatactac     180
gaagaccccg tgaagggccg gttcagcatc tcccgcgaca attccaagaa cacgctgtat     240
ctgcaaatga acagcctgcg tgccgaggac accgccgtat attactgtgc gaaaatttct     300
cagtttgggt caaatgcgtt tgactactgg ggtcagggaa cccaggtcac cgtctcgagc     360
gctagcacca gtggtccatc ggacatccag atgacccagt ctccatcctc cctgtctgca     420
tctgtaggag accgtgtcac catcacttgc cgggcaagtc gtccgattgg gacgatgtta     480
agttggtacc agcagaaacc agggaaagcc cctaagctcc tgatcttgtt tggttcccgg     540
ttgcaaagtg gggtcccatc acgtttcagt ggcagtggat ctgggacaga tttcactctc     600
accatcagca gtctgcaacc tgaagatttt gctacgtact actgtgcgca ggctgggacg     660
catcctacga cgttcggcca agggaccaag gtggaaatca aacggcggc cgcagaacaa     720
aaactcatct cagaagagga tctgaattaa                                       750
```

<210> SEQ ID NO 333
<211> LENGTH: 235
<212> TYPE: PRT
<213> ORGANISM: Homo sapiens

<400> SEQUENCE: 333

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asn Arg Tyr
             20                  25                  30

Ser Met Gly Trp Leu Arg Gln Ala Pro Gly Lys Gly Leu Glu Trp Val
         35                  40                  45
```

Ser Arg Ile Asp Ser Tyr Gly Arg Gly Thr Tyr Tyr Glu Asp Pro Val
50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
            115                 120                 125

Ile Gln Met Thr Gln Ser Pro Ser Ser Leu Ser Ala Ser Val Gly Asp
130                 135                 140

Arg Val Thr Ile Thr Cys Arg Ala Ser Arg Pro Ile Gly Thr Met Leu
145                 150                 155                 160

Ser Trp Tyr Gln Gln Lys Pro Gly Lys Ala Pro Lys Leu Leu Ile Leu
                165                 170                 175

Ala Phe Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
            195                 200                 205

Asp Phe Ala Thr Tyr Tyr Cys Ala Gln Ala Gly Thr His Pro Thr Thr
            210                 215                 220

Phe Gly Gln Gly Thr Lys Val Glu Ile Lys Arg
225                 230                 235

<210> SEQ ID NO 334
<211> LENGTH: 249
<212> TYPE: PRT
<213> ORGANISM: Artificial Sequence
<220> FEATURE:
<223> OTHER INFORMATION: Amino acid plus nucleotide plus myc tag
      sequence

<400> SEQUENCE: 334

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
            115                 120                 125

Ile Gln Met Thr Gln Ser Pro Ser Ser Leu Ser Ala Ser Val Gly Asp
130                 135                 140

Arg Val Thr Ile Thr Cys Arg Ala Ser Arg Pro Ile Gly Thr Met Leu
145                 150                 155                 160

Ser Trp Tyr Gln Gln Lys Pro Gly Lys Ala Pro Lys Leu Leu Ile Leu
                165                 170                 175

```
Ala Phe Ser Arg Leu Gln Ser Gly Val Pro Ser Arg Phe Ser Gly Ser
                180                 185                 190

Gly Ser Gly Thr Asp Phe Thr Leu Thr Ile Ser Ser Leu Gln Pro Glu
            195                 200                 205

Asp Phe Ala Thr Tyr Tyr Cys Ala Gln Ala Gly Thr His Pro Thr Thr
    210                 215                 220

Phe Gly Gln Gly Thr Lys Val Glu Ile Lys Arg Ala Ala Ala Glu Gln
225                 230                 235                 240

Lys Leu Ile Ser Glu Glu Asp Leu Asn
                245

<210> SEQ ID NO 335
<211> LENGTH: 705
<212> TYPE: DNA
<213> ORGANISM: Artificial Sequence
<220> FEATURE:
<223> OTHER INFORMATION: Nucleotide

<400> SEQUENCE: 335
gaggtgcagc tgttggagtc tgggggaggc ttggtacagc ctgggggtc cctgcgtctc      60 tcctgtgcag cctccggatt cacctttaat aggtatagta tggggtggct ccgccaggct     120
ccagggaagg gtctagagtg ggtctcacgg attgattctt atggtcgtgg tacatactac     180
gaagaccccg tgaagggccg gttcagcatc tcccgcgaca attccaagaa cacgctgtat     240
ctgcaaatga acagcctgcg tgccgaggac accgccgtat attactgtgc gaaaatttct     300
cagtttgggt caaatgcgtt tgactactgg ggtcagggaa cccaggtcac cgtctcgagc     360
gctagcacca gtggtccatc ggacatccag atgacccagt ctccatcctc cctgtctgca     420
tctgtaggag accgtgtcac catcacttgc cgggcaagtc gtccgattgg gacgatgtta     480
agttggtacc agcagaaacc agggaaagcc ctaagctcc tgatccttgc ttttccccgt     540
ttgcaaagtg gggtcccatc acgtttcagt ggcagtggat ctgggacaga tttcactctc     600
accatcagca gtctgcaacc tgaagatttt gctacgtact actgcgcgca ggctgggacg     660
catcctacga cgttcggcca agggaccaag gtggaaatca aacgg                    705

<210> SEQ ID NO 336
<211> LENGTH: 750
<212> TYPE: DNA
<213> ORGANISM: Artificial Sequence
<220> FEATURE:
<223> OTHER INFORMATION: Nucleotide plus myc tag sequence

<400> SEQUENCE: 336
gaggtgcagc tgttggagtc tgggggaggc ttggtacagc ctgggggtc cctgcgtctc      60 tcctgtgcag cctccggatt cacctttaat aggtatagta tggggtggct ccgccaggct     120
ccagggaagg gtctagagtg ggtctcacgg attgattctt atggtcgtgg tacatactac     180
gaagaccccg tgaagggccg gttcagcatc tcccgcgaca attccaagaa cacgctgtat     240
ctgcaaatga acagcctgcg tgccgaggac accgccgtat attactgtgc gaaaatttct     300
cagtttgggt caaatgcgtt tgactactgg ggtcagggaa cccaggtcac cgtctcgagc     360
gctagcacca gtggtccatc ggacatccag atgacccagt ctccatcctc cctgtctgca     420
tctgtaggag accgtgtcac catcacttgc cgggcaagtc gtccgattgg gacgatgtta     480
agttggtacc agcagaaacc agggaaagcc ctaagctcc tgatccttgc ttttccccgt     540
ttgcaaagtg gggtcccatc acgtttcagt ggcagtggat ctgggacaga tttcactctc     600
```

```
accatcagca gtctgcaacc tgaagatttt gctacgtact actgcgcgca ggctgggacg    660
catcctacga cgttcggcca agggaccaag gtggaaatca aacgggcggc cgcagaacaa    720
aaactcatct cagaagagga tctgaattaa                                     750
```

<210> SEQ ID NO 337
<211> LENGTH: 9
<212> TYPE: PRT
<213> ORGANISM: Artificial Sequence
<220> FEATURE:
<223> OTHER INFORMATION: CDR

<400> SEQUENCE: 337

Ser Gln Ser Ile Ser Ser Tyr Leu Asn
1               5

<210> SEQ ID NO 338
<211> LENGTH: 8
<212> TYPE: PRT
<213> ORGANISM: Artificial Sequence
<220> FEATURE:
<223> OTHER INFORMATION: CDR

<400> SEQUENCE: 338

Tyr Ala Ala Ser Ser Leu Gln Ser
1               5

<210> SEQ ID NO 339
<211> LENGTH: 9
<212> TYPE: PRT
<213> ORGANISM: Artificial Sequence
<220> FEATURE:
<223> OTHER INFORMATION: CDR

<400> SEQUENCE: 339

Gln Gln Ser Tyr Ser Thr Pro Asn Thr
1               5

<210> SEQ ID NO 340
<211> LENGTH: 9
<212> TYPE: PRT
<213> ORGANISM: Artificial Sequence
<220> FEATURE:
<223> OTHER INFORMATION: CDR

<400> SEQUENCE: 340

Ser Arg Pro Ile Gly Thr Thr Leu Ser
1               5

<210> SEQ ID NO 341
<211> LENGTH: 8
<212> TYPE: PRT
<213> ORGANISM: Artificial Sequence
<220> FEATURE:
<223> OTHER INFORMATION: CDR

<400> SEQUENCE: 341

Trp Phe Gly Ser Arg Leu Gln Ser
1               5

<210> SEQ ID NO 342
<211> LENGTH: 9
<212> TYPE: PRT
<213> ORGANISM: Artificial Sequence
<220> FEATURE:
<223> OTHER INFORMATION: CDR

```
<400> SEQUENCE: 342

Ala Gln Ala Gly Thr His Pro Thr Thr
1               5

<210> SEQ ID NO 343
<211> LENGTH: 9
<212> TYPE: PRT
<213> ORGANISM: Artificial Sequence
<220> FEATURE:
<223> OTHER INFORMATION: CDR

<400> SEQUENCE: 343

Ser Arg Pro Ile Gly Thr Met Leu Ser
1               5

<210> SEQ ID NO 344
<211> LENGTH: 8
<212> TYPE: PRT
<213> ORGANISM: Artificial Sequence
<220> FEATURE:
<223> OTHER INFORMATION: CDR

<400> SEQUENCE: 344

Leu Phe Gly Ser Arg Leu Gln Ser
1               5

<210> SEQ ID NO 345
<211> LENGTH: 9
<212> TYPE: PRT
<213> ORGANISM: Artificial Sequence
<220> FEATURE:
<223> OTHER INFORMATION: CDR

<400> SEQUENCE: 345

Ala Gln Ala Gly Thr His Pro Thr Thr
1               5

<210> SEQ ID NO 346
<211> LENGTH: 9
<212> TYPE: PRT
<213> ORGANISM: Artificial Sequence
<220> FEATURE:
<223> OTHER INFORMATION: CDR

<400> SEQUENCE: 346

Ser Arg Pro Ile Gly Thr Met Leu Ser
1               5

<210> SEQ ID NO 347
<211> LENGTH: 8
<212> TYPE: PRT
<213> ORGANISM: Artificial Sequence
<220> FEATURE:
<223> OTHER INFORMATION: CDR

<400> SEQUENCE: 347

Leu Ala Phe Ser Arg Leu Gln Ser
1               5

<210> SEQ ID NO 348
<211> LENGTH: 9
<212> TYPE: PRT
<213> ORGANISM: Artificial Sequence
<220> FEATURE:
<223> OTHER INFORMATION: CDR
```

```
<400> SEQUENCE: 348

Ala Gln Ala Gly Thr His Pro Thr Thr
1               5

<210> SEQ ID NO 349
<211> LENGTH: 9
<212> TYPE: PRT
<213> ORGANISM: Artificial Sequence
<220> FEATURE:
<223> OTHER INFORMATION: CDR

<400> SEQUENCE: 349

Ser Arg Pro Ile Gly Thr Met Leu Ser
1               5

<210> SEQ ID NO 350
<211> LENGTH: 8
<212> TYPE: PRT
<213> ORGANISM: Artificial Sequence
<220> FEATURE:
<223> OTHER INFORMATION: CDR

<400> SEQUENCE: 350

Trp Phe Gly Ser Arg Leu Gln Ser
1               5

<210> SEQ ID NO 351
<211> LENGTH: 9
<212> TYPE: PRT
<213> ORGANISM: Artificial Sequence
<220> FEATURE:
<223> OTHER INFORMATION: CDR

<400> SEQUENCE: 351

Ala Gln Ala Gly Thr His Pro Thr Thr
1               5

<210> SEQ ID NO 352
<211> LENGTH: 9
<212> TYPE: PRT
<213> ORGANISM: Artificial Sequence
<220> FEATURE:
<223> OTHER INFORMATION: CDR

<400> SEQUENCE: 352

Ser Arg Pro Ile Gly Thr Met Leu Ser
1               5

<210> SEQ ID NO 353
<211> LENGTH: 8
<212> TYPE: PRT
<213> ORGANISM: Artificial Sequence
<220> FEATURE:
<223> OTHER INFORMATION: CDR

<400> SEQUENCE: 353

Leu Phe Gly Ser Arg Leu Gln Ser
1               5

<210> SEQ ID NO 354
<211> LENGTH: 9
<212> TYPE: PRT
<213> ORGANISM: Artificial Sequence
<220> FEATURE:
<223> OTHER INFORMATION: CDR

<400> SEQUENCE: 354
```

Ala Gln Thr Gly Thr His Pro Thr Thr
1               5

<210> SEQ ID NO 355
<211> LENGTH: 9
<212> TYPE: PRT
<213> ORGANISM: Artificial Sequence
<220> FEATURE:
<223> OTHER INFORMATION: CDR

<400> SEQUENCE: 355

Ser Arg Pro Ile Gly Thr Thr Leu Ser
1               5

<210> SEQ ID NO 356
<211> LENGTH: 8
<212> TYPE: PRT
<213> ORGANISM: Artificial Sequence
<220> FEATURE:
<223> OTHER INFORMATION: CDR

<400> SEQUENCE: 356

Leu Trp Phe Ser Arg Leu Gln Ser
1               5

<210> SEQ ID NO 357
<211> LENGTH: 9
<212> TYPE: PRT
<213> ORGANISM: Artificial Sequence
<220> FEATURE:
<223> OTHER INFORMATION: CDR

<400> SEQUENCE: 357

Ala Gln Ala Gly Thr His Pro Thr Thr
1               5

<210> SEQ ID NO 358
<211> LENGTH: 9
<212> TYPE: PRT
<213> ORGANISM: Artificial Sequence
<220> FEATURE:
<223> OTHER INFORMATION: AlbudAb

<400> SEQUENCE: 358

Ser Gln Trp Ile Gly Ser Gln Leu Ser
1               5

<210> SEQ ID NO 359
<211> LENGTH: 8
<212> TYPE: PRT
<213> ORGANISM: Artificial Sequence
<220> FEATURE:
<223> OTHER INFORMATION: CDR

<400> SEQUENCE: 359

Met Trp Arg Ser Ser Leu Gln Ser
1               5

<210> SEQ ID NO 360
<211> LENGTH: 9
<212> TYPE: PRT
<213> ORGANISM: Artificial Sequence
<220> FEATURE:
<223> OTHER INFORMATION: CDR

<400> SEQUENCE: 360

Ala Gln Gly Ala Ala Leu Pro Arg Thr
1               5

<210> SEQ ID NO 361
<211> LENGTH: 9
<212> TYPE: PRT
<213> ORGANISM: Artificial Sequence
<220> FEATURE:
<223> OTHER INFORMATION: CDR

<400> SEQUENCE: 361

Ser Gln Trp Ile Gly Ser Gln Leu Ser
1               5

<210> SEQ ID NO 362
<211> LENGTH: 8
<212> TYPE: PRT
<213> ORGANISM: Artificial Sequence
<220> FEATURE:
<223> OTHER INFORMATION: CDR

<400> SEQUENCE: 362

Met Trp Arg Ser Ser Leu Gln Ser
1               5

<210> SEQ ID NO 363
<211> LENGTH: 9
<212> TYPE: PRT
<213> ORGANISM: Artificial Sequence
<220> FEATURE:
<223> OTHER INFORMATION: CDR

<400> SEQUENCE: 363

Ala Gln Gly Leu Arg His Pro Lys Thr
1               5

<210> SEQ ID NO 364
<211> LENGTH: 9
<212> TYPE: PRT
<213> ORGANISM: Artificial Sequence
<220> FEATURE:
<223> OTHER INFORMATION: CDR

<400> SEQUENCE: 364

Ser Gln Trp Ile Gly Ser Gln Leu Ser
1               5

<210> SEQ ID NO 365
<211> LENGTH: 8
<212> TYPE: PRT
<213> ORGANISM: Artificial Sequence
<220> FEATURE:
<223> OTHER INFORMATION: CDR

<400> SEQUENCE: 365

Met Trp Arg Ser Ser Leu Gln Ser
1               5

<210> SEQ ID NO 366
<211> LENGTH: 9
<212> TYPE: PRT
<213> ORGANISM: Artificial Sequence
<220> FEATURE:
<223> OTHER INFORMATION: CDR

<400> SEQUENCE: 366

Ala Gln Gly Leu Met Lys Pro Met Thr

```
<210> SEQ ID NO 367
<211> LENGTH: 9
<212> TYPE: PRT
<213> ORGANISM: Artificial Sequence
<220> FEATURE:
<223> OTHER INFORMATION: CDR

<400> SEQUENCE: 367

Ser Gln Trp Ile Gly Ser Gln Leu Ser
1               5

<210> SEQ ID NO 368
<211> LENGTH: 8
<212> TYPE: PRT
<213> ORGANISM: Artificial Sequence
<220> FEATURE:
<223> OTHER INFORMATION: CDR

<400> SEQUENCE: 368

Met Trp Arg Ser Ser Leu Gln Ser
1               5

<210> SEQ ID NO 369
<211> LENGTH: 9
<212> TYPE: PRT
<213> ORGANISM: Artificial Sequence
<220> FEATURE:
<223> OTHER INFORMATION: CDR

<400> SEQUENCE: 369

Ala Gln Gly Ala Ala Leu Pro Arg Thr
1               5

<210> SEQ ID NO 370
<211> LENGTH: 9
<212> TYPE: PRT
<213> ORGANISM: Artificial Sequence
<220> FEATURE:
<223> OTHER INFORMATION: CDR

<400> SEQUENCE: 370

Ser Gln Trp Ile Gly Ser Gln Leu Ser
1               5

<210> SEQ ID NO 371
<211> LENGTH: 8
<212> TYPE: PRT
<213> ORGANISM: Artificial Sequence
<220> FEATURE:
<223> OTHER INFORMATION: CDR

<400> SEQUENCE: 371

Met Trp Arg Ser Ser Leu Gln Ser
1               5

<210> SEQ ID NO 372
<211> LENGTH: 9
<212> TYPE: PRT
<213> ORGANISM: Artificial Sequence
<220> FEATURE:
<223> OTHER INFORMATION: CDR

<400> SEQUENCE: 372

Ala Gln Gly Ala Ala Leu Pro Lys Thr
1               5
```

<210> SEQ ID NO 373
<211> LENGTH: 9
<212> TYPE: PRT
<213> ORGANISM: Artificial Sequence
<220> FEATURE:
<223> OTHER INFORMATION: CDR

<400> SEQUENCE: 373

Ser Gln Trp Ile Gly Ser Gln Leu Ser
1               5

<210> SEQ ID NO 374
<211> LENGTH: 8
<212> TYPE: PRT
<213> ORGANISM: Artificial Sequence
<220> FEATURE:
<223> OTHER INFORMATION: CDR

<400> SEQUENCE: 374

Met Trp Arg Ser Ser Leu Gln Ser
1               5

<210> SEQ ID NO 375
<211> LENGTH: 9
<212> TYPE: PRT
<213> ORGANISM: Artificial Sequence
<220> FEATURE:
<223> OTHER INFORMATION: CDR

<400> SEQUENCE: 375

Ala Gln Gly Phe Lys Lys Pro Arg Thr
1               5

<210> SEQ ID NO 376
<211> LENGTH: 165
<212> TYPE: PRT
<213> ORGANISM: Homo sapiens

<400> SEQUENCE: 376

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
        50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu

<210> SEQ ID NO 377
<211> LENGTH: 495
<212> TYPE: DNA
<213> ORGANISM: Artificial Sequence
<220> FEATURE:
<223> OTHER INFORMATION: Interferon alpha 2b nucleotide

<400> SEQUENCE: 377

```
tgtgatctgc ctcaaaccca cagcctgggt agcaggagga ccttgatgct cctggcacag      60
atgaggagaa tctctctttt ctcctgcttg aaggacagac atgactttgg atttccccag     120
gaggagtttg gcaaccagtt ccaaaaggct gaaaccatcc ctgtcctcca tgagatgatc     180
cagcagatct tcaatctctt cagcacaaag gactcatctg ctgcttggga tgagaccctc     240
ctagacaaat tctacactga actctaccag cagctgaatg acctggaagc ctgtgtgata     300
caggggtgg gggtgacaga gactcccctg atgaaggagg actccattct ggctgtgagg      360
aaatacttcc aaagaatcac tctctatctg aaagagaaga atacagccc ttgtgcctgg      420
gaggttgtca gagcagaaat catgagatct ttttctttgt caacaaactt gcaagaaagt     480
ttaagaagta aggaa                                                     495
```

<210> SEQ ID NO 378
<211> LENGTH: 25
<212> TYPE: DNA
<213> ORGANISM: Artificial Sequence
<220> FEATURE:
<223> OTHER INFORMATION: IFN2b SOE fragment 5'

<400> SEQUENCE: 378

```
gcccggatcc accggctgtg atctg                                           25
```

<210> SEQ ID NO 379
<211> LENGTH: 30
<212> TYPE: DNA
<213> ORGANISM: Artificial Sequence
<220> FEATURE:
<223> OTHER INFORMATION: IFN2b SOE fragment 3'

<400> SEQUENCE: 379

```
ggaggatgga gactgggtca tctggatgtc                                      30
```

<210> SEQ ID NO 380
<211> LENGTH: 30
<212> TYPE: DNA
<213> ORGANISM: Artificial Sequence
<220> FEATURE:
<223> OTHER INFORMATION: Vk SOE fragment 5'

<400> SEQUENCE: 380

```
gacatccaga tgacccagtc tccatcctcc                                      30
```

<210> SEQ ID NO 381
<211> LENGTH: 82
<212> TYPE: DNA
<213> ORGANISM: Artificial Sequence
<220> FEATURE:
<223> OTHER INFORMATION: Vk SOE fragment 3' to also introduce a myc tag

<400> SEQUENCE: 381

```
gcgcaagctt ttattaattc agatcctctt ctgagatgag ttttttgttct gcggccgccc    60
gtttgatttc caccttggtc cc                                              82
```

<210> SEQ ID NO 382
<211> LENGTH: 25
<212> TYPE: DNA
<213> ORGANISM: Artificial Sequence
<220> FEATURE:
<223> OTHER INFORMATION: IFN2b SOE fragment 5'

<400> SEQUENCE: 382
gcccggatcc accggctgtg atctg                                      25

<210> SEQ ID NO 383
<211> LENGTH: 82
<212> TYPE: DNA
<213> ORGANISM: Artificial Sequence
<220> FEATURE:
<223> OTHER INFORMATION: NucleotideVk SOE fragment 3' to also introduce
     a myc tag

<400> SEQUENCE: 383
gcgcaagctt ttattaattc agatcctctt ctgagatgag ttttgttct gcggccgccc    60 gtttgatttc caccttggtc cc                                          82

<210> SEQ ID NO 384
<211> LENGTH: 20
<212> TYPE: PRT
<213> ORGANISM: Mouse

<400> SEQUENCE: 384

Met Glu Thr Asp Thr Leu Leu Leu Trp Val Leu Leu Leu Trp Val Pro
 1               5                  10                  15

Gly Ser Thr Gly
         20

<210> SEQ ID NO 385
<211> LENGTH: 61
<212> TYPE: DNA
<213> ORGANISM: Artificial Sequence
<220> FEATURE:
<223> OTHER INFORMATION: Nucleotide

<400> SEQUENCE: 385
atggagaccg acaccctgct gctgtgggtg ctgctgctgt gggtgcccgg atccaccggg    60
c                                                                   61

<210> SEQ ID NO 386
<211> LENGTH: 108
<212> TYPE: PRT
<213> ORGANISM: Artificial Sequence
<220> FEATURE:
<223> OTHER INFORMATION: Nucleotide

<400> SEQUENCE: 386

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
             20                  25                  30

Leu Ser Trp Tyr Gln Gln Lys Pro Gly Lys Ala Pro Lys Leu Leu Ile
         35                  40                  45

Met Trp Arg Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Ala Gln Gly Leu Arg His Pro Lys
                    85                  90                  95
Thr Phe Gly Gln Gly Thr Lys Val Glu Ile Lys Cys
                100                 105

<210> SEQ ID NO 387
<211> LENGTH: 324
<212> TYPE: DNA
<213> ORGANISM: Artificial Sequence
<220> FEATURE:
<223> OTHER INFORMATION: Nucleotide

<400> SEQUENCE: 387
gacatccaga tgacccagtc tccatcctcc ctgtctgcat ctgtaggaga ccgtgtcacc    60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat ttcactctca ccatcagcag tctgcaacct   240
gaagattttg ctacgtacta ctgtgctcag ggtttgaggc atcctaagac gttcggccaa   300
gggaccaagg tggaaatcaa atgc                                          324

<210> SEQ ID NO 388
<211> LENGTH: 108
<212> TYPE: PRT
<213> ORGANISM: Homo sapiens

<400> SEQUENCE: 388

Asp Ile Gln Met Thr Gln Ser Pro Ser Ser Leu Pro Ala Ser Val Gly
  1               5                  10                  15
Asp Arg Val Thr Ile Thr Cys Arg Ala Ser Arg Pro Ile Gly Thr Met
                 20                  25                  30
Leu Ser Trp Tyr Gln Gln Lys Pro Gly Lys Ala Pro Lys Leu Leu Ile
             35                  40                  45
Leu Ala Phe Ser Arg Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Ala Gln Ala Gly Thr His Pro Thr
                    85                  90                  95
Thr Phe Gly Gln Gly Thr Lys Val Glu Ile Lys Arg
                100                 105

<210> SEQ ID NO 389
<211> LENGTH: 324
<212> TYPE: DNA
<213> ORGANISM: Artificial Sequence
<220> FEATURE:
<223> OTHER INFORMATION: nucleic acid

<400> SEQUENCE: 389
gacatccaga tgacccagtc tccatcctcc ctgcctgcat ctgtaggaga ccgtgtcacc    60
atcacttgcc gggcaagtcg tccgattggg acgatgttaa gttggtacca gcagaaacca   120
gggaaagccc ctaagctcct gatccttgct tttcccgtt tgcaaagtgg ggtcccatca    180
cgtttcagtg gcagtggatc tgggacagat ttcactctca ccatcagcag tctgcaacct   240
gaagattttg ctacgtacta ctgcgcgcag gctgggacgc atcctacgac gttcggccaa   300
```
gggaccaagg tggaaatcaa acgg                                                  324

<210> SEQ ID NO 390
<211> LENGTH: 62
<212> TYPE: DNA
<213> ORGANISM: Artificial Sequence
<220> FEATURE:
<223> OTHER INFORMATION: Primer

<400> SEQUENCE: 390
gcaacagcgt cgacggacat ccagatgacc cagtctccat cctccctgcc tgcatctgta      60
gg                                                                      62

<210> SEQ ID NO 391
<211> LENGTH: 32
<212> TYPE: PRT
<213> ORGANISM: Homo sapiens

<400> SEQUENCE: 391

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 392
<211> LENGTH: 9
<212> TYPE: PRT
<213> ORGANISM: Homo sapiens

<400> SEQUENCE: 392

Ala Gln Ala Gly Thr His Pro Thr Thr
1               5

<210> SEQ ID NO 393
<211> LENGTH: 32
<212> TYPE: PRT
<213> ORGANISM: Homo sapiens

<400> SEQUENCE: 393

Gly Val Pro Ser Arg Phe Ser Gly Ser Gly Ser Gly Thr Asp Phe Thr
1               5                   10                  15

Leu Thr Ile Ser Asn Leu Gln Pro Glu Asp Phe Ala Thr Tyr Tyr Cys
            20                  25                  30

<210> SEQ ID NO 394
<211> LENGTH: 9
<212> TYPE: PRT
<213> ORGANISM: Homo sapiens

<400> SEQUENCE: 394

Ala Gln Ala Gly Thr His Pro Thr Thr
1               5

<210> SEQ ID NO 395
<211> LENGTH: 32
<212> TYPE: PRT
<213> ORGANISM: Homo sapiens

<400> SEQUENCE: 395

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 396
<211> LENGTH: 9
<212> TYPE: PRT
<213> ORGANISM: Homo sapiens

<400> SEQUENCE: 396

Ala Gln Ala Gly Thr His Pro Thr Thr
1               5

<210> SEQ ID NO 397
<211> LENGTH: 32
<212> TYPE: PRT
<213> ORGANISM: Homo sapiens

<400> SEQUENCE: 397

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 398
<211> LENGTH: 9
<212> TYPE: PRT
<213> ORGANISM: Homo sapiens

<400> SEQUENCE: 398

Ala Gln Ala Gly Thr His His Thr Thr
1               5

<210> SEQ ID NO 399
<211> LENGTH: 32
<212> TYPE: PRT
<213> ORGANISM: Homo sapiens

<400> SEQUENCE: 399

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 400
<211> LENGTH: 9
<212> TYPE: PRT
<213> ORGANISM: Homo sapiens

<400> SEQUENCE: 400

Ala Gln Ala Gly Val His Pro Thr Thr
1               5

<210> SEQ ID NO 401
<211> LENGTH: 96
<212> TYPE: DNA
<213> ORGANISM: Artificial Sequence
<220> FEATURE:
<223> OTHER INFORMATION: Nucleotide

<400> SEQUENCE: 401
ggggtcccat cacgtttcag tggcagtgga tctgggacag atttcactct caccatcagc        60
agtctgcaac ctgaagattt tgctacgtac tactgc                                  96

<210> SEQ ID NO 402
<211> LENGTH: 27

```
<212> TYPE: DNA
<213> ORGANISM: Artificial Sequence
<220> FEATURE:
<223> OTHER INFORMATION: Nucleotide

<400> SEQUENCE: 402
gcgcaggctg ggacgcatcc tacgacg                                              27

<210> SEQ ID NO 403
<211> LENGTH: 96
<212> TYPE: DNA
<213> ORGANISM: Artificial Sequence
<220> FEATURE:
<223> OTHER INFORMATION: Nucleotide

<400> SEQUENCE: 403
ggggtcccat cacgtttcag tggcagtgga tctgggacag atttcactct caccatcagc         60
aatctgcaac ctgaagattt tgctacgtac tactgc                                   96

<210> SEQ ID NO 404
<211> LENGTH: 27
<212> TYPE: DNA
<213> ORGANISM: Artificial Sequence
<220> FEATURE:
<223> OTHER INFORMATION: Nucleotide

<400> SEQUENCE: 404
gcgcaggctg ggacgcatcc tacgacg                                              27

<210> SEQ ID NO 405
<211> LENGTH: 96
<212> TYPE: DNA
<213> ORGANISM: Artificial Sequence
<220> FEATURE:
<223> OTHER INFORMATION: Nucleotide

<400> SEQUENCE: 405
ggggtcccat cacgtttcag tggcagtgga tctgggacag atttcactct caccatcagc         60
agtctgcaac ctgaagatgt tgctacgtac tactgt                                   96

<210> SEQ ID NO 406
<211> LENGTH: 27
<212> TYPE: DNA
<213> ORGANISM: Artificial Sequence
<220> FEATURE:
<223> OTHER INFORMATION: Nucleotide

<400> SEQUENCE: 406
gcgcaggctg ggacgcatcc tacgacg                                              27

<210> SEQ ID NO 407
<211> LENGTH: 96
<212> TYPE: DNA
<213> ORGANISM: Artificial Sequence
<220> FEATURE:
<223> OTHER INFORMATION: Nucleotide

<400> SEQUENCE: 407
ggggtcccat cacgtttcag tggcagtgga tctgggacag atttcactct caccatcagc         60
agtctgcaac ctgaagattt tgctacgtac tactgt                                   96

<210> SEQ ID NO 408
<211> LENGTH: 27
<212> TYPE: DNA
```

```
<213> ORGANISM: Artificial Sequence
<220> FEATURE:
<223> OTHER INFORMATION: Nucleotide

<400> SEQUENCE: 408
gcgcaggctg ggacgcatca tacgacg                                              27

<210> SEQ ID NO 409
<211> LENGTH: 20
<212> TYPE: DNA
<213> ORGANISM: Artificial Sequence
<220> FEATURE:
<223> OTHER INFORMATION: Nucleotide

<400> SEQUENCE: 409
attttgctac gtactactgt                                                      20

<210> SEQ ID NO 410
<211> LENGTH: 27
<212> TYPE: DNA
<213> ORGANISM: Artificial Sequence
<220> FEATURE:
<223> OTHER INFORMATION: Nucleotide

<400> SEQUENCE: 410
gcgcaggctg gggtgcatcc tacgacg                                              27

<210> SEQ ID NO 411
<211> LENGTH: 108
<212> TYPE: PRT
<213> ORGANISM: Homo sapiens

<400> SEQUENCE: 411
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
            20                  25                  30

Leu Ser Trp Tyr Gln Gln Lys Pro Gly Lys Ala Pro Lys Leu Leu Ile
        35                  40                  45

Leu Ala Phe Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His Pro Thr
                85                  90                  95

Thr Phe Gly Gln Gly Thr Lys Val Glu Ile Lys Trp
            100                 105

```
<210> SEQ ID NO 412
<211> LENGTH: 108
<212> TYPE: PRT
<213> ORGANISM: Homo sapiens

<400> SEQUENCE: 412
```

Asp Ile Gln Met Thr Gln Ser Pro Ser Ser Leu Ser Ala Ser Val Gly
1               5                   10                  15

Asp Arg Val Thr Ile Ser Cys Arg Ala Ser Arg Pro Ile Gly Thr Met
            20                  25                  30

Leu Ser Trp Tyr Gln Gln Lys Pro Gly Lys Ala Pro Lys Leu Leu Ile
        35                  40                  45

Leu Ala Phe Ser Arg Leu Gln Ser Gly Val Pro Ser Arg Phe Ser Gly

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Ala Gly Thr His Pro Thr
                 85                  90                  95

Thr Phe Gly Gln Gly Thr Lys Val Glu Ile Lys Trp
            100                 105
```

<210> SEQ ID NO 413
<211> LENGTH: 108
<212> TYPE: PRT
<213> ORGANISM: Homo sapiens

<400> SEQUENCE: 413

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Arg Pro Ile Gly Thr Met
                 20                  25                  30

Leu Ser Trp Tyr Gln Gln Lys Pro Gly Lys Ala Pro Lys Leu Leu Ile
             35                  40                  45

Leu Ala Phe Ser Arg Leu Gln Ser Gly Val Pro Ser Arg Phe Ser Gly
         50                  55                  60

Ser Gly Ser Gly Thr Asp Phe Thr Leu Thr Ile Ser Asn Leu Gln Pro
 65                  70                  75                  80

Glu Asp Phe Ala Thr Tyr Tyr Cys Ala Gln Ala Gly Thr His Pro Thr
                 85                  90                  95

Thr Phe Gly Gln Gly Thr Lys Val Glu Ile Lys Trp
            100                 105
```

<210> SEQ ID NO 414
<211> LENGTH: 108
<212> TYPE: PRT
<213> ORGANISM: Homo sapiens

<400> SEQUENCE: 414

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Arg Pro Ile Gly Thr Met
                 20                  25                  30

Leu Ser Trp Tyr Gln Gln Lys Pro Gly Lys Ala Pro Lys Leu Leu Ile
             35                  40                  45

Leu Ala Phe Ser Arg Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Ala Gln Ala Gly Thr His Pro Thr
                 85                  90                  95

Thr Phe Gly Gln Gly Thr Lys Val Glu Ile Lys Trp
            100                 105
```

<210> SEQ ID NO 415
<211> LENGTH: 108
<212> TYPE: PRT
<213> ORGANISM: Homo sapiens

<400> SEQUENCE: 415

```
Asp Ile Gln Met Thr Gln Ser Pro Ser Ser Leu Ser Ala Ser Val Gly
  1               5                  10                  15
```

```
Asp Arg Val Thr Ile Thr Cys Arg Ala Ser Arg Pro Ile Gly Thr Met
            20                  25                  30

Leu Ser Trp Tyr Gln Gln Lys Pro Gly Lys Ala Pro Lys Leu Leu Ile
        35                  40                  45

Leu Ala Phe Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His His Thr
                85                  90                  95

Thr Phe Gly Gln Gly Thr Lys Val Glu Asn Lys Trp
            100                 105
```

<210> SEQ ID NO 416
<211> LENGTH: 108
<212> TYPE: PRT
<213> ORGANISM: Homo sapiens

<400> SEQUENCE: 416

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
            20                  25                  30

Leu Ser Trp Tyr Gln Gln Lys Pro Gly Glu Ala Pro Lys Leu Leu Ile
        35                  40                  45

Leu Ala Phe Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Thr Gly Thr His Pro Thr
                85                  90                  95

Thr Phe Gly Gln Gly Thr Lys Val Glu Ile Lys Trp
            100                 105
```

<210> SEQ ID NO 417
<211> LENGTH: 108
<212> TYPE: PRT
<213> ORGANISM: Homo sapiens

<400> SEQUENCE: 417

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
            20                  25                  30

Leu Ser Trp Tyr Gln Gln Lys Pro Gly Lys Ala Pro Lys Leu Leu Ile
        35                  40                  45

Leu Ala Phe Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Val His Pro Thr
                85                  90                  95

Thr Phe Gly Gln Gly Thr Lys Val Glu Ile Lys Arg
            100                 105
```

<210> SEQ ID NO 418

```
<211> LENGTH: 108
<212> TYPE: PRT
<213> ORGANISM: Homo sapiens

<400> SEQUENCE: 418

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
                20                  25                  30

Leu Ser Trp Tyr Gln Gln Lys Pro Gly Lys Ala Pro Lys Leu Leu Ile
            35                  40                  45

Leu Ala Phe Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Thr Gly Thr His Pro Thr
                85                  90                  95

Thr Phe Gly Gln Gly Thr Lys Val Glu Ile Lys Trp
            100                 105

<210> SEQ ID NO 419
<211> LENGTH: 108
<212> TYPE: PRT
<213> ORGANISM: Homo sapiens

<400> SEQUENCE: 419

Asp Ile Gln Met Thr Gln Ser Pro Ser Ser Leu Ser Ala Ser Val Gly
1               5                   10                  15

Asp Arg Val Thr Ile Phe Cys Arg Ala Ser Arg Pro Ile Gly Thr Met
                20                  25                  30

Leu Ser Trp Tyr Gln Gln Lys Pro Gly Lys Ala Pro Lys Leu Leu Ile
            35                  40                  45

Leu Ala Phe Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His Pro Thr
                85                  90                  95

Thr Phe Gly Gln Gly Thr Lys Val Glu Ile Lys Trp
            100                 105

<210> SEQ ID NO 420
<211> LENGTH: 108
<212> TYPE: PRT
<213> ORGANISM: Homo sapiens

<400> SEQUENCE: 420

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
                20                  25                  30

Leu Ser Trp Tyr Gln Gln Lys Pro Gly Lys Ala Pro Lys Leu Leu Ile
            35                  40                  45

Leu Ala Phe Ser Arg Leu Gln Ser Gly Val Pro Ser Arg Phe Ser Gly
        50                  55                  60

Ser Gly Ser Gly Thr Asp Phe Thr Leu Thr Ile Ser Asn Leu Gln Pro
65                  70                  75                  80
```

```
Glu Asp Phe Ala Thr Tyr Tyr Cys Ala Gln Ala Gly Thr His Pro Thr
                85                  90                  95

Thr Phe Gly Gln Gly Thr Lys Val Glu Ile Lys Arg
            100                 105
```

<210> SEQ ID NO 421
<211> LENGTH: 108
<212> TYPE: PRT
<213> ORGANISM: Homo sapiens

<400> SEQUENCE: 421

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
            20                  25                  30

Leu Ser Trp Tyr Gln Gln Lys Pro Gly Lys Ala Pro Lys Leu Leu Ile
        35                  40                  45

Leu Ala Phe Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Ala Gln Ala Gly Thr His Pro Thr
                85                  90                  95

Thr Phe Gly Gln Gly Thr Lys Val Glu Ile Lys Arg
            100                 105
```

<210> SEQ ID NO 422
<211> LENGTH: 108
<212> TYPE: PRT
<213> ORGANISM: Homo sapiens

<400> SEQUENCE: 422

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
            20                  25                  30

Leu Ser Trp Tyr Gln Gln Lys Pro Gly Lys Ala Pro Lys Leu Leu Ile
        35                  40                  45

Leu Ala Phe Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His His Thr
                85                  90                  95

Thr Phe Gly Gln Gly Thr Lys Val Glu Ile Lys Arg
            100                 105
```

<210> SEQ ID NO 423
<211> LENGTH: 108
<212> TYPE: PRT
<213> ORGANISM: Homo sapiens

<400> SEQUENCE: 423

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Met
            20                  25                  30

Leu Ser Trp Tyr Gln Gln Lys Pro Gly Lys Ala Pro Lys Leu Leu Ile
```

```
              35                  40                  45
Leu Ala Phe Ser Arg Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Ala Gly Thr His His Thr
                 85                  90                  95

Thr Phe Gly Gln Gly Thr Lys Val Glu Asn Lys Arg
            100                 105
```

<210> SEQ ID NO 424
<211> LENGTH: 324
<212> TYPE: DNA
<213> ORGANISM: Artificial Sequence
<220> FEATURE:
<223> OTHER INFORMATION: Nucleotide

<400> SEQUENCE: 424

```
gacatccaga tgacccagtc tccatcctcc ctgtctgcat ctgtaggaga ccgtgtcacc    60
atcacttgcc gggcaagtcg tccgattggg acgatgttaa gttggtacca gcagaaacca   120
gggaaagccc ctaagctcct gatccttgct ttttcccgtt tgcaaagtgg ggtcccatca   180
cgtttcagtg gcagtggatc tgggacagat ttcactctca ccatcagcag tctgcaacct   240
gaagattttg ctacgtacta ctgcgcgcag gctgggacgc atcctacgac gttcggccaa   300
gggaccaagg tggaaatcaa atgg                                          324
```

<210> SEQ ID NO 425
<211> LENGTH: 324
<212> TYPE: DNA
<213> ORGANISM: Artificial Sequence
<220> FEATURE:
<223> OTHER INFORMATION: Nucleotide

<400> SEQUENCE: 425

```
gacatccaga tgacccagtc tccatcctcc ctgtctgcat ctgtaggaga ccgtgtcacc    60
atctcttgcc gggcaagtcg tccgattggg acgatgttaa gttggtacca gcagaaacca   120
gggaaagccc ctaagctcct gatccttgct ttttcccgtt tgcaaagtgg ggtcccatca   180
cgtttcagtg gcagtggatc tgggacagat ttcactctca ccatcagcag tctgcaacct   240
gaagattttg ctacgtacta ctgcgcgcag gctgggacgc atcctacgac gttcggccaa   300
gggaccaagg tggaaatcaa atgg                                          324
```

<210> SEQ ID NO 426
<211> LENGTH: 324
<212> TYPE: DNA
<213> ORGANISM: Artificial Sequence
<220> FEATURE:
<223> OTHER INFORMATION: Nucleotide

<400> SEQUENCE: 426

```
gacatccaga tgacccagtc tccatcctcc ctgtctgcat ctgtaggaga ccgtgtcacc    60
atcacttgcc gggcaagtcg tccgattggg acgatgttaa gttggtacca gcagaaacca   120
gggaaagccc ctaagctcct gatccttgct ttttcccgtt tgcaaagtgg ggtcccatca   180
cgtttcagtg gcagtggatc tgggacagat ttcactctca ccatcagcaa tctgcaacct   240
gaagattttg ctacgtacta ctgcgcgcag gctgggacgc atcctacgac gttcggccaa   300
gggaccaagg tggaaatcaa atgg                                          324
```

<210> SEQ ID NO 427
<211> LENGTH: 324
<212> TYPE: DNA
<213> ORGANISM: Artificial Sequence
<220> FEATURE:
<223> OTHER INFORMATION: Nucleotide

<400> SEQUENCE: 427

```
gacatccaga tgacccagtc tccatcctcc ctgtctgcat ctgtaggaga ccgtgtcacc      60
atcacttgcc gggcaagtcg tccgattggg acgatgttaa gttggtacca gcagaaacca     120
gggaaagccc ctaagctcct gatccttgct tttcccgtt tgcaaagtgg ggtcccatca      180
cgtttcagtg gcagtggatc tgggacagat ttcactctca ccatcagcag tctgcaacct     240
gaagatgttg ctacgtacta ctgtgcgcag gctgggacgc atcctacgac gttcggccaa     300
gggaccaagg tggaaatcaa atgg                                            324
```

<210> SEQ ID NO 428
<211> LENGTH: 324
<212> TYPE: DNA
<213> ORGANISM: Artificial Sequence
<220> FEATURE:
<223> OTHER INFORMATION: Nucleotide

<400> SEQUENCE: 428

```
gacatccaga tgacccagtc tccatcctcc ctgtctgcat ctgtaggaga ccgtgtcacc      60
atcacttgcc gggcaagtcg tccgattggg acgatgttaa gttggtacca gcagaaacca     120
gggaaagccc ctaagctcct gatccttgct tttcccgtt tgcaaagtgg ggtcccatca      180
cgtttcagtg gcagtggatc tgggacagat ttcactctca ccatcagcag tctgcaacct     240
gaagattttg ctacgtacta ctgtgcgcag gctgggacgc atcatacgac gttcggccaa     300
gggaccaagg tggaaaacaa atgg                                            324
```

<210> SEQ ID NO 429
<211> LENGTH: 324
<212> TYPE: DNA
<213> ORGANISM: Artificial Sequence
<220> FEATURE:
<223> OTHER INFORMATION: Nucleotide

<400> SEQUENCE: 429

```
gacatccaga tgacccagtc tccatcctcc ctgtctgcat ctgtaggaga ccgtgtcacc      60
atcacttgcc gggcaagtcg tccgattggg acgatgttaa gttggtacca gcagaaacca     120
ggggaagccc ctaagctcct gatccttgct tttcccgtt tgcaaagtgg ggtcccatca      180
cgtttcagtg gcagtggatc tgggacagat ttcactctca ccatcagcag tctgcaacct     240
gaagattttg ctacgtacta ctgtgcgcag actgggacgc atcctacgac gttcggccaa     300
gggaccaagg tggaaatcaa atgg                                            324
```

<210> SEQ ID NO 430
<211> LENGTH: 324
<212> TYPE: DNA
<213> ORGANISM: Artificial Sequence
<220> FEATURE:
<223> OTHER INFORMATION: Nucleotide

<400> SEQUENCE: 430

```
gacatccaga tgacccagtc tccatcctcc ctgtctgcat ctgtaggaga ccgtgtcacc      60
```

| | |
|---|---|
| atcacttgcc gggcaagtcg tccgattggg acgatgttaa gttggtacca gcagaaacca | 120 |
| gggaaagccc ctaagctcct gatccttgct ttttcccgtt tgcaaagtgg ggtcccatca | 180 |
| cgtttcagtg gcagtggatc tgggacagat ttcactctca ccatcagcag tctgcaacct | 240 |
| gaagattttg ctacgtacta ctgtgcgcag gctggggtgc atcctacgac gttcggccaa | 300 |
| gggaccaagg tggaaatcaa acgg | 324 |

<210> SEQ ID NO 431
<211> LENGTH: 324
<212> TYPE: DNA
<213> ORGANISM: Artificial Sequence
<220> FEATURE:
<223> OTHER INFORMATION: Nucleotide

<400> SEQUENCE: 431

| | |
|---|---|
| gacatccaga tgacccagtc tccatcctcc ctgtctgcat ctgtaggaga ccgtgtcacc | 60 |
| atcacttgcc gggcaagtcg tccgattggg acgatgttaa gttggtacca gcagaaacca | 120 |
| gggaaagccc ctaagctcct gatccttgct ttttcccgtt tgcaaagtgg ggtcccatca | 180 |
| cgtttcagtg gcagtggatc tgggacagat ttcactctca ccatcagcag tctgcaacct | 240 |
| gaagattttg ctacgtacta ctgtgcgcag actgggacgc atcctacgac gttcggccaa | 300 |
| gggaccaagg tggaaatcaa atgg | 324 |

<210> SEQ ID NO 432
<211> LENGTH: 324
<212> TYPE: DNA
<213> ORGANISM: Artificial Sequence
<220> FEATURE:
<223> OTHER INFORMATION: Nucleotide

<400> SEQUENCE: 432

| | |
|---|---|
| gacatccaga tgacccagtc tccatcctcc ctgtctgcat ctgtaggaga ccgtgtcacc | 60 |
| atcttttgcc gggcaagtcg tccgattggg acgatgttaa gttggtacca gcagaaacca | 120 |
| gggaaagccc ctaagctcct gatccttgct ttttcccgtt tgcaaagtgg ggtcccatca | 180 |
| cgtttcagtg gcagtggatc tgggacagat ttcactctca ccatcagcag tctgcaacct | 240 |
| gaagattttg ctacgtacta ctgcgcgcag gctgggacgc atcctacgac gttcggccaa | 300 |
| gggaccaagg tggaaatcaa atgg | 324 |

<210> SEQ ID NO 433
<211> LENGTH: 324
<212> TYPE: DNA
<213> ORGANISM: Artificial Sequence
<220> FEATURE:
<223> OTHER INFORMATION: Nucleotide

<400> SEQUENCE: 433

| | |
|---|---|
| gacatccaga tgacccagtc tccatcctcc ctgtctgcat ctgtaggaga ccgtgtcacc | 60 |
| atcacttgcc gggcaagtcg tccgattggg acgatgttaa gttggtacca gcagaaacca | 120 |
| gggaaagccc ctaagctcct gatccttgct ttttcccgtt tgcaaagtgg ggtcccatca | 180 |
| cgtttcagtg gcagtggatc tgggacagat ttcactctca ccatcagcaa tctgcaacct | 240 |
| gaagattttg ctacgtacta ctgcgcgcag gctgggacgc atcctacgac gttcggccaa | 300 |
| gggaccaagg tggaaatcaa acgg | 324 |

<210> SEQ ID NO 434
<211> LENGTH: 324

```
<212> TYPE: DNA
<213> ORGANISM: Artificial Sequence
<220> FEATURE:
<223> OTHER INFORMATION: Nucleotide

<400> SEQUENCE: 434
gacatccaga tgacccagtc tccatcctcc ctgtctgcat ctgtaggaga ccgtgtcacc      60
atcacttgcc gggcaagtcg tccgattggg acgatgttaa gttggtacca gcagaaacca     120
gggaaagccc ctaagctcct gatccttgct ttttcccgtt tgcaaagtgg ggtcccatca     180
cgtttcagtg gcagtggatc tgggacagat ttcactctca ccatcagcag tctgcaacct     240
gaagatgttg ctacgtacta ctgtgcgcag gctgggacgc atcctacgac gttcggccaa     300
gggaccaagg tggaaatcaa acgg                                             324

<210> SEQ ID NO 435
<211> LENGTH: 324
<212> TYPE: DNA
<213> ORGANISM: Artificial Sequence
<220> FEATURE:
<223> OTHER INFORMATION: Nucleotide

<400> SEQUENCE: 435
gacatccaga tgacccagtc tccatcctcc ctgtctgcat ctgtaggaga ccgtgtcacc      60
atcacttgcc gggcaagtcg tccgattggg acgatgttaa gttggtacca gcagaaacca     120
gggaaagccc ctaagctcct gatccttgct ttttcccgtt tgcaaagtgg ggtcccatca     180
cgtttcagtg gcagtggatc tgggacagat ttcactctca ccatcagcag tctgcaacct     240
gaagattttg ctacgtacta ctgtgcgcag gctgggacgc atcatacgac gttcggccaa     300
gggaccaagg tggaaatcaa acgg                                             324

<210> SEQ ID NO 436
<211> LENGTH: 324
<212> TYPE: DNA
<213> ORGANISM: Artificial Sequence
<220> FEATURE:
<223> OTHER INFORMATION: Nucleotide

<400> SEQUENCE: 436
gacatccaga tgacccagtc tccatcctcc ctgtctgcat ctgtaggaga ccgtgtcacc      60
atcacttgcc gggcaagtcg tccgattggg acgatgttaa gttggtacca gcagaaacca     120
gggaaagccc ctaagctcct gatccttgct ttttcccgtt tgcaaagtgg ggtcccatca     180
cgtttcagtg gcagtggatc tgggacagat ttcactctca ccatcagcag tctgcaacct     240
gaagattttg ctacgtacta ctgtgcgcag gctgggacgc atcatacgac gttcggccaa     300
gggaccaagg tggaaaacaa acgg                                             324

<210> SEQ ID NO 437
<211> LENGTH: 6
<212> TYPE: PRT
<213> ORGANISM: Artificial Sequence
<220> FEATURE:
<223> OTHER INFORMATION: Linker

<400> SEQUENCE: 437

Thr Val Ala Ala Pro Ser
 1               5

<210> SEQ ID NO 438
<211> LENGTH: 108
```

```
<212> TYPE: PRT
<213> ORGANISM: Homo sapiens

<400> SEQUENCE: 438

Asp Ile Gln Met Thr Gln Ser Pro Ser Ser Leu Ser Ala Ser Val Gly
 1               5                   10                  15

Asp Arg Val Thr Ile Thr Cys Arg Ala Ser Arg Pro Ile Gly Thr Thr
                20                  25                  30

Leu Ser Trp Tyr Gln Gln Lys Pro Gly Lys Ala Pro Lys Leu Leu Ile
             35                  40                  45

Trp Phe Gly Ser Arg Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His Pro Thr
                85                  90                  95

Thr Phe Gly Gln Gly Thr Lys Val Glu Ile Lys Arg
            100                 105

<210> SEQ ID NO 439
<211> LENGTH: 6
<212> TYPE: PRT
<213> ORGANISM: Artificial Sequence
<220> FEATURE:
<223> OTHER INFORMATION: Linker

<400> SEQUENCE: 439

Gly Gly Gly Gly Ser Cys
 1               5

<210> SEQ ID NO 440
<211> LENGTH: 7
<212> TYPE: PRT
<213> ORGANISM: Artificial Sequence
<220> FEATURE:
<223> OTHER INFORMATION: Linker

<400> SEQUENCE: 440

Thr Val Ala Ala Pro Ser Cys
 1               5
```